(12) United States Patent
Yokota et al.

(10) Patent No.: US 11,433,089 B2
(45) Date of Patent: Sep. 6, 2022

(54) BLOOD-BRAIN BARRIER PERMEABLE HETERODUPLEX NUCLEIC ACID

(71) Applicant: NATIONAL UNIVERSITY CORPORATION TOKYO MEDICAL AND DENTAL UNIVERSITY, Tokyo (JP)

(72) Inventors: Takanori Yokota, Tokyo (JP); Tetsuya Nagata, Tokyo (JP)

(73) Assignee: NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 0 days.

(21) Appl. No.: 16/335,017

(22) PCT Filed: Sep. 25, 2017

(86) PCT No.: PCT/JP2017/034561
§ 371 (c)(1),
(2) Date: Mar. 20, 2019

(87) PCT Pub. No.: WO2018/056442
PCT Pub. Date: Mar. 29, 2018

(65) Prior Publication Data
US 2019/0247414 A1    Aug. 15, 2019

(30) Foreign Application Priority Data
Sep. 23, 2016   (JP) .............. JP2016-185806

(51) Int. Cl.
| A61K 48/00 | (2006.01) |
| A61K 31/711 | (2006.01) |
| A61K 47/22 | (2006.01) |
| A61K 47/28 | (2006.01) |
| C12N 15/113 | (2010.01) |
| A61K 47/54 | (2017.01) |
| A61P 25/00 | (2006.01) |
| A61K 31/7088 | (2006.01) |
| C12N 15/09 | (2006.01) |
| A61P 27/02 | (2006.01) |
| A61K 9/00 | (2006.01) |
| A61K 31/7125 | (2006.01) |

(52) U.S. Cl.
CPC .......... *A61K 31/711* (2013.01); *A61K 9/0019* (2013.01); *A61K 31/7088* (2013.01); *A61K 31/7125* (2013.01); *A61K 47/22* (2013.01); *A61K 47/28* (2013.01); *A61K 47/542* (2017.08); *A61K 47/554* (2017.08); *A61K 48/00* (2013.01); *A61P 25/00* (2018.01); *A61P 27/02* (2018.01); *C12N 15/09* (2013.01); *C12N 15/113* (2013.01)

(58) Field of Classification Search
CPC .. A61K 31/711; A61K 48/00; A61K 31/7088; A61K 9/0019; A61K 31/7125; A61K 47/22; A61K 47/28; A61K 47/542; A61K 47/554; C12N 15/09; C12N 15/113; C12N 2310/3341; C12N 2320/32; C12N 2310/315; C12N 2310/345; C12N 2310/346; C12N 2310/3231; C12N 2310/3515; C12N 2310/321; C12N 2310/14; C12N 2310/341; C12N 15/111; A61P 27/02; A61P 25/00
See application file for complete search history.

(56) References Cited

U.S. PATENT DOCUMENTS

| 11,116,843 B2 | 9/2021 | Seth et al. |
| 2014/0302603 A1 | 10/2014 | Yokota et al. |
| 2016/0130583 A1 | 5/2016 | Yokota et al. |
| 2016/0287714 A1 | 10/2016 | Kataoka et al. |
| 2018/0256729 A1 | 9/2018 | Seth et al. |
| 2022/0023429 A1 | 1/2022 | Seth et al. |

FOREIGN PATENT DOCUMENTS

| JP | 2015-502134 A | 1/2015 |
| WO | 2011/123468 A1 | 10/2011 |
| WO | 2013/089283 A1 | 6/2013 |

(Continued)

OTHER PUBLICATIONS www.proteinatlas.org/ENSG00000084674-APOB/brain (retrieved Oct. 23, 2020) (Year: 2020).*

(Continued)

*Primary Examiner* — J. E. Angell
(74) *Attorney, Agent, or Firm* — Lucas & Mercanti, LLP

(57) ABSTRACT

The present invention provides a composition and a method for efficiently delivering a nucleic acid agent to the central nervous system and/or the retina and bringing about antisense effects. Provided is a composition for reducing the expression level of a target transcription product in the central nervous system and/or retina of a subject, the composition including a nucleic acid complex that includes a first nucleic acid strand and a second nucleic acid strand, wherein: the first nucleic acid strand comprises a base sequence capable of hybridizing with at least part of the target transcription product and has an antisense effect on the target transcription product; the second nucleic acid strand comprises a base sequence complementary to the first nucleic acid strand and is conjugated to tocopherol, cholesterol, or an analog thereof; and the first nucleic acid strand is annealed to the second nucleic acid strand.

12 Claims, 63 Drawing Sheets

Specification includes a Sequence Listing.

(56) References Cited

FOREIGN PATENT DOCUMENTS

| WO | 2014118267 A1 | 8/2014 |
|---|---|---|
| WO | 2014/132671 A1 | 9/2014 |
| WO | 2014/192310 A1 | 12/2014 |
| WO | 2014/203518 A1 | 12/2014 |
| WO | 2015/075942 A1 | 5/2015 |

OTHER PUBLICATIONS

Uno, Y. et al., Efficient in vivo delivery of siRNA to the Brain by Conjugation of alpha-Tocopherol, 32th The Annual Meeting of the Molecular Biology Society of Japan: abstracts, 2009, p. 248, IP-0816, entire text.

Uno, Y. et al., Efficient in vivo delivery of siRNA to the Brain by Conjugation of alpha-Tocopherol, Molecular Therapy, 2009, vol. 17, Supplement 1, p. S197, 515, entire text.

Nishina, K. et al., Novel oligonucleotide based on DNA/RNA heteroduplex structures, 57th Annual Meeting of the Japanese Society of Neurology: abstracts, May 2016, p. 194, entire text, non-official translation.

Julia F. Alterman, et al., "Hydrophobically Modified siRNAs Silence Huntingtin . . . ", Molecular Therapy—Nucleic Acids, vol. 4, No. 12, pp. e266, 2015.

Yoshitaka Uno, et al., "High-Density Lipoprote Facilitates in Vivo Delivery . . . ", Human Gene Therapy, vol. 22, No. 6, pp. 711-719, 2011.

Kazutaka Nishina, et al., "DNA/RNA Heteroduplex Oligonucleotide for Highly Efficient Gene Silencing", Nature Communications, vol. 6, No. 7969, pp. 1-13, 2015.

Supplemental European Search Report corresponding to European Application No. 17853209.9 dated Apr. 28, 2020 (5 pages).

"TTR transthyretin [*Homo sapiens* (human)]-Gene-NCBI", https://www.ncbi.nlm.nih.gov/gene/7276#gene-expression, pp. 1-9. [Gene ID: 7276, updated on Nov. 28, 2021].

"Brain tissue expression of TTR-Summary—The Human Protein Atlas", https://www.proteinatlas.org/ENSG00000118271-TTR/brain, pp. 1-3.

Jan Krutzfeldt et al., "Silencing of microRNAs in vivo with 'antagomirs'", Nature, vol. 438, pp. 685-689, 2005. [Letters].

* cited by examiner (a)

(b)

(c)

(d)

a b c d a b a b c d a Cerebral Cortex b Cerebellum c Striatum d Hippocampus a 
b 
c 
d a b c d a Cerebral Cortex b Cerebellum c Striatum d Hippocampus e Brainstem a Cerebral Cortex b Cerebellum c Striatum d Hippocampus a  Cervical Spinal Cord b  Lumbar Spinal Cord a b c d e f a b c d a Cerebral Cortex b Cerebellum c Striatum d Hippocampus a b a b a Cerebral Cortex b Cerebellum c Striatum d Hippocampus a Cerebral Cortex b Cerebellum c Striatum d Hippocampus a b

BLOOD-BRAIN BARRIER PERMEABLE HETERODUPLEX NUCLEIC ACID

CROSS-REFERENCE TO RELATED APPLICATIONS

This application is a 371 of PCT/JP2017/034561, filed Sep. 25, 2017, which claims benefit of Japanese Patent Application No. 2016-185806 filed on Sep. 23, 2016.

REFERENCE TO A SEQUENCE LISTING SUBMITTED ELECTRONICALLY VIA EFS-WEB

The content of the electronically submitted sequence listing, file name: 522-1153_Sequence_Listing.txt; size: 48,491 bytes; and date of creation: Mar. 18, 2019, filed herewith, is incorporated herein by reference in its entirety.

TECHNICAL FIELD

The present invention relates to a composition for bringing about an antisense effect in the central nervous system of a subject, and the like.

BACKGROUND ART

Recently oligonucleotides have been drawing attention in the ongoing development of pharmaceuticals called nucleic acid medicine. In particular, nucleic acid medicine using an antisense method is being actively developed, taking the high selectivity for target genes and the low toxicity into consideration. An antisense method includes a method in which the expression of a protein encoded by a target gene is selectively altered or inhibited by introducing an oligonucleotide (for example, an antisense oligonucleotide, in other words, ASO) complementary to a partial sequence of mRNA (a sense strand) of the target gene into cells. Similarly, the antisense method targets miRNA and functions to alter the activity of such a miRNA.

As a nucleic acid using an antisense method, a double-stranded nucleic acid complex obtained by annealing an antisense oligonucleotide and a strand complementary thereto has been developed by the present inventors (Patent Literature 1). Patent Literature 1 discloses that an antisense oligonucleotide annealed to a tocopherol-conjugated complementary strand is efficiently delivered to the liver and also has a high antisense effect. The present inventors have also developed a double-stranded antisense nucleic acid having an exon-skipping effect (Patent Literature 2) and a short gapmer antisense oligonucleotide wherein an additional nucleotide is added to the 5' end, 3' end, or both the 5' end and 3' end of the gapmer (antisense oligonucleotide) (Patent Literature 3). The present inventors have also developed a double-stranded agent for delivering therapeutic oligonucleotides (Patent Literature 4).

The brain has a mechanism called the blood brain barrier (BBB), which selects and limits substances transported to the brain. This mechanism plays a role to protect the brain from harmful substances. At the same time, the blood brain barrier also acts as a barrier to delivering a drug to the brain. There is a demand for a method of delivering a nucleic acid agent such as an antisense oligonucleotide to the nervous system including the brain.

CITATION LIST

Patent Literature

Patent Literature 1: WO2013/089283
Patent Literature 2: WO2014/203518
Patent Literature 3: WO2014/132671
Patent Literature 4: WO2014/192310

SUMMARY OF INVENTION

Technical Problem

A problem to be solved by the present invention is to provide a composition and method for efficiently delivering a nucleic acid agent to the central nervous system and bringing about an antisense effect.

Solution to Problem

To solve the above-mentioned problem, the present inventors have made studies earnestly, and consequently have discovered that a nucleic acid complex in which an antisense oligonucleotide and a tocopherol- or cholesterol-conjugated complementary strand are annealed is efficiently delivered to the central nervous system and/or the retina and exhibits a high antisense effect in the central nervous system and/or the retina, although the nucleic acid complex has conventionally been considered to be delivered mainly to the liver. The present inventors have also discovered that a nucleic acid complex in which an antisense oligonucleotide and an alkyl-group-conjugated complementary strand are annealed, wherein the alkyl group may have a substituent, also exhibits a high antisense effect in the central nervous system. On the basis of these findings, the present inventors have eventually completed the present invention.

The present invention thus encompasses the following.

[1] A composition for reducing the expression level of a target transcription product in the central nervous system of a subject, the composition comprising a nucleic acid complex including a first nucleic acid strand and a second nucleic acid strand, wherein the first nucleic acid strand comprises base sequence capable of hybridizing with at least part of the target transcription product and has an antisense effect on the target transcription product;

wherein the second nucleic acid strand comprises a base sequence complementary to the first nucleic acid strand and is conjugated to a tocopherol, cholesterol, or an analog thereof; and wherein the first nucleic acid strand is annealed to the second nucleic acid strand.

[2] The composition according to [1] for use in the treatment of a central nervous system disease of a subject.

[3] A composition for delivering a drug to the central nervous system of a subject, the composition comprising a nucleic acid complex including a first nucleic acid strand and a second nucleic acid strand, wherein the first nucleic acid strand and/or the second nucleic acid strand are/is conjugated to at least one drug, wherein the second nucleic acid strand comprises a base sequence complementary to the first nucleic acid strand and is conjugated to a tocopherol, cholesterol, or an analog thereof; and wherein the first nucleic acid strand is annealed to the second nucleic acid strand.

[4] The composition according to any one of [1] to [3], wherein the first nucleic acid strand comprises at least four consecutive deoxyribonucleosides.

[5] The composition according to [4], wherein the first nucleic acid strand is a gapmer.

[6] The composition according to [4] or [5], wherein the second nucleic acid strand comprises at least four consecutive ribonucleosides complementary to the at least four consecutive deoxyribonucleosides in the first nucleic acid strand.

[7] The composition according to any one of [1] to [6], wherein the first nucleic acid strand is 13 to 20 bases in length.

[8] The composition according to any one of [1] to [7], wherein the central nervous system is selected from the group consisting of cerebral cortex, basal ganglion, cerebral white matter, diencephalon, brainstem, cerebellum, and spinal cord.

[9] The composition according to any one of [1] to [7], wherein the central nervous system is selected from the group consisting of frontal lobe, temporal lobe, hippocampus, parahippocampal gyrus, parietal lobe, occipital lobe, striatum, globus pallidus, claustrum, thalamus, subthalamic nucleus, midbrain, substantia nigra, pons, medulla oblongata, cerebellar cortex, cerebellar nucleus, cervical spinal cord, thoracic spinal cord, and lumbar spinal cord.

[10] The composition according to any one of [1] to [9], wherein the composition is intravenously administered or subcutaneously administered.

[11] The composition according to any one of [1] to [10], wherein the nucleic acid complex is administered at 5 mg/kg or more per dose.

[12] The composition according to any one of [1] to [11], wherein the second nucleic acid strand does not comprise natural ribonucleosides.

[13] The composition according to any one of [1] to [12], wherein the nucleic acid moiety of the second nucleic acid strand consists of deoxyribonucleosides and/or sugar-modified nucleoside, each of which is linked by a modified or unmodified internucleoside linkage.

[14] The composition according to any one of [1] to [13], wherein a ligand is conjugated to the second nucleic acid strand via an uncleavable linker.

[15] The composition according to any one of [1] to [14], wherein the first nucleic acid strand is a mixmer.

[16] The composition according to any one of [1] to [15], wherein the nucleic acid complex permeates the blood brain barrier (BBB).

[17] A composition for regulating the expression or editing of a target RNA in the retina of a subject, the composition comprising a nucleic acid complex including a first nucleic acid strand and a second nucleic acid strand, wherein the first nucleic acid strand comprises a base sequence capable of hybridizing with at least part of the target RNA and has an antisense effect on the target RNA;

wherein the second nucleic acid strand comprises a base sequence complementary to the first nucleic acid strand and is conjugated to a tocopherol, cholesterol, or an alkyl group that may have a substituent; and wherein the first nucleic acid strand is annealed to the second nucleic acid strand.

[18] The composition according to [17], wherein the nucleic acid complex permeates the blood retina barrier (BRB).

The present Description encompasses the contents disclosed in Japanese Patent Application No. 2016-185806 that serves as a basis for the priority of the present application.

Advantageous Effects of Invention

The present invention provides a composition and method for efficiently delivering a nucleic acid agent to the central nervous system and/or the retina and bringing about an antisense effect.

DESCRIPTION OF EMBODIMENTS

<Nucleic Acid Complex>

The present invention relates to a composition including a nucleic acid complex. The nucleic acid complex includes a first nucleic acid strand and a second nucleic acid strand. The second nucleic acid strand is a nucleotide strand including a base sequence complementary to the first nucleic acid strand. In one embodiment, the second nucleic acid strand is conjugated to a tocopherol, cholesterol, or an analog thereof. In the nucleic acid complex, the first nucleic acid strand is annealed to the second nucleic acid strand.

Figure 1:
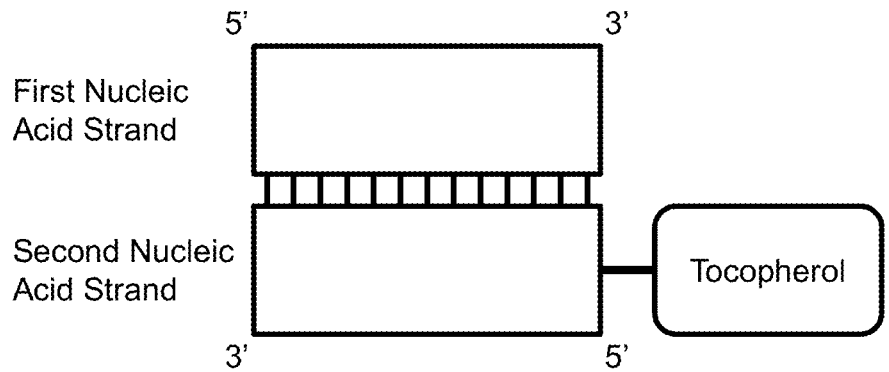
FIG. 1 is a schematic diagram depicting examples of specific embodiments of a nucleic acid complex used in the present invention.
Figure 1:
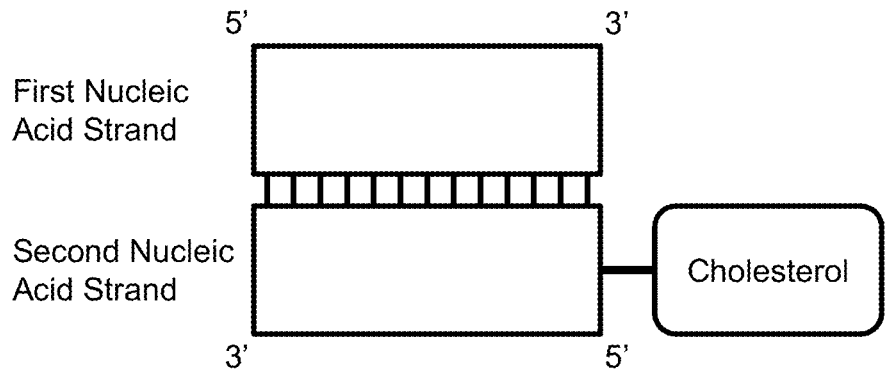
Figure 1:
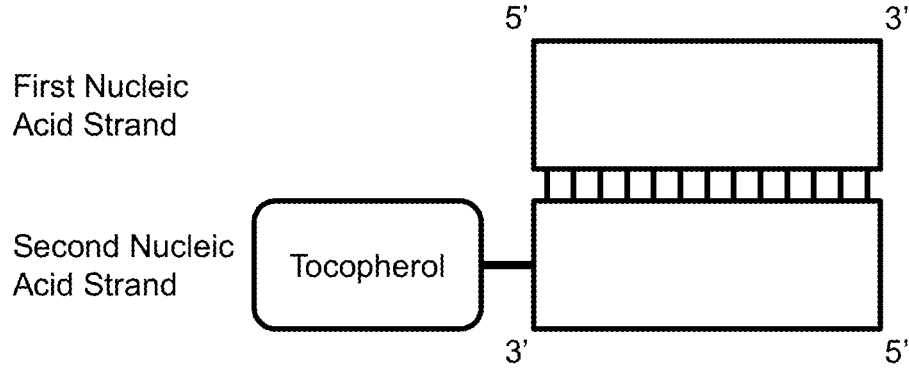
Figure 1:
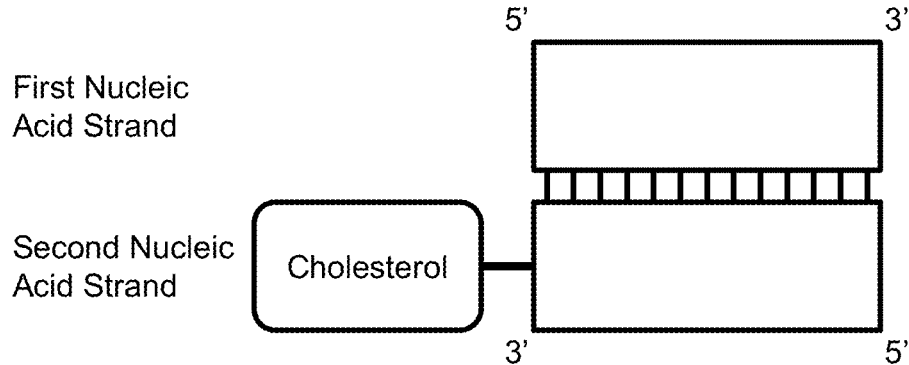

A typical schematic diagram of a nucleic acid complex is shown in FIG. 1. FIG. 1*a* depicts a nucleic acid complex having a tocopherol conjugated to the 5' end of the second nucleic acid strand. FIG. 1*b* depicts a nucleic acid complex having cholesterol conjugated to the 5' end of the second nucleic acid strand. FIG. 1*c* depicts a nucleic acid complex having a tocopherol conjugated to the 3' end of the second nucleic acid strand. FIG. 1*d* depicts a nucleic acid complex having cholesterol conjugated to the 3' end of the second nucleic acid strand. As below-mentioned, however, the tocopherol, cholesterol, or analog thereof may be conjugated to the 5' end, 3' end, or both ends of the second nucleic acid strand, or may be conjugated to a nucleotide inside the second nucleic acid strand.

In one embodiment, the first nucleic acid strand is a nucleotide strand including a base sequence capable of hybridizing with at least part of a target transcription product. In a specific embodiment, the first nucleic acid strand is a nucleotide strand having an antisense effect on a transcription product of a target gene or on a target transcription product.

Figure 2:
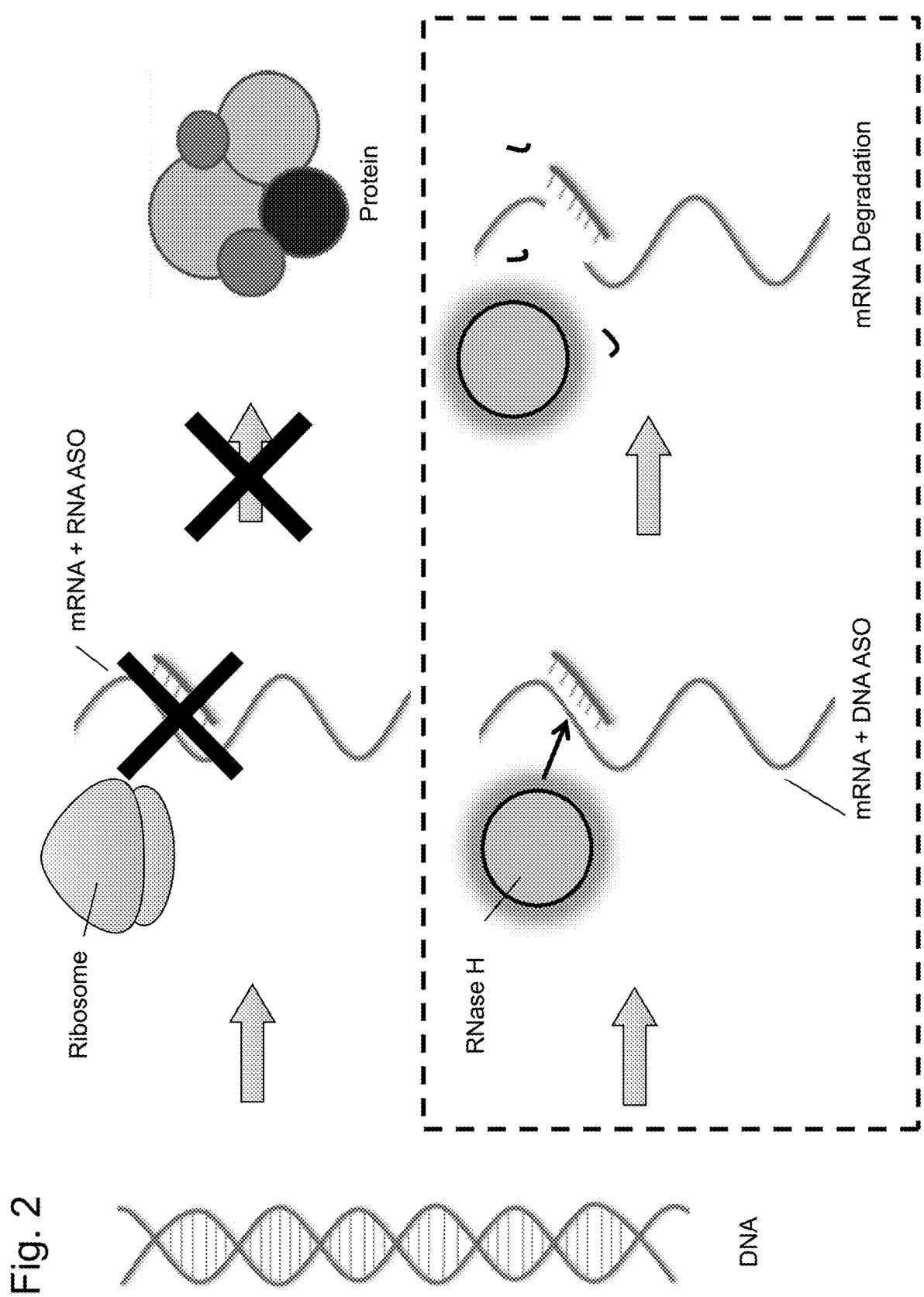
FIG. 2 is a schematic depicting an example of a general mechanism of an antisense method.

An "antisense effect" refers to suppression of expression of a target gene or suppression of the level of a target transcription product, wherein the suppression results from hybridization between a target transcription product (RNA sense strand) and, for example, a DNA strand or, more commonly, a strand that is complementary to a partial sequence of the transcription product and the like and designed to cause an antisense effect. In a specific example, translation inhibition or a splicing function alteration effect, for example, exon-skipping can be caused by hybridization of an antisense oligonucleotide (for example, a first nucleic acid strand) with a transcription product (see the depiction in the upper moiety outside the area surrounded by the dotted line in FIG. 2). Alternatively, degradation of a transcription product can result from recognition of the hybridized moiety (see the depiction in the area surrounded by the dotted line in FIG. 2). For example, in translation inhibition, an RNA-containing oligonucleotide is introduced as an antisense oligonucleotide (ASO) into a cell, and the ASO is bound to a transcription product (mRNA) of a target gene to form a partial double-strand. This double-strand plays a role as a cover for inhibiting translation by ribosome, and accordingly, the expression of the protein encoded by the target gene is inhibited (the upper moiety in FIG. 2). In addition, a DNA-containing oligonucleotide introduced as an ASO into a cell forms a partial DNA-RNA heteroduplex. This structure is recognized by an RNase H, and, as a result, the mRNA of the target gene is degraded, and accordingly, the expression of the protein encoded by the target gene is inhibited (see the lower moiety in FIG. 2). This is referred to as an RNase-H-dependent pathway. Furthermore, in a specific example, an antisense effect can be caused by targeting the introns of a pre-mRNA. An antisense effect can also be caused by targeting a miRNA. In this case, the function of the miRNA is inhibited, and the expression of a gene which is usually regulated by the miRNA can increase.

An "antisense oligonucleotide" or "antisense nucleic acid" refers to a single-stranded oligonucleotide which contains a base sequence capable of hybridizing with (in other words, complementary to) at least part of a transcription product of a target gene or a target transcription product and which can suppress expression of the transcription product of the target gene or the level of the target transcription product mainly by means of an antisense effect.

Examples of "target genes" or "target transcription products" the expression of which is suppressed, changed, or altered by means of an antisense effect include, but are not limited particularly to, genes derived from an organism to which a nucleic acid complex is to be introduced, for example, genes the expression of which is increased in various diseases. In addition, a "transcription product of a target gene" is an mRNA transcribed from a genome DNA encoding a target gene, and examples of such products further include mRNAs that have not undergone base modifications, mRNA precursors that have not undergone processing, and the like. Examples of "target transcription products" can include not only mRNAs but also non-coding RNAs (ncRNA) such as miRNAs. Furthermore, more generally, a "transcription product" may be any RNA synthesized by a DNA-dependent RNA polymerase. In one embodiment, a "target transcription product" may be, for example, a metastasis associated lung adenocarcinoma transcript 1 (malat1) non-coding RNA or a scavenger receptor B1 (SR-B1) mRNA. The base sequences of the mouse and human malat1 non-coding RNAs are shown in SEQ ID NOs: 6 and 8 respectively (however, the base sequences of RNAs are shown as the base sequences of DNAs). The base sequences of the mouse and human SR-B1 mRNAs are shown in SEQ ID NOs: 7 and 9 respectively (however, the base sequences of mRNAs are shown as the base sequences of DNAs). The target transcription product may be a DMPK (dystrophia myotonica-protein kinase) mRNA. The base sequences of the mouse and human DMPK mRNAs are shown in SEQ ID NOs: 17 and 18 respectively (however, the base sequences of RNAs are shown as the base sequences of DNAs). The base sequences of genes and transcription products are available from, for example, a known database such as the NCBI (National Center for Biotechnology Information, the U.S.A.) database.

The first nucleic acid strand can comprise a base sequence capable of hybridizing with at least part of a target transcription product (for example, any target region). The target region may include a 3' UTR, 5' UTR, exon, intron, coding region, translation initiation region, translation termination region, or another nucleic acid region. The target region of a target transcription product may comprise a base sequence of, for example, positions 1316 to 1331 of SEQ ID NO:6 in the mouse malat1 non-coding RNA, positions 2479 to 2492 of SEQ ID NO:7 in the mouse SR-B1 mRNA, and positions 2682 to 2697 of SEQ ID NO:17 in the mouse DMPK mRNA. The target region of the target transcription product may be at least 8 bases in length, for example, 10 to 35 bases in length, 12 to 25 bases in length, 13 to 20 bases in length, 14 to 19 bases in length, or 15 to 18 bases in length.

As used herein, the term "nucleic acid" may refer to a monomer nucleotide or nucleoside or may refer to an oligonucleotide composed of a plurality of monomers. As used herein, the term "nucleic acid strand" or "strand" also refers to an oligonucleotide. Nucleic acid strands can be prepared entirely or partially by a chemical synthesis method (for example, using an automated synthesis device) or an enzymic step (for example, without limitation, a polymerase, ligase, or restriction reaction).

As used herein, the term "nucleic acid base" or "base" refers to a heterocyclic ring moiety capable of pairing with a base of another nucleic acid.

As used herein, the term "purified or isolated nucleic acid complex" refers to a nucleic acid complex including at least one nucleic acid strand that does not occur naturally or essentially no natural nucleic acid substance.

As used herein, the term "complementary" refers to a relationship capable of forming what is called a Watson-Crick base pairing (natural type base pairing) or a non-Watson-Crick base pairing (Hoogsteen base pairing and the like) via hydrogen bonding. In the present invention, the first nucleic acid strand does not necessarily have to be completely complementary to at least part of a target transcription product (for example, a transcription product of a target gene), and the base sequence may have a complementarity of at least 70%, preferably at least 80%, more preferably at least 90% (for example, 95%, 96%, 97%, 98%, or 99% or more). Similarly, the first nucleic acid strand does not necessarily have to be completely complementary to the second nucleic acid strand, and the base sequence may have a complementarity of at least 70%, preferably at least 80%, more preferably at least 90% (for example, 95%, 96%, 97%, 98%, or 99% or more). The complementarity of a sequence can be determined using a BLAST program or the like. The first nucleic acid strand can "hybridize" with a target transcription product in a case where the sequence is complementary (typically, in a case where the sequence is complementary to the sequence of at least part of the target transcription product). The first nucleic acid strand can "anneal" to the second nucleic acid strand in a case where the sequence is complementary. A person skilled in the art can easily determine the conditions (temperature, salt concentration, and the like) that enable two strands to be annealed or hybridized, taking the interstrand complementarity degree into consideration. Typically, such conditions may be physiological conditions. Furthermore, a person skilled in the art can easily design an antisense nucleic acid complementary to a target transcription product, for example, on the basis of information on the base sequence of a target gene.

Hybridization conditions may be, for example, stringent conditions such as low stringent conditions and high stringent conditions. Low stringent conditions may be, for example, 30° C., 2×SSC, and 0.1% SDS. The high stringent conditions may be, for example, 65° C., 0.1×SSC, and 0.1% SDS. The stringency of hybridization can be adjusted by changing the conditions such as temperatures and salt concentrations. Here, 1×SSC comprises 150 mM sodium chloride and 15 mM sodium citrate.

The first nucleic acid strand and the second nucleic acid strand may usually be, without particular limitation, at least 8 bases in length, at least 9 bases in length, at least 10 bases in length, at least 11 bases in length, at least 12 bases in length, at least 13 bases in length, at least 14 bases in length, or at least 15 bases in length. The first nucleic acid strand and the second nucleic acid strand may be 35 bases or less in length, 30 bases or less in length, 25 bases or less in length, 24 bases or less in length, 23 bases or less in length, 22 bases or less in length, 21 bases or less in length, 20 bases or less in length, 19 bases or less in length, 18 bases or less in length, 17 bases or less in length, or 16 bases or less in length. The first nucleic acid strand and the second nucleic acid strand may be even about 100 bases in length, 10 to 35 bases in length, 12 to 25 bases in length, 13 to 20 bases in length, 14 to 19 base in length, or 15 to 18 bases in length. The first nucleic acid strand and the second nucleic acid strand may have the same length or different lengths (for example, a length different from each other by 1 to 3 bases). The double-stranded structure formed by the first nucleic acid strand and the second nucleic acid strand may include a bulge. In a specific example, the selection of the length is generally determined, for example, on the basis of cost, a synthesis yield, and, among other factors, the balance between the intensity of an antisense effect and the specificity of a nucleic acid strand to a target.

In general, a "nucleoside" is a combination of a base and a sugar. The nucleic acid base (known as a base) moiety of a nucleoside is usually a heterocyclic base moiety. A "nucleotide" further comprises a phosphate group covalently bound to the sugar moiety of the nucleoside. In a nucleoside comprising a pentofuranosyl sugar, a phosphate group can be linked to the 2', 3', or 5' hydroxyl moiety of the sugar. An oligonucleotide is formed by covalent bonds between nucleosides adjacent to each other, forming a linear polymer oligonucleotide. In general, phosphate groups are considered to form internucleoside linkages of an oligonucleotide inside the oligonucleotide structure.

Herein, a nucleic acid strand can comprise a natural nucleotide and/or an unnatural nucleotide. Herein, a "natural nucleotide" comprises a deoxyribonucleotide found in DNA and a ribonucleotide found in RNA. Herein, "deoxyribonucleotide" and "ribonucleotide" may be referred to as "DNA nucleotide" and "RNA nucleotide" respectively.

Similarly, a "natural nucleoside" as used herein comprises a deoxyribonucleoside found in DNA and a ribonucleoside found in RNA. Herein, "deoxyribonucleoside" and "ribonucleoside" may be referred to as "DNA nucleoside" and "RNA nucleoside" respectively.

An "unnatural nucleotide" refers to any nucleotide other than a natural nucleotide and encompasses a modified nucleotide and a nucleotide mimic. Similarly, an "unnatural nucleoside" as used herein refers to any nucleoside other than a natural nucleoside and encompasses a modified nucleoside and a nucleoside mimic. Herein, a "modified nucleotide" refers to a nucleotide having any one or more of a modified sugar moiety, a modified internucleoside linkage, and a modified nucleic acid base. Herein, a "modified nucleoside" refers to a nucleoside having a modified sugar moiety and/or a modified nucleic acid base. A nucleic acid strand comprising an unnatural oligonucleotide often has desirable characteristics that allow, for example, enhanced cell uptake, enhanced affinity to a nucleic acid target, increased stability in the presence of nuclease, or increased inhibitory activity, and accordingly is more preferable than a natural type.

Herein, a "modified internucleoside linkage" refers to an internucleoside linkage having a substitution or any change from a naturally-occurring internucleoside linkage (in other words, phosphodiester linkage). A modified internucleoside linkage encompasses an internucleoside linkage containing a phosphorus atom and an internucleoside linkage containing no phosphorus atom. Representative examples of phosphorus-containing internucleoside linkages include, but are not limited to, a phosphodiester linkage, phosphorothioate linkage, phosphorodithioate linkage, phosphotriester linkage, methylphosphonate linkage, methylthiophosphonate linkage, boranophosphate linkage, and phosphoramidate linkage. A phosphorothioate linkage refers to an internucleoside linkage resulting from a phosphodiester linkage whose non-bridged oxygen atom is substituted with a sulfur atom. Methods of preparing phosphorus-containing and nonphosphorus-containing linkages are well known. Modified internucleoside linkages are preferably ones having a higher nuclease resistance than naturally occurring internucleoside linkages.

Herein, a "modified nucleic acid base" or "modified base" refers to any nucleic acid base other than adenine, cytosine, guanine, thymine, or uracil. An "unmodified nucleic acid base" or "unmodified base" (natural nucleic acid base) refers to adenine (A) and guanine (G) which are purine bases and to thymine (T), cytosine (C), and uracil (U) which are pyrimidine bases. Examples of modified nucleic acid bases include, but are not limited to: 5-methylcytosine, 5-fluorocytosine, 5-bromocytosine, 5-iodocytosine, and N4-methylcytosine; N6-methyladenine and 8-bromoadenine; and N2-methylguanine or 8-bromoguanine. A modified nucleic acid base is preferably 5-methylcytosine.

Herein, a "modified sugar" refers to a sugar having a substitution and/or any change from a natural sugar moiety (in other words, a sugar moiety found in DNA (2'-H) or RNA (2'-OH)). Herein, a nucleic acid strand optionally comprises one or more modified nucleosides comprising a modified sugar. Such a sugar-modified nucleoside can confer enhanced nuclease stability, an increased binding affinity, or any other useful biological characteristics to a nucleic acid strand. In a specific embodiment, a nucleoside comprises a chemically-modified ribofuranose ring moiety. Examples of chemically-modified ribofuranose rings include, but are not limited to, those resulting from: addition of a substituent (examples thereof including 5' and 2' substituents); formation of a bicyclic nucleic acid (bridged nucleic acid, or BNA) by bridge-formation of non-geminal ring atoms; substitution of a ribosyl ring oxygen atom with S, N(R), or C(R1)(R2) (R, R1, and R2 independently represent H, $C_1$-$C_{12}$ alkyl, or a protecting group); and combinations thereof.

Herein, examples of nucleosides having a modified sugar moiety include, but are not limited to, nucleosides comprising a 5'-vinyl, 5'-methyl(R or S), 4'-S, 2'-F (2'-fluoro group), 2'-OCH$_3$ (2'-OMe group or 2'-O-methyl group), or 2'-O (CH$_2$)$_2$OCH$_3$ substituent. The substituent at the 2' position can be selected from allyl, amino, azido, thio, —O-allyl, —O—C$_1$-C$_{10}$ alkyl, —OCF$_3$, —O(CH$_2$)$_2$SCH$_3$, —O(CH$_2$)$_2$—O—N(Rm)(Rn), and —O—CH$_2$—C(=O)—N(Rm)(Rn), and each of Rm and Rn independently represents H or a substituted or unsubstituted C$_1$-C$_{10}$ alkyl. Herein, a "2'-modified sugar" refers to a furanosyl sugar modified at the 2' position.

As used herein, a "bicyclic nucleoside" refers to a modified nucleoside containing a bicyclic sugar moiety. In general, a nucleic acid containing a bicyclic sugar moiety is referred to as a bridged nucleic acid (BNA). Herein, a nucleoside containing a bicyclic sugar moiety may be referred to as a "bridged nucleoside".

A bicyclic sugar may be a sugar in which the 2' position carbon atom and 4' position carbon atom are bridged by two or more atoms. Examples of bicyclic sugars are known to a person skilled in the art. One subgroup of a nucleic acid containing a bicyclic sugar (BNA) can be described as having a 2' position carbon atom and 4' position carbon atom that are bridged by 4'-(CH$_2$)$_p$—O-2', 4'-(CH$_2$)$_p$—CH$_2$-2', 4'-(CH$_2$)$_p$—S-2', 4'-(CH$_2$)$_p$—OCO-2', or 4'-(CH$_2$)$_n$—N(R$_3$)—O—(CH$_2$)m-2' [wherein p, m, and n represent an integer of 1 to 4, an integer of 0 to 2, and an integer of 1 to 3 respectively; R$_3$ represents a hydrogen atom, alkyl group, alkenyl group, cycloalkyl group, aryl group, aralkyl group, acyl group, sulfonyl group, or unit substituent (fluorescently or chemiluminescently labeled molecule, functional group having nucleic acid cleaving activity, intracellular or intranuclear localization signal peptide, or the like)]. Furthermore, in the OR$_2$ substituent at the 3' position carbon atom and the OR$_1$ substituent at the 5' position carbon atom in BNA according to a specific embodiment, R$_1$ and R$_2$ are typically hydrogen atoms and may be the same or different, and in addition, may be a protecting group for a hydroxyl group for nucleic acid synthesis, alkyl group, alkenyl group, cycloalkyl group, aryl group, aralkyl group, acyl group, sulfonyl group, silyl group, phosphate group, phosphate group protected by a protecting group for nucleic acid synthesis, or —P(R$_4$)R$_5$ [wherein R$_4$ and R$_5$ are the same as or different from each other, and each represent a hydroxyl group, hydroxyl group protected by a protecting group for nucleic acid synthesis, mercapto group, mercapto group protected by a protecting group for nucleic acid synthesis, amino group, C$_1$-C$_5$ alkoxy group, C$_1$-C$_5$ alkylthio group, C$_1$-C$_6$ cyanoalkoxy group, or amino group substituted with a C$_1$-C$_5$ alkyl group]. Non-limiting examples of such BNAs include: methyleneoxy (4'-CH$_2$—O-2') BNA (LNA (Locked Nucleic Acid (registered trademark), also known as 2',4'-BNA), for example, α-L-methyleneoxy (4'-CH$_2$—O-2') BNA or β-D-methyleneoxy (4'-CH$_2$—O-2') BNA; ethyleneoxy (4'-(CH$_2$)$_2$—O-2') BNA (also known as ENA); β-D-thio(4'-CH$_2$—S-2') BNA; aminooxy(4'-CH$_2$—O—N(R$_3$)-2') BNA; oxyamino(4'-CH$_2$—N(R$_3$)-0-2') BNA (also known as 2',4'-BNA$^{NC}$); 2',4'-BNA$^{coc}$; 3'-amino-2',4'-BNA; 5'-methyl BNA; (4'-CH(CH$_3$)—O-2') BNA (also known as cEt BNA); (4'-CH(CH$_2$OCH$_3$)—O-2') BNA (also known as cMOE BNA); amide BNA (4'-C(O)—N(R)-2') BNA (R=H, Me) (also known as AmNA); 2'-0,4'-C-spirocyclopropylene bridged nucleic acid (also known as scpBNA); and other BNAs known to a person skilled in the art.

Herein, a bicyclic nucleoside having a methyleneoxy(4'-CH$_2$—O-2') bridge may be referred to as an LNA nucleoside.

Methods of preparing a modified sugar is well known to a person skilled in the art. In a nucleotide having a modified sugar moiety, a nucleic acid base moiety (natural one, modified one, or a combination thereof) may be maintained for hybridization with a suitable nucleic acid target.

Figure 3:
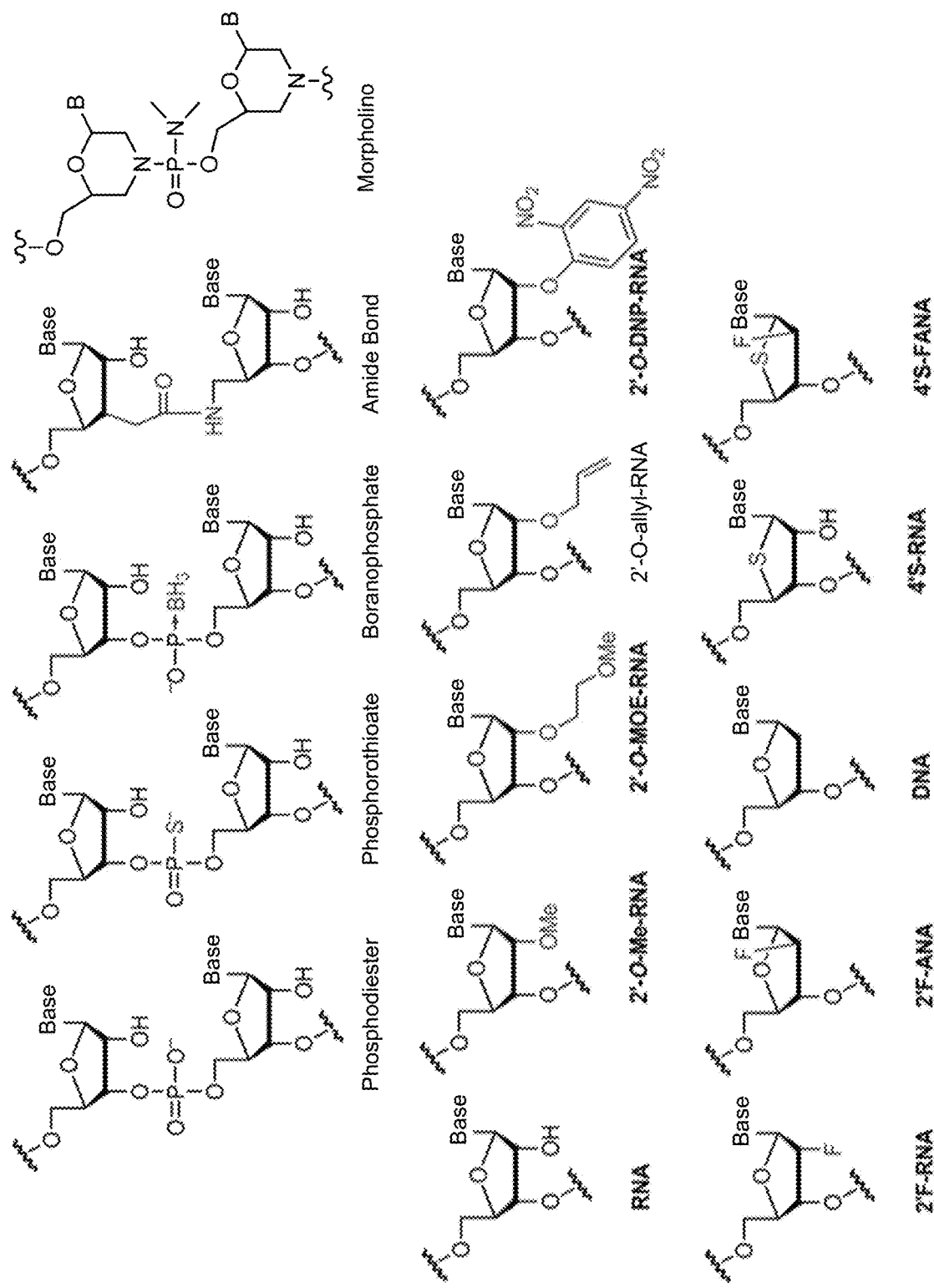
FIG. 3 is a diagram depicting the structures of various natural nucleotides or unnatural nucleotides.
Figure 4:
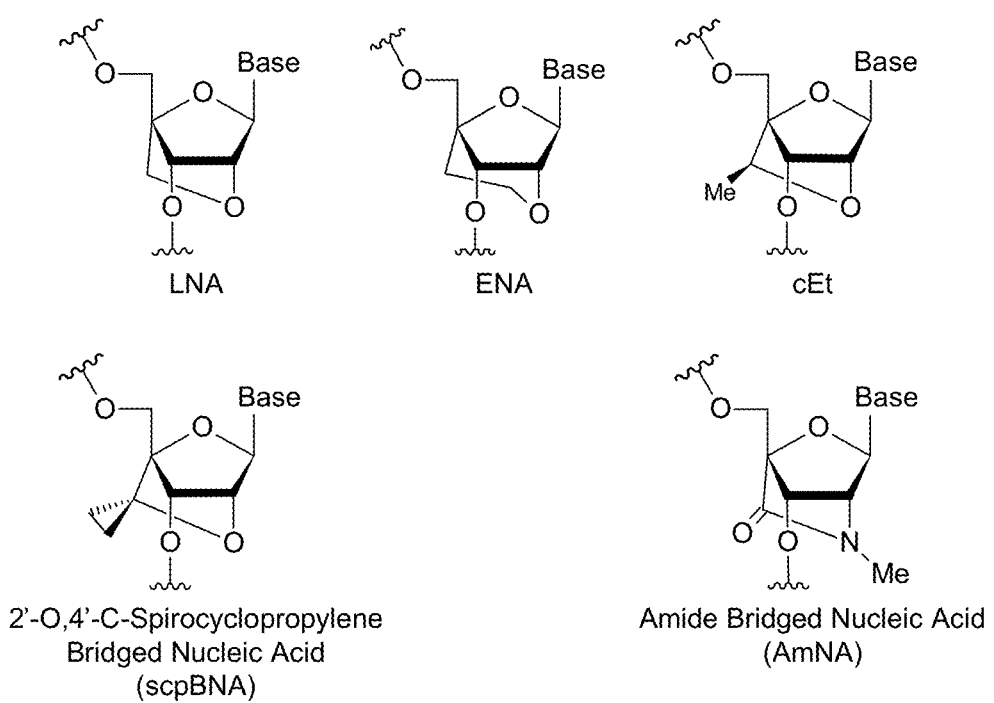
FIG. 4 is a diagram depicting the structures of various bridged nucleic acids.

Herein, a "nucleoside mimic" contains, at one or more positions in an oligomer compound, a sugar, or a sugar and a base, and optionally a structure used to substitute a linkage. An "oligomer compound" refers to a polymer of some linked monomer subunits capable of hybridizing with at least a region of a nucleic acid molecule. Examples of nucleoside mimics include morpholino, cyclohexenyl, cyclohexyl, tetrahydropyranyl, bicyclic, or tricyclic sugar mimics, for example, nucleoside mimics having a non-furanose sugar unit. A "nucleotide mimic" contains, at one or more positions in an oligomer compound, a nucleoside and a structure used to substitute a linkage. Examples of nucleotide mimics include peptide nucleic acids or morpholino nucleic acids (morpholinos linked by —N(H)—C(=O)—O— or another non-phosphodiester linkage). A peptide nucleic acid (PNA) is a nucleotide mimic having a main-chain to which N-(2-aminoethyl)glycine instead of a sugar is conjugated by an amide bond. An example of the structure of a morpholino nucleic acid is shown in FIG. 3. A "mimic" refers to a group that substitutes a sugar, nucleic acid base, and/or internucleoside linkage. In general, a mimic is used instead of a sugar or a combination of a sugar and an internucleoside linkage, and a nucleic acid base is maintained for hybridization with a selected target.

In general, modification can be carried out so that nucleotides in the same strand can independently be modified differently. To provide resistance to enzymic cleavage, the same nucleotide can have a modified internucleoside linkage (for example, a phosphorothioate bond) and further have a modified sugar (for example, a 2'-O-methyl modified sugar or a bicyclic sugar). The same nucleotide can also have a modified nucleic acid base (for example, 5-methylcytosine) and further have a modified sugar (for example, a 2'-O-methyl modified sugar or a bicyclic sugar).

The number, kind, and position of unnatural nucleotides in a nucleic acid strand can have an impact on an antisense effect provided by the nucleic acid complex according to the present invention. The selection of a modification can vary depending on the sequence of a target gene and the like, but a person skilled in the art can determine a suitable embodiment by reference to the explanation in documents related to an antisense method (for example, WO2007/143315, WO2008/043753, and WO 2008/049085). Furthermore, in a case where an antisense effect of a nucleic acid complex obtained after modification is measured, and where a measured value thus obtained is not significantly lower than a measured value of a nucleic acid complex existing before modification (for example, in a case where a measured value obtained after modification is 70% or more, 80% or more, or 90% or more of a measured value of a nucleic acid complex existing before modification), a related modification can be evaluated.

Measurement of an antisense effect can be carried out by introducing a test nucleic acid compound into a cell and then suitably using a known technique such as Northern blotting, quantitative PCR, and Western blotting to thereby measure the expression level of a target gene or the level of a target transcription product in the cell (for example, the level of mRNA, the level of RNA such as microRNA, the level of cDNA, the level of protein, and the like), the expression of which target gene or target transcription product is suppressed by the antisense effect provided by the test candidate nucleic acid complex.

For example, as shown in the following Examples, measurement of an antisense effect in the central nervous system and determination of blood brain barrier permeation can be carried out by administering a test nucleic acid compound to a subject (for example, a mouse), and measuring the expression level of a target gene or the level of a target transcription product in the central nervous system (for example, the level of mRNA, the level of RNA such as microRNA, the level of cDNA, the level of protein, and the like), for example, several days to several months later (for example, two to seven days later or one month later), the expression of which target gene or target transcription product is suppressed by the antisense effect provided by the test nucleic acid compound.

A reduction in the measured expression level of the target gene or the measured level of the target transcription product of at least 20%, at least 25%, at least 30%, or at least 40% with respect to a negative control (for example, vehicle administration) demonstrates that the test nucleic acid compound can bring about an antisense effect in the central nervous system or can permeate the blood brain barrier. In addition, determination of blood brain barrier permeation may be carried out by administering a test nucleic acid compound to a subject (for example, a mouse) and measuring the level of the test nucleic acid compound existing in the central nervous system (concentration), for example, several days to several months later (for example, two to seven days later or one month later).

Internucleoside linkages in the first nucleic acid strand and the second nucleic acid strand may be naturally-occurring internucleoside linkages and/or modified internucleoside linkages. Preferably, at least one (for example, at least two or at least three) internucleoside linkage from an end (5' end, 3' end, or both ends) of the first nucleic acid strand and/or the second nucleic acid strand is a modified internucleoside linkage. Two internucleoside linkages from the end of a nucleic acid strand refer to an internucleoside linkage most proximate to the end of the nucleic acid strand and an adjacent internucleoside linkage located at the opposite side of the former linkage from the end. A modified internucleoside linkage in the terminal region of a nucleic acid strand can inhibit undesired degradation of the nucleic acid strand, and accordingly is preferable. In one embodiment, all internucleoside linkages of the first nucleic acid strand and/or the second nucleic acid strand may be modified internucleoside linkages. Modified internucleoside linkages may be phosphorothioate bonds.

At least one (for example, three) internucleoside linkage from the 3' end of the second nucleic acid strand may be a modified internucleoside linkage (for example, a linkage having high RNase resistance, such as a phosphorothioate bond). A modified internucleoside linkage, such as a phosphorothioate-modified one, contained in the 3' end of the second nucleic acid strand enhances the gene repression activity of the double-stranded nucleic acid complex, and accordingly is preferable.

The internucleoside linkages of two to six bases at the opposite end of the second nucleic acid strand from the end to which cholesterol or a tocopherol is conjugated may be modified internucleoside linkages (for example, phosphorothioate bonds).

At least one (for example, three) nucleoside from the 3' end of the second nucleic acid strand may be a modified nucleoside (for example, a modified nucleoside having high RNase resistance, such as 2'F-RNA). A modified nucleoside, such as a 2'F-RNA, contained in the 3' end of the second nucleic acid strand enhances the gene repression activity of the double-stranded nucleic acid complex, and accordingly is preferable.

One to the five nucleosides at the opposite end of the second nucleic acid strand from the end to which cholesterol or a tocopherol is conjugated may be modified nucleosides (for example, a modified nucleoside having high RNase resistance, such as 2'F-RNA).

The nucleosides in the first nucleic acid strand and the second nucleic acid strand may each be a natural nucleoside (a deoxyribonucleoside, a ribonucleoside, or both) and/or an unnatural nucleoside.

In one embodiment, the first nucleic acid strand may contain at least four consecutive nucleosides that are recognized by RNase H when hybridized with a target transcription product. "At least four consecutive nucleosides that are recognized by RNase H" may be at least five, at least six, or at least seven consecutive nucleosides, and may usually be a region containing consecutive nucleosides of 4 to 20 bases, 5 to 16 bases, or 6 to 12 bases. In this region, a nucleoside, for example, a natural deoxyribonucleoside, which is recognized by RNase H that cleaves the RNA strand when the nucleoside is hybridized with an RNA, can be used. Modified deoxyribonucleosides and suitable nucleosides containing other bases are known in the art. It is also known that a nucleoside having a hydroxy group at the 2' position, such as ribonucleoside, is unsuitable. A person skilled in the art can easily determine the suitability of a nucleoside for use in this region containing "at least four consecutive nucleosides". In one embodiment, the first nucleic acid strand can include at least four consecutive deoxyribonucleosides.

In one embodiment, natural ribonucleosides do not represent the full length of the first nucleic acid strand. In one embodiment, natural ribonucleosides represent half or less of the full length of the first nucleic acid strand. In one embodiment, the first nucleic acid strand does not include a natural ribonucleoside.

In one embodiment, the second nucleic acid strand may include at least four consecutive ribonucleosides complementary to the above-described at least four consecutive nucleosides (for example, deoxyribonucleosides) in the first nucleic acid strand. This is because the second nucleic acid strand can thus form a partial DNA-RNA heteroduplex together with the first nucleic acid strand, and then, the heteroduplex can be recognized and cleaved by RNase H. The at least four consecutive ribonucleosides in the second nucleic acid strand are preferably linked by naturally-occurring internucleoside linkages, in other words, phosphodiester bonds.

In one embodiment, all nucleosides of the second nucleic acid strand may be constituted by ribonucleosides and/or modified nucleosides. In contrast, in one embodiment, the second nucleic acid strand may not include any ribonucleoside. In one embodiment, all nucleosides of the second nucleic acid strand may be constituted by deoxyribonucleosides and/or modified nucleosides.

In a specific embodiment, the first nucleic acid strand and/or the second nucleic acid strand may be a gapmer(s). Herein, a "gapmer" refers to a nucleic acid strand consisting of the central region (DNA gap region) containing at least four consecutive deoxyribonucleosides and the regions (the 5' wing region and 3' wing region) containing unnatural nucleosides located at the 5' terminal side and 3' terminal side of the central region. A gapmer in which the unnatural nucleosides are bridged nucleosides is referred to as a BNA/DNA gapmer. The length of the 5' wing region and that of the 3' wing region may independently be at least 2 bases in length, usually 2 to 10 bases in length, 2 to 7 bases in length, or 3 to 5 bases in length. The 5' wing region and 3' wing region have only to contain at least one unnatural nucleoside, and may further contain a natural nucleoside. The first nucleic acid strand may be a BNA/DNA gapmer including a 5' wing region containing two or three bridged nucleosides, a 3' wing region containing two or three bridged nucleosides, and a DNA gap region therebetween. The bridged nucleoside may further contain a modified nucleic acid base (for example, 5-methylcytosine). The gapmer may be an LNA/DNA gapmer in which the bridged nucleoside is an LNA nucleoside.

The first nucleic acid strand and/or the second nucleic acid strand may be constituted by (from the 5' terminal): bridged nucleosides of 2 to 7 bases in length or 3 to 5 bases in length; ribonucleosides of 4 to 15 bases in length or 8 to 12 bases in length; and bridged nucleosides of 2 to 7 bases in length or 3 to 5 bases in length.

The first nucleic acid strand and/or the second nucleic acid strand may be constituted by (from the 5' terminal): bridged nucleosides of 2 to 7 bases in length or 3 to 5 bases in length; deoxyribonucleosides of 4 to 15 bases in length or 8 to 12 bases in length; and bridged nucleosides of 2 to 7 bases in length or 3 to 5 bases in length.

In another embodiment, the first nucleic acid strand and/or the second nucleic acid strand may be a mixmer(s). As used herein, a "mixmer" refers to a nucleic acid strand that contains alternating segments of natural nucleosides (deoxyribonucleoside and/or ribonucleoside) and unnatural nucleosides of periodic or random lengths and that does not have four or more consecutive deoxyribonucleosides nor four or more consecutive ribonucleosides. A mixmer in which the unnatural nucleoside is a bridged nucleoside and in which the natural nucleoside is a deoxyribonucleoside is referred to as a BNA/DNA mixmer. A mixmer in which the unnatural nucleoside is a bridged nucleoside and in which the natural nucleoside is a ribonucleoside is referred to as a BNA/RNA mixmer. A mixmer does not necessarily need to be limited so as to contain only two kinds of nucleosides. A mixmer can contain any number of kinds of nucleosides whether the nucleoside is a natural or modified nucleoside or whether it is a nucleoside mimic. For example, a mixmer may have one or two consecutive deoxyribonucleosides separated by a bridged nucleoside (for example, an LNA nucleoside). The bridged nucleoside may further contain a modified nucleic acid base (for example, 5-methylcytosine).

At least one, at least two, at least three, or at least four nucleosides from an end (5' end, 3' end, or both ends) of the second nucleic acid strand may be a modified nucleoside(s). A modified nucleoside may contain a modified sugar and/or a modified nucleic acid base. A modified sugar may be a 2'-modified sugar (for example, a sugar containing a 2'-O-methyl group). A modified nucleic acid base may be 5-methylcytosine.

The second nucleic acid strand may be constituted by (from the 5' terminal) modified nucleosides of 2 to 7 bases in length or 3 to 5 bases in length (for example, modified nucleosides containing a 2'-modified sugar); ribonucleosides (optionally linked by a modified internucleoside linkage) of 4 to 15 bases in length or 8 to 12 bases in length; and modified nucleosides of 2 to 7 bases in length or 3 to 5 bases in length (for example, modified nucleosides containing a 2'-modified sugar). In this case, the first nucleic acid strand may be a gapmer.

The second nucleic acid strand may be constituted by (from the 5' terminal) modified nucleosides of 2 to 7 bases in length or 3 to 5 bases in length (for example, modified nucleosides containing a 2'-modified sugar); deoxyribonucleosides (optionally linked by a modified internucleoside linkage) of 4 to 15 bases in length or 8 to 12 bases in length; and modified nucleosides of 2 to 7 bases in length or 3 to 5 bases in length (for example, modified nucleosides containing a 2'-modified sugar). In this case, the first nucleic acid strand may be a gapmer.

The first nucleic acid strand and the second nucleic acid strand may contain a nucleoside mimic or a nucleotide mimic entirely or partially. The nucleotide mimic may be a peptide nucleic acid and/or a morpholino nucleic acid. The first nucleic acid strand may contain at least one modified nucleoside. The modified nucleoside may contain a 2'-modified sugar. The 2'-modified sugar may be a sugar containing a 2'-O-methyl group.

The first nucleic acid strand and second nucleic acid strand may contain any combination of the above-mentioned modified internucleoside linkages and modified nucleosides.

The second nucleic acid strand can be conjugated to a tocopherol, cholesterol, or an analog thereof. It is conventionally known that conjugating a lipid such as a tocopherol or cholesterol to a nucleic acid strand increases delivery performance to the liver and the like. The present invention is based on the present inventors' findings that a tocopherol- or cholesterol-conjugated double-stranded nucleic acid complex is unexpectedly delivered also to the central nervous system such as the brain. In some embodiments, a nucleic acid complex can permeate a blood brain barrier (BBB). Determination of blood brain barrier permeation is as above-described.

In some embodiments, a nucleic acid complex may be one which can permeate the blood retinal barrier (BRB). Blood retina barrier permeation can be determined by measuring an antisense effect in, for example, a photoreceptor cell, a retinal pigment epithelial cell, a Muller cell, and the like. BRB permeation of a drug makes it possible to regulate the gene expression of neuronal cells, epithelial cells, and/or glial cells (for example, photoreceptor cells, retinal pigment epithelial cells, Muller cells) which constitute the retina, and to treat retina-related diseases, for example, retinitis pigmentosa, macular degeneration, retrobulbar neuritis, and the like.

Herein, an "analog" refers to a compound having the same or similar basic backbone and having a similar structure and nature. An analog contains a compound and the like having, for example, a biosynthetic intermediate, a metabolite, or a substituent. A person skilled in the art can determine whether a compound is an analog of another compound.

A tocopherol can be selected from the group consisting of α-tocopherol, β-tocopherol, γ-tocopherol, and δ-tocopherol. Examples of analogs of tocopherols include various unsaturated analogs of tocopherols, for example, α-tocotrienol, β-tocotrienol, γ-tocotrienol, δ-tocotrienol, and the like. A preferable tocopherol is α-tocopherol.

Analogs of cholesterol refer to various cholesterol metabolites and analogs which are alcohols having a sterol backbone, and example of the analogs include, but are not limited to, cholestanol, lanosterol, cerebrosterol, dehydrocholesterol, coprostanol and the like.

The second nucleic acid strand bound to a tocopherol or an analog thereof may have a group represented by the following general formula (I):

[Chem. 1]

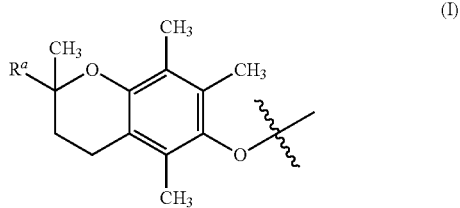

[wherein $R^a$ represents a $C_7$-$C_{15}$, preferably $C_{12}$-$C_{14}$, alkyl group optionally having a substituent (wherein the substituent is a halogen atom or a $C_1$-$C_3$ alkyl group, preferably a methyl group).]

$R^a$ may be, without limitation, $CH_3$—$CH(CH_3)$—$(CH_2)_3$—$CH(CH_3)$—$(CH_2)_3$—$CH(CH_3)$—$(CH_2)_3$—.

The second nucleic acid strand conjugated to cholesterol or an analog thereof may have a group represented by the following general formula (II):

[Chem. 2]

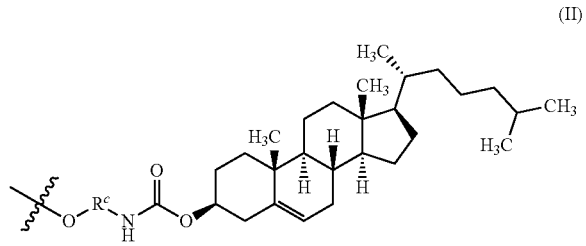

[wherein $R^c$ represents a $C_4$-$C_{18}$, preferably $C_5$-$C_{16}$, alkylene group optionally having a substituent (wherein the substituent is a halogen atom or a $C_1$-$C_3$ alkyl group optionally substituted with a hydroxy group, for example, a hydroxymethyl group; the alkylene group may be one in which carbon atoms unadjacent to each other may be replaced with oxygen atoms).]

$R^c$ may be, without limitation, —$(CH_2)_3$—O—$(CH_2)_2$—O—$(CH_2)_2$—O—$(CH_2)_2$—O—$(CH_2)_2$—, —$(CH_2)_3$—O—$(CH_2)_2$—O—$(CH_2)_2$—O—$(CH_2)_2$—O—$CH_2$—CH($CH_2OH$)—, or —$(CH_2)_6$—.

The groups represented by the general formulae (I) to (II) may be conjugated to the 5' end or 3' end of the second nucleic acid strand via a phosphate ester bond.

A tocopherol, cholesterol, or an analog thereof may be linked to the 5' end, 3' end, or both ends of the second nucleic acid strand. Alternatively, a tocopherol, cholesterol, or an analog thereof may be linked to a nucleotide inside the second nucleic acid strand. For example, cholesterol can be conjugated to the 5' end of the second nucleic acid strand. In another embodiment, the second nucleic acid strand contains two or more of tocopherols, cholesterol, and analogs thereof, and these may be linked to a plurality of positions of the second nucleic acid strand, and/or linked as one group to one position of the second nucleic acid strand. One of a tocopherol, cholesterol, and an analog thereof may be linked to each of the 5' end and 3' end of the second nucleic acid strand. One of cholesterol and an analog thereof may be linked to each of the 5' end and 3' end of the second nucleic acid strand.

The conjugation between the second nucleic acid strand and a tocopherol, cholesterol, or an analog thereof may be a direct conjugation or an indirect conjugation with another substance in-between. In a specific embodiment, however, a tocopherol, cholesterol, or an analog thereof is preferably conjugated directly to the second nucleic acid strand via covalent bonding, ionic bonding, hydrogen bonding, and the like, and covalent bonding is more preferable in the light of affording a more stable bond.

A tocopherol, cholesterol, or an analog thereof may also be conjugated to the second nucleic acid strand via a cleavable linking group (linker). A "cleavable linking group (linker)" refers to a linking group that is cleaved under physiological conditions, for example, in the cell or in the body of an animal (for example, in the body of a human). In a specific embodiment, a cleavable linker is selectively cleaved by an endogenous enzyme such as nuclease. Examples of cleavable linkers include an amide, ester, one or both esters of a phosphodiester, phosphate ester, carbamate, disulfide bond, and natural DNA linker. For example, a tocopherol, cholesterol, or an analog thereof may be linked via a disulfide bond.

A tocopherol, cholesterol, or an analog thereof may be conjugated to the second nucleic acid strand via an uncleavable linker. An "uncleavable linker" refers to a linking group that is uncleavable under physiological conditions, for example, in the cell or in the body of an animal (for example, in the body of a human). Examples of uncleavable linkers include: a phosphorothioate bond; a linker consisting of a modified or unmodified deoxyribonucleoside or a modified or unmodified ribonucleoside linked by a phosphorothioate bond; and the like. When a linker is a nucleic acid, such as DNA, or an oligonucleotide, the strand length thereof may be, without limitation, 2 to 20 bases in length, 3 to 10 bases in length, or 4 to 6 bases in length.

The second nucleic acid strand may further contain at least one functional moiety conjugated to the polynucleotide. The structure of the "functional moiety" according to a specific embodiment is not limited to a particular one as long as the functional moiety gives a desired function to a nucleic acid complex and/or a strand to which the functional moiety is conjugated. Examples of desired functions include a labeling function and a purifying function. Examples of moieties which give a labeling function include a compound such as fluorescent protein and luciferase. Examples of moieties which give a purifying function include a compound such as biotin, avidin, His-tag peptide, GST-tag peptide, and FLAG-tag peptide. The position and kind of the binding of the functional moiety in the second nucleic acid strand are as above-mentioned with reference to the conjugation between a tocopherol, cholesterol, or an analog and the second nucleic acid strand.

The present inventors have found that the nucleic acid complex exhibits a high antisense effect in the nervous system also in a case where the second nucleic acid strand to which an alkyl group instead of a cholesterol or a tocopherol is conjugated is used. Accordingly, the second nucleic acid strand may be conjugated to an alkyl group optionally having a substituent instead of being conjugated to a tocopherol or cholesterol.

Embodiments described herein about a nucleic acid complex containing a tocopherol or cholesterol can be applied to specific embodiments of a first nucleic acid strand, a second nucleic acid strand, and the conjugation between the second nucleic acid strand and an alkyl group in a nucleic acid complex containing the alkyl-group-conjugated second nucleic acid strand, wherein the alkyl group optionally has a substituent.

An alkyl group optionally having a substituent may be a $C_3$-$C_{15}$, preferably $C_6$-$C_{14}$ or $C_9$-$C_{13}$, linear alkyl group, wherein the substituent may be a hydroxy group, a halogen atom, or a $C_1$-$C_3$ alkyl group.

The second nucleic acid strand to which an alkyl group optionally having a substituent is conjugated may have a group represented by the following general formula (III):

[Chem. 3]

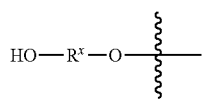
(III)

[wherein $R^x$ is a $C_3$-$C_{24}$, preferably $C_6$-$C_{14}$ or $C_9$-$C_{13}$, linear alkylene group.]

The second nucleic acid strand to which an alkyl group optionally having a substituent is conjugated may have a group represented by the following general formula (IV):

[Chem. 4]

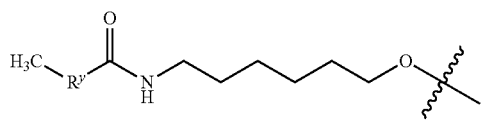
(IV)

[wherein $R^y$ is a $C_1$-$C_{15}$, preferably $C_3$-$C_{15}$, $C_6$-$C_{14}$, or $C_9$-$C_{13}$, linear alkylene group.]

As above, several suitable illustrative embodiments of the nucleic acid complex in some of the embodiments of the present invention have been described, but the nucleic acid complex is not intended to be limited to the above-mentioned illustrative embodiments. Furthermore, a person skilled in the art can produce, by selecting a known method suitably, a first nucleic acid strand and a second nucleic acid strand that constitute a nucleic acid complex according to various embodiments of the present invention. For example, nucleic acids according to some of the embodiments of the present invention can be produced by designing each base sequence of the nucleic acid based on information on the base sequence of a target transcription product (or the base sequence of a target gene in some cases), synthesizing a nucleic acid using a commercially available automated nucleic acid synthesis device (a product of Applied Biosystems, Inc., a product of Beckman Coulter, Inc., or the like), and then purifying the resulting oligonucleotide using a reversed phase column and the like. For example, the second nucleic acid strand may be produced by carrying out the above-mentioned synthesis and purification using the kind of nucleic acid that has a tocopherol, cholesterol, or an analog thereof conjugated to the nucleic acid in advance. A nucleic acid produced in this manner is mixed in a suitable buffer solution and denatured at about 90° C. to 98° C. for several minutes (for example, five minutes), the nucleic acid is then annealed at about 30° C. to 70° C. for about one to eight hours, and thus, a nucleic acid complex according to some of the embodiments of the present invention can be produced.

A nucleic acid complex according to some of the embodiments of the present invention may be prepared in a manner in which each of the first nucleic acid strand and the second nucleic acid strand is dissolved in a buffer (for example, phosphate buffered saline) at about 90° C. to 98° C., the resulting two solutions are mixed, the solution mixture is maintained at about 90° C. to 98° C. for several minutes (for example, five minutes), and then, the solution mixture is maintained at about 30° C. to 70° C. (or 30° C. to 50° C.) for about one to eight hours. A nucleic acid complex prepared in this manner suppresses the oversedation (temporal weakening) of a subject to whom/which the complex has been administered, is less burdensome for the subject, and accordingly is preferable. It is preferable to use a nucleic acid complex prepared in this manner, particularly in a case where a nucleic acid complex containing the second nucleic acid strand conjugated to cholesterol or an analog thereof is intravenously administered.

Preparation of an annealed nucleic acid complex is not limited to such a time and temperature protocol. Conditions suitable to promote annealing of strands are well known in the art. A nucleic acid complex further conjugated to a functional moiety can be produced by using the kind of nucleic acid that has a functional moiety conjugated thereto in advance and carrying out the above-mentioned synthesis, purification, and annealing. Many methods for linking a functional moiety to a nucleic acid are well known in the art. Alternatively, a nucleic acid strand according to some of the embodiments can be ordered and obtained from a manufacturer (for example, GeneDesign Inc.), in which case the base sequence and the site and type of modification should be specified.

<Composition>

In one aspect, the present invention provides a composition including a nucleic acid complex described above for reducing the expression level of a target transcription product in the central nervous system of a subject (herein, "expression level of a target transcription product" is often written as "level of a target transcription product"). The composition according to the present invention may be one for use in the treatment of a central nervous system disease of a subject. The composition may be a pharmaceutical composition.

In one aspect, the present invention provides a composition including a nucleic acid complex described above for reducing the expression level of a target transcription product in the retina of a subject. In one aspect, the present invention provides a composition including a nucleic acid complex described above for reducing the expression level of a target transcription product in neuronal cells, epithelial cells, and/or glial cells which constitute the retina of a subject.

Herein, the composition can be formulated using a known pharmaceutical manufacturing method. For example, the present composition can be used orally or parenterally in the form of capsules, tablets, pills, liquid, powder, granules, microgranules, film coated formulations, pellets, troches, sublingual formulations, peptizers, buccals, pastes, syrups, suspensions, elixirs, emulsions, coating agents, ointments, plasters, cataplasms, transdermal formulations, lotions, inhalants, aerosols, eyedrops, injection solutions, and suppositories.

With regard to formulating these formulations, pharmacologically acceptable carriers or carriers acceptable as food and beverage can be suitably incorporated, specific examples thereof including sterile water, physiological saline, plant oil, solvents, bases, emulsifying agents, suspending agents, surfactants, pH adjustors, stabilizers, flavoring agents, perfumes, excipients, vehicles, antiseptics, binders, diluents, isotonizing agents, sedatives, expanders, disintegrators, buffers, coating agents, lubricants, coloring agents, sweeteners, thickeners, flavoring substances, dissolving auxiliaries, and other additives.

Herein, preferable forms of administration of the composition are not limited to particular ones, and examples thereof include oral administration or parenteral administration, more specifically, intravenous administration, intraarterial administration, intraperitoneal administration, subcutaneously administration, intradermal administration, tracheal/bronchial administration, rectal administration, and intramuscular administration, and administration by transfusion. Administration may be carried out by intramuscular injection administration, intravenous infusion administration, or implantable type continuous subcutaneous administration. Subcutaneous administration can be done as self-injection by patients themselves, and accordingly is preferable. Without wishing to be bound by any particular theory, subcutaneous administration requires ligand to have suitable lipophilicity for coming out of the subcutaneous fat and moving into blood, and use of cholesterol ligand is considered to be preferable.

In intravenous administration, one dose of the above-mentioned nucleic acid complex can be, for example, 5 mg/kg or more, 10 mg/kg or more, 20 mg/kg or more, 30 mg/kg or more, 40 mg/kg or more, 50 mg/kg or more, 75 mg/kg or more, 100 mg/kg or more, 150 mg/kg or more, 200 mg/kg or more, 300 mg/kg or more, 400 mg/kg or more, or 500 mg/kg or more, and, for example, any dose included in the range of 5 to 500 mg/kg (for example, 5 mg/kg, 10 mg/kg, 50 mg/kg, 100 mg/kg, or 200 mg/kg) can be suitably selected.

The composition can be used for animals as subjects, such animals including humans. However, animals other than humans are not limited to particular ones, and various domestic animals, domestic fowls, pet animals, experimental animals, and the like can be subjects in some of the embodiments. A subject may be one in whose central nervous system, the expression level of a target transcription product needs to be reduced. A subject may be one whose central nervous system disease needs to be treated.

A disease to be treated can be a central nervous system disease associated with an increase or decrease in gene expression, in particular, a disease associated with an increase in expression of a target transcription product or a target gene (tumor, and the like). Examples of central nervous system diseases include, but are not limited particularly to, brain tumor, Alzheimer's disease, Parkinson's disease, amyotrophic lateral sclerosis, multiple sclerosis, Huntington's disease, and the like.

The nervous system can be classified into the central nervous system and the peripheral nervous system. The central nervous system consists of the brain and the spinal cord. The brain contains the cerebrum (cerebral cortex, cerebral white matter, and basal ganglion), diencephalon (thalamus and subthalamic nucleus), cerebellum (cerebellar cortex, and cerebellar nucleus), and brainstem (midbrain, substantia nigra, pons, and medulla oblongata). The spinal cord contains the cervical spinal cord, thoracic spinal cord, lumbar spinal cord, sacral cord, and coccygeal cord. Herein, the central nervous system may be any region of these, and, in particular, can be the cerebral cortex (frontal lobe, temporal lobe, parietal lobe, and occipital lobe), cerebellum, striatum, globus pallidus, claustrum, hippocampus, parahippocampal gyms, brainstem, cervical spinal cord, thoracic spinal cord, or lumbar spinal cord. The peripheral nerve consists of the cerebral nerve and the spinal nerve.

For example, in treatment of Alzheimer's disease, it can be efficacious to deliver a drug to the hippocampus and/or parietal lobe. In treatment of frontotemporal dementia (FTD) (frontotemporal lobar degeneration (FTLD), semantic dementia (SD), progressive nonfluent aphasia (PNFA)), and Pick disease, it can be efficacious to deliver a drug to the frontal lobe, temporal lobe, and/or substantia nigra. In treatment of Parkinson's disease dementia, it can be efficacious to deliver a drug to the occipital lobe, substantia nigra, and/or striatum. In treatment of Parkinson's disease, it can be efficacious to deliver a drug to the substantia nigra and/or striatum. In treatment of corticobasal degeneration (CBD), it can be efficacious to deliver a drug to the frontal lobe, parietal lobe, basal ganglion, and/or substantia nigra. In treatment of progressive supranuclear palsy (PSP), it can be efficacious to deliver a drug to the frontal lobe, basal ganglion, and/or substantia nigra. In treatment of amyotrophic lateral sclerosis, it can be efficacious to deliver a drug to the frontal lobe, parietal lobe, basal ganglion, and/or substantia nigra. In treatment of spinocerebellar degeneration (SCD) SCA type 1 to SCA type 34, it can be efficacious to deliver a drug to the brainstem and/or cerebellum. In treatment of dentato-rubro-pallido-luysian atrophy (DRPLA), it can be efficacious to deliver a drug to the basal ganglion, brainstem, and/or cerebellum. In treatment of spinobulbar muscular atrophy (SBMA), it can be efficacious to deliver a drug to the brainstem and/or spinal cord. In treatment of Friedreich's ataxia (FA), it can be efficacious to deliver a drug to the brainstem and/or cerebellum. In treatment of Huntington's disease, it can be efficacious to deliver a drug to the striatum, frontal lobe, parietal lobe, and/or basal ganglion. In treatment of prion disease (bovine spongiform encephalopathy, GSS), it can be efficacious to deliver a drug to the cerebral cortex, cerebral white matter, basal ganglion, and/or substantia nigra. In treatment of cerebral white matter encephalopathy, it can be efficacious to deliver a drug to the cerebral white matter. In treatment of encephalitis (viral, bacterial, mycotic, and tuberculous) and meningitis (viral, bacterial, mycotic, and tuberculous), it can be efficacious to deliver a drug to the whole brain. In treatment of metabolic encephalopathy, toxic encephalopathy, and trophic encephalopathy, it can be efficacious to deliver a drug to the whole brain. In treatment of cerebral white matter encephalopathy, it can be efficacious to deliver a drug to the cerebral white matter. In treatment of cerebral infarction, intracranial hemorrhage, subarachnoid hemorrhage, moyamoya disease, and cerebral anoxia, it can be efficacious to deliver a drug to the entire brain. In treatment of cerebral white matter encephalopathy, it can be efficacious to deliver a drug to the cerebral white matter. In treatment of diffuse axonal injury, it can be efficacious to deliver a drug to the cerebral white matter. In treatment of head injury, it can be efficacious to deliver a drug to the whole brain. In treatment of multiple sclerosis (MS) and neuromyelitis optica (NMO), it can be efficacious to deliver a drug to the cerebral white matter, cerebral cortex, optic nerve, and/or spinal cord. In treatment of myotonic dystrophy (DM1 and DM2), it can be efficacious to deliver a drug to the skeletal muscle, myocardium, cerebral cortex, and/or cerebral white matter. In treatment of familial spastic paraplegia (HSP), it can be efficacious to deliver a drug to the parietal lobe and/or spinal cord. In treatment of Fukuyama muscular dystrophy, it can be efficacious to deliver a drug to the skeletal muscle, cerebral cortex, and/or cerebral white matter. In treatment of dementia with Lewy body (DLB), it can be efficacious to deliver a drug to the substantia nigra, striatum, occipital lobe, frontal lobe, and/or parietal lobe. In treatment of multiple system atrophy (MSA), it can be efficacious to deliver a drug to the striatum, basal ganglion, cerebellum, substantia nigra, frontal lobe, and/or temporal lobe. In treatment of Alexander disease, it can be efficacious to deliver a drug to the cerebral white matter. In treatment of CADASIL and CARASIL, it can be efficacious to deliver a drug to the cerebral white matter.

Accordingly, some of the embodiments according to the present invention relate to compositions containing a nucleic acid complex for use in the treatment of the above-mentioned various diseases or relate to methods of treatment including administering such a composition. In addition, some of the embodiments according to the present invention relate to a composition containing a nucleic acid complex for regulating the expression level (for example, for reducing the expression level) of a transcription product at the above-mentioned various sites. In addition, some of the embodiments according to the present invention relate to a composition containing a nucleic acid complex for delivering a drug to the above-mentioned various sites.

In administering or taking the composition, the dose or intake amount can be suitably selected in accordance with the age, body weight, symptom, and health status of a subject, the kind of the composition (pharmaceutical, food and beverage, and the like), and the like. The effective intake amount of the composition according to a specific embodiment of the present invention can be, for example, 0.00001 mg/kg/day to 10000 mg/kg/day or 0.001 mg/kg/day to 100 mg/kg/day of the nucleic acid complex. The composition may be administered in a single dose or in multiple doses (for example, 2 to 20 times) each of which is administered every day or at suitable time intervals (for example, at intervals of one day, two days, three days, one week, two weeks, or one month). One dose of the above-mentioned nucleic acid complex can be, for example, 0.5 mg/kg or more, 1.0 mg/kg or more, 2.0 mg/kg or more, 3.0 mg/kg or more, 4.0 mg/kg or more, 5 mg/kg or more, 10 mg/kg or more, 20 mg/kg or more, 30 mg/kg or more, 40 mg/kg or more, 50 mg/kg or more, 75 mg/kg or more, 100 mg/kg or more, 150 mg/kg or more, 200 mg/kg or more, 300 mg/kg or more, 400 mg/kg or more, or 500 mg/kg or more, and, for example, any dose included in the range of 0.5 to 500 mg/kg (for example, 5 mg/kg, 10 mg/kg, 50 mg/kg, 100 mg/kg, or 200 mg/kg) can be suitably selected.

A nucleic acid complex according to one embodiment of the present invention may be administered at a dose of 3 to 10 mg/kg (for example, about 6.25 mg/kg) four times at a frequency of twice per week. Alternatively, a nucleic acid complex according to one embodiment of the present invention may be administered at a dose of 20 to 30 mg/kg (for example, about 25 mg/kg) two to four times at a frequency of once to twice per week (for example, two times at a frequency of twice per week). Adopting such a dosage regimen (divided administration) makes it possible to reduce toxicity (for example, to avoid reducing platelets) compared with administration of a higher single dose. Such divided administration is possible particularly in using cholesterol having a long half-life. Cholesterol having a long half-life can be useful for treatment of chronic diseases. On the other hand, a tocopherol having a short half-life can be useful for treatment of acute diseases or disorders for which the tocopherol is efficacious though its effect is transitory, for example, for treatment of cerebral infarction and encephalitis, and the like. In treatment of acute symptoms, there may be cases where having an effect for a short time is preferable.

There are limitations (the upper limitation) to the amount of BBB permeation and the amount of BNB permeation caused by a single dose of the nucleic acid complex, but repeated doses are considered to allow the suppression effect to work additively in cells. In other words, a single dose increased from a high dose (for example, 25 mg/kg or more) no less than the limitations of BBB permeation and BNB permeation reduces an increase in efficacy, but repeated doses administered at certain intervals (for example, half a day or longer) are considered to be capable of enhancing efficacy.

In one aspect, the present invention also provides a composition including the above-mentioned nucleic acid complex for delivering a drug to the central nervous system of a subject. In this aspect, the first nucleic acid strand and/or the second nucleic acid strand are/is conjugated to at least one drug. A nucleic acid complex including the second nucleic acid strand conjugated to a tocopherol, cholesterol, or an analog thereof and the first nucleic acid strand annealed to the second nucleic acid strand can be efficiently delivered to the nervous system, and utilization of this capability makes it possible to deliver, to the nervous system, a drug conjugated to the first nucleic acid strand and/or the second nucleic acid strand. Examples of "drugs" to be delivered to the nervous system include, but are not limited particularly to, peptide, protein or nucleic acid drugs, and other organic compounds, for example, antitumor agents, hormone agents, antibiotics, antiviral agents, antiinflammatory agents, and the like. Drugs are preferably small molecule drugs. The term, small molecule drug, is fully understood in the art. A small molecule drug typically refers to a drug having a molecular weight of less than 1,000 daltons. A drug may be a lipophilic drug. Examples of nucleic acid drugs include, but are not limited particularly to, antisense oligonucleotides, antago-miR, splice-switching oligonucleotides, aptamers, single-stranded siRNA, microRNA, pre-microRNA, and the like. The position and kind of the binding of a drug in the second nucleic acid strand are as above-mentioned with reference to the conjugation between a tocopherol, cholesterol, or an analog and the second nucleic acid strand.

In one aspect, the present invention provides a composition including the above-mentioned nucleic acid complex for delivering a drug to the retina of a subject. In one aspect, the present invention provides a composition including a nucleic acid complex described above for delivering a drug to neuronal cells, epithelial cells, and/or glial cells which constitute the retina of a subject.

As disclosed in the below-mentioned Examples, a composition containing a nucleic acid complex according to some of the embodiments can be highly efficiently delivered to the central nervous system, and can highly effectively alter or suppress the expression of a target gene or the level of a target transcription product. Accordingly, provided is a method of reducing the expression level of a target transcription product in the central nervous system of a subject, the method including administering a composition containing the nucleic acid complex described above to a subject. The method may be a method of treating a central nervous system disease of a subject. In addition, provided is a method of delivering a drug to the central nervous system of a subject, the method including administering a composition containing the nucleic acid complex described above to a subject.

In addition, provided is the nucleic acid complex described above for use in reducing the expression level of a target transcription product in the central nervous system of a subject. The nucleic acid complex may be used for treating a central nervous system disease of a subject. In addition, provided is the nucleic acid complex for use in delivering a drug to the central nervous system of a subject.

The present invention also relates to a composition for reducing the expression level of a target transcription product in the central nervous system of a subject, the composition including a nucleic acid complex including a first nucleic acid strand and a second nucleic acid strand, wherein the first nucleic acid strand contains a base sequence capable of hybridizing with at least part of the target transcription product and has an antisense effect on the target transcription product;

wherein the second nucleic acid strand contains a base sequence complementary to the first nucleic acid strand and is conjugated to an alkyl group that may have a substituent; and wherein the first nucleic acid strand is annealed to the second nucleic acid strand.

The present invention also relates to a composition for delivering a drug to the central nervous system of a subject, the composition including a nucleic acid complex including a first nucleic acid strand and a second nucleic acid strand, wherein the first nucleic acid strand and/or the second nucleic acid strand are/is conjugated to at least one drug, wherein the second nucleic acid strand comprises a base sequence complementary to the first nucleic acid strand and is conjugated to an alkyl group that may have a substituent; and wherein the first nucleic acid strand is annealed to the second nucleic acid strand.

The present invention also relates to a composition for inhibiting the effect of a target miRNA in the central nervous system of a subject, the composition including a nucleic acid complex including a first nucleic acid strand and a second nucleic acid strand, wherein the first nucleic acid strand comprises a base sequence capable of hybridizing with at least part of the target miRNA and has an antisense effect on the target miRNA;

wherein the second nucleic acid strand comprises a base sequence complementary to the first nucleic acid strand and is conjugated to a tocopherol, cholesterol, or an alkyl group that may have a substituent; and wherein the first nucleic acid strand is annealed to the second nucleic acid strand. For example, inhibiting the effect of a target miRNA makes it possible to up-regulate the expression of a gene usually down-regulated by the miRNA.

The present invention also relates to a composition for regulating the expression or editing of a target RNA in the central nervous system of a subject, the composition including a nucleic acid complex including a first nucleic acid strand and a second nucleic acid strand, wherein the first nucleic acid strand comprises a base sequence capable of hybridizing with at least part of the target RNA and has an antisense effect on the target RNA;

wherein the second nucleic acid strand comprises a base sequence complementary to the first nucleic acid strand and is conjugated to a tocopherol, cholesterol, or an alkyl group that may have a substituent; and wherein the first nucleic acid strand is annealed to the second nucleic acid strand. Here, regulation of expression of a target RNA encompasses, for example, up-regulation and down-regulation of the expression level. Regulation of editing of a target RNA encompasses regulation of splicing by editing RNA, examples of such regulation including exon skipping and exon inclusion. In some embodiments, a target RNA may be an RNA of a virus or bacteria or a toxic RNA.

The present invention also relates to a composition for inhibiting the translation of a target mRNA in the central nervous system of a subject, the composition including a nucleic acid complex including a first nucleic acid strand and a second nucleic acid strand, wherein the first nucleic acid strand comprises a base sequence capable of hybridizing with at least part of the target mRNA and has an antisense effect on the target mRNA;

wherein the second nucleic acid strand comprises a base sequence complementary to the first nucleic acid strand and is conjugated to a tocopherol, cholesterol, or an alkyl group that may have a substituent; and wherein the first nucleic acid strand is annealed to the second nucleic acid strand. Binding of the first nucleic acid strand to a target mRNA generates steric blocks and thereby inhibits the translation of the mRNA.

The present invention also relates to a composition for reducing the expression level of a target transcription product in the retina of a subject, the composition including a nucleic acid complex including a first nucleic acid strand and a second nucleic acid strand, wherein the first nucleic acid strand comprises a base sequence capable of hybridizing with at least part of the target transcription product and has an antisense effect on the target transcription product;

wherein the second nucleic acid strand comprises a base sequence complementary to the first nucleic acid strand and is conjugated to a tocopherol, cholesterol, or an alkyl group that may have a substituent; and wherein the first nucleic acid strand is annealed to the second nucleic acid strand.

The present invention also relates to a composition for delivering a drug to the retina of a subject, the composition including a nucleic acid complex including a first nucleic acid strand and a second nucleic acid strand, wherein the first nucleic acid strand and/or the second nucleic acid strand are/is bound to at least one drug, wherein the second nucleic acid strand comprises a base sequence complementary to the first nucleic acid strand and is conjugated to a tocopherol, cholesterol, or an alkyl group that may have a substituent; and wherein the first nucleic acid strand is annealed to the second nucleic acid strand.

The present invention also relates to a composition for inhibiting the effect of a target miRNA in the retina of a subject, the composition including a nucleic acid complex including a first nucleic acid strand and a second nucleic acid strand, wherein the first nucleic acid strand comprises a base sequence capable of hybridizing with at least part of the target miRNA and has an antisense effect on the target miRNA;

wherein the second nucleic acid strand comprises a base sequence complementary to the first nucleic acid strand and is conjugated to a tocopherol, cholesterol, or an alkyl group that may have a substituent; and wherein the first nucleic acid strand is annealed to the second nucleic acid strand.

The present invention also relates to a composition for regulating the expression or editing of a target RNA in the retina of a subject, the composition including a nucleic acid complex including a first nucleic acid strand and a second nucleic acid strand, wherein the first nucleic acid strand comprises a base sequence capable of hybridizing with at least part of the target RNA and has an antisense effect on the target RNA;

wherein the second nucleic acid strand comprises a base sequence complementary to the first nucleic acid strand and is conjugated to a tocopherol, cholesterol, or an alkyl group that may have a substituent; and wherein the first nucleic acid strand is annealed to the second nucleic acid strand.

The present invention also relates to a composition for inhibiting the translation of a target mRNA in the retina of a subject, the composition including a nucleic acid complex including a first nucleic acid strand and a second nucleic acid strand, wherein the first nucleic acid strand comprises a base sequence capable of hybridizing with at least part of the target mRNA and has an antisense effect on the target mRNA;

wherein the second nucleic acid strand comprises a base sequence complementary to the first nucleic acid strand and is conjugated to a tocopherol, cholesterol, or an alkyl group that may have a substituent; and wherein the first nucleic acid strand is annealed to the second nucleic acid strand.

EXAMPLES

Below, the present invention will be described more specifically with reference to Examples. However, the technical scope of the present invention is not to be limited to these Examples.

The oligonucleotide sequences used in the following Examples are shown together in Table 1. The oligonucleotides were synthesized by GeneDesign Inc. (Osaka, Japan).

TABLE 1

Oligonucleotides used in Examples

| SEQ ID NO: | Sequence | Name of Oligonucleotide | Example |
|---|---|---|---|
| 1 | 5'-C*T*A*g*t*t*c*a*c*t*g*a*a*T*G*C-3' | ASO(mMalat1) | 1, 2, 4-7, 10-15, 19, 20, 22-26, 28-31, 33, 34 |
| 10 | 5'-Toc#1-g*c*a*UUCAGUGAAC*u*a*g-3' | Toc#1-cRNA(mMalat1) | 1, 2, 20, 24, 28 |
| 3 | 5'-T*C*a*g*t*c*a*t*g*a*c*t*T*C-3' | ASO(mSR-B1) | 3, 21 |
| 11 | 5'-Toc#1-g*a*AGUCAUGACU*g*a-3' | Toc#1-cRNA(mSR-B1) | 3 |
| 10 | 5'-Chol#1-g*c*a*UUCAGUGAAC*u*a*g-3' | Chol#1-cRNA(mMalat1) | 4, 13-15, 22, 24, 32, 34 |
| 10 | 5'-g*c*a*UUCAGUGAAC*u*a*g-Chol#3-3' | Chol#3-cRNA(mMalat1) | 5 |
| 12 | 5'-Toc#1-G*C*A*ttcagtgaac*T*A*G-3' | Toc#1-cDNA(mMalat1) | 6 |
| 12 | 5'-Chol#1-G*C*A*ttcagtgaac*T*A*G-3' | Chol#1-cDNA(mMalat1) | 7 |
| 13 | 5'-A*C*A*a*t*a*a*a*t*a*c*c*g*A*G*G-3' | ASO(mDMPK) | 8, 16 |
| 14 | 5'-Chol#1-c*c*u*CGGUAUUUAU*u*g*u-3' | Chol#1-cRNA(mDMPK) | 8 |
| 15 | 5'-A*G*T*a*c*t*a*t*a*g*c*a*t*C*T*G-3' | ASO(mfMalat1) | 9 |
| 16 | 5'-Toc#1-c*a*g*AUGCUAUAGU*a*c*u-3' | Toc#1-cRNA(mfMalat1) | 9 |
| 10 | 5'-Chol#2-g*c*a*UUCAGUGAAC*u*a*g-3' | Chol#2-cRNA(mMalat1) | 10 |
| 10 | 5'-Chol#4-g*c*a*UUCAGUGAAC*u*a*g-3' | Chol#4-cRNA(mMalat1) | 11 |
| 10 | 5'-g*c*a*UUCAGUGAAC*u*a*g-Chol#5-3' | Chol#5-cRNA(mMalat1) | 12 |
| 14 | 5'-Tocl#1-c*c*u*CGGUAUUUAU*u*g*u-3' | Toc#1-cRNA(mDMPK) | 16 |
| 19 | 5'-Toc#1-guauaaACAUuCGCAuCGCAUAgGUuC*U*U-3' | Toc#1-AS(mBACE1) | 17 |
| 20 | 5'-GAAcCuAuGCGAuGCGAAuGUUUAU*A*C-3' | SS(mBACE1)27mer | 17 |
| 21 | 5'-Chol#1-a*cAUuCGCAuCGCAUAgGUuC*U*U-3' | Chol#1-AS(mBACE1) | 18 |
| 22 | 5'-GAAcCuAuGCGAuGCGAAuG*U-3' | SS(mBACE1)21mer | 18 |
| 10 | 5'-DHA-g*c*a*UUCAGUGAAC*u*a*g-3' | DHA-cRNA(mMalat1) | 19 |
| 11 | 5'-Chol#1-g*a*AGUCAUGACU*g*a-3' | Chol#1-cRNA(mSR-B1) | 21 |
| 10 | 5'-Chol#1-gcaUUCAGUGAACuag-3' | Chol#1-cRNA(mMalat1)(PO) | 23 |
| 10 | 5'-Chol#1-g*c*a*UUCAGUGAACuag-3' | Chol#1-cRNA(mMalat1)(5'PS) | 23 |
| 10 | 5'-Chol#1-gcaUUCAGUGAAC*u*a*g-3' | Chol#1-cRNA(mMalat1)(3'PS) | 23 |
| 10 | 5'-Chol#1-g*c*a*UUCAGUGAAC*u*a*g-Chol#3-3' | Chol#1-cRNA-Chol#3(mMalat1) | 25 |

TABLE 1-continued

Oligonucleotides used in Examples

| SEQ ID NO: | Sequence | Name of Oligonucleotide | Example |
|---|---|---|---|
| 24 | 5'-Chol#1-g*c*a*ttcagtgaac*t*a*g-3' | Chol#1-cDNA(mMalat1) Full DNA | 26 |
| 25 | 5'-Chol#1-g*c*a*t*t*c*a*g*t*g*a*a*c*u*a*g-3' | Chol#1-cDNA(mMalat1) Full PS | 26 |
| 25 | 5'-Chol#1-gcattcagtgaacuag-3' | Chol#1-cDNA(mMalat1) Full PO | 26 |
| 26 | 5'-T*c*A*g*t*C*T*g*a*T*a*A*g*C*T-3' | ASO(anti-miR21) | 27 |
| 27 | 5'-Chol#1-a*g*c*UUAUCAGAC*u*g*a-3' | Chol#1-cRNA(anti-miR21) | 27 |
| 28 | 5'-Chol#1-G*C*A*UUCAGUGAAC*T*A*G-3' | Chol#1-cRNA(LNA)(mMalat1) | 29 |
| 10 | 5'-Chol#1*g*c*a*UUCAGUGAAC*u*a*g-3' | Chol#1-cRNA(PS)(mMalat1) | 30 |
| 29 | 5'-Chol#1-cttcg*c*a*UUCAGUGAAC*u*a*g-3' | Chol#1-cRNA(DNA)(mMalat1) | 30 |
| 10 | 5'-C6(OH)-g*c*a*UUCAGUGAAC*u*a*g-3' | C6(OH)-cRNA(mMalat1) | 31 |
| 10 | 5'-C9(OH)-g*c*a*UUCAGUGAAC*u*a*g-3' | C9(OH)-cRNA(mMalat1) | 31 |
| 10 | 5'-C12(OH)-g*c*a*UUCAGUGAAC*u*a*g-3' | C12(OH)-cRNA(mMalat1) | 31 |
| 30 | 5'-C*T*A*G*U*U*C*A*C*U*G*A*A*T*G*C-3' | ASO(RNA)(mMalat1) | 32 |
| 10 | 5'-C3-g*c*a*UUCAGUGAAC*u*a*g-3' | C3-cRNA(mMalat1) | 33 |
| 10 | 5'-C4-g*c*a*UUCAGUGAAC*u*a*g-3' | C4-cRNA(mMalat1) | 33 |
| 10 | 5'-C8-g*c*a*UUCAGUGAAC*u*a*g-3' | C8-cRNA(mMalat1) | 33 |
| 10 | 5'-C10-g*c*a*UUCAGUGAAC*u*a*g-3' | C10-cRNA(mMalat1) | 33 |
| 10 | 5'-C12-g*c*a*UUCAGUGAAC*u*a*g-3' | C12-cRNA(mMalat1) | 33 |

Upper case letters/underlined: LNA(C = 5-methylcytosine LNA),
Lower case letters: DNA,
Upper case letters: RNA,
Lower case letters/underlined: 2'-O-Me RNA,
*: phosphorothioated,
Toc#1: α-tocopherol#1,
Chol#1 to 5: cholesterol#1 to 5
DHA: docosahexaenoic acid The 5' terminal structure of the oligonucleotides, Toc#1-cRNA(mMalat1), Toc#1-cRNA(mSR-B1), Toc#1-cDNA(mMalat1), Toc#1-cRNA(mfMalat1), Toc#1-cRNA(mDMPK), and Toc#1-AS(mBACE1), shown in Table 1 is shown below. In this regard, the expression "oligo" in the following chemical formulae represents an oligonucleotide.

[Chem. 5]

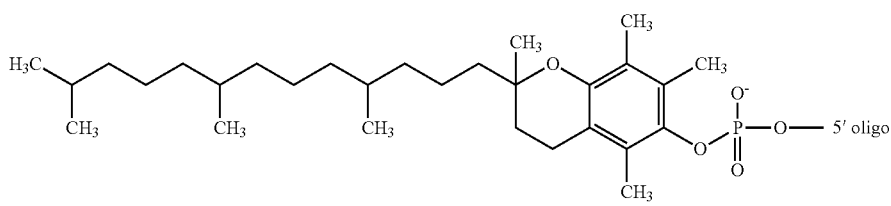

α-tocopherol#1

The 5' terminal structure of the oligonucleotides, Chol#1-cRNA(mMalat1), Chol#1-cDNA(mMalat1), Chol#1-cRNA(mDMPK), Chol#1-AS(mBACE1), Chol#1-cRNA(mSR-B1), Chol#1-cRNA(mMalat1)(PO), Chol#1-cRNA(mMalat1)(5' PS), Chol#1-cRNA(mMalat1)(3' PS), Chol#1-cRNA-Chol#3(mMalat1), Chol#1-cDNA(mMalat1) Full DNA, Chol#1-cDNA(mMalat1) Full PS, Chol#1-cDNA(mMalat1) Full PO, Chol#1-cRNA(anti-miR21), Chol#1-cRNA(LNA)(mMalat1), and Chol#1-cRNA(DNA)(mMalat1), shown in Table 1 is shown below.

[Chem. 6]

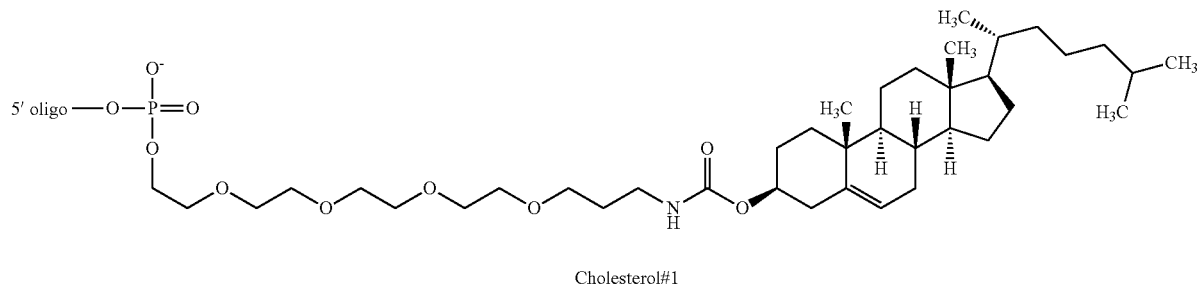

Cholesterol#1

The 5' terminal structure of the oligonucleotide, Chol#2-cRNA(mMalat1), shown in Table 1 is shown below.

[Chem. 7]

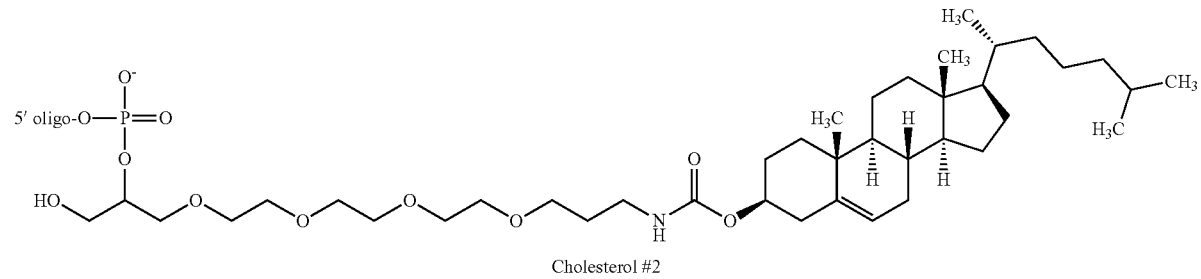

Cholesterol #2

The 3' terminal structure of the oligonucleotides, Chol#3-cRNA(mMalat1) and Chol#1-cRNA-Chol#3(mMalat1), shown in Table 1 is shown below.

[Chem. 8]

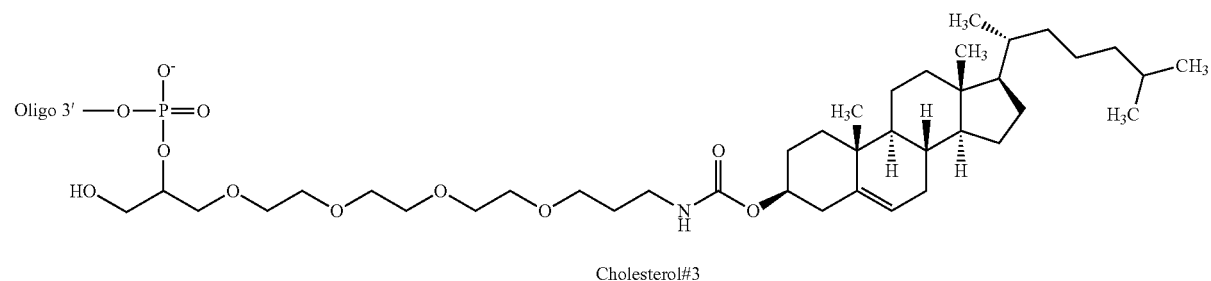

Cholesterol#3

The 5' terminal structure of the oligonucleotide, Chol#4-cRNA(mMalat1), shown in Table 1 is shown below.

[Chem. 9]

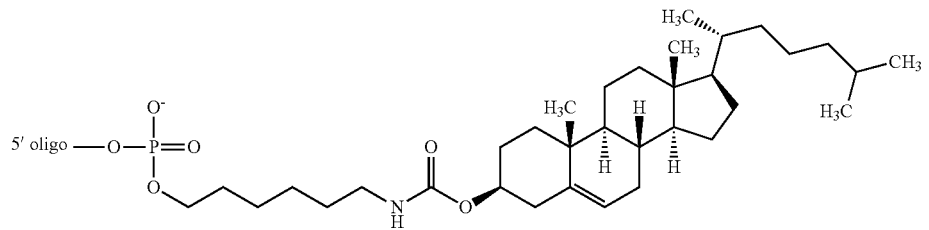

Cholesterol#4

The 3' terminal structure of the oligonucleotide, Chol#5-cRNA(mMalat1), shown in Table 1 is shown below.

[Chem. 10]

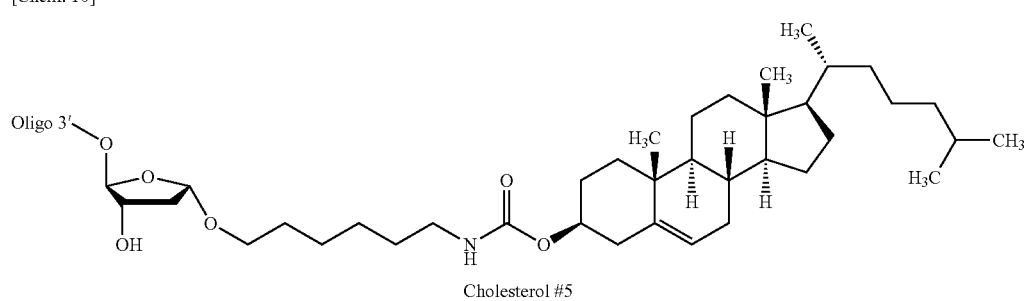

Cholesterol #5

The 5' terminal structure of the oligonucleotide, Chol#1-cRNA(PS)(mMalat1), shown in Table 1 is shown below.

[Chem. 11]

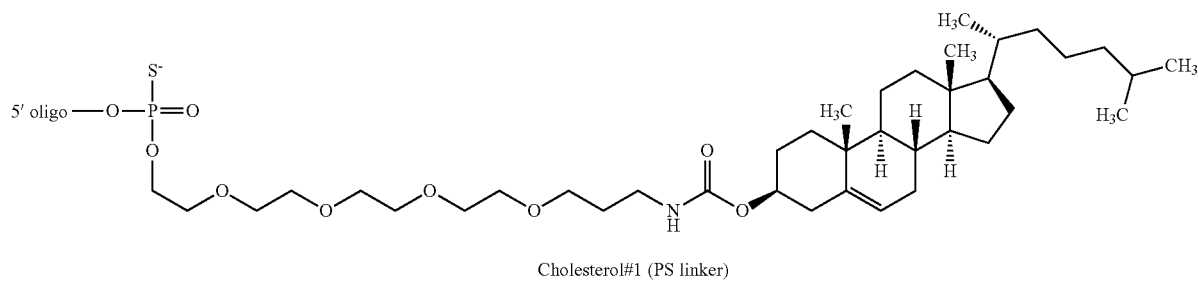

Cholesterol#1 (PS linker)

The 5' terminal structure of the oligonucleotide, DHA-cRNA(mMalat1), shown in Table 1 is shown below.

[Chem. 12]

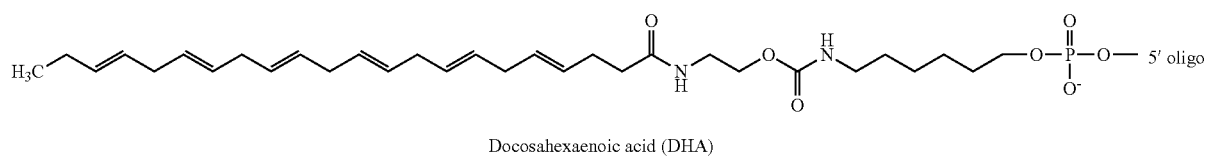

Docosahexaenoic acid (DHA)

The 5' terminal structure of the oligonucleotide, C6(OH)-cRNA(mMalat1), shown in Table 1 is shown below.

[Chem. 13]

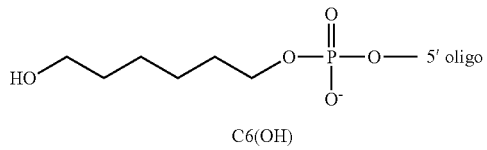

C6(OH)

The 5' terminal structure of the oligonucleotide, C9(OH)-cRNA(mMalat1), shown in Table 1 is shown below.

[Chem. 14]

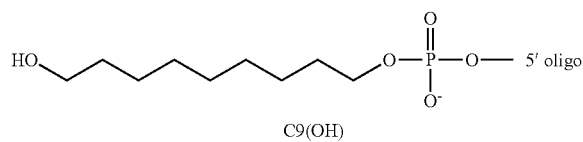

C9(OH)

The 5' terminal structure of the oligonucleotide, C12(OH)-cRNA(mMalat1), shown in Table 1 is shown below.

[Chem. 15]

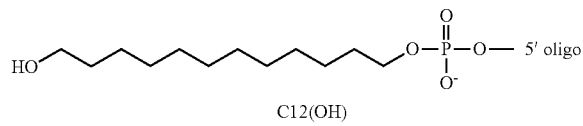

C12(OH)

The 5' terminal structure of the oligonucleotide, C3-cRNA(mMalat1), shown in Table 1 is shown below.

[Chem. 16]

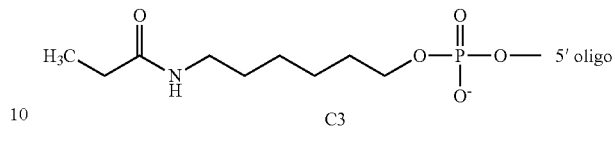

C3

The 5' terminal structure of the oligonucleotide, C4-cRNA(mMalat1), shown in Table 1 is shown below.

[Chem. 17]

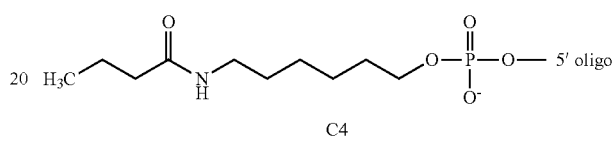

C4

The 5' terminal structure of the oligonucleotide, C8-cRNA(mMalat1), shown in Table 1 is shown below.

[Chem. 18]

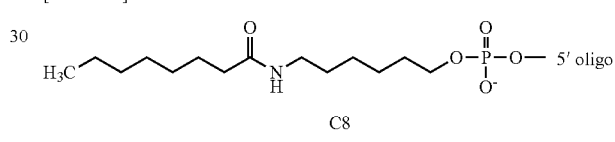

C8

The 5' terminal structure of the oligonucleotide, C10-cRNA(mMalat1), shown in Table 1 is shown below.

[Chem. 19]

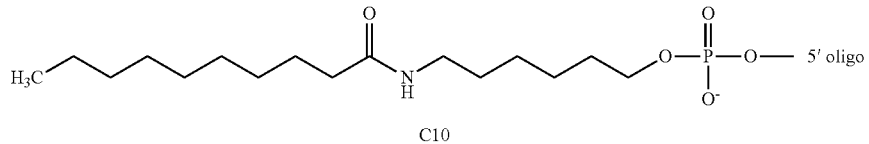

C10

The 5' terminal structure of the oligonucleotide, C12-cRNA(mMalat1), shown in Table 1 is shown below.

[Chem. 20]

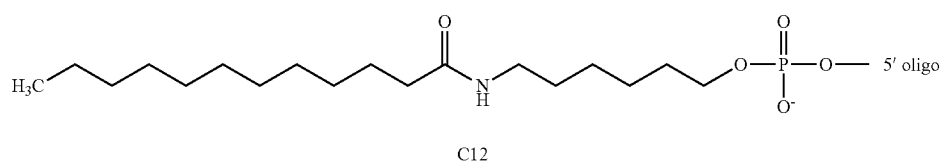

C12

Example 1

Evaluation of Antisense Effect Brought about in Brain by Administration of Single Dose of Double-Stranded Nucleic Acid Complex Consisting of Antisense Oligonucleotide Targeted at Malat1 and Tocopherol-Conjugated Complementary Strand An experiment was carried out to evaluate the in vivo inhibition potency against RNA expression in the brain by a double-stranded nucleic acid agent consisting of an antisense oligonucleotide and a tocopherol-conjugated complementary strand.

(Preparation of Nucleic Acid Agent)

The double-stranded agent was compared with a conventional single-stranded antisense oligonucleotide (ASO) control. The control (ASO) was a 16-mer single-stranded LNA/DNA gapmer (ASO(mMalat1), SEQ ID NO: 1) targeted at a metastasis associated lung adenocarcinoma transcription product (malat1) non-coding RNA. This LNA/DNA gapmer comprises three LNA nucleosides to the 5' end, three LNA nucleosides to the 3' end, and ten DNA nucleosides therebetween. This LNA/DNA gapmer has a base sequence complementary to positions 1316 to 1331 of the malat1 non-coding RNA (GenBank Accession No. NR_002847, SEQ ID NO: 6) of a mouse. By annealing this LNA/DNA gapmer (a first strand) to a tocopherol-conjugated complementary strand RNA (Toc#1-cRNA(mMalat1), SEQ ID NO: 10) (a second strand), a tocopherol-conjugated heteroduplex oligonucleotide (Toc-HDO), which is a double-stranded nucleic acid agent, was prepared. The double-stranded nucleic acid agent described above was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice. The prepared double-stranded nucleic acid agent is referred to as Toc#1HDO.

The names and sequences of the first strand and the second strand used in this Example are shown below.

```
First Strand: ASO(mMalat1)
                                          (SEQ ID NO: 1)
5'-C*T*A*g*t*t*c*a*c*t*g*a*a*T*G*C-3'

Second Strand: Toc#1-cRNA(mMalat1)
                                         (SEQ ID NO: 10)
5'-Toc#1-g*c*a*UUCAGUGAAC*u*a*g-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Toc#1 represents the above-mentioned α-tocopherol #1.

(In Vivo Experiment)

The mice were 6- to 7-week old male C57BL/6 mice having a body weight of 20 g. The experiments involving use of mice were all carried out with n=3. The nucleic acid agent was intravenously injected at a dose of 50 mg/kg (single dose administration) into each mouse through the tail veins. In addition, a mouse into which PBS alone (instead of a nucleic acid agent) was injected was prepared as a negative control group.

(Analysis of Expression)

Seventy-two hours after injection, PBS was perfused into the mice, and then, the mice were dissected to isolate the cerebral cortex. Subsequently, RNA was extracted using a fully automated high-throughput nucleic acid extraction device, MagNA Pure 96 (from Roche Life Science) in accordance with the protocol. cDNA was synthesized using Transcriptor Universal cDNA Master (from Roche Life Science) in accordance with the protocol. Quantitative RT-PCR was carried out using TaqMan (from Roche Life Science). The primers used in quantitative RT-PCR were products designed and produced based on various numbers of genes by Thermo Fisher Scientific Inc. (formerly known as Life Technologies Corp.). The amplification conditions (temperature and duration) were as follows: 95° C. for 15 seconds, 60° C. for 30 seconds, and 72° C. for one second (in one cycle), and this cycle was repeated 40 times. On the basis of the thus obtained results of quantitative RT-PCR, a non-coding RNA(malat1) expression level and an mRNA (GAPDH; internal standard gene) expression level were each calculated, and relative expression levels were obtained. The average value and standard error of the relative expression levels were calculated. In addition, the results of different groups were compared, and the results were further evaluated by t-test.

(Results)

Figure 5:
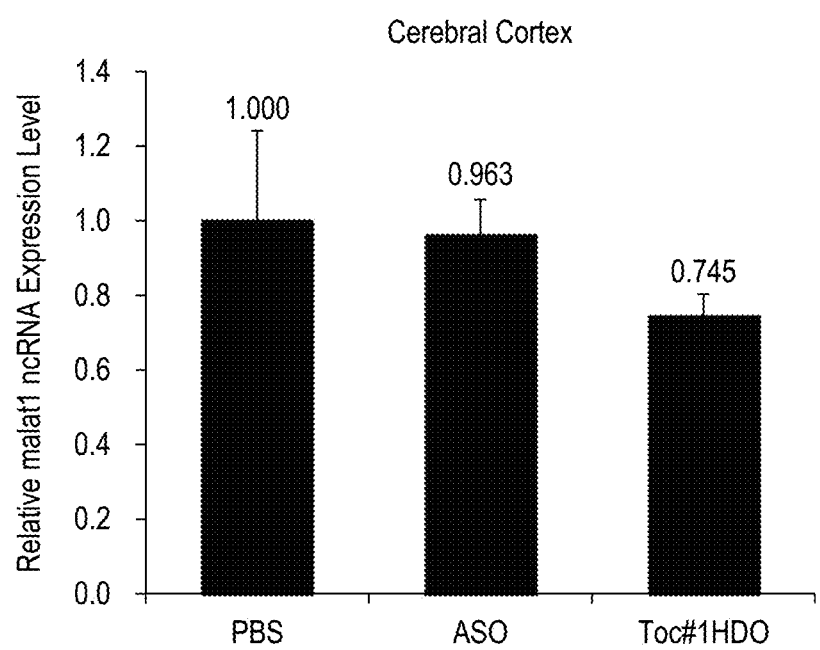
FIG. 5 is a graph showing the results of the experiment described in Example 1, and the graph shows the suppression effects on the expression of the target transcription product (malat1) by a tocopherol-conjugated nucleic acid complex in the cerebral cortex. The error bars represent standard errors.

The results of Example 1 are shown by the graph in FIG. 5. The single-stranded ASO suppressed the expression of the malat1 non-coding RNA in the cerebral cortex to the same degree as the negative control (PBS alone) did. On the other hand, Toc#1HDO remarkably suppressed the expression of the malat1 non-coding RNA in the cerebral cortex, compared with ASO.

These results have revealed that the double-stranded nucleic acid complex consisting of an antisense oligonucleotide and a tocopherol-conjugated complementary strand and targeted at malat1 was efficiently delivered to the brain and brought an antisense effect on the malat1 non-coding RNA in the brain.

Example 2

Evaluation of Antisense Effect Brought about in Various Sites of Brain and Spinal Cord by Administration of Multiple Doses of Double-Stranded Nucleic Acid Complex Consisting of Antisense Oligonucleotide Targeted at Malat1 and Tocopherol-Conjugated Complementary Strand An experiment was carried out to evaluate the in vivo inhibition potency against RNA expression in the brain by administration of multiple doses of a double-stranded nucleic acid agent consisting of an antisense oligonucleotide and a tocopherol-conjugated complementary strand.

(Preparation of Nucleic Acid Agent)

The same nucleic acid agents as used in Example 1, in other words, a single-stranded ASO and a tocopherol-conjugated heteroduplex oligonucleotide (Toc#1HDO), were used.

(In Vivo Experiment)

The mice were 6- to 7-week old male C57BL/6 mice having a body weight of 20 g. The experiments involving use of mice were all carried out with n=4. The nucleic acid agent in an amount of 50 mg/kg per dose was intravenously injected into a mouse through the tail veins. The dose was administered once a week, a total of four times in four weeks. In addition, a mouse into which PBS alone (instead of a nucleic acid agent) was injected was prepared as a negative control group.

(Analysis of Expression)

Seventy-two hours after the final administration, PBS was perfused into the mice, and then, the mice were dissected to isolate the brain and spinal cord. The cerebral cortex, cerebellum, striatum, hippocampus, and brainstem were separately collected from the brain. The cervical spinal cord, thoracic spinal cord, and lumbar spinal cord were separately collected from the spinal cord. In addition, the retina was collected from each mouse. Using the obtained tissues, RNA extraction, cDNA synthesis, and quantitative RT-PCR were carried out as described in Example 1, and the expression level of the malat1 non-coding RNA was evaluated.

In addition, the concentration of the nucleic acid agent in the cerebral cortex was measured by quantitative RT-PCR using TaqMan Small Assay (from Roche Life Science) in accordance with the protocol.

(Results)

Figure 6:
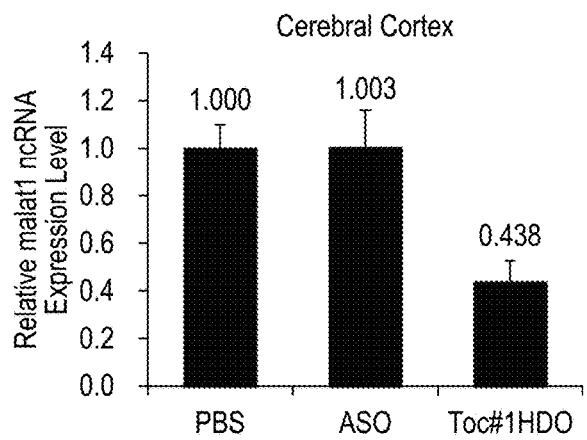
FIG. 6 shows graphs for part of the results of the experiment described in Example 2, and the graphs show comparisons of suppression effects on the expression of the target transcription product (malat1) by a tocopherol-conjugated nucleic acid complex in various sites in the brain. The results are shown for (a) cerebral cortex, (b) cerebellum, (c) striatum, (d) hippocampus, and (e) brainstem. The error bars represent standard errors.
Figure 6:
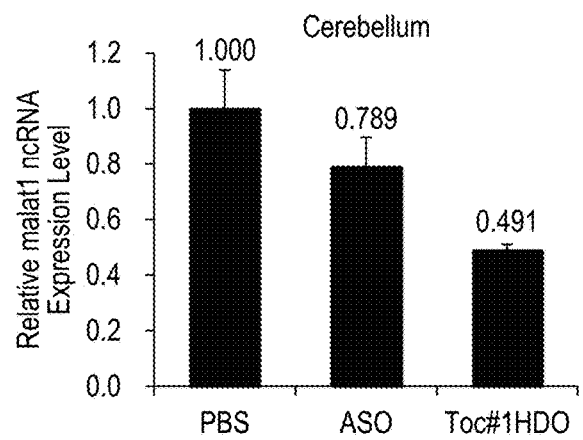
Figure 6:
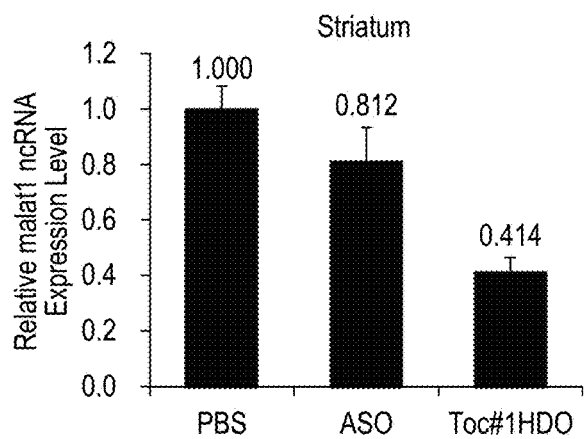
Figure 6:
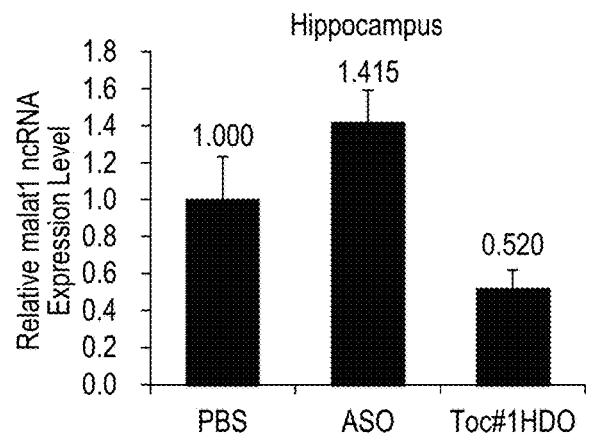
Figure 6:
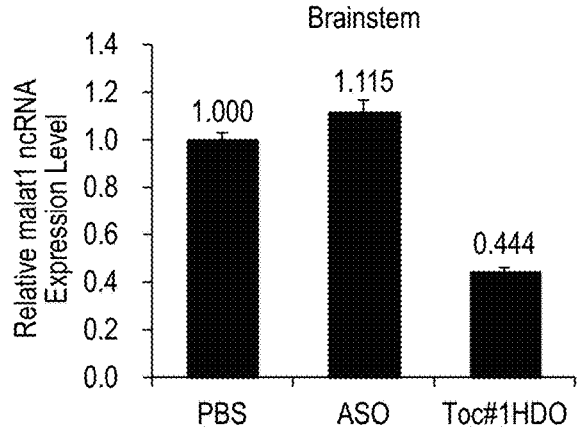
Figure 7:
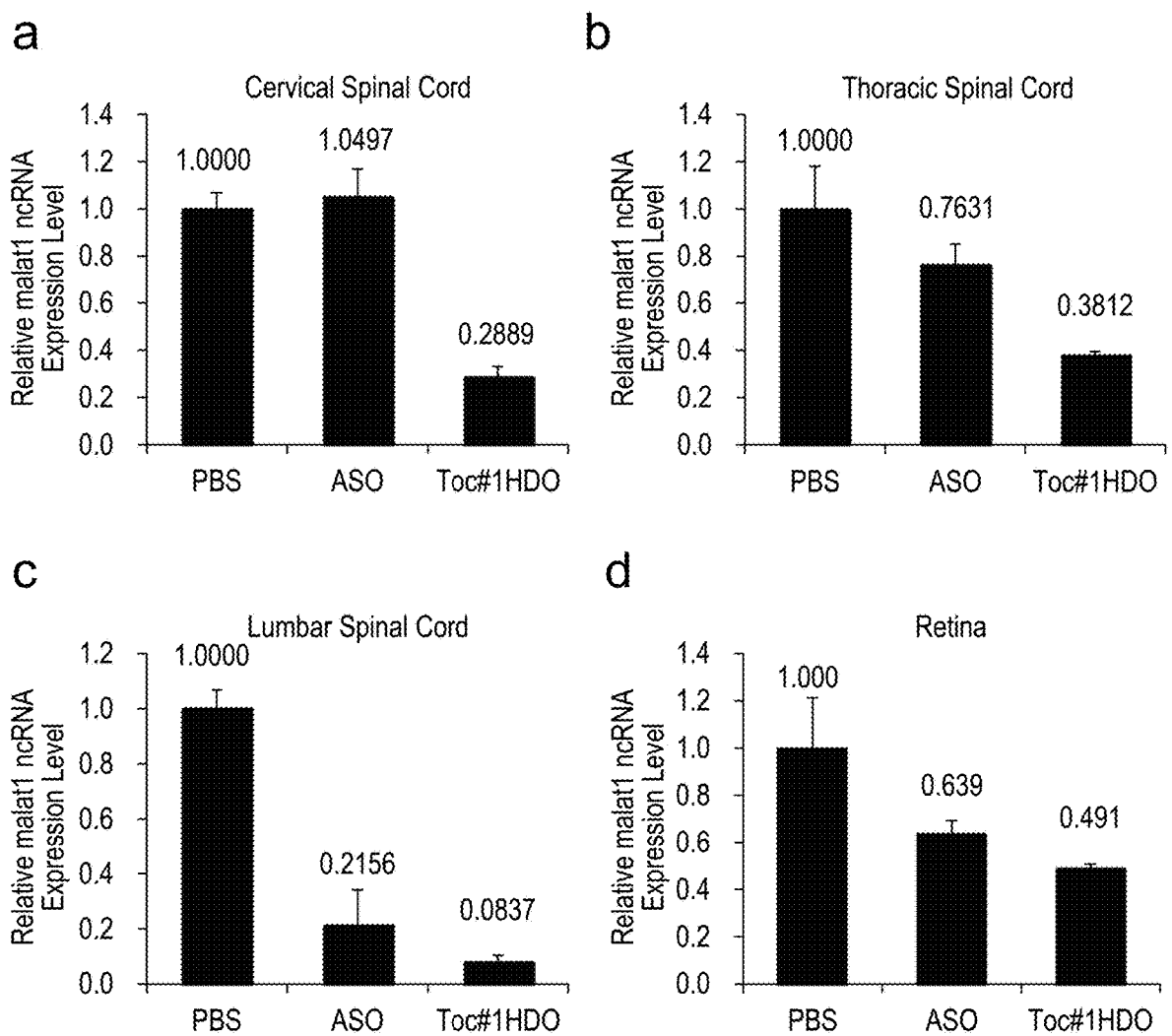
FIG. 7 shows graphs for part of the results of the experiment described in Example 2, and the graphs show comparisons of suppression effects on the expression of the target transcription product (malat1) by a tocopherol-conjugated nucleic acid complex in various sites in the spinal cord and the retina. The results are shown for (a) cervical spinal cord, (b) thoracic spinal cord, (c) lumbar spinal cord, and (d) retina. The error bars represent standard errors.
Figure 8:
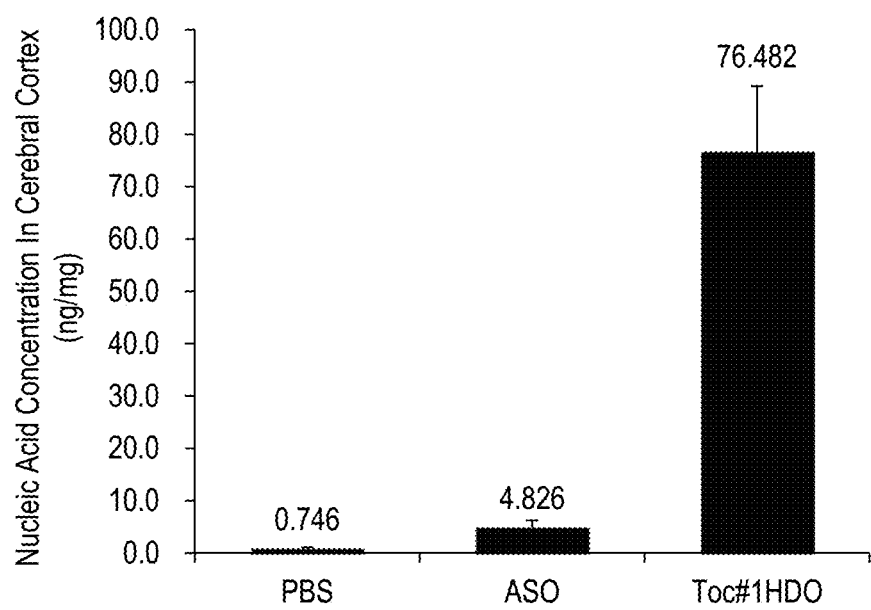
FIG. 8 is a graph showing part of the results of the experiment described in Example 2, and the graph shows the concentration of a tocopherol-conjugated nucleic acid complex in the cerebral cortex. The error bars represent standard errors.

The results of Example 2 are shown by the graphs in FIGS. 6 to 8. Toc#1HDO remarkably suppressed the expression of the malat1 non-coding RNA in any of the cerebral cortex, cerebellum, striatum, hippocampus, brainstem, cervical spinal cord, thoracic spinal cord, lumbar spinal cord, and retina, compared with the negative control (PBS alone) and the single-stranded ASO (FIGS. 6 and 7). Furthermore, the concentration of the nucleic acid agent, Toc#1HDO, in the cerebral cortex was remarkably higher than that of ASO (FIG. 8).

These results have revealed that the tocopherol-conjugated double-stranded nucleic acid complex can be efficiently delivered in a large amount to various sites in the brain and spinal cord and to the retina, and bring about an antisense effect.

Example 3

Evaluation of Antisense Effect Brought about in Brain by Administration of Single Dose of Double-Stranded Nucleic Acid Complex Consisting of Antisense Oligonucleotide Targeted at SR-B1 and Tocopherol-Conjugated Complementary Strand An experiment was carried out to evaluate the in vivo inhibition potency against mRNA expression in the brain by a double-stranded nucleic acid agent consisting of an antisense oligonucleotide and a tocopherol-conjugated complementary strand targeted at an SR-B1 gene, which is different from Examples 1 and 2.

(Preparation of Nucleic Acid Agent)

The double-stranded agent was compared with a conventional single-stranded antisense oligonucleotide (ASO) control. The control (ASO) was a 14-mer single-stranded LNA/DNA gapmer (ASO(mSR-B1), SEQ ID NO: 3) targeted at a scavenger receptor B1 (SR-B1) mRNA. This LNA/DNA gapmer comprises two LNA nucleosides to the 5' end, two LNA nucleosides to the 3' end, and ten DNA nucleosides therebetween. This LNA/DNA gapmer has a base sequence complementary to positions 2479 to 2492 of the SR-B1 mRNA (GenBank Accession No. NM_016741, SEQ ID NO: 7) of a mouse. By annealing this LNA/DNA gapmer (a first strand) to a tocopherol-conjugated complementary strand RNA (Toc#1-cRNA(mSR-B1), SEQ ID NO: 11) (a second strand), a tocopherol-conjugated heteroduplex oligonucleotide (Toc-HDO), which is a double-stranded nucleic acid agent, was prepared. The double-stranded nucleic acid agent was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice. The prepared double-stranded nucleic acid agent is referred to as Toc#1HDO.

The names and sequences of the first strand and the second strand used in this Example are shown below.

```
First Strand: ASO(mSR-B1)
                                        (SEQ ID NO: 3)
5'-T*C*a*g*t*c*a*t*g*a*c*t*T*C-3'

Second Strand: Toc#1-cRNA(mSR-B1)
                                       (SEQ ID NO: 11)
5'-Toc#1-g*a*AGUCAUGACU*g*a-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Toc#1 represents the above-mentioned α-tocopherol #1.

(In Vivo Experiment)

The mice were 6- to 7-week old male C57BL/6 mice having a body weight of 20 g. The experiments involving use of mice were all carried out with n=4. The nucleic acid agent was intravenously injected at an amount of 50 mg/kg (single dose administration) into a mouse through the tail veins. In addition, a mouse into which PBS alone (instead of a nucleic acid agent) was injected was prepared as a negative control group.

(Analysis of Expression)

Seventy-two hours after injection, PBS was perfused into the mice, and then, the mice were dissected to isolate the cerebral cortex, cerebellum, striatum, hippocampus, brainstem, cervical spinal cord, and lumbar spinal cord. Subsequently, mRNA was extracted from each tissue using a fully automated high-throughput nucleic acid extraction device, MagNA Pure 96 (from Roche Life Science) in accordance with the protocol. cDNA was synthesized using Transcriptor Universal cDNA Master (from Roche Life Science) in accordance with the protocol. Quantitative RT-PCR was carried out using TaqMan (from Roche Life Science). The primers used in quantitative RT-PCR were products designed and produced based on various numbers of genes by Thermo Fisher Scientific Inc. The amplification conditions (temperature and duration) were as follows: 95° C. for 15 seconds, 60° C. for 30 seconds, and 72° C. for one second (in one cycle), and this cycle was repeated 40 times. On the basis of the thus obtained results of quantitative RT-PCR, an mRNA(SR-B1) expression level/an mRNA (GAPDH; internal standard gene) expression level were each calculated, and a relative expression level was obtained. The average value and standard error of the relative expression level were calculated. In addition, the results of different groups were compared, and the results were further evaluated by t-test.

(Results)

Figure 9:
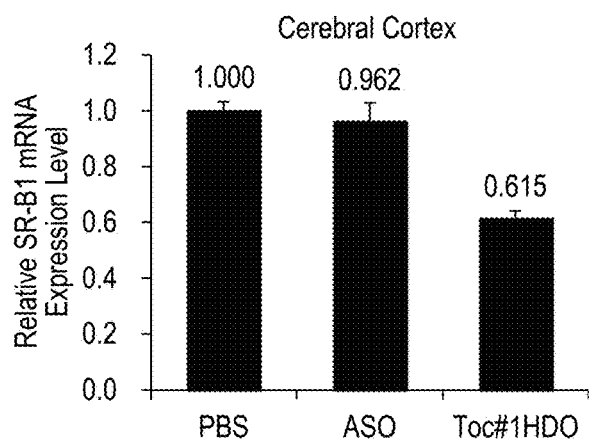
FIG. 9 shows graphs for the results of the experiment described in Example 3, and the graphs show suppression effects on the expression of the target gene (SR-B1) by a tocopherol-conjugated nucleic acid complex in various sites in the brain. The results are shown for (a) cerebral cortex, (b) cerebellum, (c) striatum, and (d) hippocampus. The error bars represent standard errors.
Figure 9:
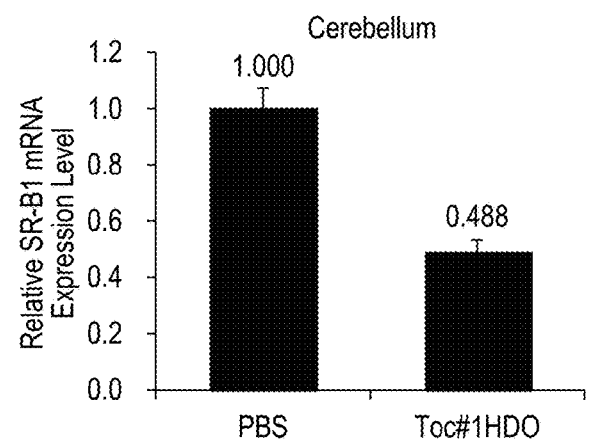
Figure 9:
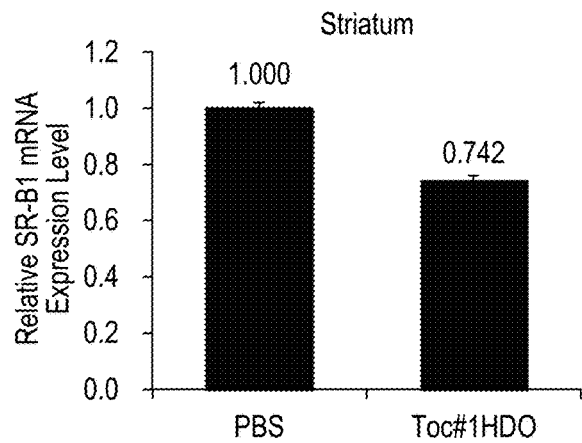
Figure 9:
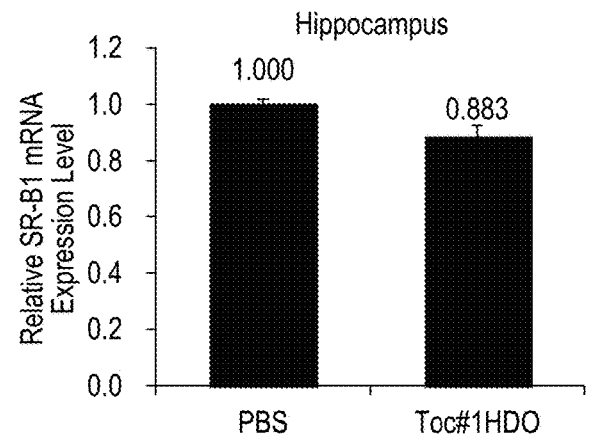
Figure 10:
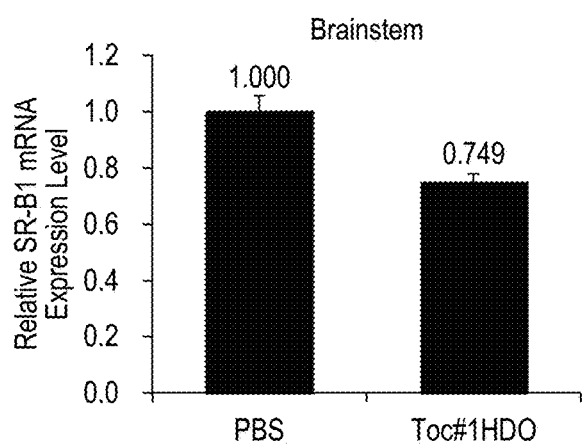
FIG. 10 shows graphs for the results of the experiment described in Example 3, and the graphs show suppression effects on the expression of the target gene (SR-B1) by a tocopherol-conjugated nucleic acid complex in various sites in the brain and spinal cord. The results are shown for (a) brainstem, (b) cervical spinal cord, and (c) lumbar spinal cord. The error bars represent standard errors.
Figure 10:
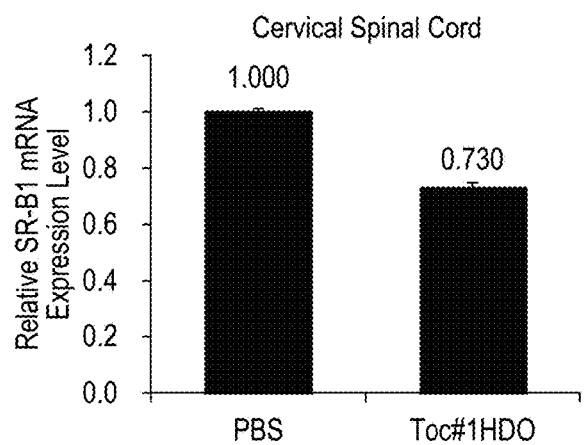
Figure 10:
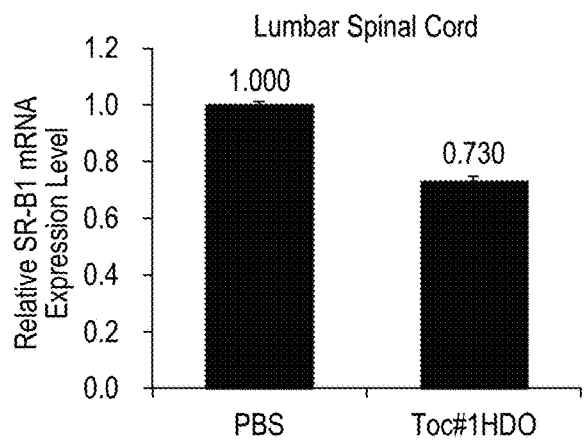

The results of Example 3 are shown by the graphs in FIGS. 9 and 10. The single-stranded ASO suppressed the expression of the SR-B1 mRNA in the cerebral cortex to the same degree as the negative control (PBS alone) did. On the other hand, Toc#1HDO remarkably suppressed the expression of the SR-B1 mRNA in the cerebral cortex, cerebellum, striatum, hippocampus, brainstem, cervical spinal cord, and lumbar spinal cord, compared with ASO.

These results have revealed that the antisense effect of the double-stranded nucleic acid complex in the brain is not specific to malat1 and can be targeted at various gene transcription products.

Example 4

Evaluation of Antisense Effect Brought about in Various Sites of Brain by Administration of Multiple Doses of Double-Stranded Nucleic Acid Complex Consisting of Antisense Oligonucleotide Targeted at Malat1 and Cholesterol-Conjugated Complementary Strand An experiment was carried out to evaluate the in vivo inhibition potency against RNA expression in the brain by administration of multiple doses of a double-stranded nucleic acid agent consisting of an antisense oligonucleotide targeted at malat1 and a cholesterol-conjugated complementary strand unlike in Examples 1 and 3.

(Preparation of Nucleic Acid Agent)

The control (ASO) was a 16-mer single-stranded LNA/DNA gapmer (ASO(mMalat1), SEQ ID NO: 1) targeted at a malat1 non-coding RNA and used in Example 1. By annealing this LNA/DNA gapmer (a first strand) to a cholesterol-conjugated complementary strand RNA (Chol#1-cRNA(mMalat1), SEQ ID NO: 10) (a second strand), a cholesterol-conjugated heteroduplex oligonucleotide (Chol-HDO), which is a double-stranded nucleic acid agent, was prepared. Specifically, the double-stranded nucleic acid agent described above was prepared by adding the second strand (powder) to phosphate buffered saline (PBS) heated to 95° C., dissolving the strand by vortexing, mixing the resulting solution with the first strand solution heated to 95° C., maintaining the resulting solution mixture at 95° C. for five minutes, then maintaining the solution mixture at 37° C. for one hour, and thus annealing the nucleic acid strands. The annealed nucleic acid was stored at 4° C. or on ice. The prepared double-stranded nucleic acid agent is referred to as Chol#1HDO.

The names and sequences of the first strand and the second strand used in this Example are shown below.

```
First Strand: ASO(mMalat1)
                                    (SEQ ID NO: 1)
5'-C*T*A*g*t*t*c*a*c*t*g*a*a*T*G*C-3'

Second Strand: Chol#1-cRNA(mMalat1)
                                    (SEQ ID NO: 10)
5'-Chol#1-g*c*a*UUCAGUGAAC*u*a*g-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#1 represents the above-mentioned cholesterol #1.

(In Vivo Experiment)

The mice were 6- to 7-week old male C57BL/6 mice having a body weight of 20 g. The experiments involving use of mice were all carried out with n=4. The nucleic acid agent in an amount of 50 mg/kg per dose was intravenously injected into a mouse through the tail veins. The dose was administered once a week, a total of four times in four weeks. In addition, a mouse into which PBS alone (instead of a nucleic acid agent) was injected was prepared as a negative control group.

(Analysis of Expression)

Seventy-two hours after the final administration, PBS was perfused into the mice, and then, the mice were dissected to isolate the cerebral cortex, cerebellum, striatum, hippocampus, brainstem, cervical spinal cord, and lumbar spinal cord. Using the obtained each tissue, RNA extraction, cDNA synthesis, and quantitative RT-PCR were carried out as described in Example 1, and the expression level of the malat1 non-coding RNA was evaluated.

(Results)

Figure 11:
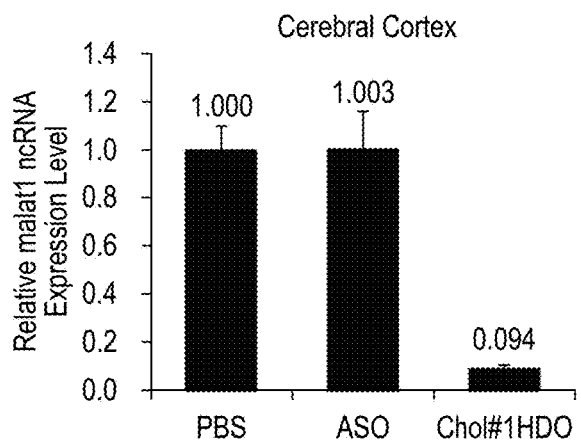
FIG. 11 shows graphs for the results of the experiment described in Example 4, and the graphs show comparisons of suppression effects on the expression of the target transcription product (malat1) by a cholesterol-conjugated nucleic acid complex in various sites in the brain. The results are shown for (a) cerebral cortex, (b) cerebellum, (c) striatum, (d) hippocampus, and (e) brainstem. The error bars represent standard errors.
Figure 11:
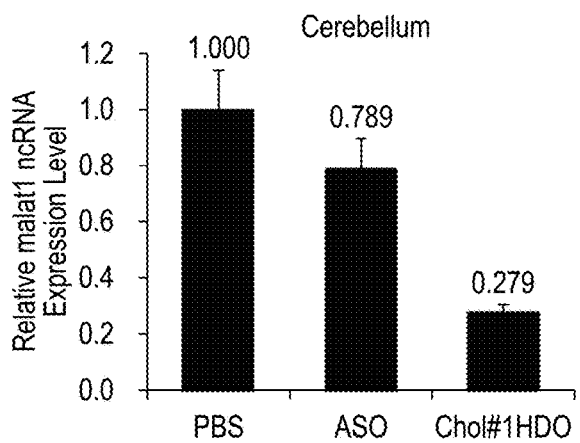
Figure 11:
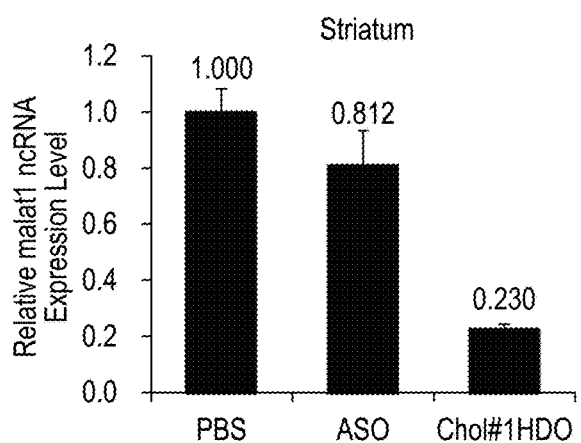
Figure 11:
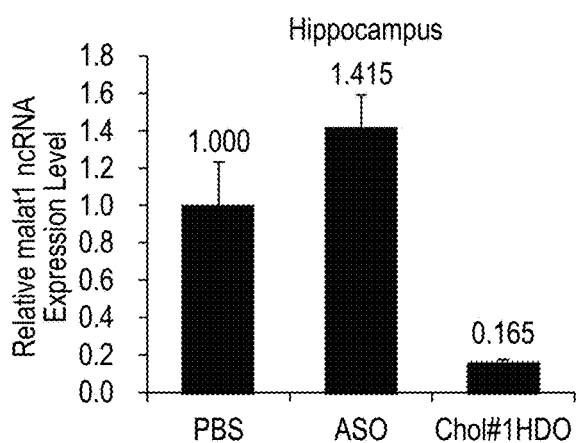
Figure 11:
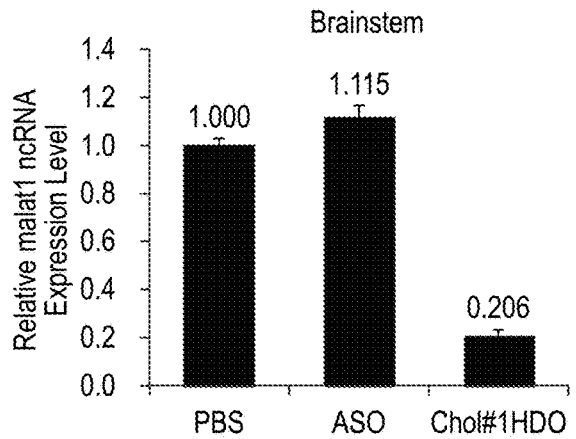
Figure 12:
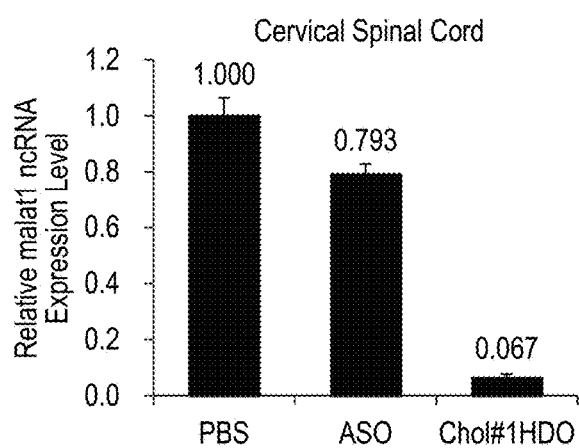
FIG. 12 shows graphs for the results of the experiment described in Example 4, and the graphs show comparisons of suppression effects on the expression of the target transcription product (malat1) by a cholesterol-conjugated nucleic acid complex in various sites in the spinal cord. The results are shown for (a) cervical spinal cord and (b) lumbar spinal cord. The error bars represent standard errors.
Figure 12:
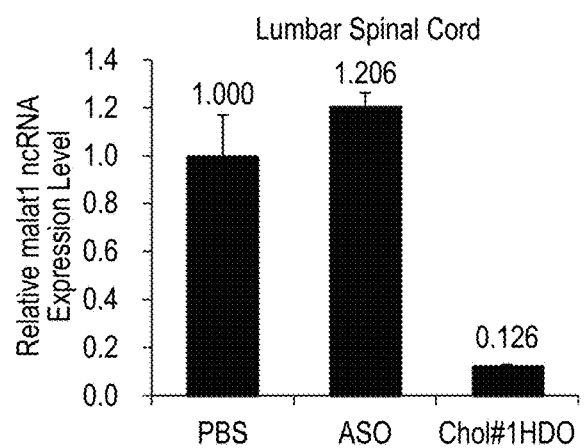

The results of Example 4 are shown by the graphs in FIGS. 11 and 12. Chol#1HDO remarkably suppressed the expression of the malat1 non-coding RNA in any of the cerebral cortex, cerebellum, striatum, hippocampus, brainstem, cervical spinal cord, and lumbar spinal cord, compared with the negative control (PBS alone) and the single-stranded ASO.

These results have revealed that the cholesterol-conjugated double-stranded nucleic acid complex can be delivered to various sites in the brain and bring about an antisense effect.

Example 5

Evaluation of Antisense Effect Brought about in Various Sites of Brain by Administration of Multiple Doses of Double-Stranded Nucleic Acid Complex Consisting of Antisense Oligonucleotide and Cholesterol-Conjugated Complementary Strand An experiment was carried out to evaluate the in vivo inhibition potency against RNA expression in the brain by administration of multiple doses of a double-stranded nucleic acid agent consisting of an antisense oligonucleotide targeted at malat1 and a complementary strand conjugated to cholesterol at the 3' end, unlike in Example 4.

(Preparation of Nucleic Acid Agent)

The double-stranded nucleic acid agent was prepared by allowing a 16-mer single-stranded LNA/DNA gapmer targeted at malat1 non-coding RNA (ASO(mMalat1), SEQ ID NO: 1) (a first strand) to be annealed to a cholesterol-conjugated complementary strand RNA having cholesterol conjugated to the 3' end (Chol#3-cRNA(mMalat1), SEQ ID NO: 10) (a second strand). The double-stranded nucleic acid agent described above was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice. The prepared double-stranded nucleic acid agent is referred to as Chol#3HDO.

The names and sequences of the first strand and the second strand used in this Example are shown below.

```
First Strand: ASO(mMalat1)
                                    (SEQ ID NO: 1)
5'-C*T*A*g*t*t*c*a*c*t*g*a*a*T*G*C-3

Second Strand: Chol#3-cRNA(mMalat1)
                                    (SEQ ID NO: 10)
5'-g*c*a*UUCAGUGAAC*u*a*g-Chol#3-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#3 represents the above-mentioned cholesterol #3.

(In Vivo Experiment)

As described in Example 4, multiple doses of the nucleic acid agent were administered to the mouse.

(Analysis of Expression)

Seventy-two hours after the final administration, PBS was perfused into the mice, and then, the mice were dissected to collect the cerebral cortex, cerebellum, hippocampus, and brainstem separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 13:
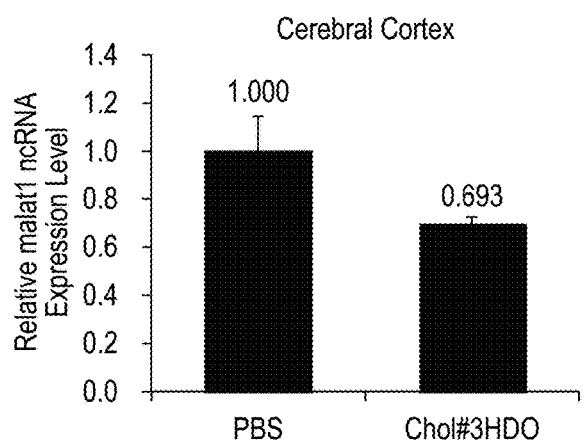
FIG. 13 shows graphs for the results of the experiment described in Example 5, and the graphs show suppression effects on the expression of the target transcription product (malat1) by a cholesterol-conjugated nucleic acid complex in various sites in the brain. The results are shown for (a) cerebral cortex, (b) cerebellum, (c) hippocampus, and (d) brainstem. The error bars represent standard errors.
Figure 13:
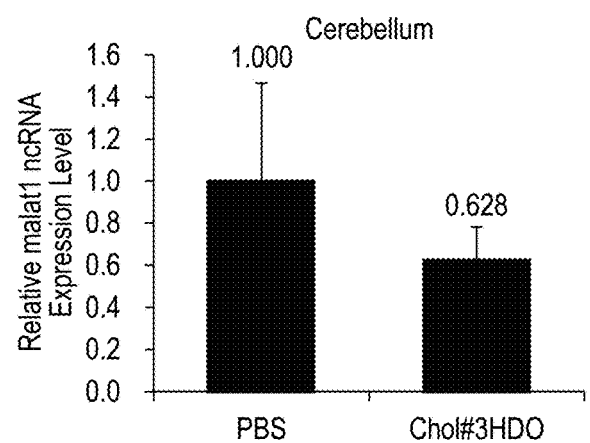
Figure 13:
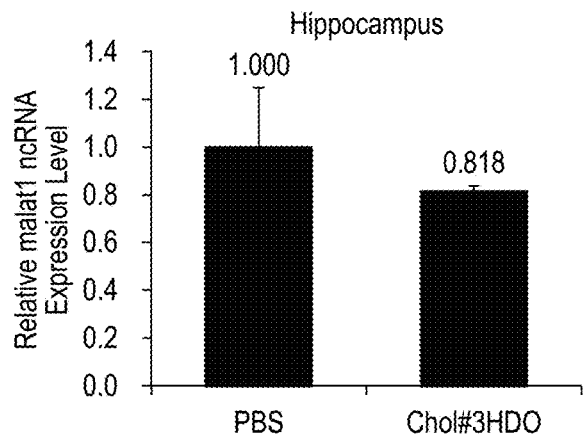
Figure 13:
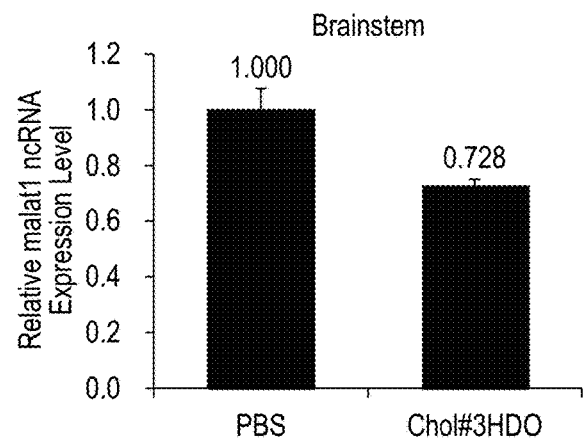

The results of Example 5 are shown by the graph in FIG. 13. Chol#3HDO suppressed the expression of the malat1 non-coding RNA in any of the cerebral cortex, cerebellum, hippocampus, and brainstem, compared with the negative control (PBS alone).

These results have revealed that the double-stranded nucleic acid agent consisting of an antisense oligonucleotide and a complementary strand conjugated to cholesterol at the 3' end can be delivered to various sites in the brain and bring about an antisense effect.

Example 6

Evaluation of Antisense Effect Brought about in Various Sites of Brain by Administration of Multiple Doses of Double-Stranded Nucleic Acid Complex Consisting of Antisense Oligonucleotide and Tocopherol-Conjugated DNA Complementary Strand An experiment was carried out to evaluate the in vivo inhibition potency against RNA expression in the brain by administration of multiple doses of a double-stranded nucleic acid agent consisting of an antisense oligonucleotide targeted at malat1 and a DNA complementary strand unlike in Examples 1 to 5.

(Preparation of Nucleic Acid Agent)

The double-stranded nucleic acid agent described above was prepared by allowing a 16-mer single-stranded LNA/DNA gapmer targeted at malat1 non-coding RNA (ASO (mMalat1), SEQ ID NO: 1) (a first strand) to be annealed to a tocopherol-conjugated complementary strand DNA (Toc#1-cDNA(mMalat1), SEQ ID NO: 12) (a second strand). This tocopherol-conjugated complementary strand DNA (a second strand) comprises three LNA nucleosides to the 5' end, three LNA nucleosides to the 3' end, and ten DNA nucleosides therebetween. The double-stranded nucleic acid agent was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice. The prepared double-stranded nucleic acid agent is referred to as Toc#1DNA/DNA.

The names and sequences of the first strand and the second strand used in this Example are shown below.

```
First Strand: ASO(mMalat1)
                                (SEQ ID NO: 1)
5'-C*T*A*g*t*t*c*a*c*t*g*a*a*T*G*C-3'

Second Strand: Toc#1-cDNA(mMalat1)
                                (SEQ ID NO: 12)
5'-Toc#1-G*C*A*ttcagtgaac*T*A*G-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Toc#1 represents the above-mentioned α-tocopherol #1.

(In Vivo Experiment)

As described in Example 4, multiple doses of the nucleic acid agents were administered to the mouse.

(Analysis of Expression)

Seventy-two hours after the final administration, PBS was perfused into the mice, and then, the mice were dissected to collect the cerebral cortex, cerebellum, striatum, hippocampus, and brainstem separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 14:
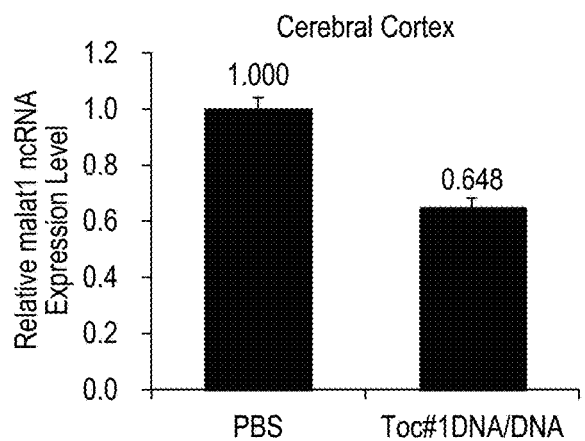
FIG. 14 shows graphs for the results of the experiment described in Example 6, and the graphs show suppression effects on the expression of the target transcription product (malat1) by a tocopherol-conjugated nucleic acid complex in various sites in the brain. The results are shown for (a) cerebral cortex, (b) cerebellum, (c) striatum, and (d) hippocampus. The error bars represent standard errors.
Figure 14:
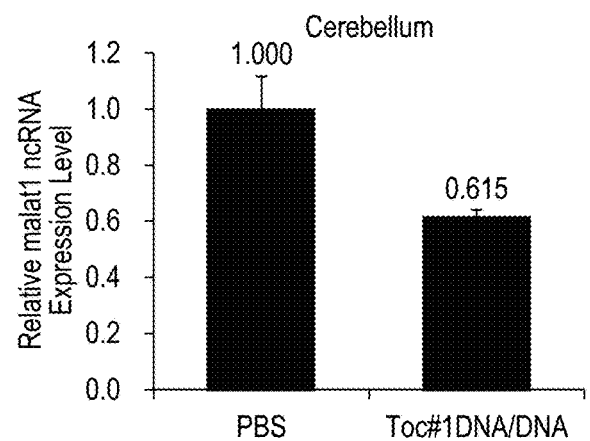
Figure 14:
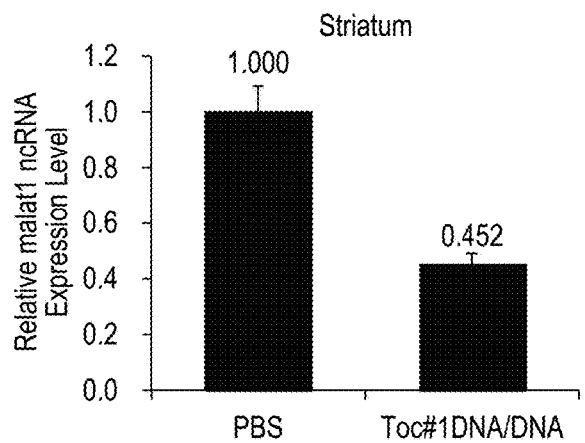
Figure 14:
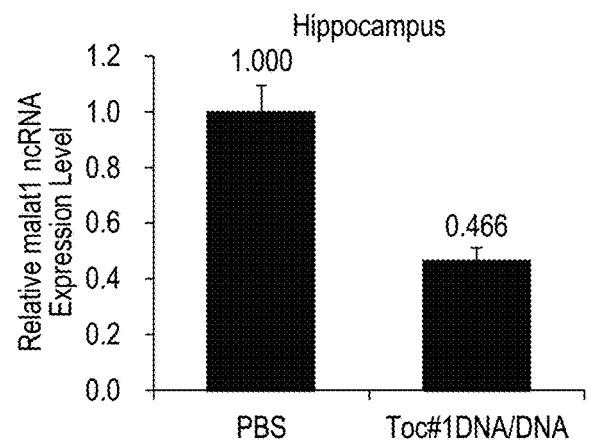
Figure 15:
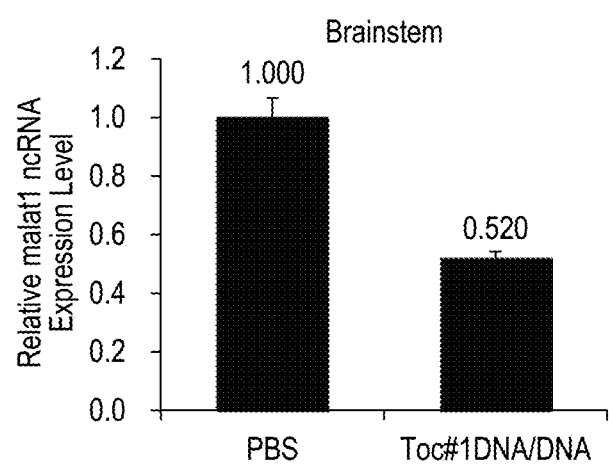
FIG. 15 is a graph showing the results of the experiment described in Example 6, and the graph shows suppression effects on the expression of the target transcription product (malat1) by a tocopherol-conjugated nucleic acid complex in the brainstem. The error bars represent standard errors.

The results of Example 6 are shown by the graphs in FIGS. 14 and 15. Toc#1DNA/DNA remarkably suppressed the expression of the malat1 non-coding RNA in any of the cerebral cortex, cerebellum, striatum, hippocampus, and brainstem, compared with the negative control (PBS alone).

These results have revealed that the double-stranded nucleic acid agent consisting of an antisense oligonucleotide and a tocopherol-conjugated DNA complementary strand can be delivered to various sites in the brain and bring about an antisense effect.

Example 7

Evaluation of Antisense Effect Brought about in Various Sites of Brain by Administration of Single Dose of Double-Stranded Nucleic Acid Complex Consisting of Antisense Oligonucleotide and Cholesterol-Conjugated DNA Complementary Strand An experiment was carried out to evaluate the in vivo inhibition potency against RNA expression in the brain by administration of a single dose of a double-stranded nucleic acid agent consisting of an antisense oligonucleotide targeted at malat1 and a DNA complementary strand unlike in Examples 1 to 5.

(Preparation of Nucleic Acid Agent)

The double-stranded nucleic acid agent was prepared by allowing a 16-mer single-stranded LNA/DNA gapmer targeted at malat1 non-coding RNA (ASO(mMalat1), SEQ ID NO: 1) (a first strand) to be annealed to a cholesterol-conjugated complementary strand DNA (Chol#1-cDNA (mMalat1), SEQ ID NO: 12) (a second strand). This cholesterol-conjugated complementary strand DNA (a second strand) comprises three LNA nucleosides to the 5' end, three LNA nucleosides to the 3' end, and ten DNA nucleosides therebetween. The double-stranded nucleic acid agent was prepared by adding the second strand (powder) to phosphate buffered saline (PBS) heated to 95° C., dissolving the strand by vortexing, mixing the resulting solution with the first strand solution heated to 95° C., maintaining the resulting solution mixture at 95° C. for five minutes, then maintaining the solution mixture at 37° C. for one hour, and thus annealing the nucleic acid strands. The annealed nucleic acid was stored at 4° C. or on ice. The prepared double-stranded nucleic acid agent is referred to as Chol#1DNA/DNA.

The names and sequences of the first strand and the second strand used in this Example are shown below.

```
First Strand: ASO(mMalat1)
                                (SEQ ID NO: 1)
5'-C*T*A*g*t*t*c*a*c*t*g*a*a*T*G*C-3'

Second Strand: Chol#1-cDNA(mMalat1)
                                (SEQ ID NO: 12)
5'-Chol#1-G*C*A*ttcagtgaac*T*A*G-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#1 represents the above-mentioned cholesterol #1.

(In Vivo Experiment)

As described in Example 3, a single dose of the nucleic acid agent was administered to the mouse.

(Analysis of Expression)

Seventy-two hours after administration, PBS was perfused into the mice, and then, the mice were dissected to collect the cerebral cortex, cerebellum, striatum, hippocampus, and brainstem separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 16:
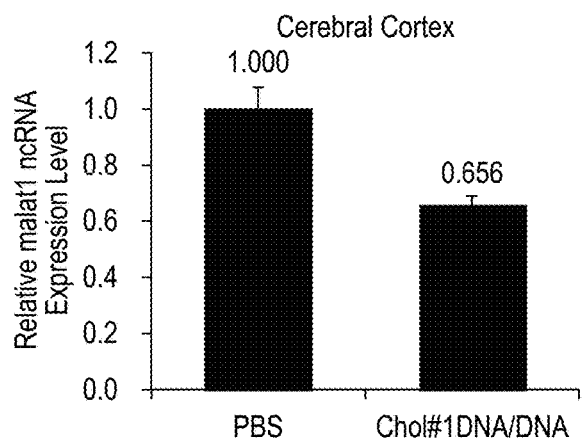
FIG. 16 shows graphs for the results of the experiment described in Example 7, and the graphs show suppression effects on the expression of the target transcription product (malat1) by a cholesterol-conjugated nucleic acid complex in various sites in the brain. The results are shown for (a) cerebral cortex, (b) cerebellum, (c) striatum, and (d) hippocampus. The error bars represent standard errors.
Figure 16:
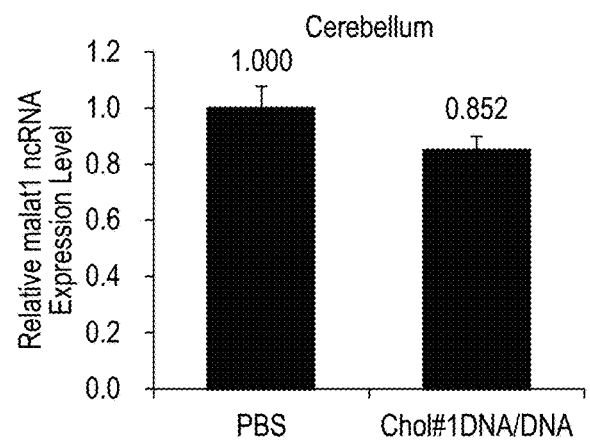
Figure 16:
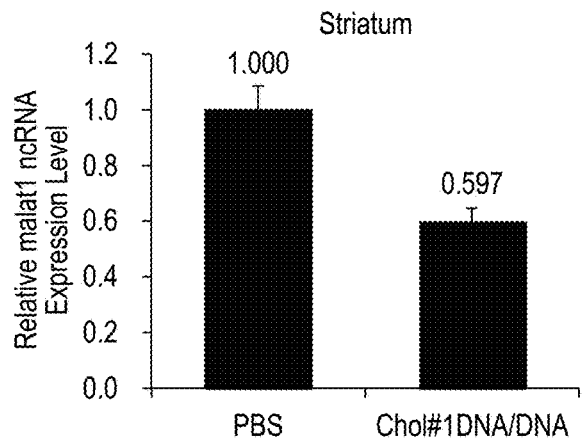
Figure 16:
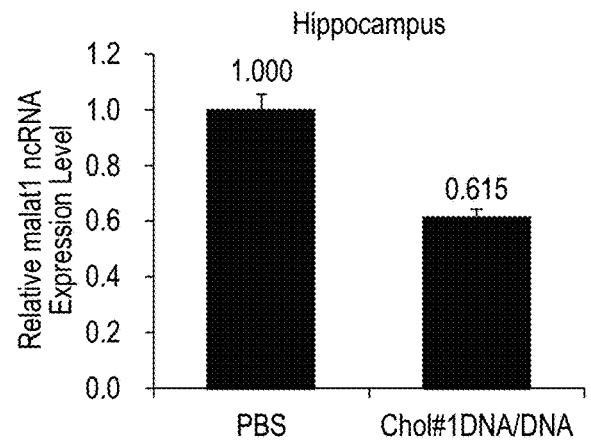
Figure 17:
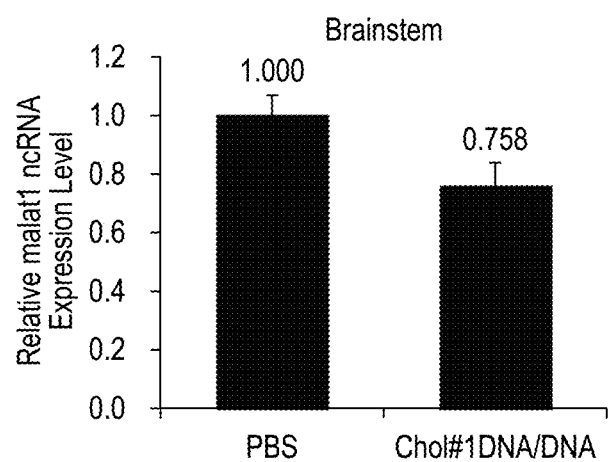
FIG. 17 is a graph showing the results of the experiment described in Example 7, and the graph shows suppression effects on the expression of the target transcription product (malat1) by a cholesterol-conjugated nucleic acid complex in the brainstem. The error bars represent standard errors.

The results of Example 7 are shown by the graphs in FIGS. 16 and 17. Chol#1DNA/DNA remarkably suppressed the expression of the malat1 non-coding RNA in any of the cerebral cortex, cerebellum, striatum, hippocampus, and brainstem, compared with the negative control (PBS alone).

These results have revealed that the double-stranded nucleic acid agent consisting of an antisense oligonucleotide and a cholesterol-conjugated DNA complementary strand can be delivered to various sites in the brain and bring about an antisense effect.

Example 8

Evaluation of Antisense Effect Brought about in Various Sites of Brain and Spinal Cord by Administration of Multiple Doses of Double-Stranded Nucleic Acid Complex Consisting of Antisense Oligonucleotide and Cholesterol-Conjugated Complementary Strand An experiment was carried out to evaluate the in vivo inhibition potency brought against RNA expression in the brain by administration of multiple doses of a double-stranded nucleic acid agent consisting of an antisense oligonucleotide targeted at DMPK unlike in Examples 1 and 7 and a cholesterol-conjugated complementary strand.

(Preparation of Nucleic Acid Agent)

The first strand was a 16-mer single-stranded LNA/DNA gapmer (ASO(mDMPK), SEQ ID NO: 13) targeted at DMPK (dystrophia myotonica-protein kinase) mRNA. This LNA/DNA gapmer comprises three LNA nucleosides to the 5' end, three LNA nucleosides to the 3' end, and ten DNA nucleosides therebetween. This LNA/DNA gapmer has a base sequence complementary to positions 2682 to 2697 of the DMPK mRNA (GenBank Accession No. NM_032418, SEQ ID NO: 17) of a mouse. The double-stranded nucleic acid agent was prepared by allowing this LNA/DNA gapmer (the first strand) to be annealed to a cholesterol-conjugated complementary strand RNA (Chol#1-cRNA(mDMPK), SEQ ID NO: 14) (the second strand). The double-stranded nucleic acid agent described above was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice. The prepared double-stranded nucleic acid agent is referred to as Chol#1HDO.

The names and sequences of the first strand and the second strand used in this Example are shown below.

```
First Strand: ASO(mDMPK)
                                    (SEQ ID NO: 13)
5'-A*C*A*a*t*a*a*a*t*a*c*c*g*A*G*G-3'

Second Strand: Chol#1-cRNA(mDMPK)
                                    (SEQ ID NO: 14)
5'-Chol#1-c*c*u*CGGUAUUUAU*u*g*u-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#1 represents the above-mentioned cholesterol #1.

(In Vivo Experiment)

Multiple doses of the nucleic acid agents were administered to the mouse in the same manner as described in Example 4 except that a dose was administered twice a week, a total of four times.

(Analysis of Expression)

Seventy-two hours after the final administration, PBS was perfused into the mice, and then, the mice were dissected to collect the cerebral cortex, cerebellum, striatum, hippocampus, brainstem, lumbar spinal cord, and dorsal root ganglia separately. Using obtained each tissue, RNA extraction, cDNA synthesis, and quantitative RT-PCR were carried out, and the expression level of the DMPK mRNA was evaluated in the same manner as described in Example 1 except that a primer to amplify DMPK mRNA was used instead of malat1 in the quantitative RT-PCR and that actin was used as an internal standard gene instead of GAPDH.

(Results)

Figure 18:
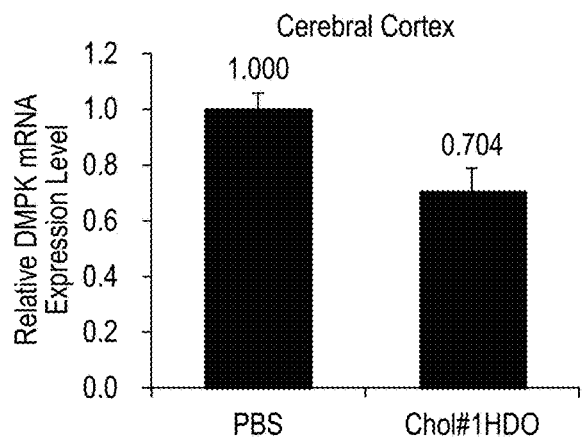
FIG. 18 shows graphs for the results of the experiment described in Example 8, and the graphs show suppression effects on the expression of the target gene (DMPK) by a cholesterol-conjugated nucleic acid complex in various sites in the brain. The results are shown for (a) cerebral cortex, (b) cerebellum, (c) striatum, (d) hippocampus, and (e) brainstem. The error bars represent standard errors.
Figure 18:
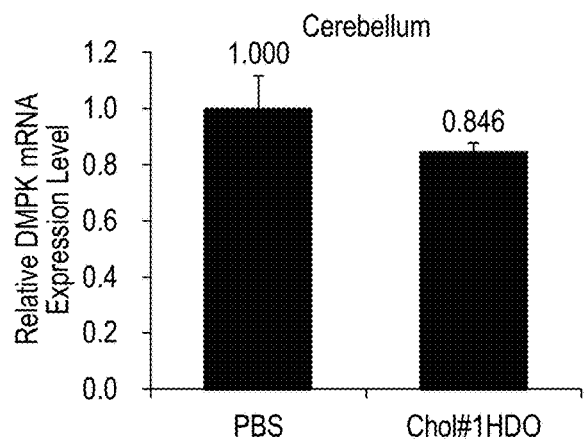
Figure 18:
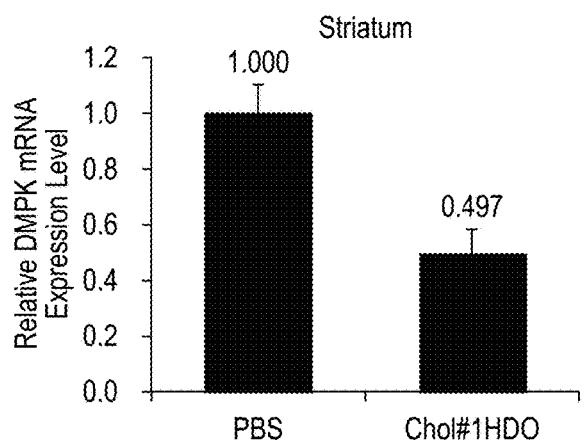
Figure 18:
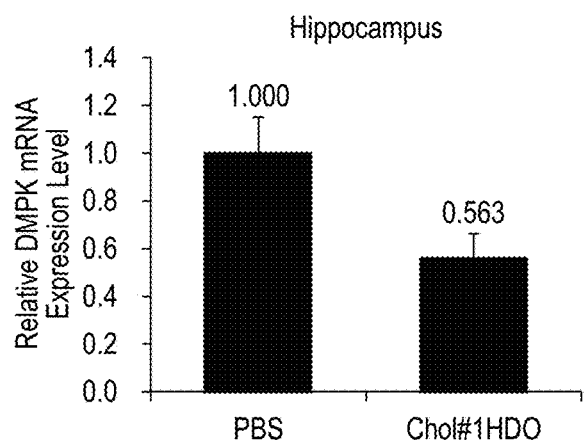
Figure 18:
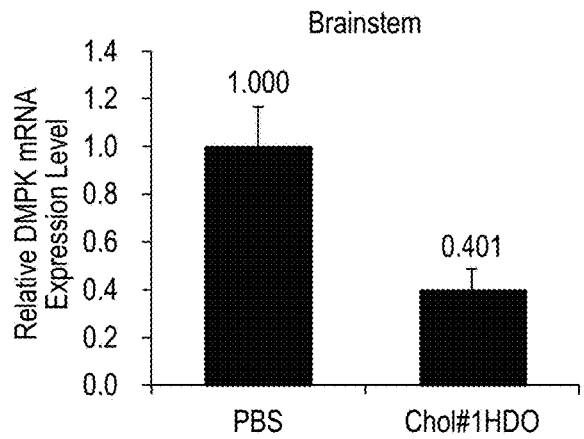
Figure 19:
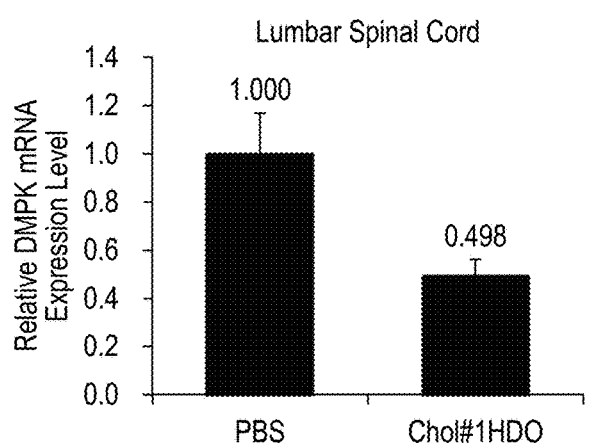
FIG. 19 shows graphs for the results of the experiment described in Example 8, and the graphs show suppression effects on the expression of the target gene (DMPK) of a cholesterol-conjugated nucleic acid complex in various sites in the spinal cord. The results are shown for (a) lumbar spinal cord and (b) dorsal root ganglia. The error bars represent standard errors.
Figure 19:
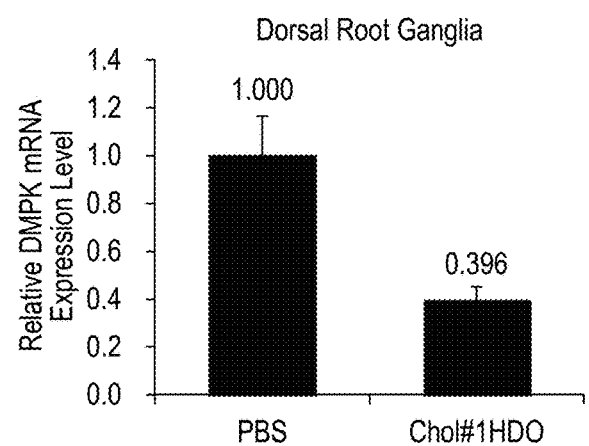

The results of Example 8 are shown by the graphs in FIGS. 18 and 19. Chol#1HDO remarkably suppressed the expression of the DMPK mRNA in any of the cerebral cortex, cerebellum, striatum, hippocampus, brainstem, lumbar spinal cord, and dorsal root ganglia, compared with the negative control (PBS alone).

These results have revealed that the double-stranded nucleic acid complex according to one embodiment of the present invention can be targeted at various gene transcription products.

Example 9

Evaluation of Antisense Effect Brought about in Various Sites of Brain and Spinal Cord by Administration of Single Dose of Double-Stranded Nucleic Acid Complex Consisting of Antisense Oligonucleotide and Tocopherol-Conjugated Complementary Strand to Primate An experiment was carried out to evaluate the in vivo inhibition potency against RNA expression in the brain by administering, to a primate (cynomolgus monkey), a single dose of a double-stranded nucleic acid agent consisting of an antisense oligonucleotide targeted at malat1 and a tocopherol-conjugated complementary strand.

(Preparation of Nucleic Acid Agent)

The first strand was a 16-mer single-stranded LNA/DNA gapmer (ASO(mfMalat1), SEQ ID NO: 15) targeted at a malat1 non-coding RNA of a cynomolgus monkey. The base sequence of this LNA/DNA gapmer was designed by reference to Hung G. et al. (Characterization of Target mRNA Reduction Through In Situ RNA Hybridization in Multiple Organ Systems Following Systemic Antisense Treatment in Animal, Nucleic Acid Therapeutics. 23(6): 369-378 (2013)). This LNA/DNA gapmer comprises three LNA nucleosides to the 5' end, three LNA nucleosides to the 3' end, and ten DNA nucleosides therebetween. The double-stranded nucleic acid agent was prepared by allowing this LNA/DNA gapmer (the first strand) to be annealed to a tocopherol-conjugated complementary strand RNA (Toc#1-cRNA(mf-Malat1), SEQ ID NO: 16) (the second strand). The double-stranded nucleic acid agent was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice. The prepared double-stranded nucleic acid agent is referred to as Toc#1HDO.

The names and sequences of the first strand and the second strand used in this Example are shown below.

```
First Strand: ASO(mfMalat1)
                                (SEQ ID NO: 15)
5'-A*G*T*a*c*t*a*t*a*g*c*a*t*C*T*G-3'

Second Strand: Toc#1-cRNA(mfMalat1)
                                (SEQ ID NO: 16)
5'-Toc#1-c*a*g*AUGCUAUAGU*a*c*u-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Toc#1 represents the above-mentioned α-tocopherol #1.

(In Vivo Experiment)

The cynomolgus monkeys were male, having a body weight of 1.8 kg. The experiments were all carried out with n=1. The nucleic acid agent was intravenously injected at a dose of 50 mg/kg into each cynomolgus monkey through the saphenous veins. In addition, cynomolgus monkeys into which PBS alone or the first strand (ASO) was injected were prepared as a negative control group.

(Analysis of Expression)

Seventy-two hours after administration, PBS was perfused into the cynomolgus monkeys, and then, the cynomolgus monkeys were dissected to collect the cerebral cortex, striatum, brainstem, cervical spinal cord, and thoracic spinal cord separately. Samples were obtained from four locations from each tissue. Using obtained each sample, RNA extraction, cDNA synthesis, and quantitative RT-PCR were carried out, and the expression level of the malat1 non-coding RNA was evaluated in the same manner as described in Example 1 except that a primer to amplify cynomolgus monkey malat1 was used instead of mouse malat1 in the quantitative RT-PCR and that actin was used as an internal standard gene instead of GAPDH.

(Results)

Figure 20:
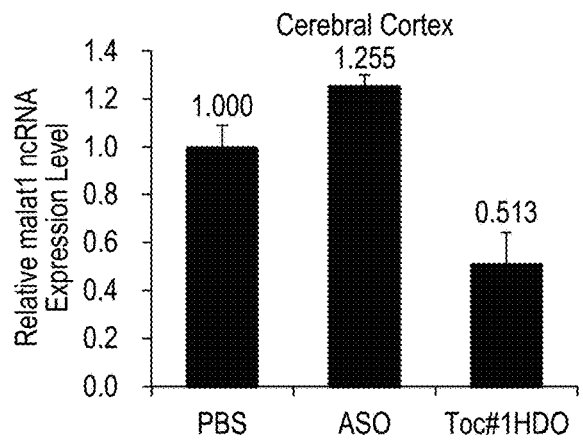
FIG. 20 shows graphs for the results of the experiment described in Example 9, and the graphs show suppression effects on the expression of the target transcription product (malat1) by a tocopherol-conjugated nucleic acid complex in various sites in the brain and spinal cord. The results are shown for (a) cerebral cortex, (b) striatum, (c) brainstem, (d) cervical spinal cord, and (e) thoracic spinal cord. The error bars represent standard errors.
Figure 20:
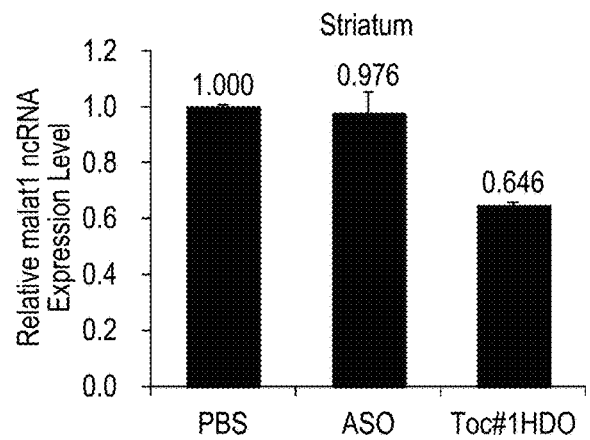
Figure 20:
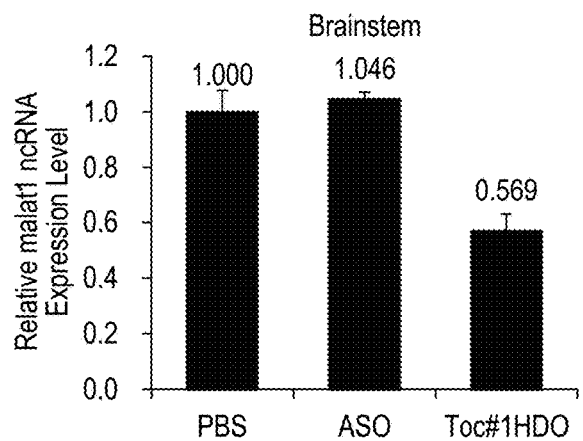
Figure 20:
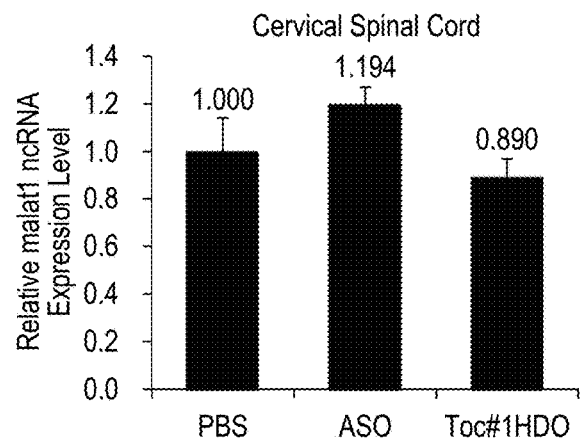
Figure 20:
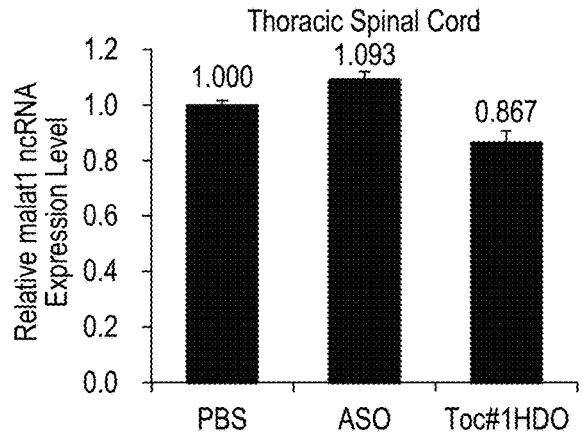

The results of Example 9 are shown by the graph in FIG. 20. Toc#1HDO remarkably suppressed the expression of the malat1 non-coding RNA in any of the cerebral cortex, striatum, brainstem, cervical spinal cord, and thoracic spinal cord, compared with the negative control (PBS alone).

These results have revealed that the double-stranded nucleic acid agent according to one embodiment of the present invention can be delivered to various sites in the brain and spinal cord of primates and bring about an antisense effect.

Example 10

Evaluation of Antisense Effect Brought about in Various Sites of Brain and Spinal Cord by Administration of Single Dose of Double-Stranded Nucleic Acid Complex Consisting of Antisense Oligonucleotide and Cholesterol-Conjugated Complementary Strand An experiment was carried out to evaluate the in vivo inhibition potency against RNA expression in the brain by administration of a single dose of a double-stranded nucleic acid agent consisting of an antisense oligonucleotide targeted at malat1 and a cholesterol-conjugated complementary strand.

(Preparation of Nucleic Acid Agent)

The double-stranded nucleic acid agent was prepared by allowing a 16-mer single-stranded LNA/DNA gapmer targeted at malat1 non-coding RNA (ASO(mMalat1), SEQ ID NO: 1) (a first strand) to be annealed to a cholesterol-conjugated complementary strand RNA (Chol#2-cRNA(mMalat1), SEQ ID NO: 10) (a second strand). Specifically, the double-stranded nucleic acid agent described above was prepared by adding the second strand (powder) to phosphate buffered saline (PBS) heated to 95° C., dissolving the strand by vortexing, mixing the resulting solution with the first strand solution heated to 95° C., maintaining the resulting solution mixture at 95° C. for five minutes, then maintaining the solution mixture at 37° C. for one hour, and thus annealing the nucleic acid strands. The annealed nucleic acid was stored at 4° C. or on ice. The prepared double-stranded nucleic acid agent is referred to as Chol#2HDO.

The names and sequences of the first strand and the second strand used in this Example are shown below.

```
First Strand: ASO(mMalat1)
                                (SEQ ID NO: 1)
5'-C*T*A*g*t*t*c*a*c*t*g*a*a*T*G*C-3

Second Strand: Chol#2-cRNA(mMalat1)
                                (SEQ ID NO: 10)
5'-Chol#2-g*c*a*UUCAGUGAAC*u*a*g-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#2 represents the above-mentioned cholesterol #2.

(In Vivo Experiment)

As described in Example 3, a single dose of the nucleic acid agent was administered to the mouse.

(Analysis of Expression)

Seventy-two hours after administration, PBS was perfused into the mice, and then, the mice were dissected to collect the cerebral cortex, cerebellum, striatum, hippocampus, brainstem, cervical spinal cord, and lumbar spinal cord separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 21:
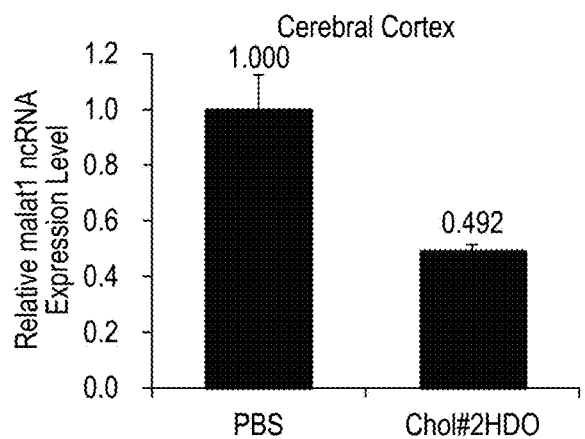
FIG. 21 shows graphs for the results of the experiment described in Example 10, and the graphs show suppression effects on the expression of the target transcription product (malat1) by a cholesterol-conjugated nucleic acid complex in various sites in the brain. The results are shown for (a) cerebral cortex, (b) cerebellum, (c) striatum, (d) hippocampus, and (e) brainstem. The error bars represent standard errors.
Figure 21:
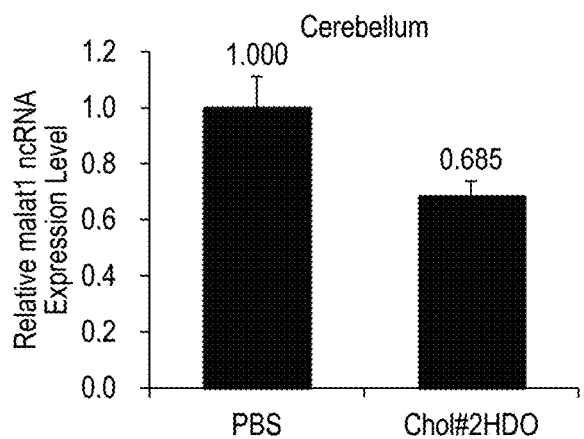
Figure 21:
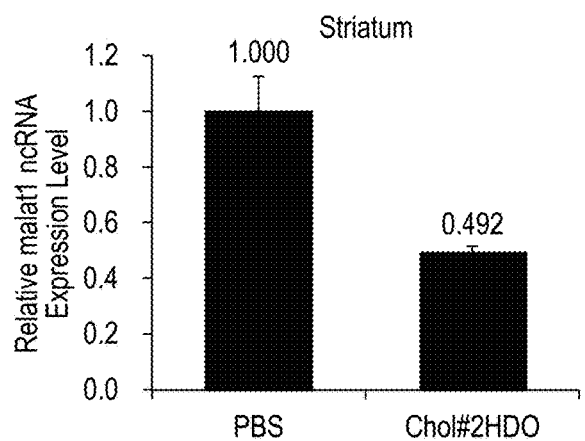
Figure 21:
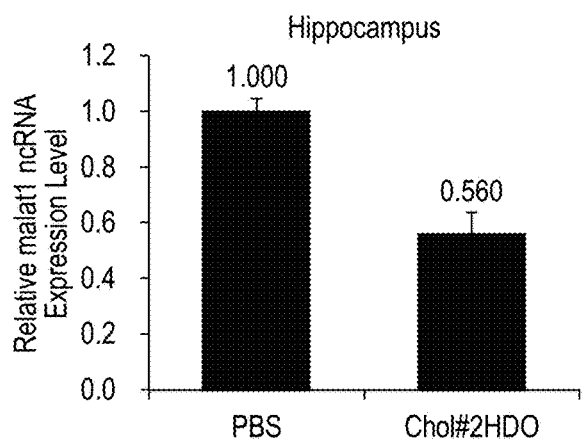
Figure 21:
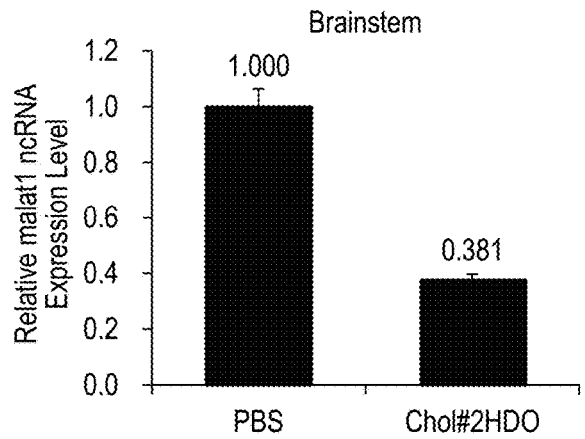
Figure 22:
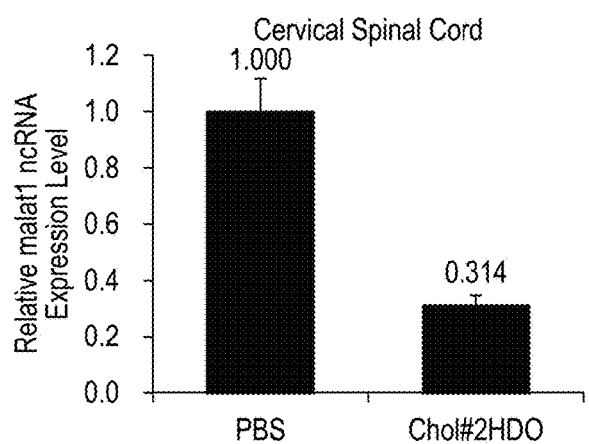
FIG. 22 shows graphs for the results of the experiment described in Example 10, and the graphs show suppression effects on the expression of the target transcription product (malat1) by a cholesterol-conjugated nucleic acid complex in various sites in the spinal cord. The results are shown for (a) cervical spinal cord and (b) lumbar spinal cord. The error bars represent standard errors.
Figure 22:
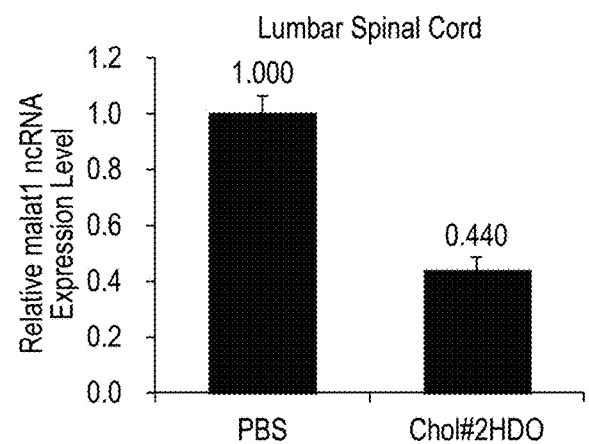

The results of Example 10 are shown by the graphs in FIGS. 21 and 22. Chol#2HDO remarkably suppressed the expression of the malat1 non-coding RNA in any of the cerebral cortex, cerebellum, striatum, hippocampus, brainstem, cervical spinal cord, and lumbar spinal cord, compared with the negative control (PBS alone).

These results have revealed that the double-stranded nucleic acid agent consisting of an antisense oligonucleotide and a cholesterol-conjugated complementary strand can be delivered to various sites in the brain and spinal cord and bring about an antisense effect.

Example 11

Evaluation of Antisense Effect Brought about in Various Sites of Brain by Administration of Single Dose of Double-Stranded Nucleic Acid Complex Consisting of Antisense Oligonucleotide and Cholesterol-Conjugated Complementary Strand An experiment was carried out to evaluate the in vivo inhibition potency against RNA expression in the brain by administration of a single dose of a double-stranded nucleic acid agent consisting of an antisense oligonucleotide targeted at malat1 and a cholesterol-conjugated complementary strand.

(Preparation of Nucleic Acid Agent)

The double-stranded nucleic acid agent was prepared by allowing a 16-mer single-stranded LNA/DNA gapmer targeted at malat1 non-coding RNA (ASO(mMalat1), SEQ ID NO: 1) (a first strand) to be annealed to a cholesterol-conjugated complementary strand RNA (Chol#4-cRNA (mMalat1), SEQ ID NO: 10) (a second strand). Specifically, the double-stranded nucleic acid agent was prepared by adding the second strand (powder) to phosphate buffered saline (PBS) heated to 95° C., dissolving the strand by vortexing, mixing the resulting solution with the first strand solution heated to 95° C., maintaining the resulting solution mixture at 95° C. for five minutes, then maintaining the solution mixture at 37° C. for one hour, and thus annealing the nucleic acid strands. The annealed nucleic acid was stored at 4° C. or on ice. The prepared double-stranded nucleic acid agent is referred to as Chol#4HDO.

The names and sequences of the first strand and the second strand used in this Example are shown below.

```
First Strand: ASO(mMalat1)
                                    (SEQ ID NO: 1)
5'-C*T*A*g*t*t*c*a*c*t*g*a*a*T*G*C-3'

Second Strand: Chol#4-cRNA(mMalat1)
                                   (SEQ ID NO: 10)
5'-Chol#4-g*c*a*UUCAGUGAAC*u*a*g-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#4 represents the above-mentioned cholesterol #4.

(In Vivo Experiment)

As described in Example 3, a single dose of the nucleic acid agent was administered to the mouse.

(Analysis of Expression)

Seventy-two hours after administration, PBS was perfused into the mice, and then, the mice were dissected to collect the cerebral cortex, cerebellum, striatum, hippocampus, and brainstem separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 23:
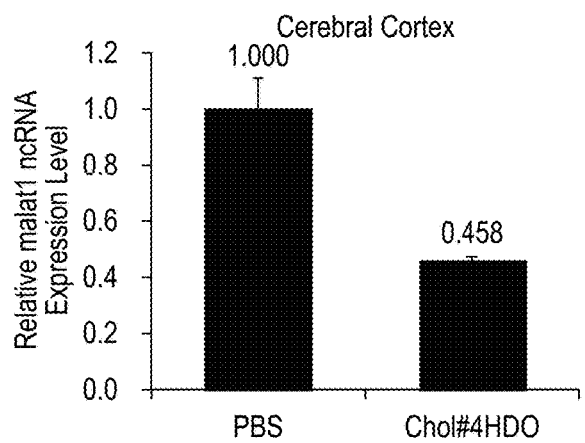
FIG. 23 shows graphs for the results of the experiment described in Example 11, and the graphs show suppression effects on the expression of the target transcription product (malat1) by a cholesterol-conjugated nucleic acid complex in various sites in the brain. The results are shown for (a) cerebral cortex, (b) cerebellum, (c) striatum, and (d) hippocampus. The error bars represent standard errors.
Figure 23:
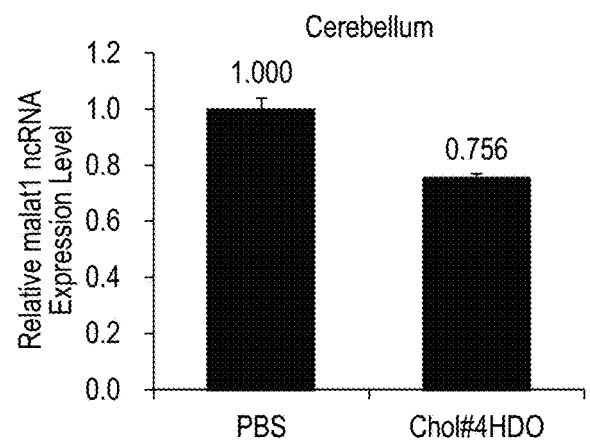
Figure 23:
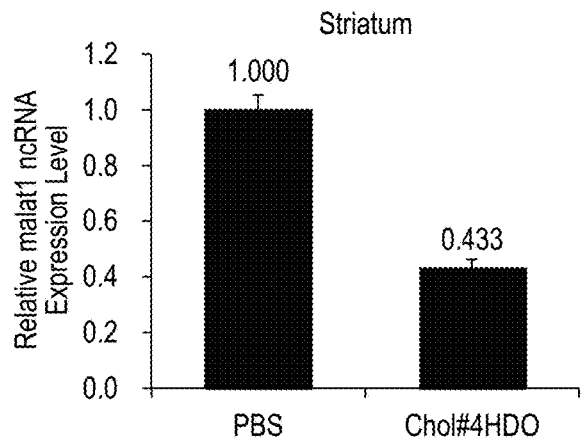
Figure 23:
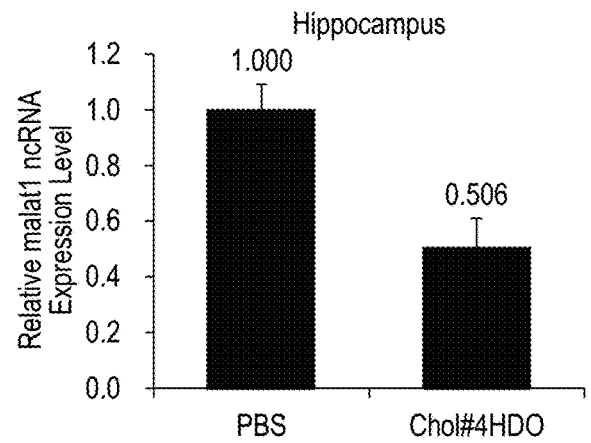
Figure 24:
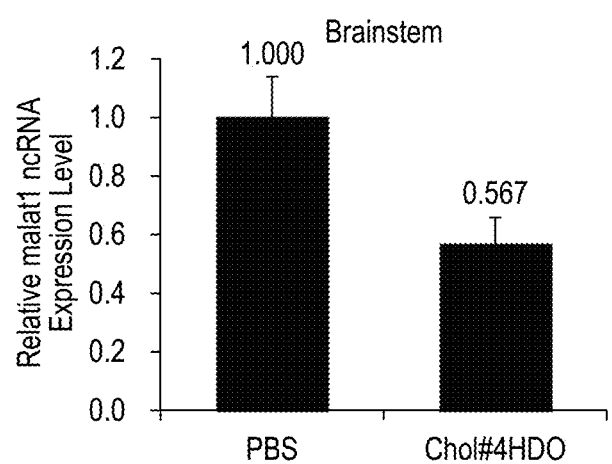
FIG. 24 is a graph showing the results of the experiment described in Example 11, and the graph shows suppression effects of the expression of the target transcription product (malat1) by a cholesterol-conjugated nucleic acid complex in the brainstem. The error bars represent standard errors.

The results of Example 11 are shown by the graphs in FIGS. 23 and 24. Chol#4HDO remarkably suppressed the expression of the malat1 non-coding RNA in any of the cerebral cortex, cerebellum, striatum, hippocampus, and brainstem, compared with the negative control (PBS alone).

These results have revealed that the double-stranded nucleic acid agent consisting of an antisense oligonucleotide and a cholesterol-conjugated complementary strand can be delivered to various sites in the brain and bring about an antisense effect.

Example 12

Evaluation of Antisense Effect Brought about in Various Sites of Brain by Administration of Single Dose of Double-Stranded Nucleic Acid Complex Consisting of Antisense Oligonucleotide and Cholesterol-Conjugated Complementary Strand An experiment was carried out to evaluate the in vivo inhibition potency against RNA expression in the brain by administration of a single dose of a double-stranded nucleic acid agent consisting of an antisense oligonucleotide targeted at malat1 and a cholesterol-conjugated complementary strand.

(Preparation of Nucleic Acid Agent)

The double-stranded nucleic acid agent was prepared by allowing a 16-mer single-stranded LNA/DNA gapmer targeted at malat1 non-coding RNA (ASO(mMalat1), SEQ ID NO: 1) (a first strand) to be annealed to a cholesterol-conjugated complementary strand RNA (Chol#5-cRNA (mMalat1), SEQ ID NO: 10) (a second strand). The double-stranded nucleic acid agent described above was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice. The prepared double-stranded nucleic acid agent is referred to as Chol#5HDO.

The names and sequences of the first strand and the second strand used in this Example are shown below.

```
First Strand: ASO(mMalat1)
                                    (SEQ ID NO: 1)
5'-C*T*A*g*t*t*c*a*c*t*g*a*a*T*G*C-3'

Second Strand: Chol#5-cRNA(mMalat1)
                                   (SEQ ID NO: 10)
5'-g*c*a*UUCAGUGAAC*u*a*g-Chol#5-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#5 represents the above-mentioned cholesterol #5.

(In Vivo Experiment)

As described in Example 3, a single dose of the nucleic acid agent was administered to the mouse.

(Analysis of Expression)

Seventy-two hours after administration, PBS was perfused into the mice, and then, the mice were dissected to collect the cerebral cortex, striatum, hippocampus, and brainstem separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 25:
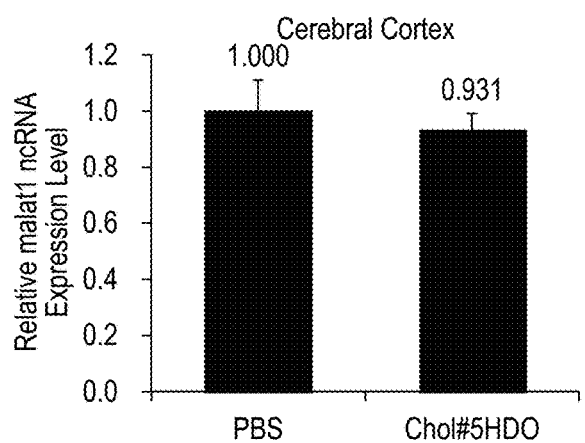
FIG. 25 shows graphs for the results of the experiment described in Example 12, and the graphs show suppression effects on the expression of the target transcription product (malat1) by a cholesterol-conjugated nucleic acid complex in various sites in the brain. The results are shown for (a) cerebral cortex, (b) striatum, (c) hippocampus, and (d) brainstem. The error bars represent standard errors.
Figure 25:
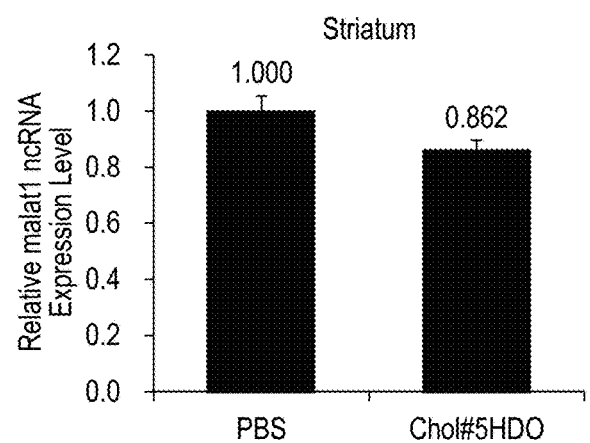
Figure 25:
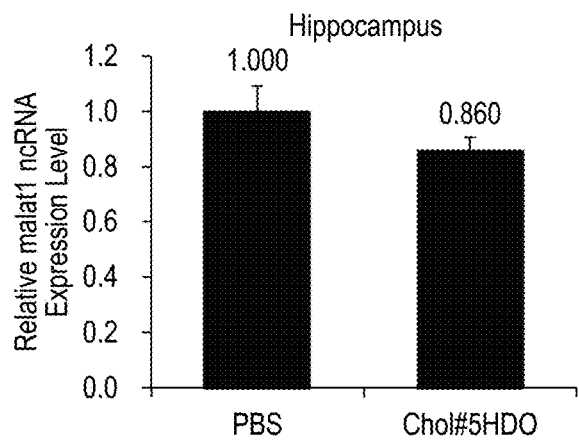
Figure 25:
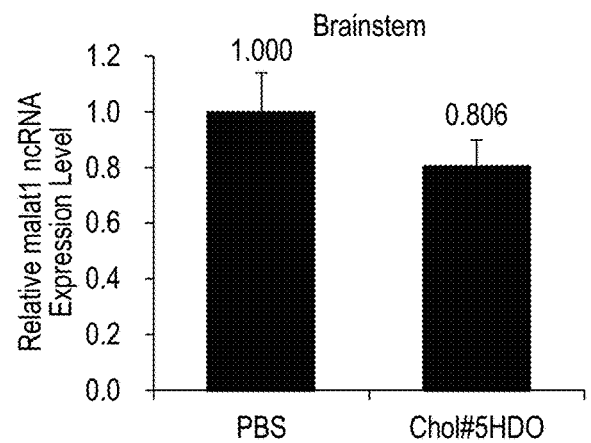

The results of Example 12 are shown by the graph in FIG. 25. Chol#5HDO suppressed the expression of the malat1 non-coding RNA in any of the cerebral cortex, striatum, hippocampus, and brainstem, compared with the negative control (PBS alone).

These results have revealed that the double-stranded nucleic acid agent consisting of an antisense oligonucleotide and a cholesterol-conjugated complementary strand can be delivered to various sites in the brain and bring about an antisense effect.

Example 13

Evaluation of Antisense Effect Brought about in Various Sites of Brain and Spinal Cord by Subcutaneous Administration of Single Dose of Double-Stranded Nucleic Acid Complex Consisting of Antisense Oligonucleotide and Cholesterol-Bound Complementary Strand An experiment was carried out to evaluate the in vivo inhibition potency against RNA expression in the brain by subcutaneous administration of a single dose of a double-stranded nucleic acid agent consisting of an antisense oligonucleotide targeted at malat1 and a cholesterol-conjugated complementary strand.

(Preparation of Nucleic Acid Agent)

The double-stranded nucleic acid agent was prepared by allowing a 16-mer single-stranded LNA/DNA gapmer targeted at malat1 non-coding RNA (ASO(mMalat1), SEQ ID NO: 1) (a first strand) to be annealed to a cholesterol-conjugated complementary strand RNA (Chol#1-cRNA (mMalat1), SEQ ID NO: 10) (a second strand). Specifically, the double-stranded nucleic acid agent described above was prepared by adding the second strand (powder) to phosphate buffered saline (PBS) heated to 95° C., dissolving the strand by vortexing, mixing the resulting solution with the first strand solution heated to 95° C., maintaining the resulting solution mixture at 95° C. for five minutes, then maintaining the solution mixture at 37° C. for one hour, and thus annealing the nucleic acid strands. The annealed nucleic acid was stored at 4° C. or on ice. The prepared double-stranded nucleic acid agent is referred to as Chol#1HDO.

The names and sequences of the first strand and the second strand used in this Example are shown below.

```
First Strand: ASO(mMalat1)
                                    (SEQ ID NO: 1)
5'-C*T*A*g*t*t*c*a*c*t*g*a*a*T*G*C-3'

Second Strand: Chol#1-cRNA(mMalat1)
                                    (SEQ ID NO: 10)
5'-Chol#1-g*c*a*UUCAGUGAAC*u*a*g-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#1 represents the above-mentioned cholesterol #1.

(In Vivo Experiment)

A single dose of the nucleic acid agent was administered to the mouse in the same manner as described in Example 3 except that a dose was administered by subcutaneous injection instead of intravenous injection through the tail veins.

(Analysis of Expression)

Seventy-two hours after administration, PBS was perfused into the mice, and then, the mice were dissected to collect the cerebral cortex, cerebellum, striatum, hippocampus, brainstem, cervical spinal cord, lumbar spinal cord, and dorsal root ganglia separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 26:
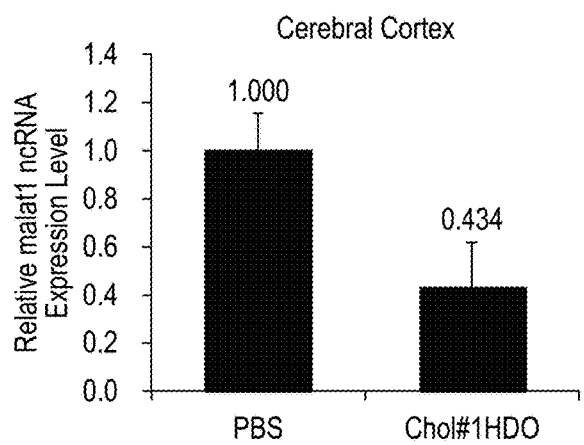
FIG. 26 shows graphs for the results of the experiment described in Example 13, and the graphs show suppression effects on the expression of the target transcription product (malat1) by a cholesterol-conjugated nucleic acid complex in various sites in the brain and spinal cord. The results are shown for (a) cerebral cortex, (b) cerebellum, (c) striatum, (d) hippocampus, (e) brainstem, and (f) cervical spinal cord. The error bars represent standard errors.
Figure 26:
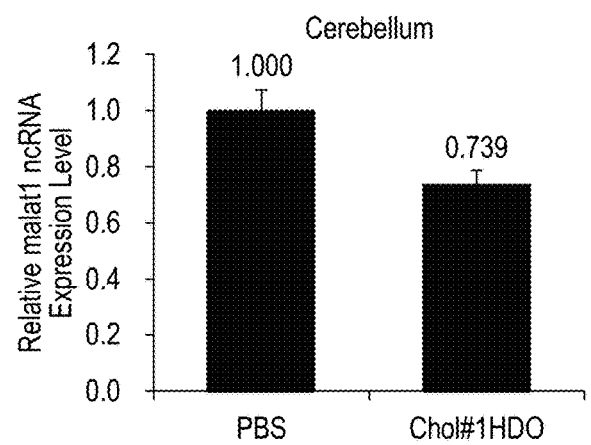
Figure 26:
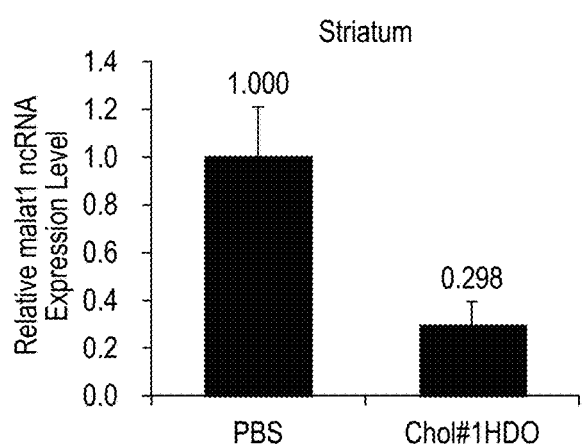
Figure 26:
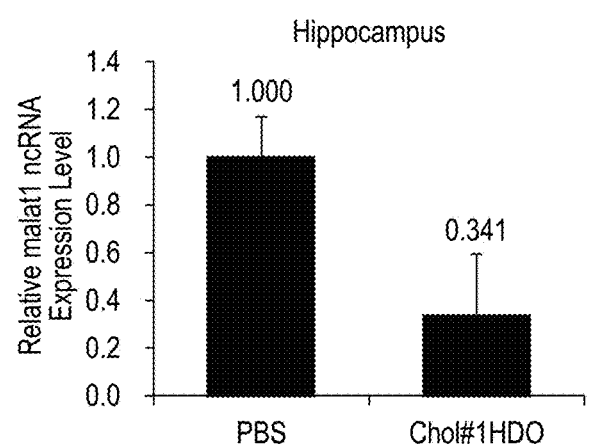
Figure 26:
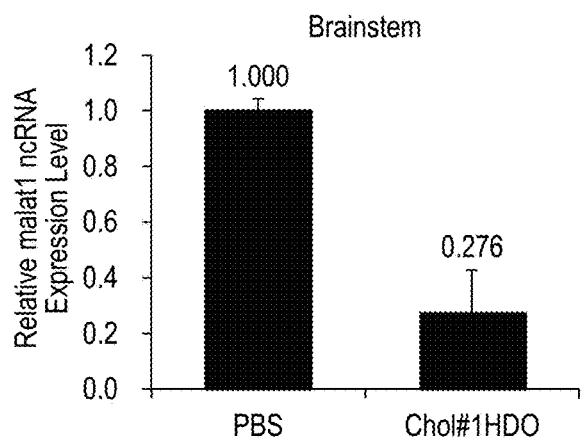
Figure 26:
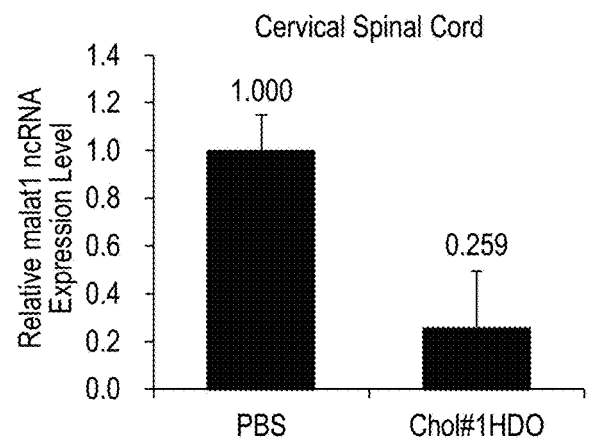
Figure 27:
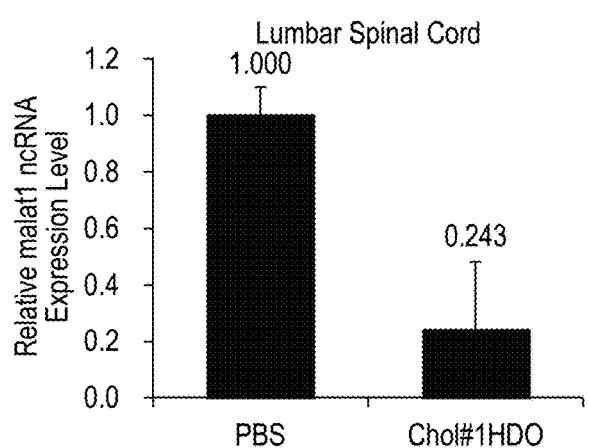
FIG. 27 shows graphs for the results of the experiment described in Example 13, and the graphs show suppression effects on the expression of the target transcription product (malat1) by a cholesterol-conjugated nucleic acid complex in various sites in the spinal cord. The results are shown for (a) lumbar spinal cord and (b) dorsal root ganglia. The error bars represent standard errors.
Figure 27:
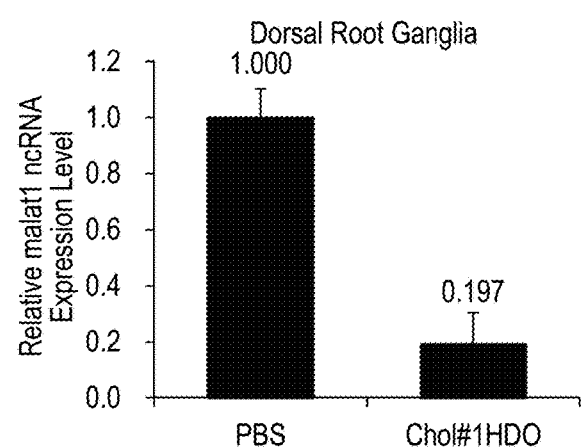

The results of Example 13 are shown by the graphs in FIGS. 26 and 27. Chol#1HDO remarkably suppressed the expression of the malat1 non-coding RNA in any of the cerebral cortex, cerebellum, striatum, hippocampus, brainstem, cervical spinal cord, lumbar spinal cord, and dorsal root ganglia, compared with the negative control (PBS alone).

These results have revealed that the double-stranded nucleic acid agent according to one embodiment of the present invention can be delivered to various sites in the brain and spinal cord by subcutaneous administration and bring about an antisense effect.

Example 14

Evaluation of Long-Term Effect of Double-Stranded Nucleic Acid Complex

An experiment was carried out to evaluate the long-term in vivo inhibition potency of the double-stranded nucleic acid agent.

(Preparation of Nucleic Acid Agent)

The double-stranded nucleic acid agent, Chol#1HDO described in Example 13 was used.

(In Vivo Experiment)

As described in Example 3, a single dose of the nucleic acid agent was administered to the mouse.

(Analysis of Expression)

Three days, seven days, 14 days, 28 days, and 56 days after administration, PBS was perfused into the mice, and then, the mice were dissected to collect the cerebral cortex, cerebellum, striatum, hippocampus, brainstem, cervical spinal cord, and lumbar spinal cord separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 28:
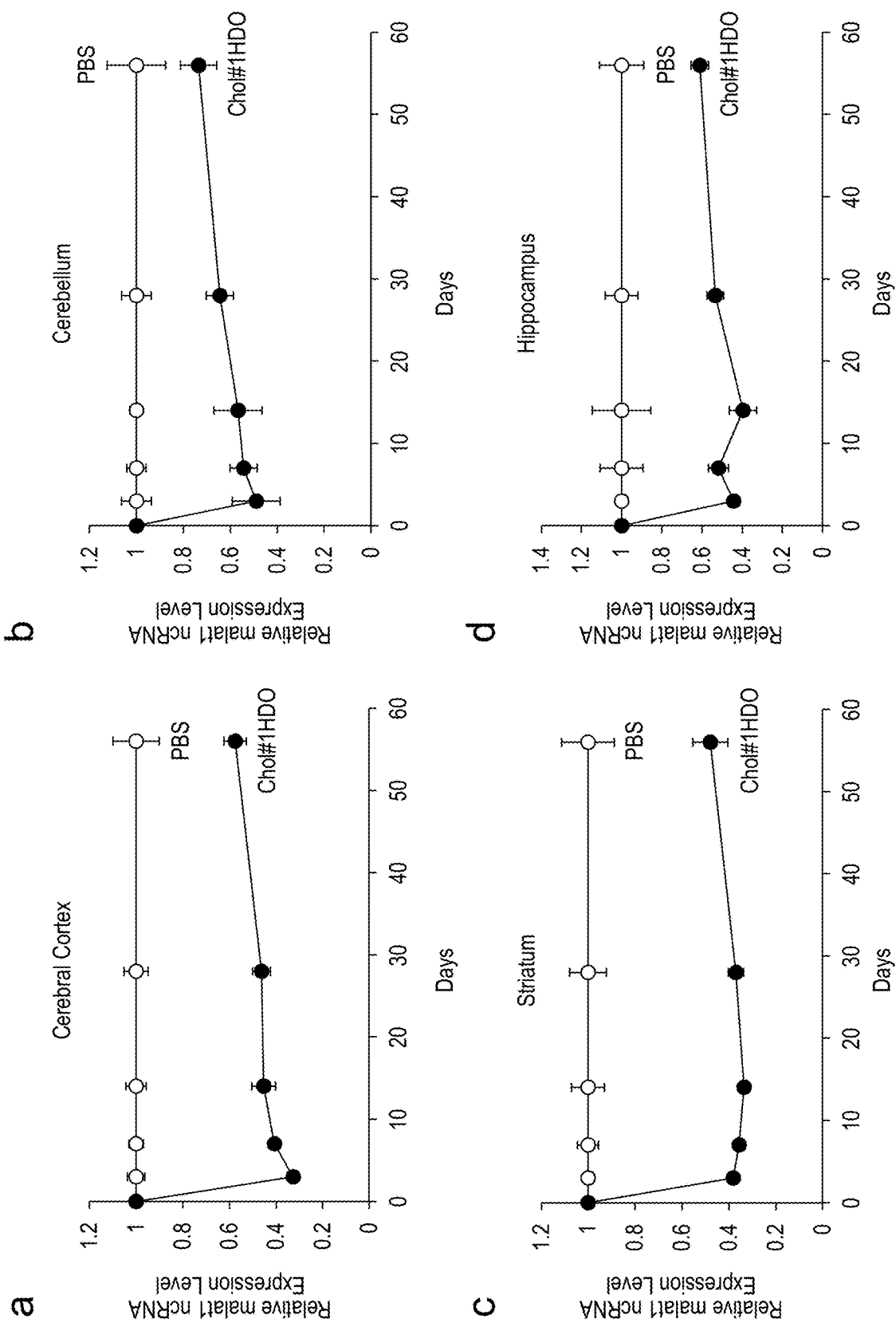
FIG. 28 shows graphs for the results of the experiment described in Example 14, and the graphs show suppression effects on the expression of the target transcription product (malat1) by a cholesterol-conjugated nucleic acid complex in various sites in the brain. The results are shown for (a) cerebral cortex, (b) cerebellum, (c) striatum, and (d) hippocampus. The error bars represent standard errors.
Figure 29:
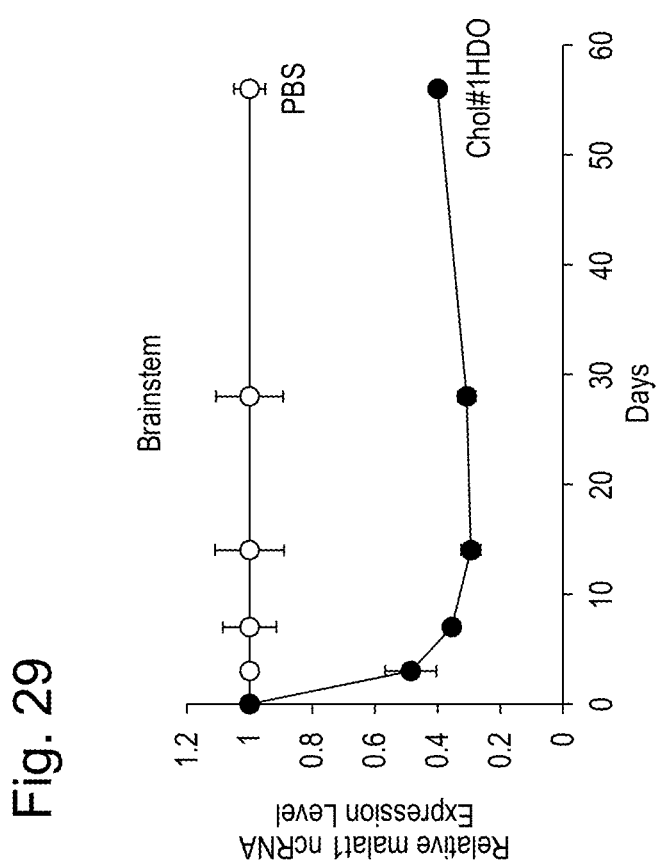
FIG. 29 is a graph showing the results of the experiment described in Example 14, and the graph shows suppression effects on the expression of the target transcription product (malat1) by a cholesterol-conjugated nucleic acid complex in the brainstem. The error bars represent standard errors.
Figure 30:
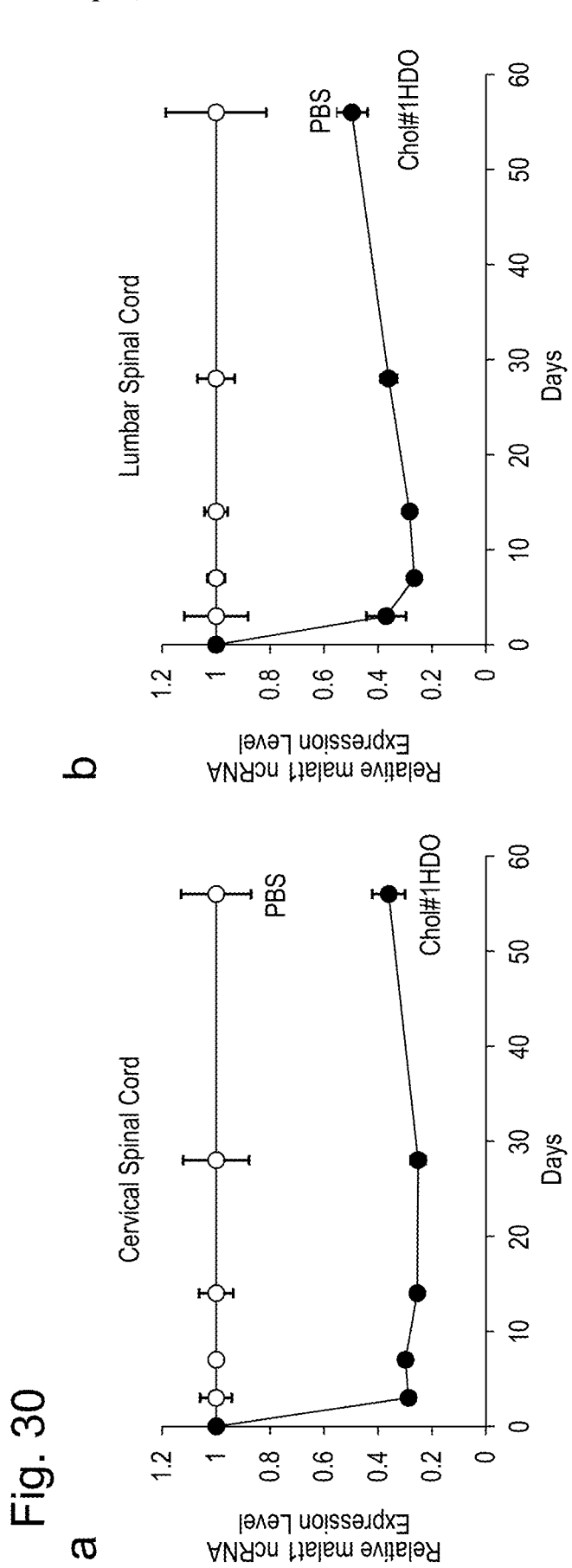
FIG. 30 shows graphs for the results of the experiment described in Example 14, and the graphs show suppression effects on the expression of the target transcription product (malat1) by a cholesterol-conjugated nucleic acid complex in various sites in the spinal cord. The results are shown for (a) cervical spinal cord and (b) lumbar spinal cord. The error bars represent standard errors.

The results of Example 14 are shown by the graphs in FIGS. 28 to 30. Chol#1HDO remarkably suppressed the expression of the malat1 non-coding RNA in any of the cerebral cortex, cerebellum, striatum, hippocampus, brainstem, cervical spinal cord, and lumbar spinal cord for a long period of time, compared with the negative control (PBS alone).

Example 15

Study of Dose of Double-Stranded Nucleic Acid Complex

An experiment was carried out to evaluate the in vivo inhibition potency of the double-stranded nucleic acid agent in different doses.

(Preparation of Nucleic Acid Agent)

The double-stranded nucleic acid agent, Chol#1HDO described in Example 13 was used.

(In Vivo Experiment)

A single dose of the nucleic acid agent was administered to the mouse in the same manner as described in Example 3 except that a dose of 12.5 mg/kg, 25.0 mg/kg, 50 mg/kg, or 75 mg/kg was used.

(Analysis of Expression)

Seventy-two hours after administration, PBS was perfused into the mice, and then, the mice were dissected to collect the cerebral cortex, cerebellum, striatum, hippocampus, brainstem, cervical spinal cord, and lumbar spinal cord separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 31:
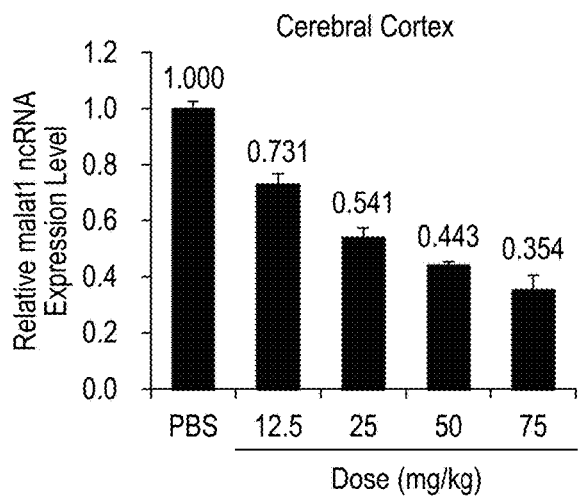
FIG. 31 shows graphs for the results of the experiment described in Example 15, and the graphs show suppression effects on the expression of the target transcription product (malat1) by a cholesterol-conjugated nucleic acid complex in various sites in the brain. The results are shown for (a) cerebral cortex, (b) cerebellum, (c) striatum, (d) hippocampus, and (e) brainstem. The error bars represent standard errors.
Figure 31:
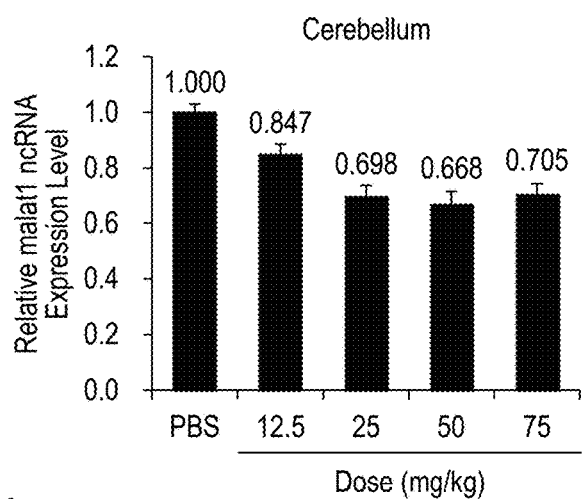
Figure 31:
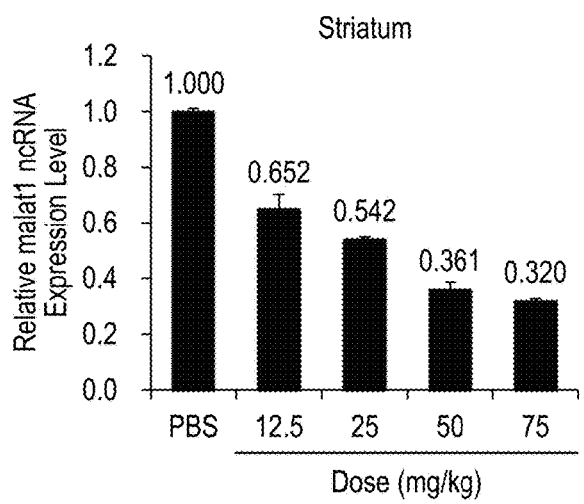
Figure 31:
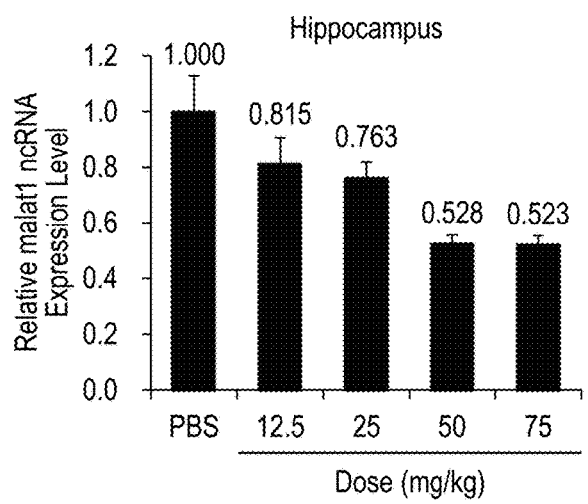
Figure 31:
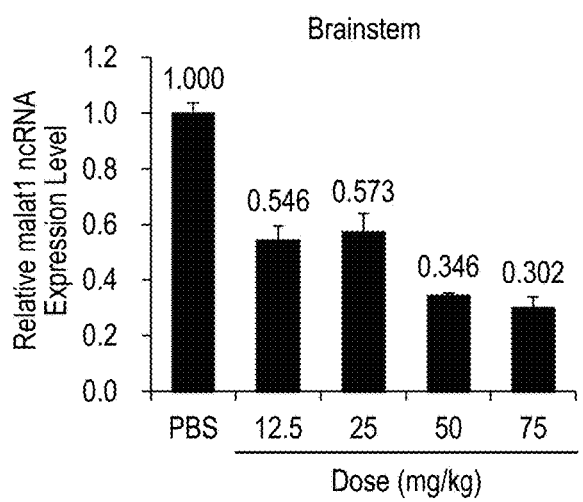
Figure 32:
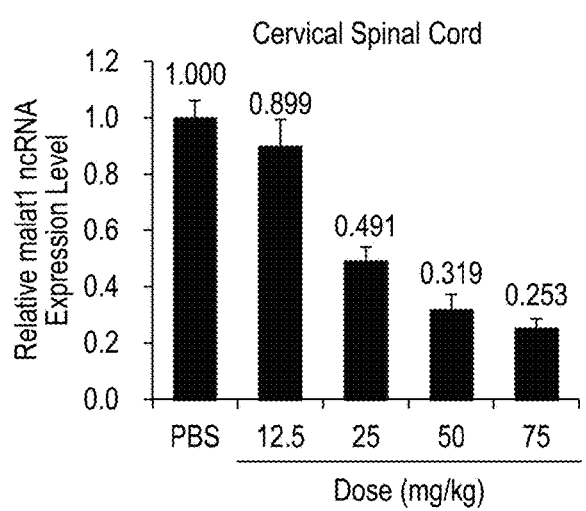
FIG. 32 shows graphs for the results of the experiment described in Example 15, and the graphs show suppression effects on the target transcription product (malat1) by a cholesterol-conjugated nucleic acid complex in various sites in the spinal cord. The results are shown for (a) cervical spinal cord and (b) lumbar spinal cord. The error bars represent standard errors.
Figure 32:
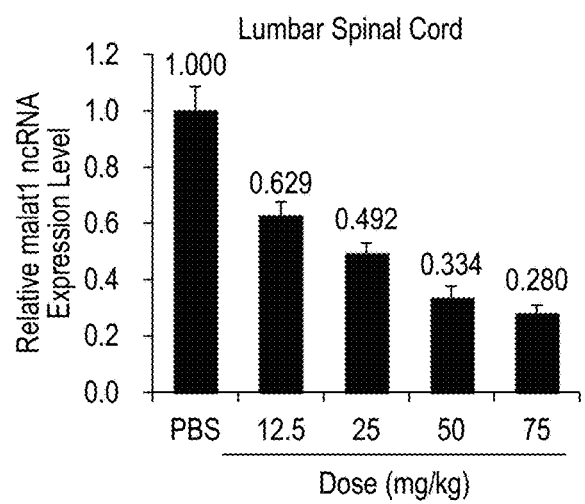

The results of Example 15 are shown by the graphs in FIGS. 31 and 32. Chol#1HDO exhibited a tendency to suppress the expression of the malat1 non-coding RNA dose-dependently in any of the cerebral cortex, cerebellum, striatum, hippocampus, brainstem, cervical spinal cord, and lumbar spinal cord.

Example 16

Evaluation of Antisense Effect Brought about in Various Sites of Brain by Administration of Multiple Doses of Double-Stranded Nucleic Acid Complex Consisting of Antisense Oligonucleotide and Tocopherol-Conjugated Complementary Strand An experiment was carried out to evaluate the in vivo inhibition potency against RNA expression in the brain by administration of multiple doses of a double-stranded nucleic acid agent consisting of an antisense oligonucleotide targeted at DMPK and a complementary strand conjugated to a tocopherol at the 5' end.

(Preparation of Nucleic Acid Agent)

The first strand was a 16-mer single-stranded LNA/DNA gapmer (ASO(mDMPK), SEQ ID NO: 13) targeted at DMPK (dystrophia myotonica-protein kinase) mRNA. This LNA/DNA gapmer comprises three LNA nucleosides to the 5' end, three LNA nucleosides to the 3' end, and ten DNA nucleosides therebetween. This LNA/DNA gapmer has a base sequence complementary to positions 2682 to 2697 of the DMPK mRNA (GenBank Accession No. NM_032418, SEQ ID NO: 17) of a mouse. The double-stranded nucleic acid agent was prepared by allowing this LNA/DNA gapmer (the first strand) to be annealed to a tocopherol-conjugated complementary strand RNA (Toc#1-cRNA(mDMPK), SEQ ID NO: 14) (the second strand). The double-stranded nucleic acid agent was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice. The prepared double-stranded nucleic acid agent is referred to as Toc#1HDO.

The names and sequences of the first strand and the second strand used in this Example are shown below.

```
First Strand: ASO(mDMPK)
                                       (SEQ ID NO: 13)
5'-A*C*A*a*t*a*a*a*t*a*c*c*g*A*G*G-3'

Second Strand: Toc#1-cRNA(mDMPK)
                                       (SEQ ID NO: 14)
5'-Toc#1-c*c*u*CGGUAUUUAU*u*g*u-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Toc#1 represents the above-mentioned tocopherol #1.

(In Vivo Experiment)

The nucleic acid agent was intravenously administered to the mouse once a week, a total of four times. In addition, a mouse into which PBS alone (instead of a nucleic acid agent) or the first strand (ASO) was injected was prepared as a negative control group.

(Analysis of Expression)

Seventy-two hours after the final administration, PBS was perfused into the mice, and then, the mice were dissected to collect the whole brain. Using obtained each tissue, RNA extraction, cDNA synthesis, and quantitative RT-PCR were carried out, and the expression level of the DMPK mRNA was evaluated in the same manner as described in Example 1 except that a primer to amplify DMPK mRNA was used instead of malat1 in the quantitative RT-PCR and that actin was used as an internal standard gene instead of GAPDH.

(Results)

Figure 33:
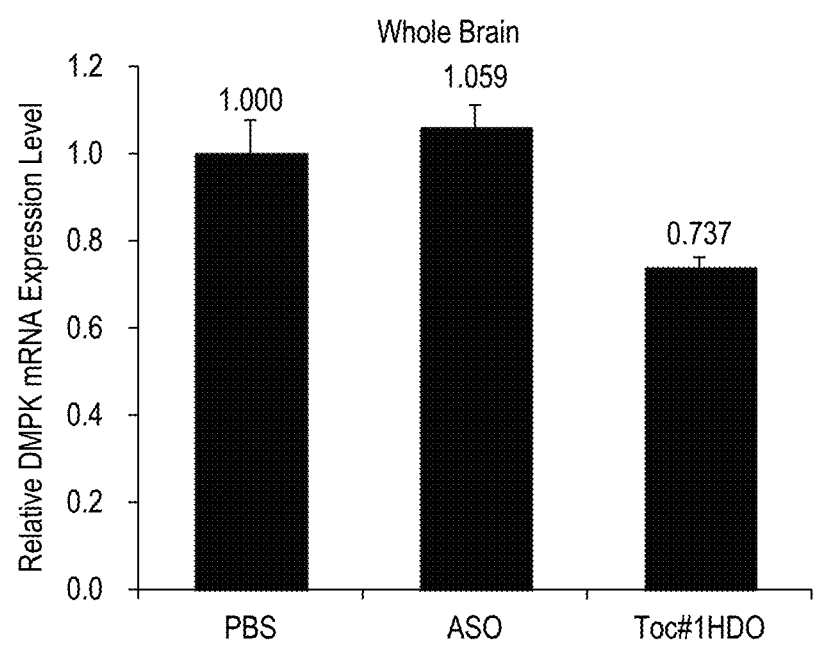
FIG. 33 is a graph showing the results of the experiment described in Example 16, and the graph shows suppression effects on the target gene (DMPK) by a tocopherol-conjugated nucleic acid complex in the whole brain. The error bars represent standard errors.

The results of Example 16 are shown by the graph in FIG. 33. Toc#1HDO remarkably suppressed the expression of the DMPK mRNA in the whole brain, compared with the negative control (PBS alone or ASO alone).

These results have revealed that the double-stranded nucleic acid complex according to one embodiment of the present invention can be targeted at various gene transcription products.

Example 17

Evaluation of Gene Repression Effect Brought about in Various Sites of Brain and Spinal Cord by Administration of Tocopherol-Conjugated siRNA An experiment was carried out to evaluate the in vivo inhibition potency against RNA expression in the brain by administration of a single dose of a double-stranded (siRNA) nucleic acid agent consisting of an antisense strand conjugated to a tocopherol at the 5' end targeted at BACE1 (Beta-secretase 1) and a complementary strand.

(Preparation of Nucleic Acid Agent)

The antisense strand was a single-stranded oligonucleotide (Toc#1-AS(mBACE1), SEQ ID NO: 19) consisting of a 29-mer RNA targeted at BACE1 (Beta-secretase 1) mRNA and 2'-O-Me RNA. This antisense strand has a base sequence complementary to positions 2522 to 2550 of the BACE1 mRNA (GenBank Accession No. NM_011792.6, SEQ ID NO: 23) of a mouse. This antisense strand has a tocopherol conjugated to the 5' end. The double-stranded nucleic acid agent was prepared by allowing this antisense strand (the first strand) to be annealed to a 27-mer sense strand oligonucleotide (the second strand) consisting of RNA and 2'-O-Me RNA. The double-stranded nucleic acid agent described above was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice. The prepared double-stranded nucleic acid agent is referred to as Toc#1siRNA.

The names and sequences of the first strand and the second strand used in this Example are shown below.

```
First Strand: Toc#1-AS(mBACE1)
                                      (SEQ ID NO: 19)
5'-Toc#1-guauaaACAUuCGCAuCGCAUAgGUuC*U*U-3'

Second Strand: SS(mBACE1) 27-mer
                                      (SEQ ID NO: 20)
5'-GAAcCuAuGCGAuGCGAAuGUUUAU*A*C-3'
```

The upper case letters represent RNA, the underlined lower case letters represent 2'-O-methylated RNA, and the asterisks represent a phosphorothioate bond. Toc#1 represents the above-mentioned tocopherol #1.

(In Vivo Experiment)

The mice were 6- to 7-week old male C57BL/6 mice having a body weight of 20 g. The experiments involving use of mice were all carried out with n=4. The nucleic acid agent was intravenously injected into a mouse through the tail veins such that the antisense strand was administered at a dose of 92 mg/kg (equimolar to the amount of the antisense strand used in administering 50 mg/kg of the heteroduplex oligonucleotide in Example 1) (a single dose administration). In addition, a mouse into which PBS alone (instead of a nucleic acid agent) was injected was prepared as a negative control group.

(Analysis of Expression)

Seventy-two hours after the final administration, PBS was perfused into the mice, and then, the mice were dissected to collect the cerebral cortex, cerebellum, striatum, hippocampus, brainstem, lumbar spinal cord, and dorsal root ganglia separately. Using obtained each tissue, RNA extraction, cDNA synthesis, and quantitative RT-PCR were carried out, and the expression level of the BACE1 mRNA was evaluated in the same manner as described in Example 1 except that a primer to amplify BACE1 mRNA was used instead of malat1 in the quantitative RT-PCR and that actin was used as an internal standard gene instead of GAPDH.

(Results)

Figure 34:
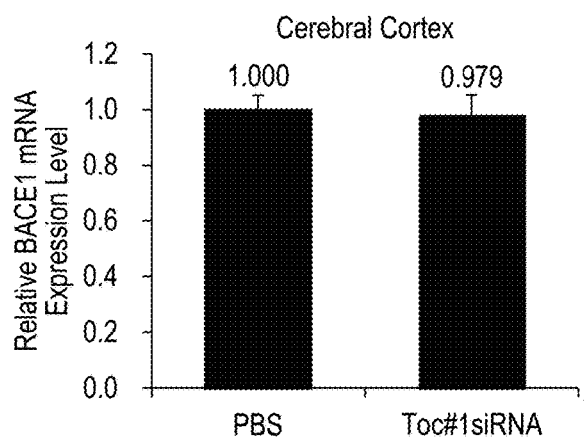
FIG. 34 shows graphs for the results of the experiment described in Example 17, and the graphs show suppression effects on the target gene (BACE1) by a tocopherol-conjugated siRNA in various sites in the brain. The results are shown for (a) cerebral cortex, (b) cerebellum, (c) striatum, and (d) hippocampus. The error bars represent standard errors.
Figure 34:
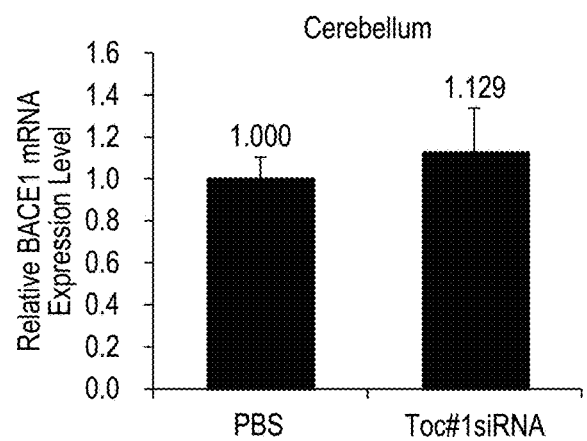
Figure 34:
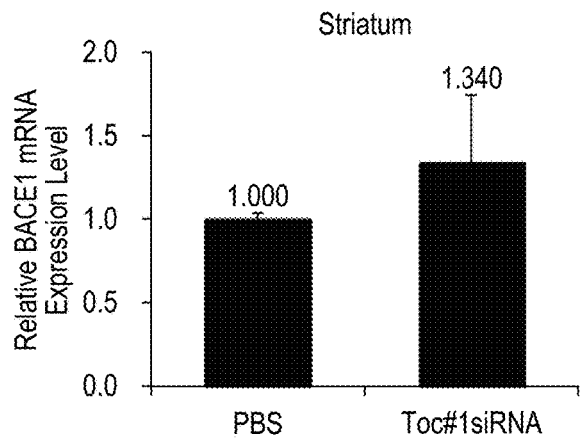
Figure 34:
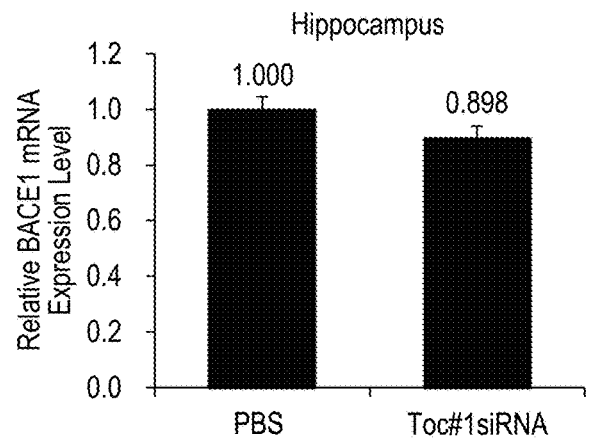
Figure 35:
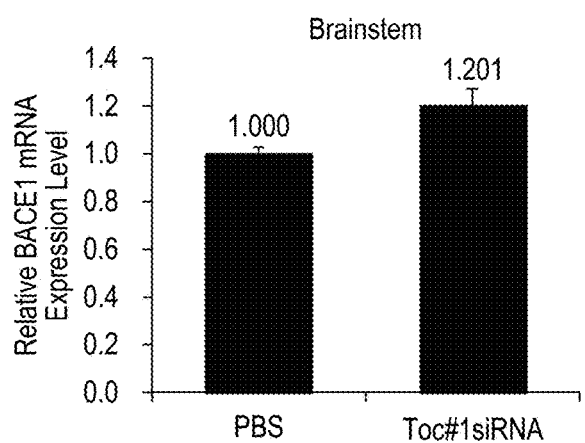
FIG. 35 shows graphs for the results of the experiment described in Example 17, and the graphs show suppression effects on the target gene (BACE1) by a tocopherol-conjugated siRNA in various sites in the brain and spinal cord. The results are shown for (a) brainstem, (b) lumbar spinal cord, and (c) dorsal root ganglia. The error bars represent standard errors.
Figure 35:
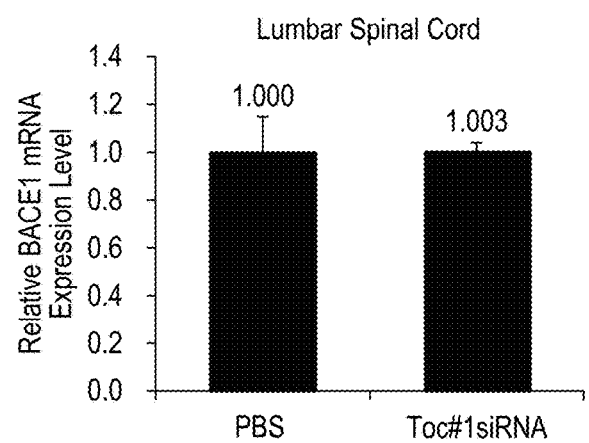
Figure 35:
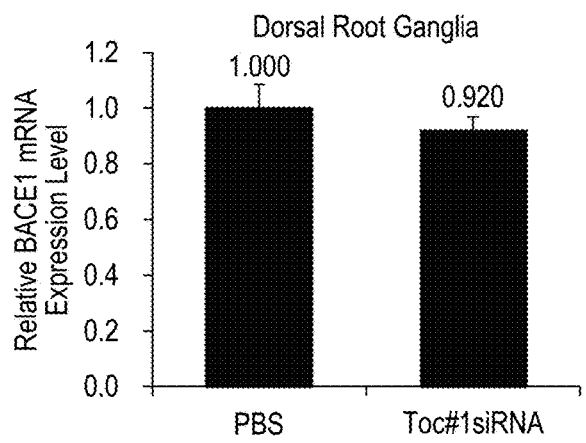

The results of Example 17 are shown by the graphs in FIGS. 34 and 35. Toc#1siRNA did not exhibit any BACE1 expression suppression effect, compared with the negative control (PBS alone).

These results have revealed that the peripheral administration of the siRNA having a lipid ligand conjugated to the antisense strand (the first strand) does not show gene repression effects in the brain.

Example 18

Evaluation of Gene Repression Effect Brought about in Various Sites of Brain by Administration of Cholesterol-Conjugated siRNA An experiment was carried out to evaluate the in vivo inhibition potency against RNA expression in the brain by administration of a single dose of a double-stranded (siRNA) nucleic acid agent consisting of an antisense strand having cholesterol conjugated to the 5' end and targeted at BACE1 (Beta-secretase 1) and a sense strand.

(Preparation of Nucleic Acid Agent)

The antisense strand was a single-stranded oligonucleotide (Chol#1-AS(mBACE1), SEQ ID NO: 21) consisting of a 23-mer RNA targeted at BACE1 (Beta-secretase 1) mRNA and 2'-O-Me RNA. This antisense strand has a base sequence complementary to positions 2522 to 2544 of the BACE1 mRNA (GenBank Accession No. NM_011792.6, SEQ ID NO: 23) of a mouse. This antisense strand has cholesterol conjugated to the 5' end. The double-stranded nucleic acid agent was prepared by allowing this antisense strand (the first strand) to be annealed to a 21-mer sense strand oligonucleotide (the second strand) consisting of RNA and 2'-O-Me RNA. The double-stranded nucleic acid agent described above was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice. The prepared double-stranded nucleic acid agent is referred to as Chol#1siRNA.

The names and sequences of the first strand and the second strand used in this Example are shown below.

```
First Strand: Chol#1-AS(mBACE1)
                                      (SEQ ID NO: 21)
5'-Chol#1-a*cAUuCGCAuCGCAUAgGUuC*U*U-3'

Second Strand: SS(mBACE1) 21mer
                                      (SEQ ID NO: 22)
5'-GAAcCuAuGCGAuGCGAAuG*U-3'
```

The upper case letters represent RNA, the underlined lower case letters represent 2'-O-methylated RNA, and the asterisks represent a phosphorothioate bond. Chol#1 represents the above-mentioned cholesterol #1.

(In Vivo Experiment)

The mice were 6- to 7-week old male C57BL/6 mice having a body weight of 20 g. The experiments involving use of mice were all carried out with n=4. The nucleic acid agent was intravenously injected into a mouse through the tail veins such that the antisense strand was administered at a dose of 73 mg/kg (equimolar to the amount of the antisense strand used in administering 50 mg/kg of the heteroduplex oligonucleotide in Example 1) (a single dose administration). In addition, a mouse into which PBS alone (instead of a nucleic acid agent) was injected was prepared as a negative control group.

(Analysis of Expression)

Seventy-two hours after the final administration, PBS was perfused into the mice, and then, the mice were dissected to isolate the brain. The cerebral cortex, cerebellum, striatum, hippocampus, and brainstem were separately collected from the brain. Using obtained each tissue, RNA extraction, cDNA synthesis, and quantitative RT-PCR were carried out, and the expression level of the BACE1 mRNA was evaluated in the same manner as described in Example 1 except that a primer to amplify BACE1 mRNA was used instead of malat1 in the quantitative RT-PCR and that actin was used as an internal standard gene instead of GAPDH.

(Results)

Figure 36:
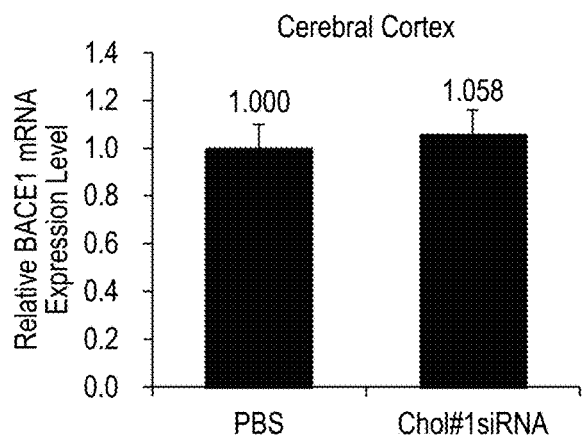
FIG. 36 shows graphs for the results of the experiment described in Example 18, and the graphs show suppression effects on the target gene (BACE1) by a cholesterol-conjugated siRNA in various sites in the brain. The results are shown for (a) cerebral cortex, (b) cerebellum, (c) striatum, (d) hippocampus, and (e) brainstem. The error bars represent standard errors.
Figure 36:
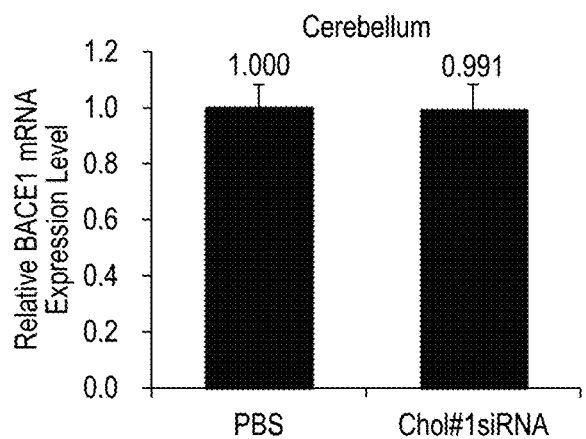
Figure 36:
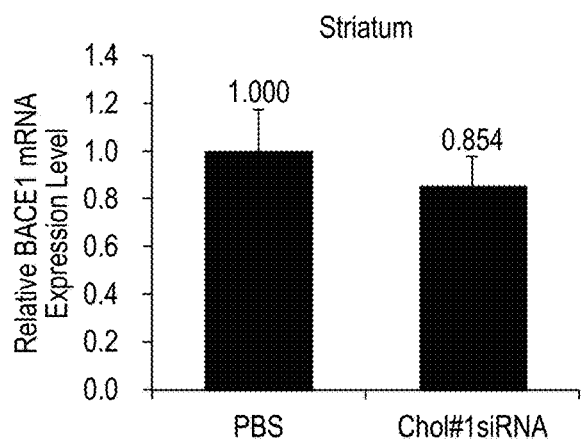
Figure 36:
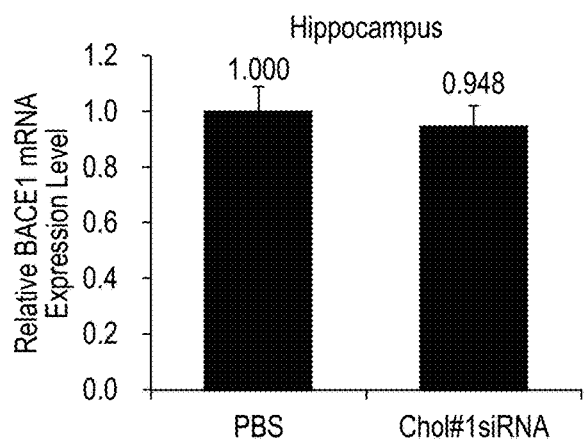
Figure 36:
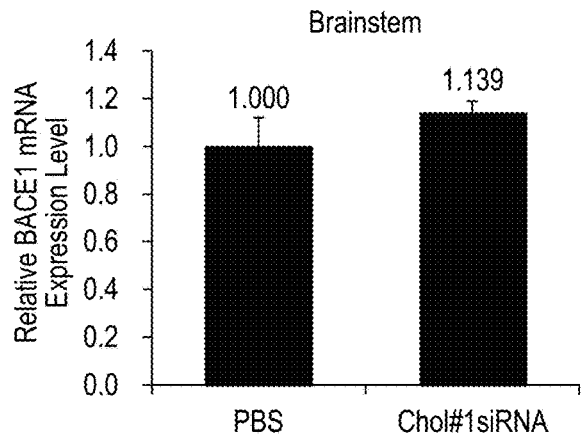

The results of Example 18 are shown by the graph in FIG. 36. Chol#1siRNA did not exhibit any BACE1 expression suppression effect, compared with the negative control (PBS alone).

These results have revealed that the peripheral administration of the siRNA having a lipid ligand conjugated to the antisense strand (the first strand) does not show gene repression effects in the brain.

Example 19

Evaluation of Antisense Effect Brought about in Various Sites of Brain by Administration of Single Dose of Double-Stranded Nucleic Acid Complex Consisting of Antisense Oligonucleotide and Docosahexaenoic Acid (DHA)-Conjugated Complementary Strand An experiment was carried out to evaluate the in vivo inhibition potency against RNA expression in the brain by administration of a single dose of a double-stranded nucleic acid agent consisting of an antisense oligonucleotide targeted at malat1 and a complementary strand conjugated to DHA at the 5' end, unlike in Example 4.

(Preparation of Nucleic Acid Agent)

The double-stranded nucleic acid agent was prepared by allowing a 16-mer single-stranded LNA/DNA gapmer targeted at malat1 non-coding RNA (ASO(mMalat1), SEQ ID NO: 1) (a first strand) to be annealed to a DHA-conjugated complementary strand RNA having DHA conjugated to the 5' end (DHA-cRNA(mMalat1), SEQ ID NO: 10) (a second strand). The double-stranded nucleic acid agent described above was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice. The prepared double-stranded nucleic acid agent is referred to as DHA-HDO.

The names and sequences of the first strand and the second strand used in this Example are shown below.

```
First Strand: ASO(mMalat1)
                                    (SEQ ID NO: 1)
5'-C*T*A*g*t*t*c*a*c*t*g*a*a*T*G*C-3'

Second Strand: DHA-cRNA(mMalat1)
                                    (SEQ ID NO: 10)
5'-DHA-g*c*a*UUCAGUGAAC*u*a*g-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond.

(In Vivo Experiment)

The mice were 6- to 7-week old male C57BL/6 mice having a body weight of 20 g. The experiments involving use of mice were all carried out with n=4. The nucleic acid agent was intravenously injected at a dose of 50 mg/kg (single dose administration) into a mouse through the tail veins. In addition, a mouse into which PBS alone (instead of a nucleic acid agent) was injected was prepared as a negative control group.

(Analysis of Expression)

Seventy-two hours after the final administration, PBS was perfused into the mice, and then, the mice were dissected to collect the cerebral cortex, cerebellum, striatum, hippocampus, and brainstem separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 37:
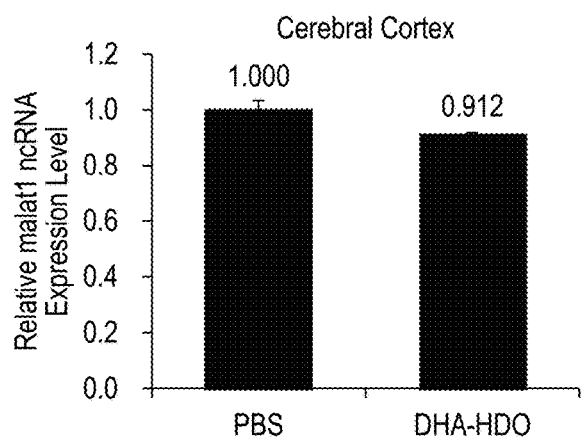
FIG. 37 shows graphs for the results of the experiment described in Example 19, and the graphs show suppression effects on the target transcription product (malat1) by a docosahexaenoic acid (DHA)-conjugated nucleic acid complex in various sites in the brain. The results are shown for (a) cerebral cortex, (b) cerebellum, (c) striatum, and (d) hippocampus. The error bars represent standard errors.
Figure 37:
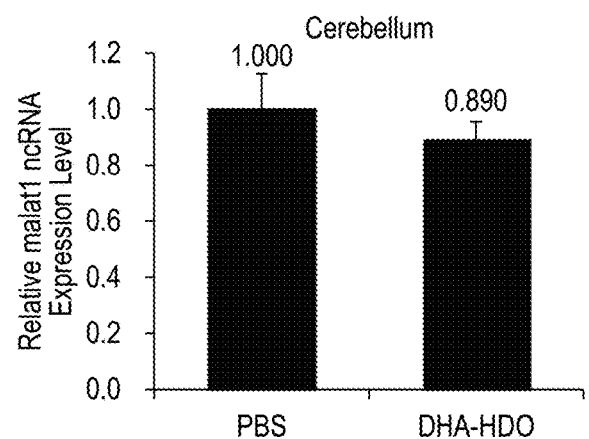
Figure 37:
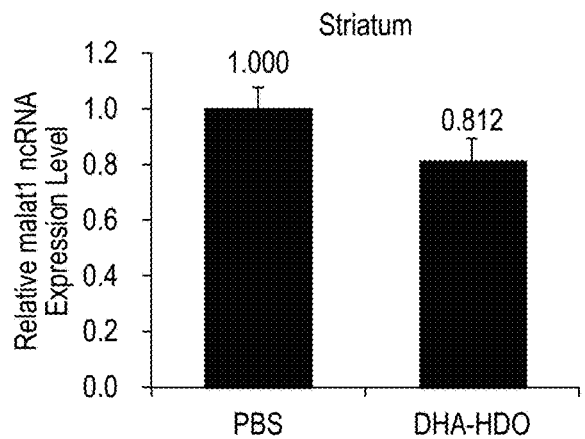
Figure 37:
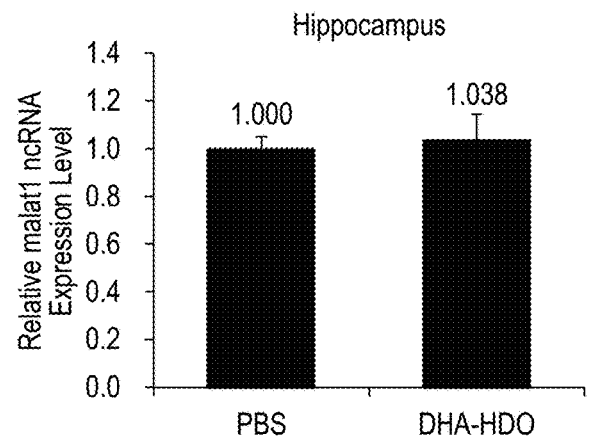
Figure 38:
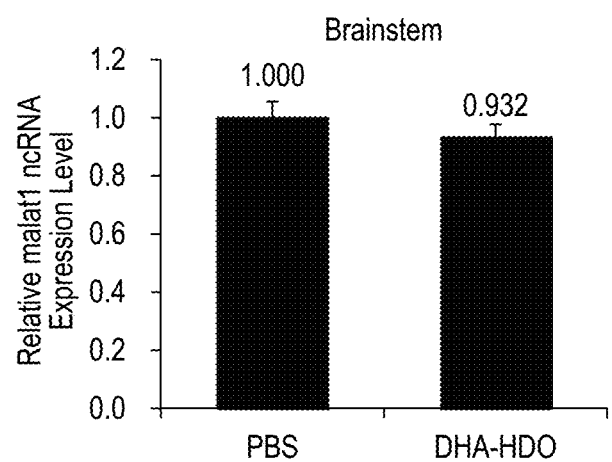
FIG. 38 is a graph showing the results of the experiment described in Example 19, and the graph shows suppression effects on the target transcription product (malat1) expression suppression effect of a docosahexaenoic acid (DHA)-conjugated nucleic acid complex in the brainstem. The error bars represent standard errors.

The results of Example 19 are shown by the graphs in FIGS. 37 and 38. DHA-HDO did not suppress the expression of the malat1 non-coding RNA in any of the cerebral cortex, cerebellum, striatum, hippocampus, and brainstem, compared with the negative control (PBS alone).

Example 20

Evaluation of Long-Term Effect of Double-Stranded Nucleic Acid Complex (Tocopherol)

An experiment was carried out to evaluate the long-term in vivo inhibition potency of the double-stranded nucleic acid agent.

(Preparation of Nucleic Acid Agent)

The double-stranded nucleic acid agent, Toc#1HDO described in Example 1 was used.

(In Vivo Experiment)

As described in Example 3, a single dose of the nucleic acid agent was administered to the mouse.

(Analysis of Expression)

Three days, seven days, 14 days, and 28 days after administration, PBS was perfused into the mice, and then, the mice were dissected to collect the whole brain. Using obtained each tissue, RNA extraction, cDNA synthesis, and quantitative RT-PCR with GAPDH used as an internal standard gene in the quantitative RT-PCR were carried out, and the expression level of the malat1 non-coding RNA was evaluated in the same manner as described in Example 1.

(Results)

Figure 39:
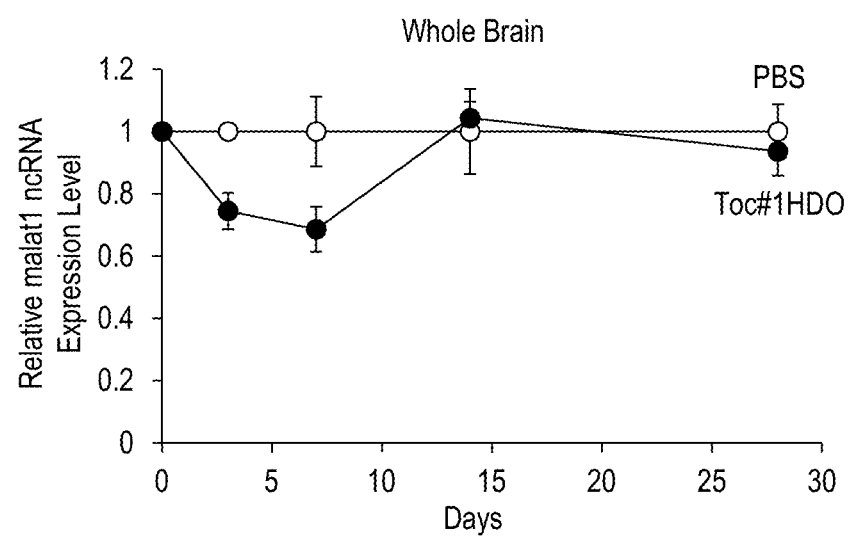
FIG. 39 is a graph showing the results of the experiment described in Example 20, and the graph shows suppression effects on the target transcription product (malat1) by a tocopherol-conjugated nucleic acid complex in the brain. The error bars represent standard errors.

The results of Example 20 are shown by the graph in FIG. 39. Toc#1HDO suppressed the expression of the malat1 non-coding RNA in the whole brain for two weeks, compared with the negative control (PBS alone).

Example 21

Evaluation of Antisense Effect Brought about in Brain by Administration of Single Dose of Double-Stranded Nucleic Acid Complex Consisting of Antisense Oligonucleotide Targeted at SR-B1 and Cholesterol-Conjugated Complementary Strand An experiment was carried out to evaluate the in vivo inhibition potency against mRNA expression in the brain by a double-stranded nucleic acid agent consisting of an antisense oligonucleotide targeted at an SR-B1 gene, which is different from Examples 1 and 2, and a cholesterol-conjugated complementary strand.

(Preparation of Nucleic Acid Agent)

The double-stranded nucleic acid agent was prepared by allowing a 16-mer single-stranded LNA/DNA gapmer (ASO (mSR-B1), SEQ ID NO: 3) targeted at SR-B1 mRNA (a first strand) to be annealed to a cholesterol-conjugated complementary strand RNA (Chol#1-cRNA(mSR-B1), SEQ ID NO: 11) (a second strand). The double-stranded nucleic acid agent described above was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice. The prepared double-stranded nucleic acid agent is referred to as Chol#1HDO.

The names and sequences of the first strand and the second strand used in this Example are shown below.

```
First Strand: ASO(mSR-B1)
                                    (SEQ ID NO: 3)
5'-T*C*a*g*t*c*a*t*g*a*c*t*T*C-3'

Second Strand: Chol#1-cRNA(mSR-B1)
                                    (SEQ ID NO: 11)
5'-Chol#1-g*a*AGUCAUGACU*g*a-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. CHol#1 represents the above-mentioned cholesterol #1.

(In Vivo Experiment)

The mice were 6- to 7-week old male C57BL/6 mice having a body weight of 20 g. The experiments involving use of mice were all carried out with n=4. The nucleic acid agent was intravenously injected at a dose of 50 mg/kg (single dose administration) into a mouse through the tail veins. In addition, a mouse into which PBS alone (instead of a nucleic acid agent) was injected was prepared as a negative control group.

(Analysis of Expression)

Seventy-two hours after injection, PBS was perfused into the mice, and then, the mice were dissected to isolate the cerebral cortex, cerebellum, striatum, hippocampus, brainstem, cervical spinal cord, and lumbar spinal cord. Subsequently, mRNA was extracted using a fully automated high-throughput nucleic acid extraction device, MagNA Pure 96 (from Roche Life Science) in accordance with the protocol. cDNA was synthesized using Transcriptor Universal cDNA Master (from Roche Life Science) in accordance with the protocol. Quantitative RT-PCR was carried out using TaqMan (from Roche Life Science). The primers used in quantitative RT-PCR were products designed and produced based on various numbers of genes by Thermo Fisher Scientific Inc. The amplification conditions (temperature and duration) were as follows: 95° C. for 15 seconds, 60° C. for 30 seconds, and 72° C. for one second (in one cycle), and this cycle was repeated 40 times. On the basis of the thus obtained results of quantitative RT-PCR, an mRNA(SR-B1) expression level/an mRNA (actin; internal standard gene) expression level were each calculated, and a relative expression level was obtained. The average value and standard error of the relative expression level were calculated. In addition, the results of different groups were compared, and the results were further evaluated by t-test.

(Results)

Figure 40:
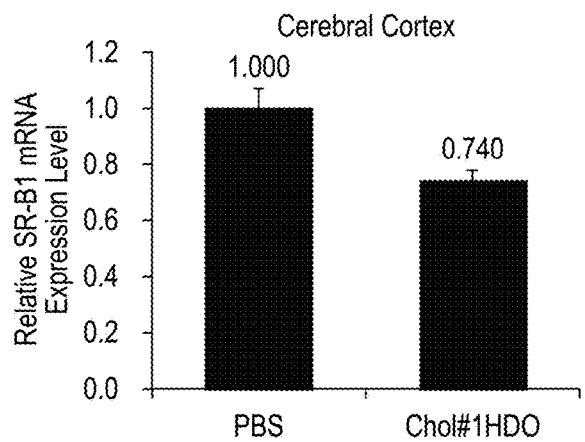
FIG. 40 shows graphs for the results of the experiment described in Example 21, and the graphs show suppression effects on the target gene (SR-B1) by a cholesterol-conjugated nucleic acid complex in various sites in the brain. The results are shown for (a) cerebral cortex, (b) cerebellum, (c) striatum, (d) hippocampus, and (e) brainstem. The error bars represent standard errors.
Figure 40:
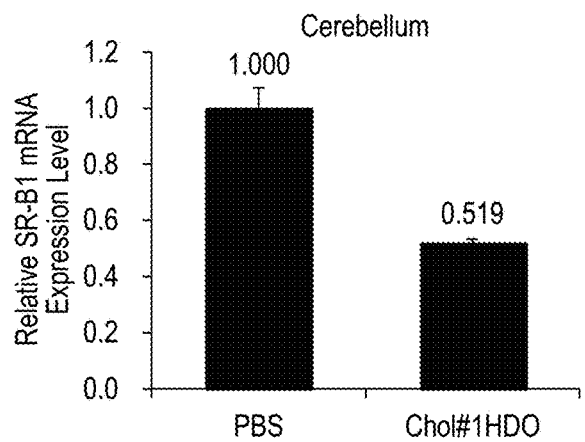
Figure 40:
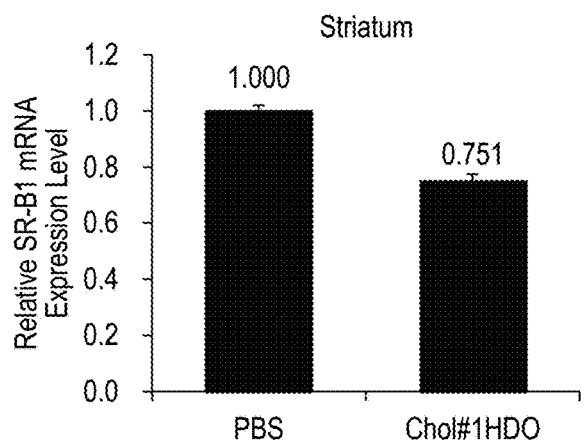
Figure 40:
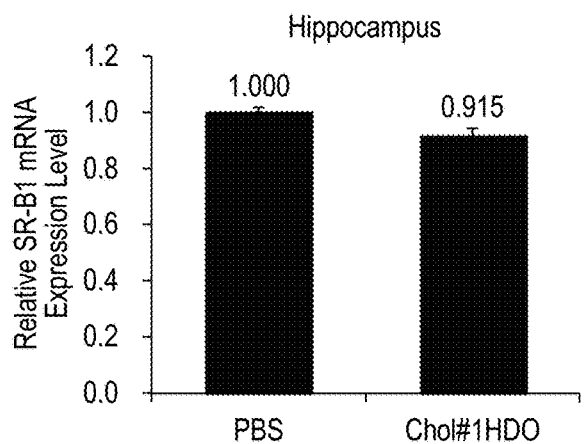
Figure 40:
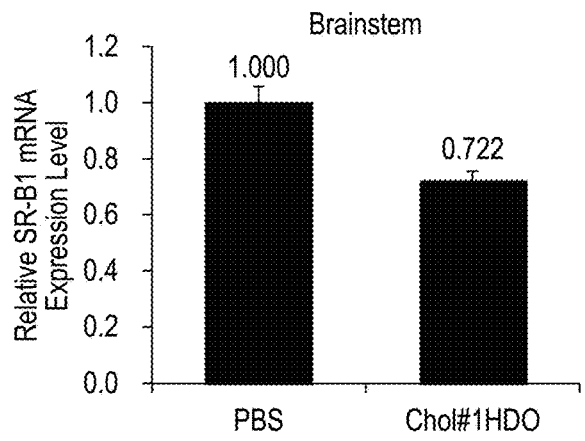
Figure 41:
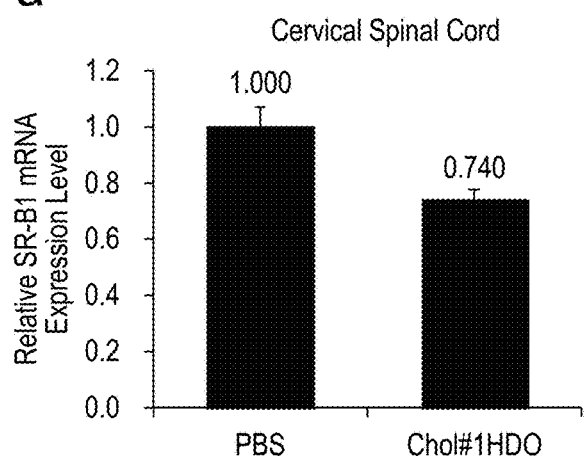
FIG. 41 shows graphs for the results of the experiment described in Example 21, and the graphs show suppression effects on the target gene (SR-B1) by a cholesterol-conjugated nucleic acid complex in various sites in the spinal cord. The results are shown for (a) cervical spinal cord and (b) lumbar spinal cord. The error bars represent standard errors.
Figure 41:
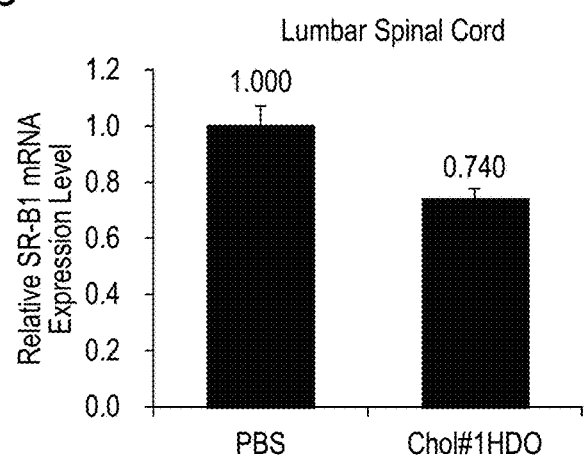

The results of Example 21 are shown by the graphs in FIGS. 40 and 41. These results have revealed that Chol#1HDO remarkably suppressed the expression of the SR-B1 mRNA in the cerebral cortex, cerebellum, striatum, hippocampus, brainstem, cervical spinal cord, and lumbar spinal cord.

Example 22

Evaluation of Antisense Effect Brought about in Various Sites of Brain and Spinal Cord by Administration of Multiple Small Doses of Double-Stranded Nucleic Acid Complex Consisting of Antisense Oligonucleotide and Cholesterol-Conjugated Complementary Strand An experiment was carried out to evaluate the in vivo inhibition potency against RNA expression in the brain by administration of multiple doses of a double-stranded nucleic acid agent consisting of an antisense oligonucleotide targeted at malat1 and a cholesterol-conjugated complementary strand.

(Preparation of Nucleic Acid Agent)

The double-stranded nucleic acid agent was prepared by allowing a 16-mer single-stranded LNA/DNA gapmer targeted at malat1 non-coding RNA (ASO(mMalat1), SEQ ID NO: 1) (a first strand) to be annealed to a cholesterol-conjugated complementary strand RNA (Chol#1-cRNA (mMalat1), SEQ ID NO: 10) (a second strand). The double-stranded nucleic acid agent described above was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice. The prepared double-stranded nucleic acid agent is referred to as Chol#1HDO.

The names and sequences of the first strand and the second strand used in this Example are shown below.

```
First Strand: ASO(mMalat1)
                              (SEQ ID NO: 1)
5'-C*T*A*g*t*t*c*a*c*t*g*a*a*T*G*C-3'

Second Strand: Chol#1-cRNA(mMalat1)
                              (SEQ ID NO: 10)
5'-Chol#1-g*c*a*UUCAGUGAAC*u*a*g-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#1 represents the above-mentioned cholesterol #1.

(In Vivo Experiment)

The nucleic acid agent was intravenously injected at a dose of 6.25 mg/kg into a mouse through the tail veins. The dose was administered twice a week, a total of four times. In addition, a mouse into which PBS alone (instead of a nucleic acid agent) was injected was prepared as a negative control group.

(Analysis of Expression)

Seventy-two hours after administration, PBS was perfused into the mice, and then, the mice were dissected to collect the cerebral cortex, cerebellum, striatum, hippocampus, brainstem, cervical spinal cord, and lumbar spinal cord separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 42:
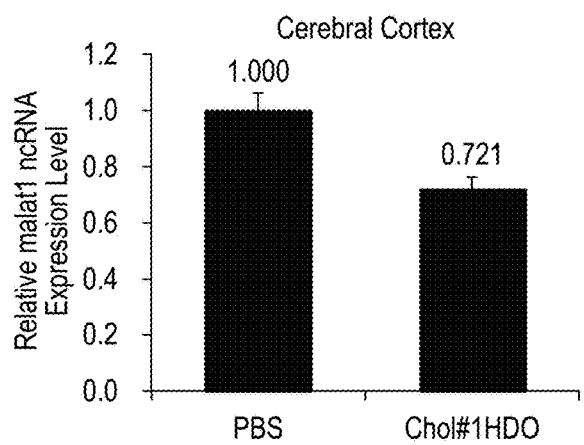
FIG. 42 shows graphs for the results of the experiment described in Example 22, and the graphs show comparisons of the target transcription product (malat1) by administration of a small dose of a cholesterol-conjugated nucleic acid complex in various sites in the brain and spinal cord. The results are shown for (a) cerebral cortex, (b) cerebellum, (c) striatum, (d) hippocampus, (e) brainstem, and (f) cervical spinal cord. The error bars represent standard errors.
Figure 42:
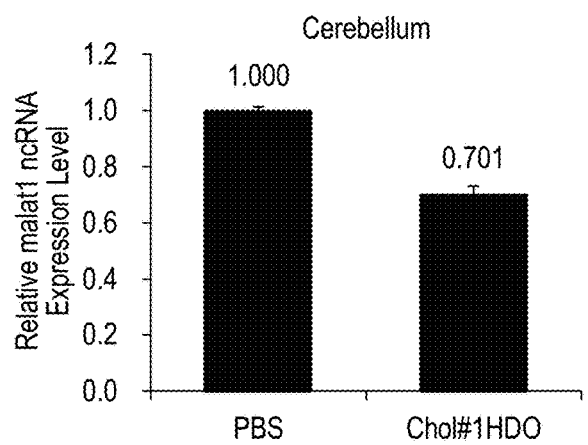
Figure 42:
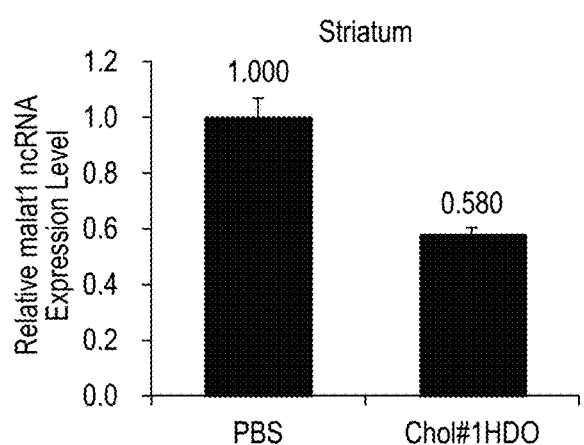
Figure 42:
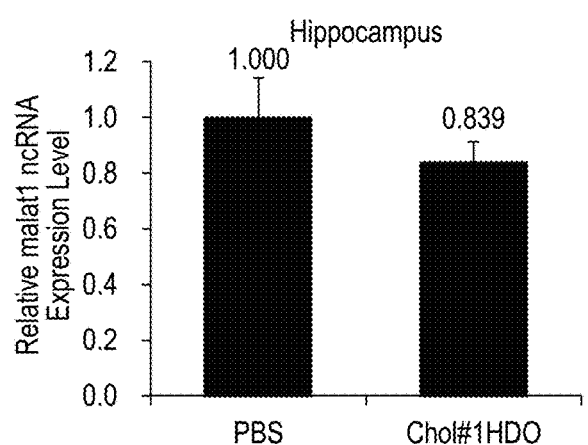
Figure 42:
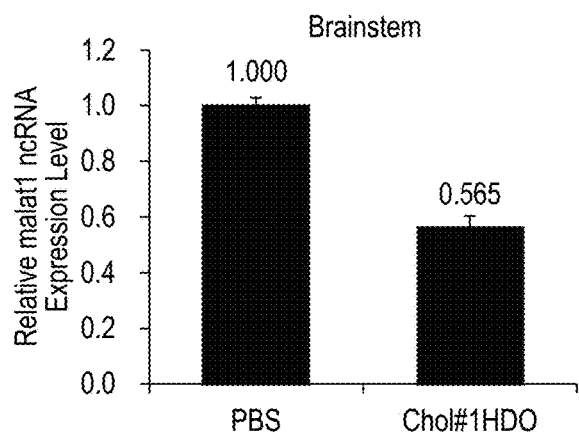
Figure 42:
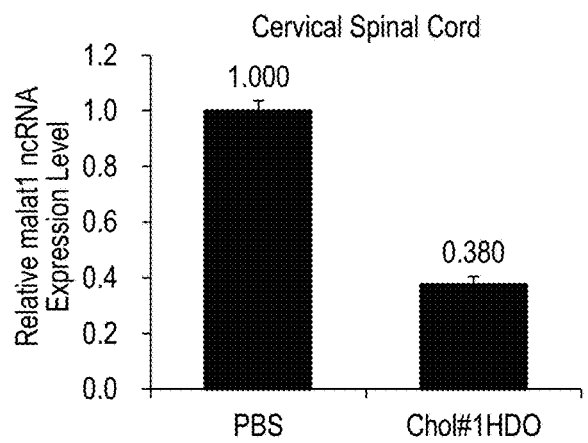
Figure 43:
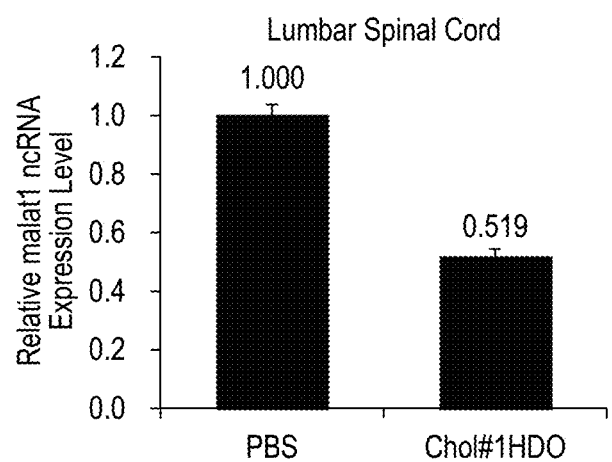
FIG. 43 is a graph showing the results of the experiment described in Example 22, and the graph shows comparisons of suppression effects on the target transcription product (malat1) by administration of a small dose of a cholesterol-conjugated nucleic acid complex in the lumbar spinal cord. The error bars represent standard errors.

The results of Example 22 are shown by the graphs in FIGS. 42 and 43. Chol#1HDO remarkably suppressed the expression of the malat1 non-coding RNA in any of the cerebral cortex, cerebellum, striatum, hippocampus, brainstem, cervical spinal cord, and lumbar spinal cord, compared with the negative control (PBS alone).

Example 23

Evaluation of Antisense Effect Brought about in Various Sites of Brain by Double-Stranded Nucleic Acid Complex Consisting of Antisense Oligonucleotide and Cholesterol-Conjugated Complementary Strand Having Internucleoside Linkages of Different Modification Patterns An experiment was carried out to evaluate the in vivo inhibition potency against RNA expression in the brain by a double-stranded nucleic acid agent consisting of an antisense oligonucleotide targeted at malat1 and a cholesterol-conjugated complementary strand having internucleoside linkages of different modification patterns.

(Preparation of Nucleic Acid Agent)

The double-stranded nucleic acid agent was prepared by allowing a 16-mer single-stranded LNA/DNA gapmer targeted at malat1 non-coding RNA (ASO(mMalat1), SEQ ID NO: 1) (a first strand) to be annealed to cholesterol-conjugated complementary strand RNAs having internucleoside linkages of different modification patterns (a second strand). Three kinds of second strands were prepared as below-mentioned. The double-stranded nucleic acid agent described above was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice.

The double-stranded nucleic acid agent prepared using Chol#1-cRNA(mMalat1)(PO) as the second strand is referred to as Chol#1HDO(PO). The double-stranded nucleic acid agent prepared using Chol#1-cRNA(mMalat1) (5'PS) as the second strand is referred to as Chol#1HDO (5'PS). The double-stranded nucleic acid agent prepared using Chol#1-cRNA(mMalat1)(3'PS) as the second strand is referred to as Chol#1HDO(3'PS).

The names and sequences of the first strand and the second strand used in this Example are shown below.

```
First Strand: ASO(mMalat1)
                                          (SEQ ID NO: 1)
5'-C*T*A*g*t*t*c*a*c*t*g*a*a*T*G*C-3'

Second Strand: Chol#1-cRNA(mMalat1)(PO)
                                         (SEQ ID NO: 10)
5'-Chol#1-gcaUUCAGUGAACuag-3'

Second Strand: Chol#1-cRNA(mMalat1)(5'PS)
                                         (SEQ ID NO: 10)
5'-Chol#1-g*c*a*UUCAGUGAACuag-3'

Second Strand: Chol#1-cRNA(mMalat1)(3'PS)
                                         (SEQ ID NO: 10)
5'-Chol#1-gcaUUCAGUGAAC*u*a*g-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#1 represents the above-mentioned cholesterol #1.

(In Vivo Experiment)

The nucleic acid agent was intravenously injected once at a dose of 50 mg/kg into a mouse through the tail veins. In addition, a mouse into which PBS alone (instead of a nucleic acid agent) was injected was prepared as a negative control group.

(Analysis of Expression)

Seventy-two hours after administration, PBS was perfused into the mice, and then, the mice were dissected to collect the cerebral cortex, cerebellum, striatum, hippocampus, and brainstem separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 44:
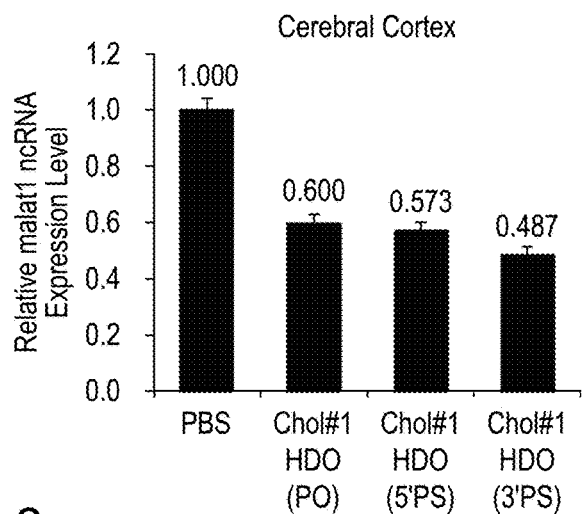
FIG. 44 shows graphs for the results of the experiment described in Example 23, and the graphs show the target transcription product (malat1) by cholesterol-conjugated nucleic acid complexes in various sites in the brain, wherein the second strands of the complexes have different modification patterns of internucleoside linkages. The results are shown for (a) cerebral cortex, (b) cerebellum, (c) striatum, and (d) hippocampus. The error bars represent standard errors.
Figure 44:
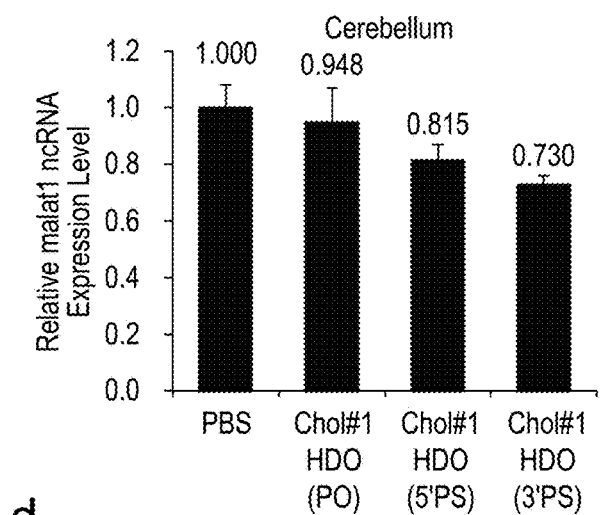
Figure 44:
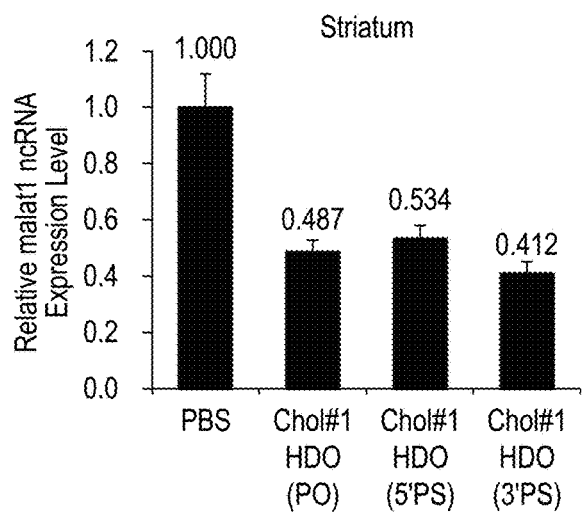
Figure 44:
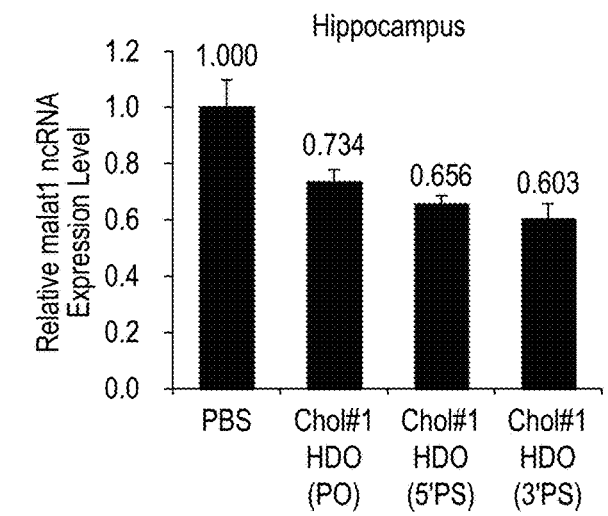
Figure 45:
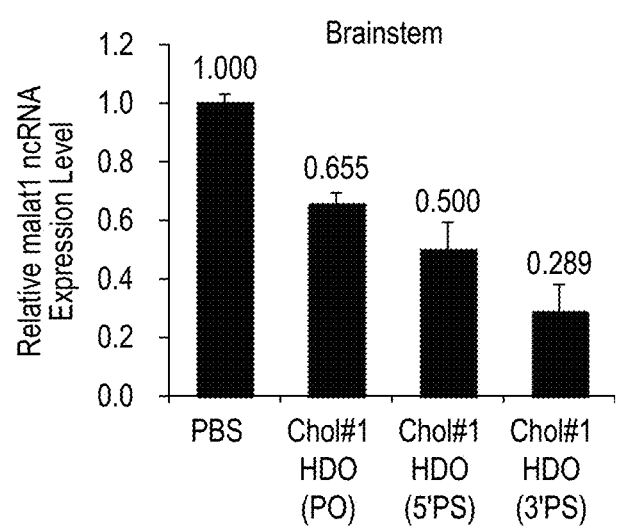
FIG. 45 is a graph showing the results of the experiment described in Example 23, and the graph shows suppression effects on the target transcription product (malat1) by cholesterol-conjugated nucleic acid complexes in the brainstem, wherein the second strands of the complexes have different modification patterns of internucleoside linkages. The error bars represent standard errors.

The results of Example 23 are shown by the graphs in FIGS. 44 and 45. The double-stranded agents, Chol#1HDO (PO), Chol#1HDO(5'PS), and Chol#1HDO(3'PS), remarkably suppressed the expression of the malat1 non-coding RNA in any of the cerebral cortex, cerebellum, striatum, hippocampus, and brainstem, compared with the negative control (PBS alone). In particular, a tendency to increase activity was exhibited when modified internucleoside linkages were introduced from the 3' end.

Example 24

Evaluation of Antisense Effect Brought about in Various Sites of Brain by Twice-a-Week Administration of Double-Stranded Nucleic Acid Complex Consisting of Antisense Oligonucleotide and Tocopherol-Conjugated or Cholesterol-Conjugated Complementary Strand An experiment was carried out to evaluate the in vivo inhibition potency brought against RNA expression in the brain by twice-a-week administration of a double-stranded nucleic acid agent consisting of an antisense oligonucleotide targeted at malat1 and a tocopherol-conjugated or cholesterol-conjugated complementary strand.

(Preparation of Nucleic Acid Agent)

The double-stranded nucleic acid agent was prepared by allowing a 16-mer single-stranded LNA/DNA gapmer targeted at malat1 non-coding RNA (ASO(mMalat1), SEQ ID NO: 1) (a first strand) to be annealed to a tocopherol-conjugated complementary strand RNA (Toc#1-cRNA (mMalat1), SEQ ID NO: 10) (a second strand) or a cholesterol-conjugated complementary strand RNA (Chol#1-cRNA(mMalat1), SEQ ID NO: 10) (a second strand). The double-stranded nucleic acid agent described above was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice.

The double-stranded nucleic acid agent prepared using Toc#1-cRNA(mMalat1) as the second strand is referred to as Toc#1HDO. The double-stranded nucleic acid agent prepared using Chol#1-cRNA(mMalat1) as the second strand is referred to as Chol#1HDO.

The names and sequences of the first strand and the second strand used in this Example are shown below.

```
First Strand: ASO(mMalat1)
                                          (SEQ ID NO: 1)
5'-C*T*A*g*t*t*c*a*c*t*g*a*a*T*G*C-3'

Second Strand: Toc#1-cRNA(mMalat1)
                                         (SEQ ID NO: 10)
5'-Toc#1-g*c*a*UUCAGUGAAC*u*a*g-3'

Second Strand: Chol#1-cRNA(mMalat1)
                                         (SEQ ID NO: 10)
5'-Chol#1-g*c*a*UUCAGUGAAC*u*a*g-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Toc#1 represents the above-mentioned α-tocopherol #1. Chol#1 represents the above-mentioned cholesterol #1.

(In Vivo Experiment)

The mice were 6- to 7-week old male C57BL/6 mice having a body weight of 20 g. The experiments involving use of mice were all carried out with n=4. The nucleic acid agent in an amount of 25 mg/kg or 50 mg/kg per dose was intravenously injected into a mouse through the tail veins. The dose was administered twice a week. In addition, a mouse into which PBS alone (instead of a nucleic acid agent) was injected was prepared as a negative control group.

(Analysis of Expression)

Seventy-two hours after the final administration, PBS was perfused into the mice, and then, the mice were dissected to isolate the brain. The cerebral cortex, cerebellum, striatum, hippocampus, and brainstem were separately collected from the brain. Using obtained each tissue, RNA extraction, cDNA synthesis, and quantitative RT-PCR were carried out as described in Example 1, and the expression level of the malat1 non-coding RNA was evaluated.

(Results)

Figure 46:
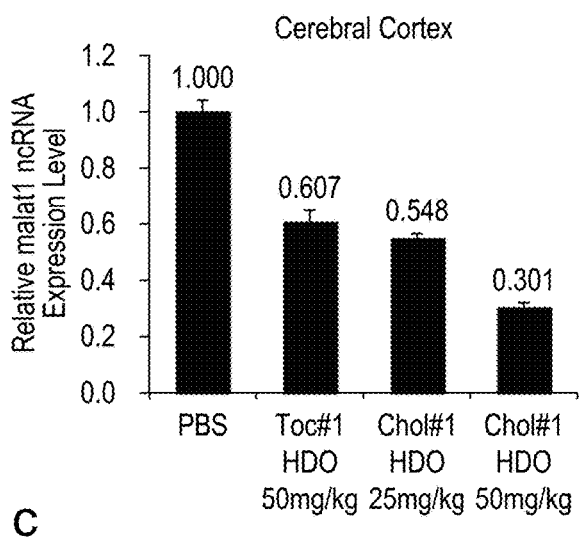
FIG. 46 shows graphs for the results of the experiment described in Example 24, and the graphs show suppression effects on the target transcription product (malat1) by twice a week administration of a tocopherol- or cholesterol-conjugated nucleic acid complex in various sites in the brain. The results are shown for (a) cerebral cortex, (b) cerebellum, (c) striatum, (d) hippocampus, and (e) brainstem. The error bars represent standard errors.
Figure 46:
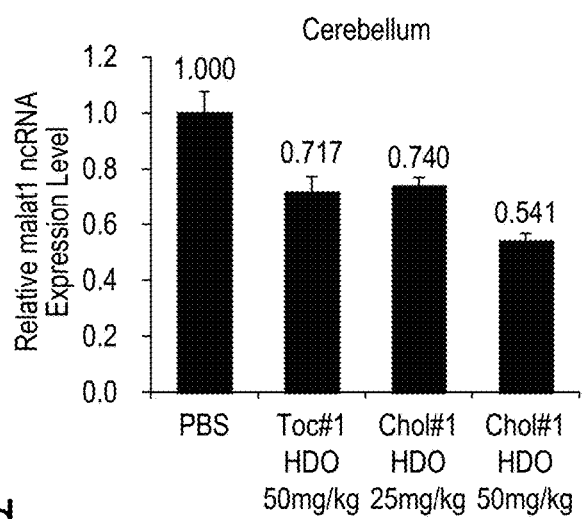
Figure 46:
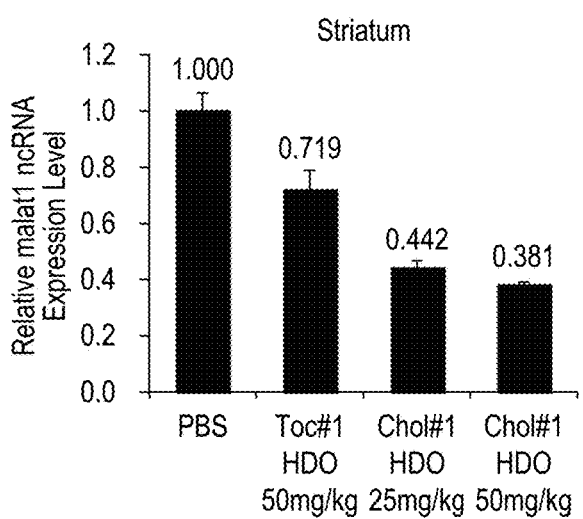
Figure 46:
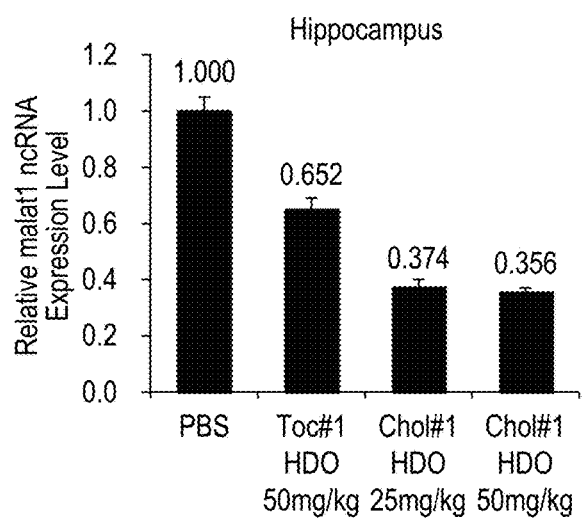
Figure 46:
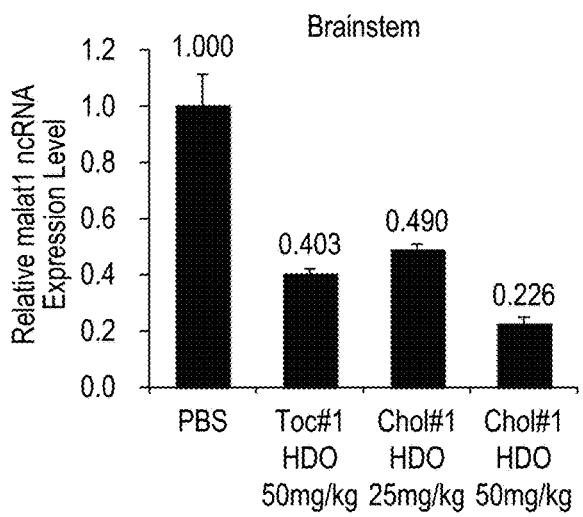

The results of Example 24 are shown by the graph in FIG. 46. Toc#1HDO and Chol#1HDO remarkably suppressed the expression of the malat1 non-coding RNA in any of the cerebral cortex, cerebellum, striatum, hippocampus, and brainstem, compared with the negative control (PBS alone).

Example 25

Evaluation of Antisense Effect Brought about in Various Sites of Brain by Subcutaneous Administration of Single Dose of Double-Stranded Nucleic Acid Complex Consisting of Antisense Oligonucleotide and Cholesterol-Conjugated Complementary Strand An experiment was carried out to evaluate the in vivo inhibition potency against RNA expression in the brain by subcutaneous administration of a single dose of a double-stranded nucleic acid agent consisting of an antisense oligonucleotide targeted at malat1 and a cholesterol-conjugated complementary strand.

(Preparation of Nucleic Acid Agent)

The double-stranded nucleic acid agent was prepared by allowing a 16-mer single-stranded LNA/DNA gapmer targeted at malat1 non-coding RNA (ASO(mMalat1), SEQ ID NO: 1) (a first strand) to be annealed to a cholesterol-conjugated complementary strand RNA (Chol#1-cRNA-Chol#3(mMalat1), SEQ ID NO: 10) (a second strand). Specifically, the double-stranded nucleic acid agent described above was prepared by adding the second strand (powder) to phosphate buffered saline (PBS) heated to 95° C., dissolving the strand by vortexing, mixing the resulting solution with the first strand solution heated to 95° C., maintaining the resulting solution mixture at 95° C. for five minutes, then maintaining the solution mixture at 37° C. for one hour, and thus annealing the nucleic acid strands. The annealed nucleic acid was stored at 4° C. or on ice. The prepared double-stranded nucleic acid agent is referred to as Chol#1HDOChol#3.

The names and sequences of the first strand and the second strand used in this Example are shown below.

```
First Strand: ASO(mMalat1)
                                        (SEQ ID NO: 1)
5'-C*T*A*g*t*t*c*a*c*t*g*a*a*T*G*C-3'

Second Strand: Chol#1-cRNA-Chol#3(mMalat1)
                                        (SEQ ID NO: 10)
5'-Chol#1-g*c*a*UUCAGUGAAC*u*a*g-Chol#3-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#1 represents the above-mentioned cholesterol #1. Chol#3 represents the above-mentioned cholesterol #3.

(In Vivo Experiment)

A single dose of the nucleic acid agent was administered to the mouse in the same manner as described in Example 3 except that a dose was administered by subcutaneous injection instead of intravenous injection through the tail veins.

(Analysis of Expression)

Seventy-two hours after administration, PBS was perfused into the mice, and then, the mice were dissected to collect the cerebral cortex, cerebellum, striatum, and brainstem separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 47:
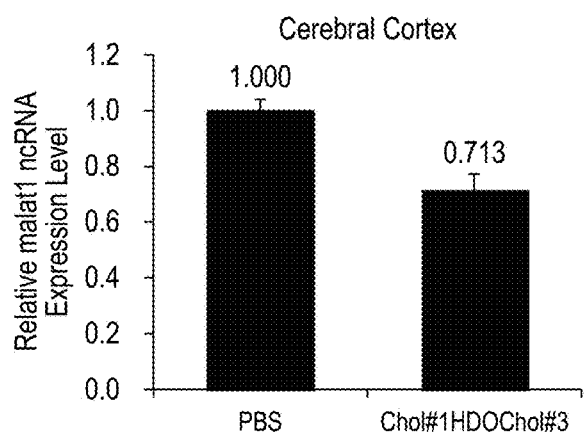
FIG. 47 shows graphs for the results of the experiment described in Example 25, and the graphs show suppression effects on the target transcription product (malat1) by a cholesterol-conjugated nucleic acid complex in various sites in the brain. The results are shown for (a) cerebral cortex, (b) cerebellum, (c) striatum. The error bars represent standard errors.
Figure 47:
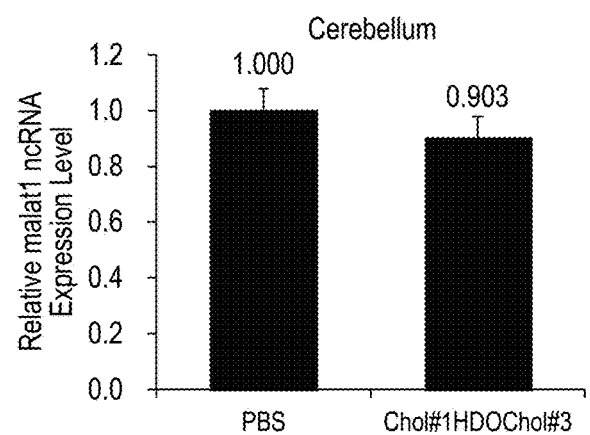
Figure 47:
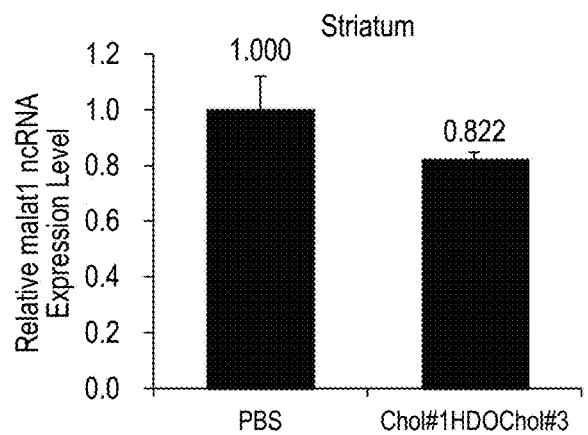
Figure 48:
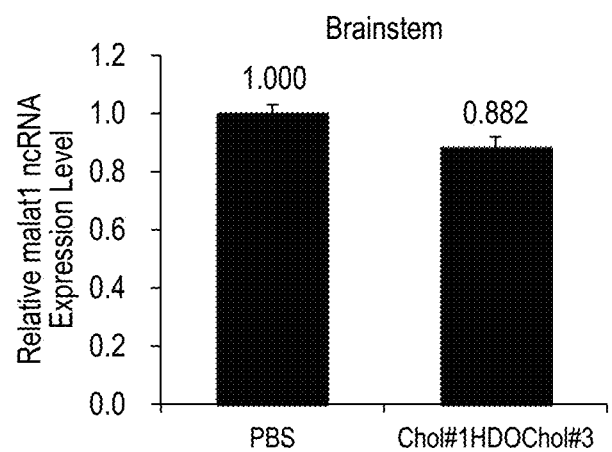
FIG. 48 is a graph showing the results of the experiment described in Example 25, and the graph shows suppression effects on the target transcription product (malat1) by a cholesterol-conjugated nucleic acid complex in the brainstem. The error bars represent standard errors.

The results of Example 25 are shown by the graphs in FIGS. 47 and 48. Chol#1HDOChol#3 suppressed the expression of the malat1 non-coding RNA in any of the cerebral cortex, cerebellum, striatum, and brainstem, compared with the negative control (PBS alone).

These results have revealed that the double-stranded nucleic acid agent according to one embodiment of the present invention can be delivered to various sites in the brain by subcutaneous administration and bring about an antisense effect.

Example 26

Evaluation of Antisense Effect Brought about in Various Sites of Brain by Administration of Single Dose of Double-Stranded Nucleic Acid Complex Consisting of Antisense Oligonucleotide and Cholesterol-Conjugated DNA Complementary Strand An experiment was carried out to evaluate the in vivo inhibition potency against RNA expression in the brain by administration of a single dose of a double-stranded nucleic acid agent consisting of an antisense oligonucleotide targeted at malat1 and a DNA complementary strand unlike in Examples 1 to 5.

(Preparation of Nucleic Acid Agent)

The double-stranded nucleic acid agent was prepared by allowing a 16-mer single-stranded LNA/DNA gapmer targeted at malat1 non-coding RNA (ASO(mMalat1), SEQ ID NO: 1) (a first strand) to be annealed to a cholesterol-conjugated complementary strand DNA (a second strand). Three kinds of second strands were used as below-mentioned. The double-stranded nucleic acid agent described above was prepared by adding the second strand (powder) to phosphate buffered saline (PBS) heated to 95° C., dissolving the strand by vortexing, mixing the resulting solution with the first strand solution heated to 95° C., maintaining the resulting solution mixture at 95° C. for five minutes, then maintaining the solution mixture at 37° C. for one hour, and thus annealing the nucleic acid strands. The annealed nucleic acid was stored at 4° C. or on ice.

The double-stranded nucleic acid agent prepared using Chol#1-cDNA(mMalat1) Full DNA as the second strand is referred to as Chol#1DNA/DNA full DNA. The double-stranded nucleic acid agent prepared using Chol#1-cDNA(mMalat1) Full PS as the second strand is referred to as Chol#1DNA/DNA full PS. The double-stranded nucleic acid agent prepared using Chol#1-cDNA(mMalat1) Full PO as the second strand is referred to as Chol#1DNA/DNA full PO.

The names and sequences of the first strand and the second strand used in this Example are shown below.

```
First Strand: ASO(mMalat1)
                                           (SEQ ID NO: 1)
5'-C*T*A*g*t*t*c*a*c*t*g*a*a*T*G*C-3'

Second Strand: Chol#1-cDNA(mMalat1) Full DNA
                                          (SEQ ID NO: 24)
5'-Chol#1-g*c*a*ttcagtgaac*t*a*g-3'

Second Strand: Chol#1-cDNA(mMalat1) Full PS
                                          (SEQ ID NO: 25)
5'-Chol#1-g*c*a*t*t*c*a*g*t*g*a*a*c*u*a*g-3'

Second Strand: Chol#1-cDNA(mMalat1) Full PO
                                          (SEQ ID NO: 25)
5'-Chol#1-gcattcagtgaacuag-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#1 represents the above-mentioned cholesterol #1.

(In Vivo Experiment)

As described in Example 3, a single dose of the nucleic acid agent was administered to the mouse.

(Analysis of Expression)

Seventy-two hours after administration, PBS was perfused into the mice, and then, the mice were dissected to collect the cerebral cortex, cerebellum, striatum, hippocampus, brainstem, cervical spinal cord, and lumbar spinal cord separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 49:
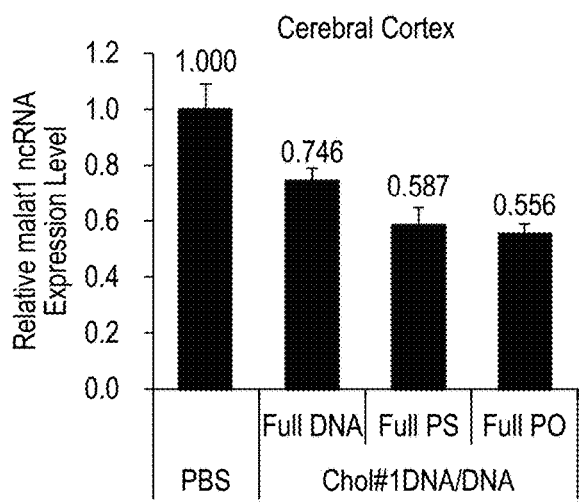
FIG. 49 shows graphs for the results of the experiment described in Example 26, and the graphs show suppression effects on the target transcription product (malat1) by cholesterol-conjugated nucleic acid complexes in various sites in the brain. The results are shown for (a) cerebral cortex, (b) cerebellum, (c) striatum, (d) hippocampus, and (e) brainstem. The error bars represent standard errors.
Figure 49:
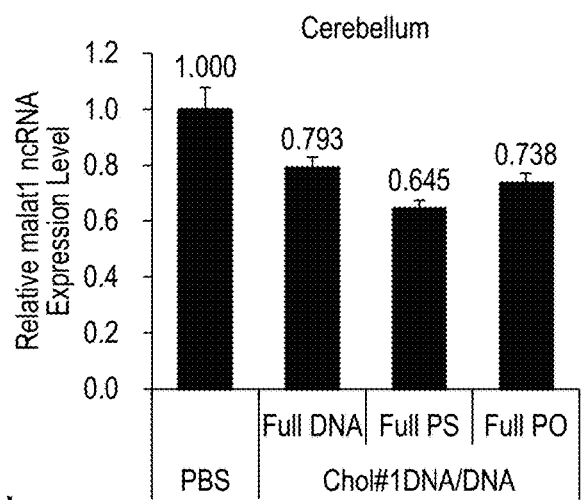
Figure 49:
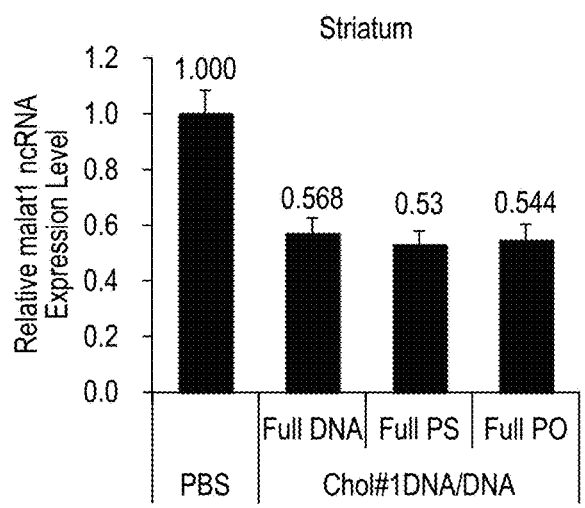
Figure 49:
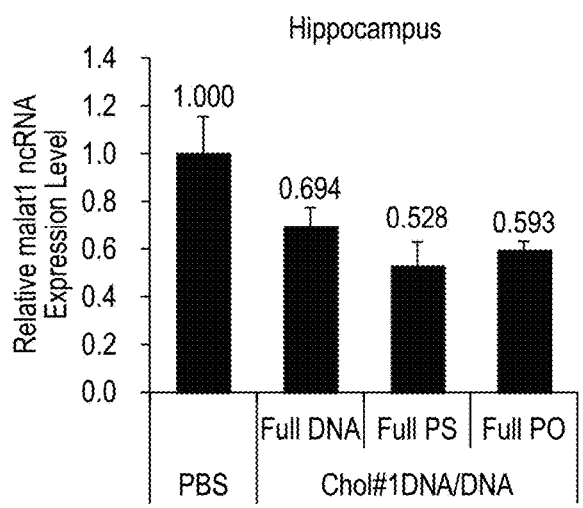
Figure 49:
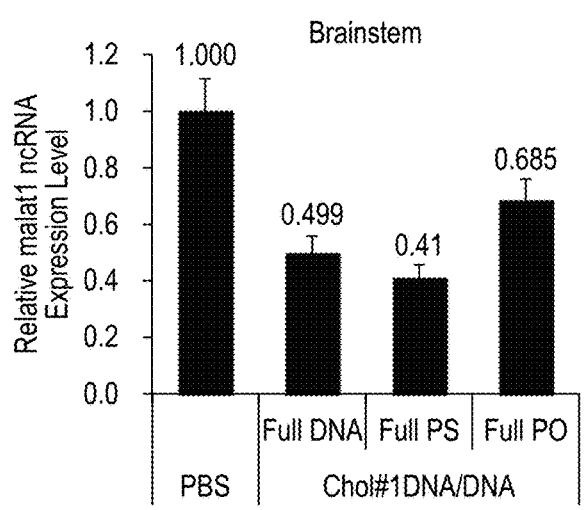
Figure 50:
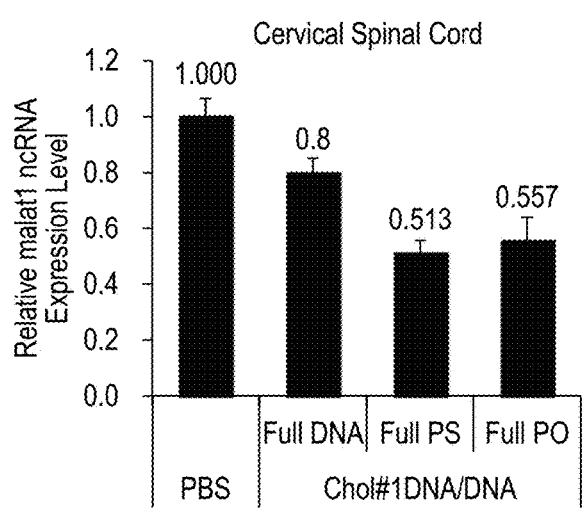
FIG. 50 shows graphs for the results of the experiment described in Example 26, and the graphs show suppression effects on the target transcription product (malat1) by cholesterol-conjugated nucleic acid complexes in various sites in the spinal cord. The results are shown for (a) cervical spinal cord and (b) lumbar spinal cord. The error bars represent standard errors.
Figure 50:
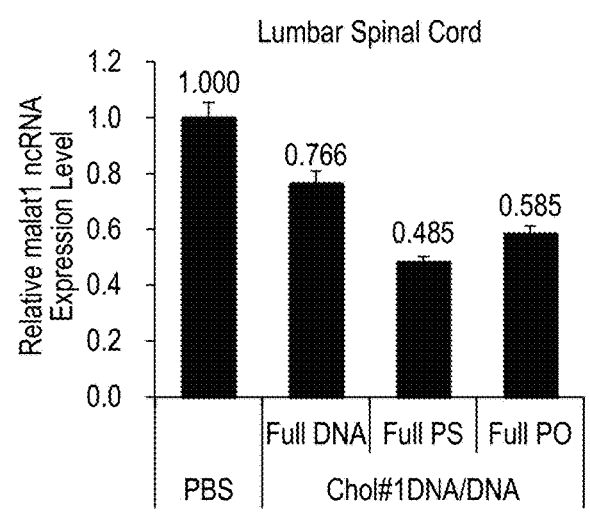

The results of Example 26 are shown by the graphs in FIGS. 49 and 50. The double-stranded agents, Chol#1DNA/DNA full DNA, Chol#1DNA/DNA full PS, and Chol#1DNA/DNA full PO, remarkably suppressed the expression of the malat1 non-coding RNA in any of the cerebral cortex, cerebellum, striatum, hippocampus, brainstem, cervical spinal cord, and lumbar spinal cord, compared with the negative control (PBS alone).

These results have revealed that the double-stranded nucleic acid agent consisting of an antisense oligonucleotide and a cholesterol-conjugated DNA complementary strand can be delivered to various sites in the brain and spinal cord and bring about an antisense effect.

Example 27

Evaluation of miRNA Suppression Effect Brought about in Various Sites of Brain by Administration of Single Dose of Double-Stranded Nucleic Acid Complex Consisting of Antisense Oligonucleotide and Cholesterol-Conjugated DNA Complementary Strand An experiment was carried out to evaluate the in vivo inhibition potency against miRNA expression in the brain by administration of a single dose of a double-stranded nucleic acid agent consisting of an antisense oligonucleotide targeted at miRNA-21(miR21) and a complementary strand.

(Preparation of Nucleic Acid Agent)

The double-stranded nucleic acid agent was prepared by allowing a 15-mer single-stranded LNA/DNA mixmer (ASO(anti-miR21), SEQ ID NO: 26) targeted at miR21 (a first strand) to be annealed to a cholesterol-conjugated complementary strand RNA (Chol#1-cRNA(anti-miR21), SEQ ID NO: 27) (a second strand). The double-stranded nucleic acid agent described above was prepared by adding the second strand (powder) to phosphate buffered saline (PBS) heated to 95° C., dissolving the strand by vortexing, mixing the resulting solution with the first strand solution heated to 95° C., maintaining the resulting solution mixture at 95° C. for five minutes, then maintaining the solution mixture at 37° C. for one hour, and thus annealing the nucleic acid strands. The annealed nucleic acid was stored at 4° C. or on ice. The prepared double-stranded nucleic acid agent is referred to as Chol#1HDO(antimiR21).

The names and sequences of the first strand and the second strand used in this Example are shown below.

```
First Strand: ASO(anti-miR21)
                                          (SEQ ID NO: 26)
5'-T*c*A*g*t*C*T*g*a*T*a*A*g*C*T-3'

Second Strand: Chol#1-cRNA(anti-miR21)
                                          (SEQ ID NO: 27)
5'-Chol#1-a*g*c*UUAUCAGAC*u*g*a-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#1 represents the above-mentioned cholesterol #1.

(In Vivo Experiment)

As described in Example 3, a single dose of the nucleic acid agent was administered to the mouse.

(Analysis of Expression)

Seventy-two hours after administration, PBS was perfused into the mice, and then, the mice were dissected to collect the cerebral cortex, cerebellum, striatum, hippocampus, and brainstem separately. RNA was extracted using miRNeasy Mini Kit (Qiagen N.V.) in accordance with the protocol. cDNA was synthesized using TaqMan MicroRNA Reverse Transcription Kit (Thermo Fisher Scientific Inc.) in accordance with the protocol. Quantitative RT-PCR was carried out using TaqMan (from Roche Life Science). In addition, U6 was used as an internal standard gene in quantitative RT-PCR.

(Results)

Figure 51:
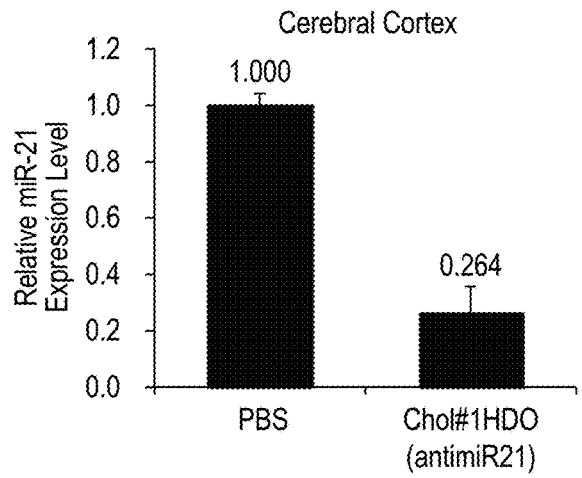
FIG. 51 shows graphs for the results of the experiment described in Example 27, and the graphs show suppression effects on the target transcription product (miR-21) by a cholesterol-conjugated nucleic acid complex in various sites in the brain. The results are shown for (a) cerebral cortex, (b) cerebellum, (c) striatum, (d) hippocampus, and (e) brainstem. The error bars represent standard errors.
Figure 51:
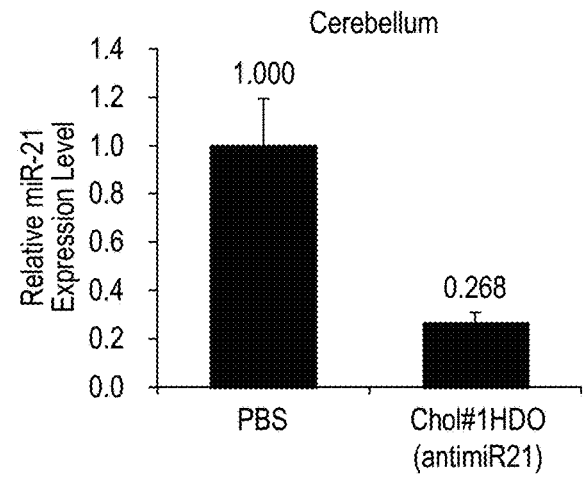
Figure 51:
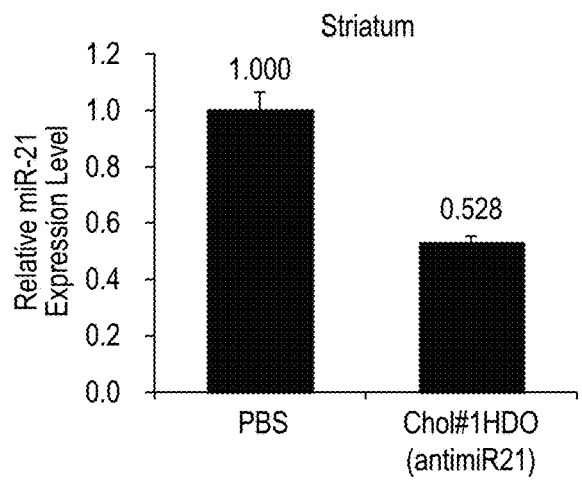
Figure 51:
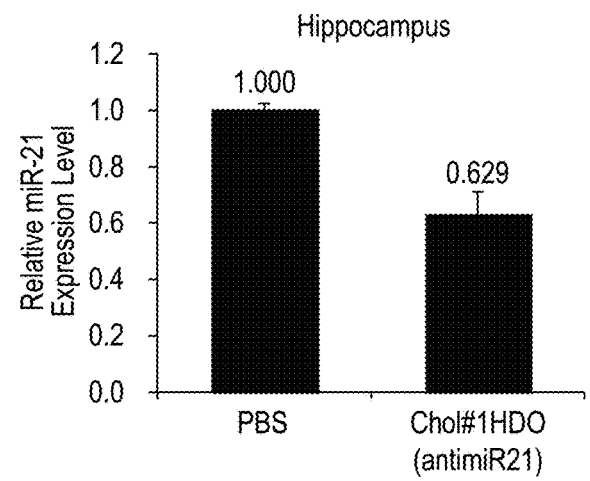
Figure 51:
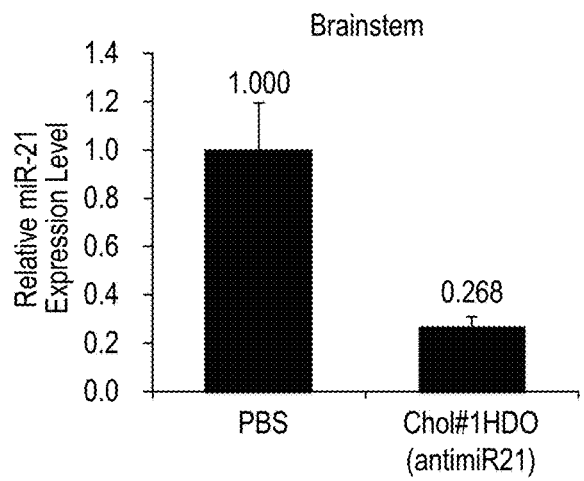

The results of Example 27 are shown by the graph in FIG. 51. Chol#1HDO(anti-miR21) remarkably suppressed the expression of miR21 in any of the cerebral cortex, cerebellum, striatum, hippocampus, and brainstem, compared with the negative control (PBS alone).

These results have revealed that the double-stranded nucleic acid agent consisting of an antisense oligonucleotide and a cholesterol-conjugated DNA complementary strand can be delivered to various sites in the brain and bring about an anti-miR effect.

Example 28

Evaluation of Antisense Effect Brought about in Various Sites of Brain by Administration of Single Dose of Double-Stranded Nucleic Acid Complex Consisting of Antisense Oligonucleotide and Tocopherol-Conjugated Complementary Strand An experiment was carried out to evaluate the in vivo inhibition potency against RNA expression in the brain by administration of a single dose of a double-stranded nucleic acid agent consisting of an antisense oligonucleotide targeted at malat1 and a tocopherol-conjugated complementary strand. The effect brought about seven days after administration was evaluated, unlike in Example 1.

(Preparation of Nucleic Acid Agent)

The double-stranded nucleic acid agent was prepared by allowing a 16-mer single-stranded LNA/DNA gapmer targeted at malat1 non-coding RNA (ASO(mMalat1), SEQ ID NO: 1) (a first strand) to be annealed to a tocopherol-conjugated complementary strand RNA (Toc#1-cRNA (mMalat1), SEQ ID NO: 10) (a second strand). The double-stranded nucleic acid agent described above was prepared by mixing the first strand and the second strand in equimolar amounts, heating the solution at 95° C. for five minutes, then cooling the solution at 37° C., maintaining the solution for one hour, and thus annealing the nucleic acid strands. The annealed nucleic acid was stored at 4° C. or on ice. The prepared double-stranded nucleic acid agent is referred to as Toc#1HDO.

The names and sequences of the first strand and the second strand used in this Example are shown below.

```
First Strand: ASO(mMalat1)
                                (SEQ ID NO: 1)
5'-C*T*A*g*t*t*c*a*c*t*g*a*a*T*G*C-3'

Second Strand: Toc#1-cRNA(mMalat1)
                                (SEQ ID NO: 10)
5'-Toc#1-g*c*a*UUCAGUGAAC*u*a*g-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Toc#1 represents the above-mentioned tocopherol #1.

(In Vivo Experiment)

As described in Example 1, a single dose of the nucleic acid agent was administered to the mouse.

(Analysis of Expression)

Seven days after administration, PBS was perfused into the mice, and then, the mice were dissected to collect the cerebral cortex, cerebellum, striatum, hippocampus, and brainstem separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 52:
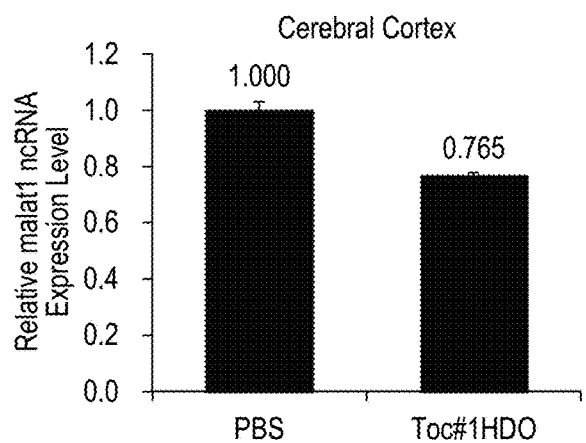
FIG. 52 shows graphs for the results of the experiment described in Example 28, and the graphs show suppression effects on the target transcription product (malat1) by a tocopherol-conjugated nucleic acid complex in various sites in the brain. The results obtained seven days after administration are shown. The results are shown for (a) cerebral cortex, (b) cerebellum, (c) striatum, and (d) hippocampus. The error bars represent standard errors.
Figure 52:
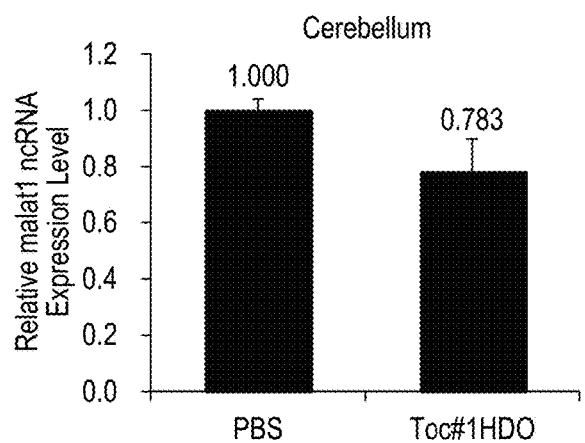
Figure 52:
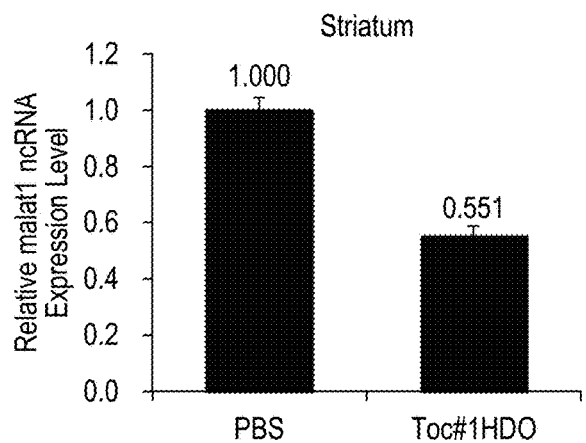
Figure 52:
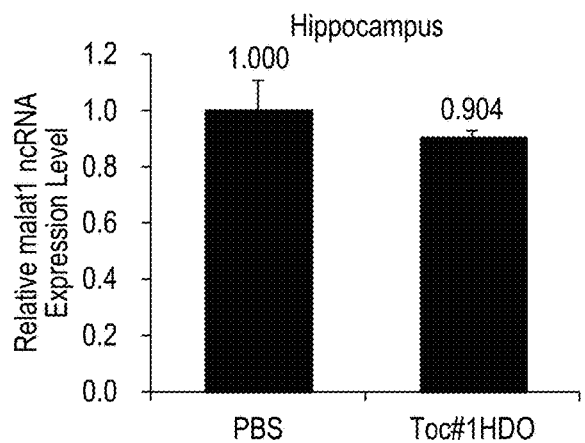
Figure 53:
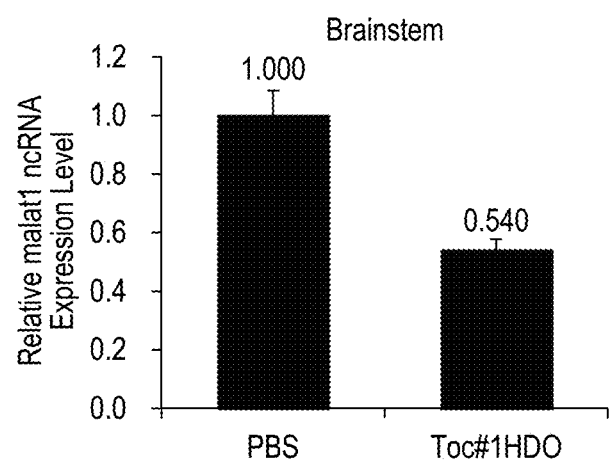
FIG. 53 is a graph showing the results of the experiment described in Example 28, and the graph shows suppression effects on the target transcription product (malat1) by a tocopherol-conjugated nucleic acid complex in the brainstem. The results obtained seven days after administration are shown. The error bars represent standard errors.

The results of Example 28 are shown by the graphs in FIG. 52 or 53. Toc#1HDO remarkably suppressed the expression of the malat1 non-coding RNA in any of the cerebral cortex, cerebellum, striatum, hippocampus, and brainstem even after seven days, compared with the negative control (PBS alone).

These results have revealed that the double-stranded nucleic acid agent consisting of an antisense oligonucleotide and a tocopherol-conjugated complementary strand can be delivered to various sites in the brain and bring about an antisense effect for a long time.

Example 29

Evaluation of Antisense Effect Brought about in Various Sites of Brain and Spinal Cord by Administration of Single Dose of Double-Stranded Nucleic Acid Complex Consisting of Antisense Oligonucleotide and Cholesterol-Conjugated Complementary Strand An experiment was carried out to evaluate the in vivo inhibition potency of the double-stranded nucleic acid agent with a complementary strand (a second strand) having a changed structure.

(Preparation of Nucleic Acid Agent)

The control (ASO) was a 16-mer single-stranded LNA/DNA gapmer (ASO(mMalat1), SEQ ID NO: 1) targeted at a malat1 non-coding RNA used in Example 1. By annealing this LNA/DNA gapmer (a first strand) to a cholesterol-conjugated complementary strand RNA (Chol#1-cRNA (LNA)(mMalat1), SEQ ID NO: 28) (a second strand), a cholesterol-conjugated heteroduplex oligonucleotide (Chol-HDO), which is a double-stranded nucleic acid agent, was prepared. Specifically, the double-stranded nucleic acid agent described above was prepared by adding the second strand (powder) to phosphate buffered saline (PBS) heated to 95° C., dissolving the strand by vortexing, mixing the resulting solution with the first strand solution heated to 95° C., maintaining the resulting solution mixture at 95° C. for five minutes, then maintaining the solution mixture at 37° C. for one hour, and thus annealing the nucleic acid strands. The annealed nucleic acid was stored at 4° C. or on ice. The prepared double-stranded nucleic acid agent is referred to as Chol#1HDO(LNA/LNA).

The names and sequences of the first strand and the second strand used in this Example are shown below.

```
First Strand: ASO(mMalat1)
                                (SEQ ID NO: 1)
5'-C*T*A*g*t*t*c*a*c*t*g*a*a*T*G*C-3'

Second Strand: Chol#1-cRNA(LNA)(mMalat1)
                                (SEQ ID NO: 28)
5'-Chol#1-G*C*A*UUCAGUGAAC*T*A*G-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#1 represents the above-mentioned cholesterol #1.

(In Vivo Experiment)

As described in Example 3, a single dose of the nucleic acid agent was administered to the mouse.

(Analysis of Expression)

Seventy-two hours after administration, PBS was perfused into the mice, and then, the mice were dissected to collect the cerebral cortex, cerebellum, striatum, hippocampus, brainstem, and cervical spinal cord separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 54:
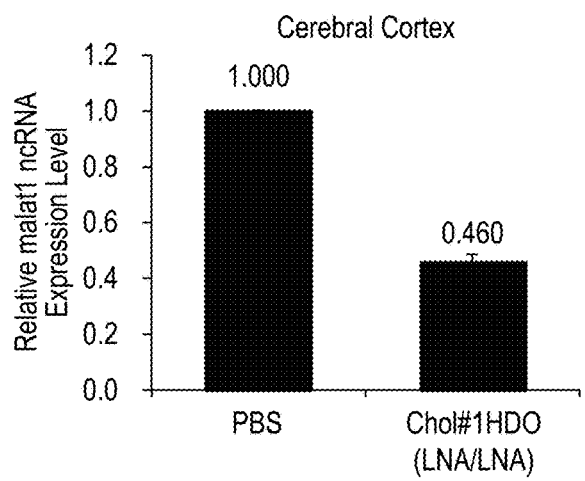
FIG. 54 shows graphs for the results of the experiment described in Example 29, and the graphs show suppression effects on the target transcription product (malat1) by a cholesterol-conjugated nucleic acid complex in various sites in the brain. The results are shown for (a) cerebral cortex, (b) cerebellum, (c) striatum, and (d) hippocampus. The error bars represent standard errors.
Figure 54:
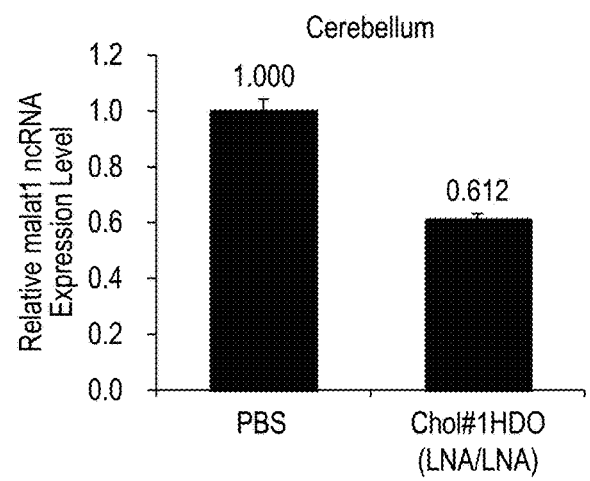
Figure 54:
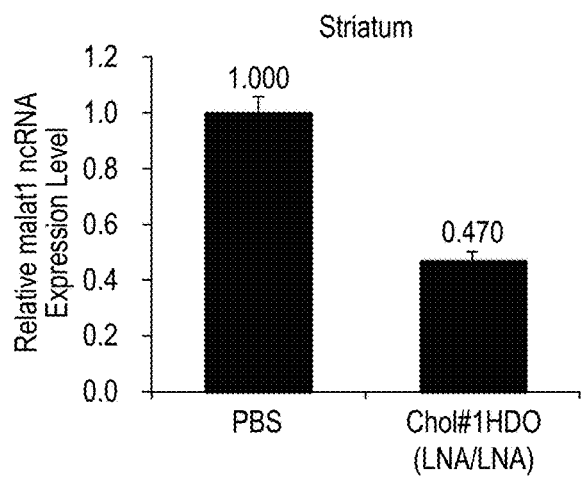
Figure 54:
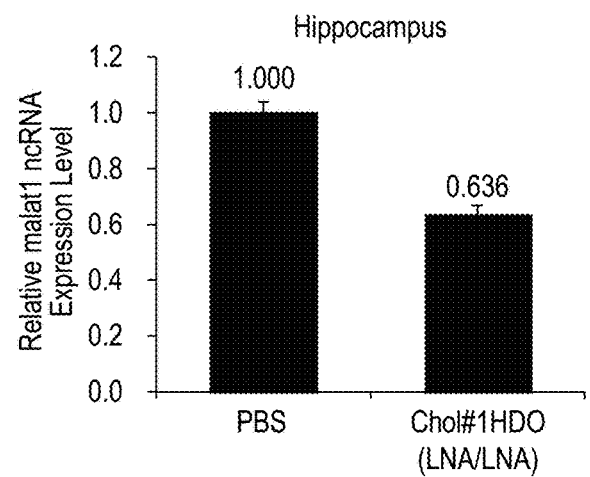
Figure 55:
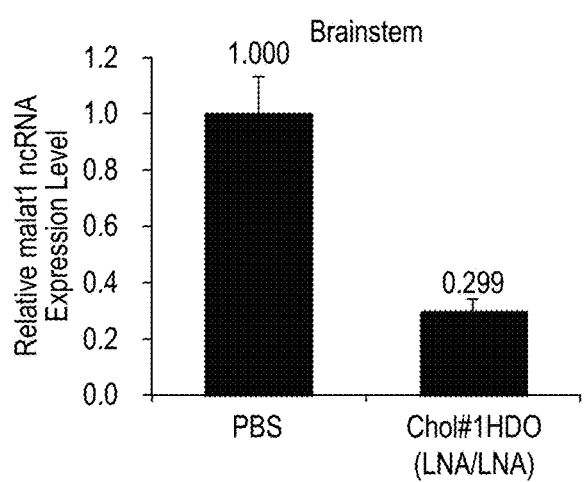
FIG. 55 shows graphs for the results of the experiment described in Example 29, and the graphs show suppression effects on the target transcription product (malat1) by a cholesterol-conjugated nucleic acid complex in various sites in the brain and spinal cord. The results are shown for (a) brainstem and (b) cervical spinal cord. The error bars represent standard errors.
Figure 55:
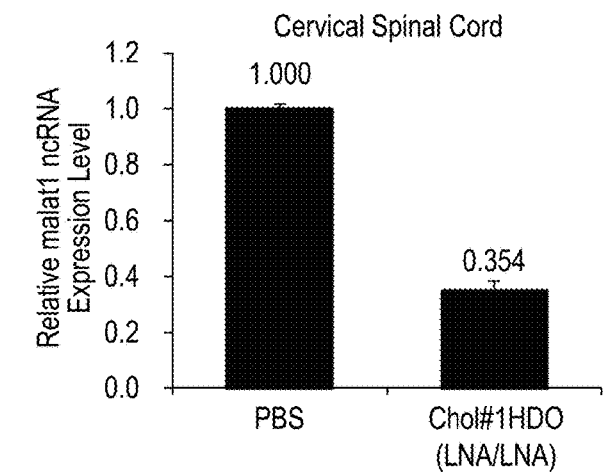

The results of Example 29 are shown by the graphs in FIG. 54 or 55. Chol#1HDO(LNA/LNA) suppressed the expression of the malat1 non-coding RNA in any of the cerebral cortex, cerebellum, striatum, hippocampus, brainstem, and cervical spinal cord, compared with the negative control (PBS alone).

These results have revealed that the double-stranded nucleic acid agent having a complementary strand (a second strand) having LNA positioned at both ends can be delivered to various sites in the brain and spinal cord and bring about an antisense effect.

Example 30

Evaluation of Antisense Effect Brought about in Various Sites of Brain and Spinal Cord by Administration of Single Dose of Double-Stranded Nucleic Acid Complex Consisting of Antisense Oligonucleotide and Cholesterol-Conjugated Complementary Strand An experiment was carried out to evaluate the in vivo inhibition potency of the double-stranded nucleic acid agent having a complementary strand (a second strand) wherein the conjugation between oligonucleotide and cholesterol are changed.

(Preparation of Nucleic Acid Agent)

The control (ASO) was a 16-mer single-stranded LNA/DNA gapmer (ASO(mMalat1), SEQ ID NO: 1) targeted at a malat1 non-coding RNA used in Example 1. By annealing this LNA/DNA gapmer (a first strand) to a cholesterol-conjugated complementary strand RNA (a second strand), a cholesterol-conjugated heteroduplex oligonucleotide (Chol-HDO), which is a double-stranded nucleic acid agent, was prepared. Two kinds of second strands were used as below-mentioned. The double-stranded nucleic acid agent described above was prepared by adding the second strand (powder) to phosphate buffered saline (PBS) heated to 95° C., dissolving the strand by vortexing, mixing the resulting solution with the first strand solution heated to 95° C., maintaining the resulting solution mixture at 95° C. for five minutes, then maintaining the solution mixture at 37° C. for one hour, and thus annealing the nucleic acid strands. The annealed nucleic acid was stored at 4° C. or on ice.

The double-stranded nucleic acid agent prepared using Chol#1-cRNA(PS)(mMalat1) as the second strand is referred to as Chol#1HDO(PS). Chol#1-cRNA(PS)(mMalat1) has a phosphorothioate conjugation between cholesterol and g at the 5' end of an oligonucleotide.

The double-stranded nucleic acid agent prepared using Chol#1-cRNA(DNA)(mMalat1) as the second strand is referred to as Chol#1HDO(DNA). In Chol#1-cRNA(DNA)(mMalat1) cholesterol and g at the 5' end are linked by DNA of 4 bases in length.

The names and sequences of the first strand and the second strand used in this Example are shown below.

```
First Strand: ASO(mMalat1)
                                          (SEQ ID NO: 1)
5'-C*T*A*g*t*t*c*a*c*t*g*a*a*T*G*C-3'

Second Strand: Chol#1-cRNA(PS)(mMalat1)
                                         (SEQ ID NO: 10)
5'-Chol#1*g*c*a*UUCAGUGAAC*u*a*g-3'

Second Strand: Chol#1-cRNA(DNA)(mMalat1)
                                         (SEQ ID NO: 29)
5'-Chol#1-cttcg*c*a*UUCAGUGAAC*u*a*g-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#1 represents the above-mentioned cholesterol #1.

(In Vivo Experiment)

As described in Example 3, a single dose of the nucleic acid agent was administered to the mouse.

(Analysis of Expression)

Seventy-two hours after administration, PBS was perfused into the mice, and then, the mice were dissected to collect the cerebral cortex, cerebellum, striatum, hippocampus, brainstem, cervical spinal cord, and lumbar spinal cord separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 56:
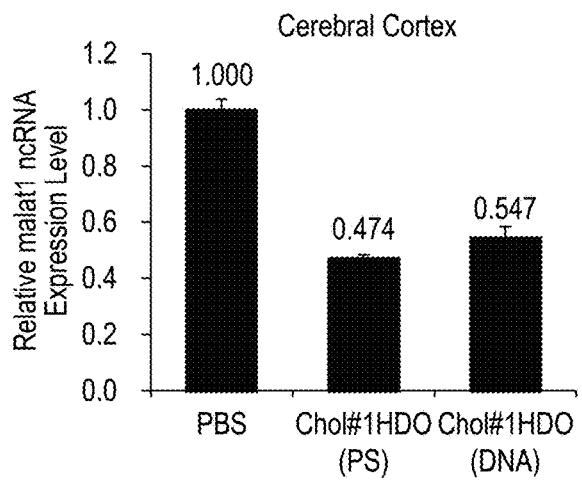
FIG. 56 shows graphs for the results of the experiment described in Example 30, and the graphs show suppression effects on the target transcription product (malat1) by cholesterol-conjugated nucleic acid complexes in various sites in the brain. The results are shown for (a) cerebral cortex, (b) cerebellum, (c) striatum, (d) hippocampus, and (e) brainstem. The error bars represent standard errors.
Figure 56:
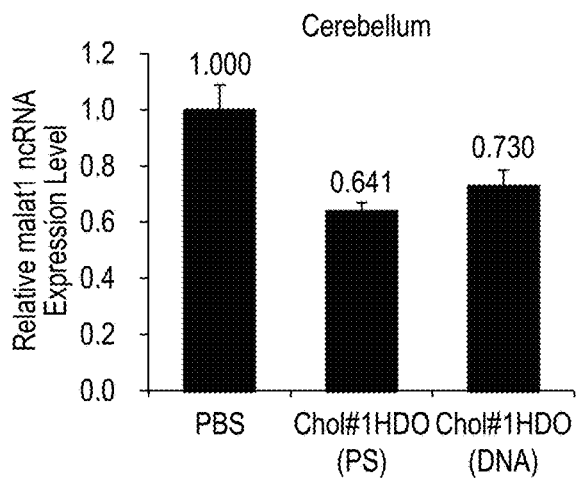
Figure 56:
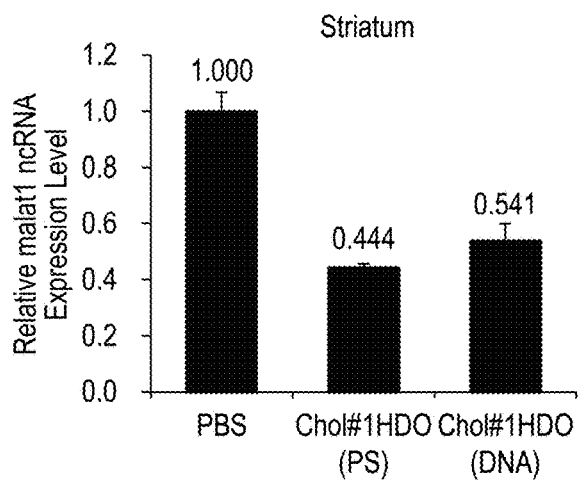
Figure 56:
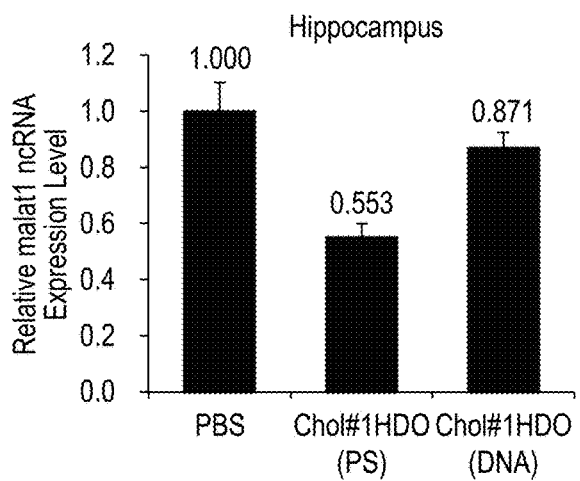
Figure 56:
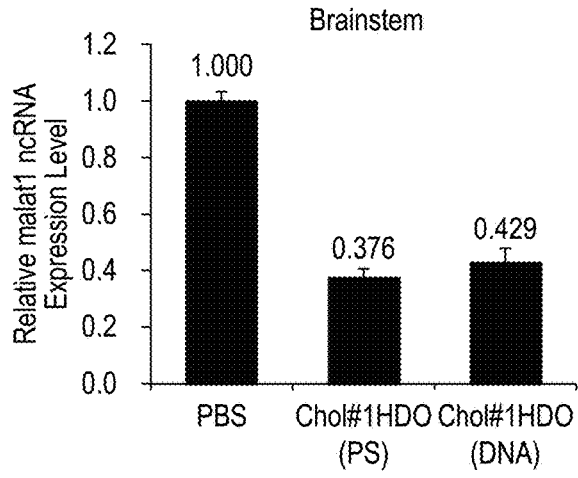
Figure 57:
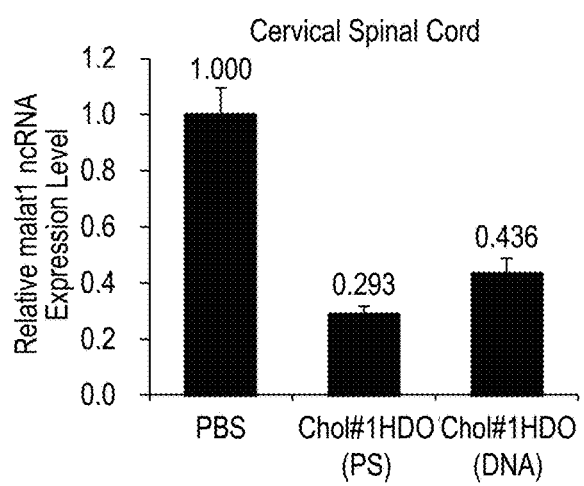
FIG. 57 shows graphs for the results of the experiment described in Example 30, and the graphs show suppression effects on the target transcription product (malat1) by cholesterol-conjugated nucleic acid complexes in various sites in the spinal cord. The results are shown for (a) cervical spinal cord and (b) lumbar spinal cord. The error bars represent standard errors.
Figure 57:
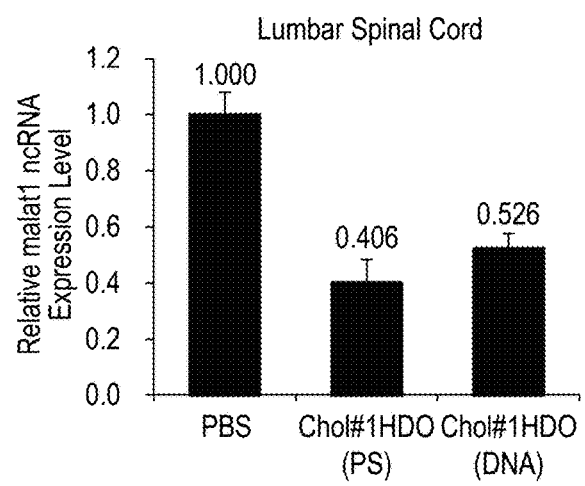

The results of Example 30 are shown by the graphs in FIG. 56 or 57. Chol#1HDO(PS) or Chol#1HDO(DNA) suppressed the expression of the malat1 non-coding RNA in any of the cerebral cortex, cerebellum, striatum, hippocampus, brainstem, cervical spinal cord, and lumbar spinal cord, compared with the negative control (PBS alone).

These results have revealed that Chol#1HDO(PS) or Chol#1HDO(DNA) can be delivered to various sites in the brain and spinal cord and bring about an antisense effect. Chol#1HDO(PS) exhibited a tendency to have a higher effect, compared with Chol#1HDO(DNA).

Example 31

Evaluation of Antisense Effect Brought about in Various Sites of Brain by Administration of Single Dose of Double-Stranded Nucleic Acid Complex Consisting of Antisense Oligonucleotide and Alkyl-Group-Conjugated Complementary Strand, Wherein the Alkyl Group has OH Group at an End An experiment was carried out to evaluate the in vivo inhibition potency of the double-stranded nucleic acid agent to which an alkyl group instead of a tocopherol or cholesterol is conjugated, wherein the alkyl group has an OH group at an end.

(Preparation of Nucleic Acid Agent)

The control (ASO) was a 16-mer single-stranded LNA/DNA gapmer (ASO(mMalat1), SEQ ID NO: 1) targeted at a malat1 non-coding RNA used in Example 1. By annealing this LNA/DNA gapmer (a first strand) to an alkyl-group-conjugated complementary strand RNA (a second strand), an alkyl-group-conjugated heteroduplex oligonucleotide, which is a double-stranded nucleic acid agent, was prepared. Three kinds of second strands were used as below-mentioned. The double-stranded nucleic acid agent described above was prepared by adding the second strand (powder) to phosphate buffered saline (PBS) heated to 95° C., dissolving the strand by vortexing, mixing the resulting solution with the first strand solution heated to 95° C., maintaining the resulting solution mixture at 95° C. for five minutes, then maintaining the solution mixture at 37° C. for one hour, and thus annealing the nucleic acid strands. The annealed nucleic acid was stored at 4° C. or on ice.

The double-stranded nucleic acid agent prepared using C6(OH)-cRNA(mMalat1) as the second strand is referred to as C6(OH)HDO.

The double-stranded nucleic acid agent prepared using C9(OH)-cRNA(mMalat1) as the second strand is referred to as C9(OH)HDO.

The double-stranded nucleic acid agent prepared using C12(OH)-cRNA(mMalat1) as the second strand is referred to as C12(OH)HDO.

The names and sequences of the first strand and the second strand used in this Example are shown below.

```
First Strand: ASO(mMalat1)
                                    (SEQ ID NO: 1)
5'-C*T*A*g*t*t*c*a*c*t*g*a*a*T*G*C-3'

Second Strand: C6(OH)-cRNA(mMalat1)
                                   (SEQ ID NO: 10)
5'-C6(OH)-g*c*a*UUCAGUGAAC*u*a*g-3'

Second Strand: C9(OH)-cRNA(mMalat1)
                                   (SEQ ID NO: 10)
5'-C9(OH)-g*c*a*UUCAGUGAAC*u*a*g-3'

Second Strand: C12(OH)-cRNA(mMalat1)
                                   (SEQ ID NO: 10)
5'-C12(OH)-g*c*a*UUCAGUGAAC*u*a*g-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. The structures of C6(OH), C9(OH), and C12(OH) are described above.

(In Vivo Experiment)

As described in Example 3, a single dose of the nucleic acid agent was administered to the mouse.

(Analysis of Expression)

Seventy-two hours after administration, PBS was perfused into the mice, and then, the mice were dissected to collect the cerebral cortex, cerebellum, striatum, hippocampus, and brainstem separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 58:
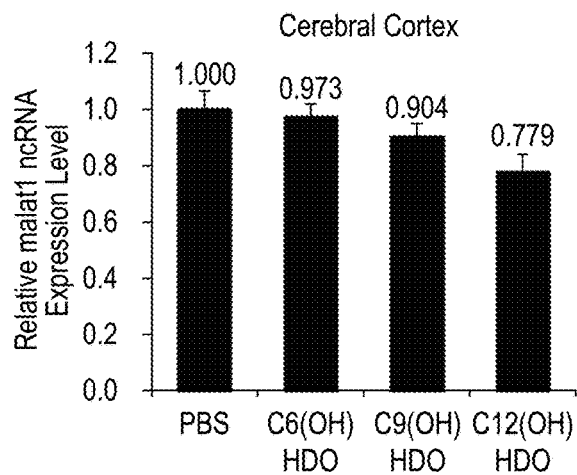
FIG. 58 shows graphs for the results of the experiment described in Example 31, and the graphs show suppression effects on the target transcription product (malat1) by nucleic acid complexes in various sites in the brain, wherein an alkyl group having an OH group at an end thereof is-conjugated to the nucleic acid complexes. The results are shown for (a) cerebral cortex, (b) cerebellum, (c) striatum, and (d) hippocampus. The error bars represent standard errors.
Figure 58:
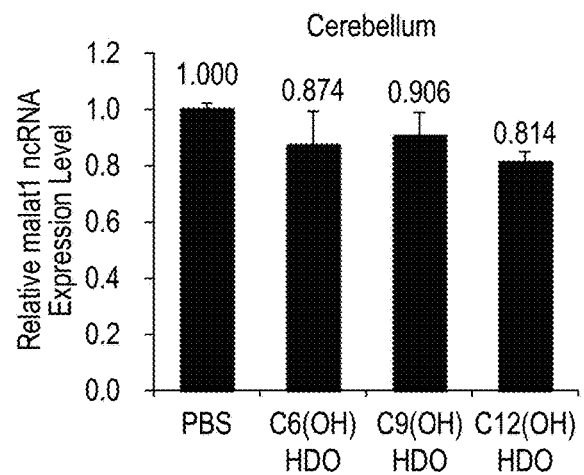
Figure 58:
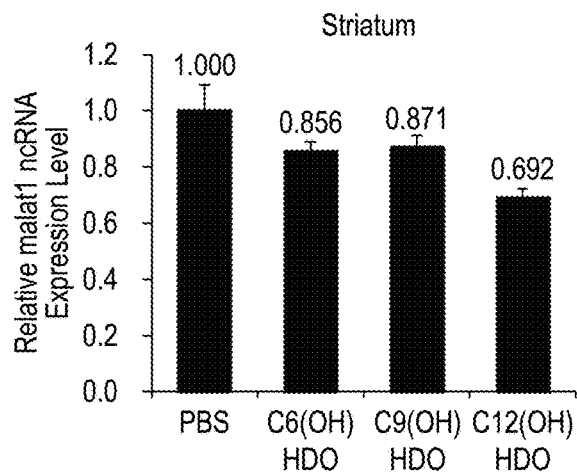
Figure 58:
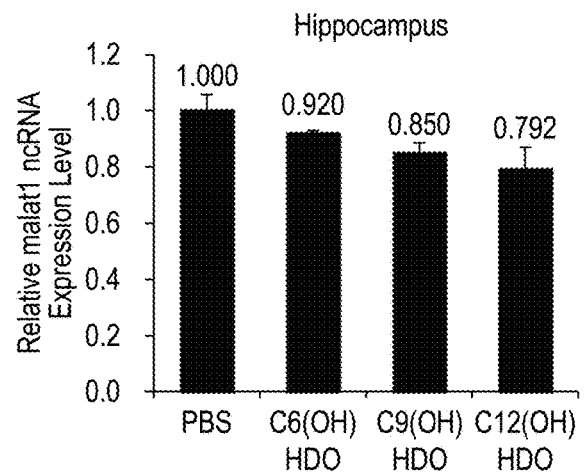
Figure 59:
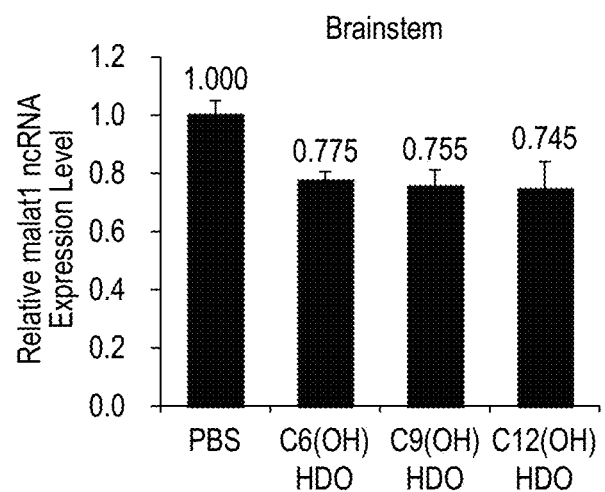
FIG. 59 is a graph showing the results of the experiment described in Example 31, and the graph shows suppression effects on the target transcription product (malat1) by nucleic acid complexes in the brainstem, wherein an alkyl group having an OH group at an end thereof is-conjugated to the nucleic acid complexes. The error bars represent standard errors.

The results of Example 31 are shown by the graphs in FIG. 58 or 59. C6(OH)HDO, C9(OH)HDO, and C12(OH)HDO suppressed the expression of the malat1 non-coding RNA in any of the cerebral cortex, cerebellum, striatum, hippocampus, and brainstem, compared with the negative control (PBS alone).

These results have revealed that C6(OH)HDO, C9(OH)HDO, or C12(OH)HDO can be delivered to various sites in the brain and bring about an antisense effect. C12(OH)HDO exhibited a tendency to have a higher effect, compared with C6(OH)HDO and C9(OH)HDO.

Example 32

Evaluation of Antisense Effect Brought about in Various Sites of Brain by Administration of Single Dose of Double-Stranded Nucleic Acid Complex Consisting of Antisense Oligonucleotide and Cholesterol-Conjugated Complementary Strand An experiment was carried out to evaluate the in vivo inhibition potency of the double-stranded nucleic acid agent wherein the structure of antisense oligonucleotide (a first strand) is changed to RNA having LNA positioned on both sides.

(Preparation of Nucleic Acid Agent)

The control (ASO) was a 16-mer single-stranded LNA/RNA gapmer (ASO(RNA)(mMalat1), SEQ ID NO: 30) targeted at a malat1 non-coding RNA. By annealing this LNA/RNA gapmer (a first strand) to a cholesterol-conjugated complementary strand RNA (Chol#1-cRNA (mMalat1), SEQ ID NO: 10) (a second strand), a cholesterol-conjugated heteroduplex oligonucleotide (Chol-HDO), which is a double-stranded nucleic acid agent, was prepared. Specifically, the double-stranded nucleic acid agent described above was prepared by adding the second strand (powder) to phosphate buffered saline (PBS) heated to 95° C., dissolving the strand by vortexing, mixing the resulting solution with the first strand solution heated to 95° C., maintaining the resulting solution mixture at 95° C. for five minutes, then maintaining the solution mixture at 37° C. for one hour, and thus annealing the nucleic acid strands. The annealed nucleic acid was stored at 4° C. or on ice. The prepared double-stranded nucleic acid agent is referred to as Chol#1HDO(RNA/RNA).

The names and sequences of the first strand and the second strand used in this Example are shown below.

```
First Strand: ASO(RNA)(mMalat1)
                                   (SEQ ID NO: 30)
5'-C*T*A*G*U*U*C*A*C*U*G*A*A*T*G*C-3'

Second Strand: Chol#1-cRNA(mMalat1)
                                   (SEQ ID NO: 10)
5'-Chol#1-g*c*a*UUCAGUGAAC*u*a*g-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#1 represents the above-mentioned cholesterol #1.

(In Vivo Experiment)

As described in Example 3, a single dose of the nucleic acid agent was administered to the mouse.

(Analysis of Expression)

Seventy-two hours after administration, PBS was perfused into the mice, and then, the mice were dissected to collect the cerebral cortex, cerebellum, striatum, hippocampus, and brainstem separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 60:
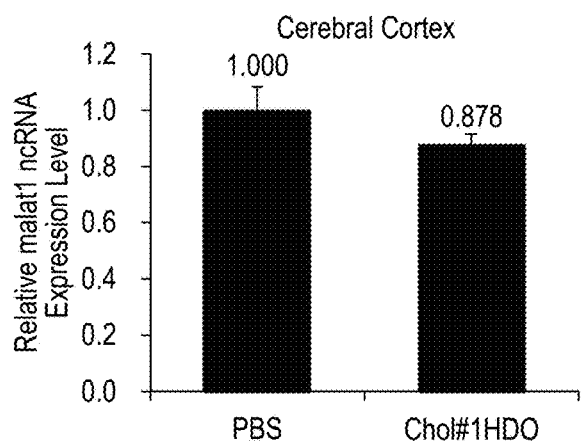
FIG. 60 shows graphs for the results of the experiment described in Example 32, and the graphs show suppression effects on the target transcription product (malat1) by a cholesterol-conjugated nucleic acid complex in various sites in the brain. The results are shown for (a) cerebral cortex, (b) cerebellum, (c) striatum, (d) hippocampus, and (e) brainstem. The error bars represent standard errors.
Figure 60:
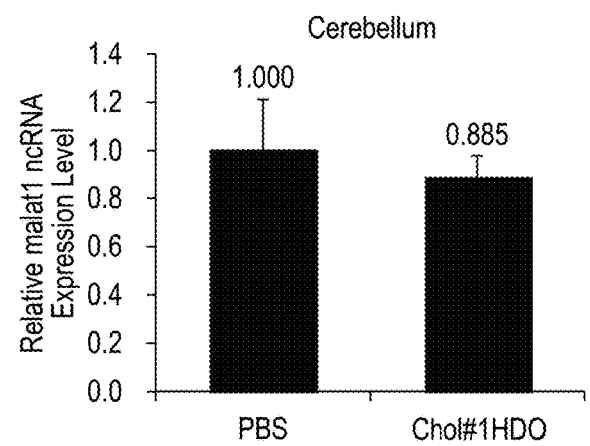
Figure 60:
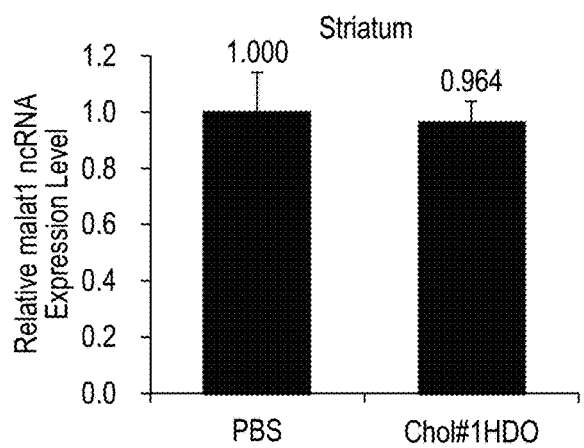
Figure 60:
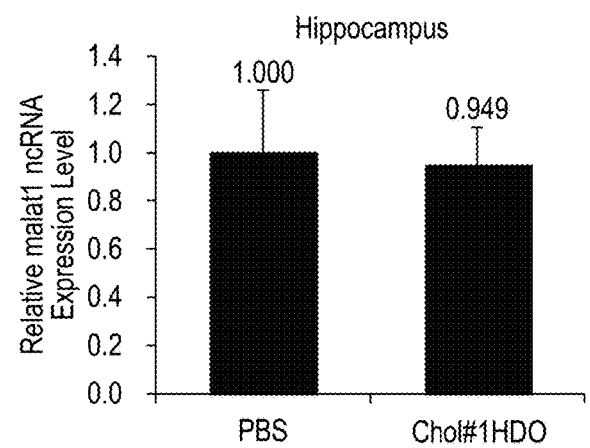
Figure 60:
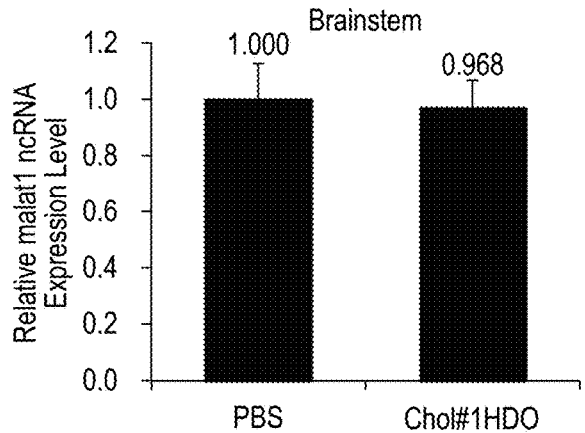

The results of Example 32 are shown by the graph in FIG. 60. Chol#1HDO(RNA/RNA) suppressed the expression of the malat1 non-coding RNA in any of the cerebral cortex, cerebellum, striatum, hippocampus, and brainstem, compared with the negative control (PBS alone).

Example 33

Evaluation of Antisense Effect Brought about in Various Sites of Brain by Administration of Single Dose of Double-Stranded Nucleic Acid Complex Consisting of Antisense Oligonucleotide and Alkyl-Group-Conjugated Complementary Strand An experiment was carried out to evaluate the in vivo inhibition potency of the double-stranded nucleic acid agent to which an alkyl group instead of a tocopherol or cholesterol is conjugated.

(Preparation of Nucleic Acid Agent)

The control (ASO) was a 16-mer single-stranded LNA/DNA gapmer (ASO(mMalat1), SEQ ID NO: 1) targeted at a malat1 non-coding RNA used in Example 1. By annealing this LNA/DNA gapmer (a first strand) to an alkyl-group-conjugated complementary strand RNA (a second strand), an alkyl-group-conjugated heteroduplex oligonucleotide, which is a double-stranded nucleic acid agent, was prepared. Five kinds of second strands were used as below-mentioned. The double-stranded nucleic acid agent described above was prepared by adding the second strand (powder) to phosphate buffered saline (PBS) heated to 95° C., dissolving the strand by vortexing, mixing the resulting solution with the first strand solution heated to 95° C., maintaining the resulting solution mixture at 95° C. for five minutes, then maintaining the solution mixture at 37° C. for one hour, and thus annealing the nucleic acid strands. The annealed nucleic acid was stored at 4° C. or on ice.

The double-stranded nucleic acid agent prepared using C3-cRNA(mMalat1) as the second strand is referred to as C3HDO.

The double-stranded nucleic acid agent prepared using C4-cRNA(mMalat1) as the second strand is referred to as C4HDO.

The double-stranded nucleic acid agent prepared using C8-cRNA(mMalat1) as the second strand is referred to as C8HDO.

The double-stranded nucleic acid agent prepared using C10-cRNA(mMalat1) as the second strand is referred to as C10HDO.

The double-stranded nucleic acid agent prepared using C12-cRNA(mMalat1) as the second strand is referred to as C12HDO.

The names and sequences of the first strand and the second strand used in this Example are shown below.

```
First Strand: ASO(mMalat1)
                                          (SEQ ID NO: 1)
5'-C*T*A*g*t*t*c*a*c*t*g*a*a*T*G*C-3'

Second Strand: C3-cRNA(mMalat1)
                                         (SEQ ID NO: 10)
5'-C3-g*c*a*UUCAGUGAAC*u*a*g-3'

Second Strand: C4-cRNA(mMalat1)
                                         (SEQ ID NO: 10)
5'-C4-g*c*a*UUCAGUGAAC*u*a*g-3'

Second Strand: C8-cRNA(mMalat1)
                                         (SEQ ID NO: 10)
5'-C8-g*c*a*UUCAGUGAAC*u*a*g-3'

Second Strand: C10-cRNA(mMalat1)
                                         (SEQ ID NO: 10)
5'-C10-g*c*a*UUCAGUGAAC*u*a*g-3'

Second Strand: C12-cRNA(mMalat1)
                                         (SEQ ID NO: 10)
5'-C12-g*c*a*UUCAGUGAAC*u*a*g-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. The structures of C3, C4, C8, C10, and C12 are described above.

(In Vivo Experiment)

As described in Example 3, a single dose of the nucleic acid agent was administered to the mouse.

(Analysis of Expression)

Seventy-two hours after administration, PBS was perfused into the mice, and then, the mice were dissected to collect the cerebral cortex, cerebellum, striatum, hippocampus, and brainstem separately. Using obtained each tissue, RNA extraction, cDNA synthesis, and quantitative RT-PCR were carried out, and the expression level of the malat1 non-coding RNA was evaluated in the same manner as described in Example 1 except that actin was used as an internal standard gene instead of GAPDH in the quantitative RT-PCR.

(Results)

Figure 61:
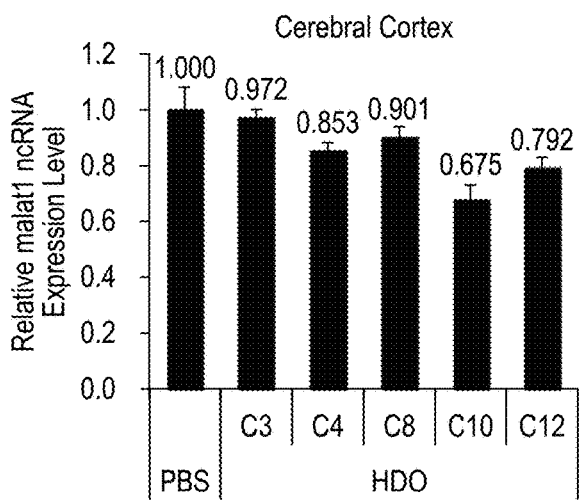
FIG. 61 shows graphs for the results of the experiment described in Example 33, and the graphs show suppression effects on the target transcription product (malat1) by alkyl-group-conjugated nucleic acid complexes in various sites in the brain. The results are shown for (a) cerebral cortex, (b) cerebellum, (c) striatum, and (d) hippocampus. The error bars represent standard errors.
Figure 61:
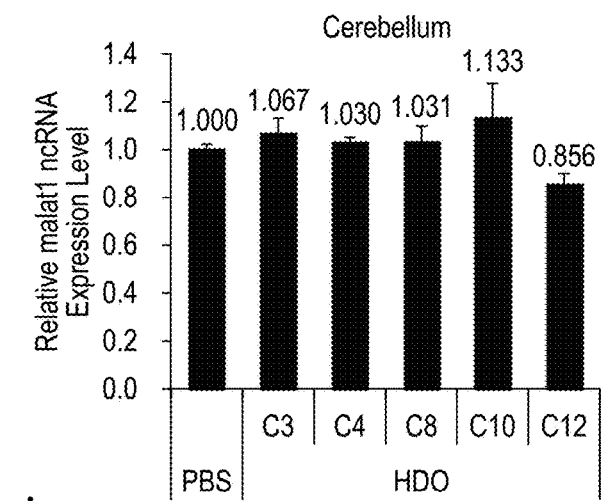
Figure 61:
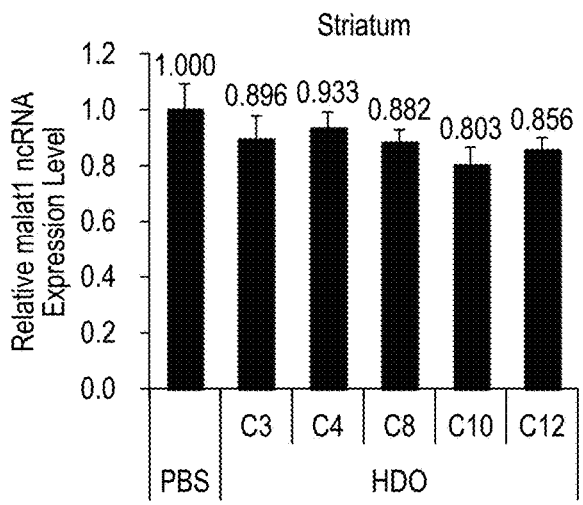
Figure 61:
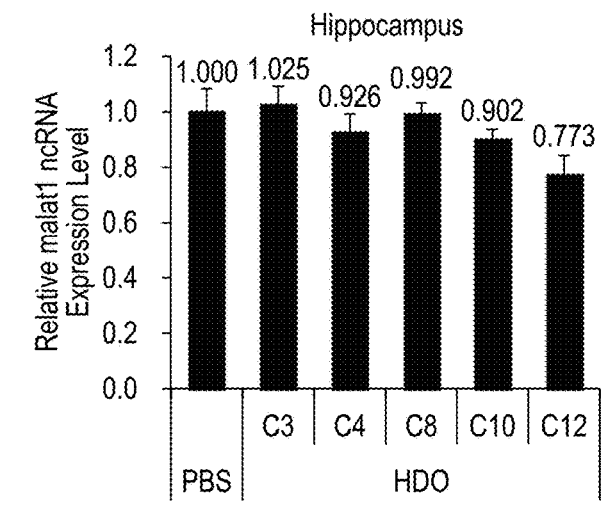
Figure 62:
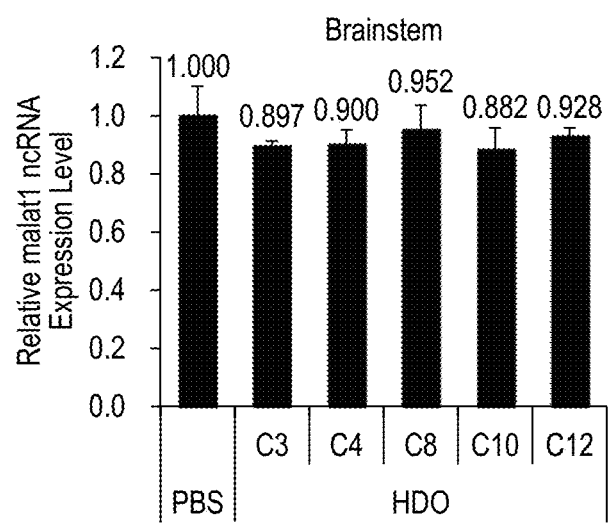
FIG. 62 is a graph showing the results of the experiment described in Example 33, and the graph shows suppression effects on the target transcription product (malat1) by alkyl-group-conjugated nucleic acid complexes in the brainstem. The error bars represent standard errors.

The results of Example 33 are shown by the graphs in FIG. 61 or 62. C3HDO, C4HDO, C8HDO, C10HDO, and C12HDO suppressed the expression of the malat1 non-coding RNA in any of the cerebral cortex, cerebellum, striatum, hippocampus, and brainstem, compared with the negative control (PBS alone).

Example 34

Evaluation of Impact on Platelet Numbers by Administration of Double-Stranded Nucleic Acid Complex Consisting of Antisense Oligonucleotide and Cholesterol-Conjugated Complementary Strand An experiment was carried out to evaluate the impact on platelet numbers by the double-stranded nucleic acid agent.

(Preparation of Nucleic Acid Agent)

The control (ASO) was a 16-mer single-stranded LNA/DNA gapmer (ASO(mMalat1), SEQ ID NO: 1) targeted at a malat1 non-coding RNA used in Example 1. By annealing this LNA/DNA gapmer (a first strand) to a cholesterol-conjugated complementary strand RNA (Chol#1-cRNA (mMalat1), SEQ ID NO: 10) (a second strand), a cholesterol-conjugated heteroduplex oligonucleotide (Chol-HDO), which is a double-stranded nucleic acid agent, was prepared. Specifically, the double-stranded nucleic acid agent described above was prepared by adding the second strand (powder) to phosphate buffered saline (PBS) heated to 95° C., dissolving the strand by vortexing, mixing the resulting solution with the first strand solution heated to 95° C., maintaining the resulting solution mixture at 95° C. for five minutes, then maintaining the solution mixture at 37° C. for one hour, and thus annealing the nucleic acid strands. The annealed nucleic acid was stored at 4° C. or on ice. The prepared double-stranded nucleic acid agent is referred to as Chol#1HDO.

The names and sequences of the first strand and the second strand used in this Example are shown below.

```
First Strand: ASO(mMalat1)
                                          (SEQ ID NO: 1)
5'-C*T*A*g*t*t*c*a*c*t*g*a*a*T*G*C-3'

Second Strand: Chol#1-cRNA(mMalat1)
                                         (SEQ ID NO: 10)
5'-Chol#1-g*c*a*UUCAGUGAAC*u*a*g-3'
```

The underlined upper case letters represent LNA (C represents 5-methylcytosine LNA), the lower case letters represent DNA, the upper case letters represent RNA, the underlined lower case letters represent 2'-O-methylated RNA, and the asterisks represent a phosphorothioate bond. Chol#1 represents the above-mentioned cholesterol #1.

(In Vivo Experiment)

The number of platelets was measured after administering the nucleic acid agent to the mouse intravenously at a dose of 25 mg/kg twice (at intervals of three days) or administering intravenously at a dose of 50 mg/kg once. In addition, the number of platelets was measured after administering the nucleic acid agent to the mouse intravenously at a dose of 50 mg/kg once or administering subcutaneously at a dose of 50 mg/kg once.

(Analysis of Number of Platelets)

Seventy-two hours or seven days after administration, blood was collected, and the number of platelets was measured by LSI Medience Corporation.

(Results)

Figure 63:
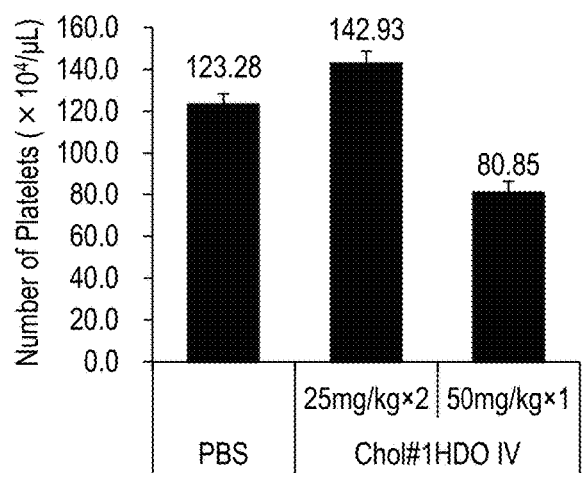
FIG. 63 shows graphs for the results of the experiment described in Example 34, and the graphs show platelet inhibition effects by a cholesterol-conjugated nucleic acid complex. (a) A comparison between one dose of 50 mg/kg and two doses of 25 mg/kg each in intravenous administration of a cholesterol-conjugated nucleic acid complex. (b) A comparison between intravenous administration and subcutaneous administration of a single dose of a 50 mg/kg cholesterol-conjugated nucleic acid complex. The error bars represent standard errors.
Figure 63:
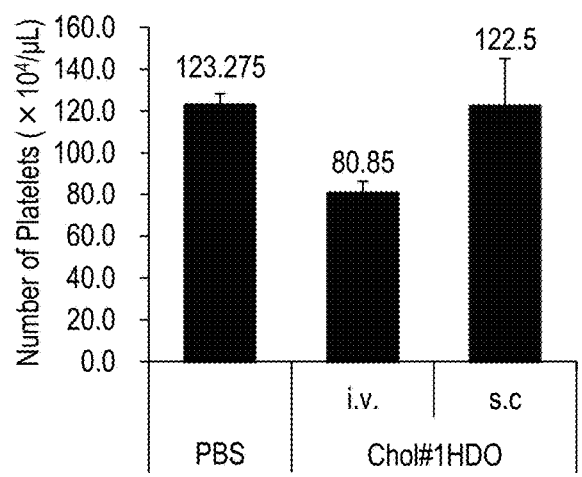

The results of Example 34 are shown by the graph in FIG. 63. Administering a dose of 25 mg/kg intravenously twice did not exhibit a reduction in the number of platelets, compared with administering a dose of 50 mg/kg intravenously once. In addition, administering a dose of 50 mg/kg subcutaneously once did not exhibit a reduction in the number of platelets, compared with administering a dose of 50 mg/kg intravenously once.

These results have revealed that the double-stranded nucleic acid agent according to the present invention can avoid a reduction in the number of platelets by reducing the amount of one dose or subcutaneously administering a dose.

All publications, patents, and patent applications cited herein are incorporated herein by reference in their entirety.

The invention claimed is:

1. A method for treating a central nervous system disease of a subject by reducing the expression level of a target transcription product in the central nervous system of the subject, comprising intravenously or subcutaneously administering to the subject a double-stranded nucleic acid agent consisting of a first nucleic acid strand and a second nucleic acid strand,
   wherein the first nucleic acid strand comprises a base sequence capable of hybridizing with at least part of the target transcription product and has an antisense effect on the target transcription product;
   wherein the second nucleic acid strand comprises a base sequence complementary to the first nucleic acid strand and is conjugated to a tocopherol, cholesterol, or an analog thereof;
   wherein the first nucleic acid strand is annealed to the second nucleic acid strand;
   wherein the first nucleic acid strand is a gapmer or a mixmer, and
wherein the subject has a central nervous system disease.

2. The method according to claim 1, wherein the first nucleic acid strand comprises at least four consecutive deoxyribonucleosides.

3. The method according to claim 2, wherein the second nucleic acid strand comprises at least four consecutive ribonucleosides complementary to the at least four consecutive deoxyribonucleosides in the first nucleic acid strand.

4. The method according to claim 1, wherein the first nucleic acid strand is 13 to 20 bases in length.

5. The method according to claim 1, wherein the central nervous system is selected from the group consisting of cerebral cortex, basal ganglion, cerebral white matter, diencephalon, brainstem, cerebellum, and spinal cord.

6. The method according to claim 1, wherein the central nervous system is selected from the group consisting of frontal lobe, temporal lobe, hippocampus, parahippocampal gyms, parietal lobe, occipital lobe, striatum, globus pallidus, claustrum, thalamus, subthalamic nucleus, midbrain, substantia nigra, pons, medulla oblongata, cerebellar cortex, cerebellar nucleus, cervical spinal cord, thoracic spinal cord, and lumbar spinal cord.

7. The method according to claim 1, wherein the double-stranded nucleic acid agent is administered at 5 mg/kg or more per dose.

8. The method according to claim 1, wherein the second nucleic acid strand does not comprise natural ribonucleosides.

9. The method according to claim 1, wherein the nucleic acid portion of the second nucleic acid strand consists of deoxyribonucleosides and/or sugar-modified nucleosides, wherein the deoxyribonucleosides and/or sugar-modified nucleosides are linked by a modified or unmodified internucleoside linkage.

10. The method according to claim 1, wherein a ligand is conjugated to the second nucleic acid strand via an uncleavable linker.

11. The method according to claim 1, wherein the double-stranded nucleic acid agent permeates the blood brain barrier (BBB).

12. The method according to claim 1, wherein the second nucleic acid is conjugated to a tocopherol.

* * * * *

SEQUENCE LISTING

```
<160> NUMBER OF SEQ ID NOS: 30

<210> SEQ ID NO 1
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2)..(3), (14)..(15)
<223> OTHER INFORMATION: LNA
<220> FEATURE:
<221> NAME/KEY: misc_feature
<222> LOCATION: (1)..(1), (16)..(16)
<223> OTHER INFORMATION: 5-methylcytosine LNA

<400> SEQUENCE: 1
ctagttcact gaatgc                                                       16

<210> SEQ ID NO 2
<211> LENGTH: 16
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (2)..(3), (14)..(16)
<223> OTHER INFORMATION: 2'-O-Me RNA
<220> FEATURE:
<221> NAME/KEY: misc_feature
<222> LOCATION: (1)..(1)
<223> OTHER INFORMATION: Tocopherol-conjugated 2'-O-Me RNA

<400> SEQUENCE: 2
gcauucagug aacuag                                                       16

<210> SEQ ID NO 3
<211> LENGTH: 14
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1), (13)..(13)
<223> OTHER INFORMATION: LNA
<220> FEATURE:
<221> NAME/KEY: misc_feature
<222> LOCATION: (2)..(2), (14)..(14)
<223> OTHER INFORMATION: 5-methylcytosine LNA

<400> SEQUENCE: 3
tcagtcatga cttc                                                         14
```

-continued

```
<210> SEQ ID NO 4
<211> LENGTH: 14
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (2)..(2), (13)..(14)
<223> OTHER INFORMATION: 2'-O-Me RNA
<220> FEATURE:
<221> NAME/KEY: misc_feature
<222> LOCATION: (1)..(1)
<223> OTHER INFORMATION: Tocopherol-conjugated 2'-O-Me RNA

<400> SEQUENCE: 4
gaagucauga cuga                                                       14

<210> SEQ ID NO 5
<211> LENGTH: 16
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (2)..(3), (14)..(16)
<223> OTHER INFORMATION: 2'-O-Me RNA
<220> FEATURE:
<221> NAME/KEY: misc_feature
<222> LOCATION: (1)..(1)
<223> OTHER INFORMATION: Cholesterol-conjugated 2'-O-Me RNA

<400> SEQUENCE: 5
gcauucagug aacuag                                                     16

<210> SEQ ID NO 6
<211> LENGTH: 6982
<212> TYPE: DNA
<213> ORGANISM: Mus musculus

<400> SEQUENCE: 6
aggcattcag gcagcgagag cagagcagcg tagagcagca cagctgagct cgtgaggcag      60
gagactcagc ccgaggaaat cgcagataag ttttaattaa aaagattga gcagtaaaaa      120 gaattagaac tctaaactta agctaataga gtagcttatc gaaatattac ttagtcttaa     180
taatctaaga agatcttaag agataacatg aaggcttatt taaacagttt gaaaaaggaa     240
atgaggagaa aagtatttgt actgtataat ggaggctgac cagagcagtt taggagattg     300
taaagggagg ttttgtgaag ttctaaaagg ttctagtttg aaggtcggcc ttgtagatta     360
aaacgaaggt tacctaaata gaatctaagt ggcatttaaa acagtaaagt tgtagagaat     420
agtttgaaaa tgaggtgtag ttttaaagaa ttgagaaaag taggttaagt tgacggccgt     480
tataaaaatc cttcgactgg cgcatgtacg tttgaaggca tgagttggaa acagggaaga     540
tggaagtgtt aggctagccg ggcgatggtg gcgcacgcct ttaatcctag cacttgggag     600
gcagaggcag gcggatttct gagttcgagg ccagcctggt ctacagagtg agttccagga     660
cagccagggc tacacagaga aaccctgtct tgaaaaaaca aaaaggttag gctagtattt     720
ggagaaagaa gattagaaaa tggaagtgaa agacgaagaa gacatacagg aaggtgaaga     780
aaaagctgtt agagaagata ggaaaataga agacaaagca tctttagaag acagaaaagg     840
tacttaaagg cacaggtagt aggaagccga agaatagaag atagaaagaa gcaagataga     900
aaaacaaaat ggaagttaag acaactttgg atgccagcat tcaagatagg caaagaagat     960
```

```
aagattgagg ccaaaaggtt ggataagata taaagtcaga aggaaattat ctttaaagcc    1020
ataagttcaa atttctgatg gagcgagcag tttagaagag tctttagaca gccacataca    1080
agattgaagc tagcaatcaa agctactagg actgaagtaa aaagttaagg cagaatgcct    1140
ttgaagagtt agaagaatat taaaagcctt aacttgtagc ttaattttgc ttgatgacaa    1200
aaggactttt gataacagtt tcaagattgt cagcattttg cattggactt gagctgaggt    1260
gcttttaaaa tcctaacgac tagcattggc agctgaccca ggtctacaca gaagtgcatt    1320
cagtgaacta ggaagacagg agcggcagac aggagtcccg aagccagttt ggtgaagcta    1380
ggaaggactg aggagccagc agcagcagtg catggtgaag atagcccagg aaagagtgcg    1440
gttcggtgga ggaagctagg aagaaggagc catacggatg tggtggtgaa gctgggaaag    1500
ggttccagga tggtggagcg agagcgagtt ggtgatgaag ctagctggcg gcttggcttg    1560
tcaactgcgc ggaggaggcg agcaggcatt gtggagagga tagatagcgg ctcctagacc    1620
agcatgccag tgtgcaagaa aggctgcagg gagagcatgc ggtgcggtaa cattccttga    1680
ggtcggcaac atggtggtgg ttttctgtaa cttggatggt aacttgttta ctttgtctta    1740
atagttatgg gggagttgta ggcttctgtg taaagagata tatctggggc tgtatgtagg    1800
cctttgcggg tgttgtaggt ttttcttttt caggggttatg tcctcttgca tcttgtcaga    1860
agcttttgag ggctgactgc caaggcccag aaagaagaat ggtagatggc aagttgtctt    1920
taaccgctca gaggggaatg aatggtagag ccagcacaac ctcccagttt tgtaagacgt    1980
tgtagtttga acagatgacc taccacaagc ctcactcctg tgtaggggag gtaattgggc    2040 aaaagtgcttt tgggggaatg ggggcaaaat atattttgag ttcttttccc cttaggtctg    2100
tctagaatcc taaaggcaga tgactcaagg gaaccagaaa aaaggaaatc cactctcagg    2160
ataagcagag ctcgccaggt ttacagtttg taggaagtag aggatggatg ctagctttca    2220
cactgagtgt ggaggagctg gccatggcgg aattgctggt agtttactct ttccccctcc    2280
cttaatgaga tttgtaaaat cctaaacact tttacttgaa atatttggga gtggtcttaa    2340
cagggaggag tgggtggggg aaacgttttt tttctaagat tttccacaga tgctatagtt    2400
gtgttgacac actgggttag agaaggcgtg tactgctatg ctgttggcac gacaccttca    2460
gggactggag ctgccttttg tccttggaag agttttccca gttgccgctg aagtcagcac    2520
agtgcggctt tggttcacag tcacctcagg agaacctcag gagcttggct aggccagagg    2580
ttgaagttaa gttttacagc accgtgattt aaaatatttc attaaggggg aggggtaaaa    2640
cttagttggc tgtggccttg tgtttgggtg ggtgggggtg ttaggtaatt gtttagttta    2700
tgatttcaga taatcatacc agagaactta aatatttgga aaaacaggaa atctcagctt    2760
tcaagttggc aagtaactcc caatccagtt tttgcttctt ttttccttttt tcttttttttg    2820 aggcgggcag ctaaggaagg ttggttcctc tgccggtccc tcgaaagcgt agggcttggg    2880
ggttggtctg gtccactggg atgatgtgat gctacagtgg ggactcttct gaagctgttg    2940
gatgaatata gattgtagtg tgtggttctc ttttgaaatt ttttcaggt gacttaatgt    3000 atcttaataa ctactatagg aacaaaggaa gtggctttaa tgaccctgaa ggaatttctt    3060
ctggtgatag ctttttatatt atcaagtaag agatactatc tcagttttgt ataagcaagt    3120 cttttttccta gtgtaggaga aatgattttc cttgtgacta aacaagatgt aaaggtatgc    3180
tttttttctt cttgtgcatt gtatacttgt gtttatttgt aacttataat ttaagaatta    3240
tgataattca gcctgaatgt cttttagagg gtgggctttt gttgatgagg gaggggaaac    3300
cttttttttt ctgtagacct ttttcagata acaccatctg agtcataacc agcctggcag    3360
```

-continued

```
tgtgatgacg tagatgcaga gggagcagct ccttggtgaa tgagtgataa gtaaaggcag    3420
aaaaaataat gtcatgtctc catggggaat gagcatgagc cagagattgt tcctactgat    3480
gaaaagctgc atatgcaaaa atttaagcaa atgaaagcaa ccagtataaa gttatggcaa    3540
tacctttaaa agttatggct tatctaccaa gctttatcca caaaagtaaa gaattgatga    3600
aaaacagtga agatcaaatg ttcatctcaa aactgctttt acaaaagcag aatagaaatg    3660
aagtgaaaat gctgcattaa gcctggagta aaaagaagct gagcttgttg agatgagtgg    3720
gatcgagcgg ctgcgaggcg gtgcagtgtg ccaatgtttc gtttgcctca gacaggtttc    3780
tcttcataag cagaagagtt gcttcattcc atctcggagc aggaaacagc agactgctgt    3840
tgacagataa gtgtaacttg gatctgcagt attgcatgtt agggatagat aagtgccttt    3900
tttctctttt tccaaaaaga cctgtagagc tgttgaatgt ttgcagctgg cccctcttag    3960
gcagttcaga attttgagta gttttcccat ccagcctctt aaaaattcct aagccttgca    4020
ccgatgggct ttcatgatgg atagctaat aggcttttgc atcgtaaact tcaacacaaa    4080
agcctacatg attaatgcct actttaatta cattgcttac aagattaagg aatctttatc    4140
ttgaagaccc catgaaaggg atcattatgt gctgaaaatt agatgttcat attgctaaaa    4200
tttaaatgtg ctccaatgta cttgtgctta aaatcattaa attatacaaa ttaataaaat    4260
acttcactag agaatgtatg tatttagaag gctgtctcct tatttaaata aagtcttgtt    4320
tgttgtctgt agttagtgtg ggcaattttg gggggatgtt cttctctaat cttttcagaa    4380
acttgacttc gaacacttaa gtggaccaga tcaggatttg agccagaaga ccgaaattaa    4440
ctttaaggca ggaaagacaa attttattct ccatgcagtg atgagcattt ataattgca    4500 ggcctggcat agaggccgtc taactaagga ctaagtacct taggcaggtg ggagatgatg    4560
gtcagagtaa aaggtaacta catattttgt ttccagaaag tcaggggtct aatttgacca    4620
tggctaaaca tctagggtaa gacacttttc ccccacattt ccaaatatgc atgttgagtt    4680
taaatgctta cgatcatctc atccacttta gccttttgtc acctcacttg agccacgagt    4740
ggggtcaggc atgtgggttt aaagagtttt cctttgcaga gcctcatttc atccttcatg    4800
gagctgctca ggactttgca tataagcgct tgcctctgtc ttctgttctg ctagtgagtg    4860
tgtgatgtga gaccttgcag tgagtttgtt tttcctggaa tgtggaggga gggggggatg    4920
gggcttactt gttctagctt tttttttaca gaccacacag aatgcaggtg tcttgacttc    4980
aggtcatgtc tgttctttgg caagtaatat gtgcagtact gttccaatct gctgctatta    5040
gaatgcattg tgacgcgact ggagtatgat taaagaaagt tgtgtttccc caagtgtttg    5100
gagtagtggt tgttggagga aaagccatga gtaacaggct gagtgttgag gaaatggctc    5160
tctgcagctt taagtaaccc gtgtttgtga ttggagccga gtccctttgc tgtgctgcct    5220
taggtaaatg ttttttgttca tttctggtga ggggggttgg gagcactgaa gcctttagtc    5280
tcttccagat tcaacttaaa atctgacaag aaataaatca gacaagcaac attcttgaag    5340
aaattttaac tggcaagtgg aaatgttttg aacagttccg tggtctttag tgcattatct    5400
ttgtgtaggt gttctctctc ccctcccttg gtcttaattc ttacatgcag gaacattgac    5460
aacagcagac atctatctat tcaaggggcc agagaatcca gacccagtaa ggaaaaatag    5520
cccatttact ttaaatcgat aagtgaagca gacatgccat tttcagtgtg gggattggga    5580
agccctagtt ctttcagatg tacttcagac tgtagaagga gcttccagtt gaattgaaat    5640
tcaccagtgg acaaaatgag gacaacaggt gaacgagcct tttcttgttt aagattagct    5700
```

-continued

```
actggtaatc tagtgttgaa tcctctccag cttcatgctg gagcagctag catgtgatgt    5760
aatgttggcc ttggggtgga ggggtgaggt gggcgctaag cctttttta agattttca     5820 ggtacccctc actaaaggca ctgaaggctt aatgtaggac agcggagcct tcctgtgtgg    5880
caagaatcaa gcaagcagta ttgtatcgag accaaagtgg tatcatggtc ggttttgatt    5940
agcagtgggg actaccctac cgtaacacct tgttggaatt gaagcatcca agaaaatac    6000 ttgagaggcc ctgggcttgt tttaacatct ggaaaaaagg ctgttttat agcagcggtt    6060 accagcccaa acctcaagtt gtgcttgcag gggagggaaa aggggaaag cgggcaacca   6120 gtttccccag cttttccaga atcctgttac aaggtctccc cacaagtgat ttctctgcca    6180
catcgccacc atgggccttt ggcctaatca cagacccttc acccctcacc ttgatgcagc    6240
cagtagctgg atccttgagg tcacgttgca tatcggtttc aaggtaacca tggtgccaag    6300
gtcctgtggg ttgcaccaga aaaggccatc aattttcccc ttgcctgtaa tttaacatta    6360
aaaccatagc taagatgttt tatacatagc acctatgcag agtaaacaaa ccagtatggg    6420
tatagtatgt ttgataccag tgctgggtgg gaatgtagga agtcgatga aaagcaagcc    6480 tttgtaggaa gttgttgggg tgggattgca aaaattctct gctaagactt tttcaggtgg    6540
acataacaga cttggccaag ctagcatctt agtggaagca gattcgtcag tagggttgta    6600 aaggttttc ttttcctgag aaaacaacct tttgttttct caggttttgc ttttggcct     6660 ttccctagct ttaaaaaaaa aaagcaaaa acgctggtg gctggcactc ctggtttcca     6720
ggacggggtt caagtccctg cggtgtcttt gcttgactct tatatcatga ggccattaca    6780
tttttcttgg agggttctaa aggctctggg tatggtagct gatatcactg gaacactccc    6840
cagcctcagt gttgaactct tgataattaa ctgcattgtc tttcaggtta tgcccaattc    6900
gtcttattac ctctgagtcg acacacctcc tactatttat tgaatacttt gattttatga    6960
aataaaaact aaatatctct ca                                            6982
```

<210> SEQ ID NO 7
<211> LENGTH: 2534
<212> TYPE: DNA
<213> ORGANISM: Mus musculus

<400> SEQUENCE: 7

```
ggaatcccgc gccgaactcg ggggcgggct gcccgggcca tggcgcataa agcctctggc      60
cacctgcagg gctactgctg ctccggccac cgccaggcac acaccttgct gctgagggag     120
tctcggcttc tgtcatctct gtggcctccg tcacctctgt ctccgtctcc ttcaggtcct     180
gagccccgag agccccttcc gcgcacgcgg acatgggcgg cagctccagg gcgcgctggg     240
tggccttggg gttgggcgcc ctggggctgc tgtttgctgc gctcggcgtt gtcatgatcc     300
tcatggtgcc ctccctcatc aagcagcagg tgctcaagaa tgtccgcata gacccgagca     360
gcctgtcctt cggatgtgg aaggagatcc ccgtcccttt ctacttgtct gtctacttct     420
tcgaagtggt caacccaaac gaggtcctca acggccagaa gccagtagtc cgggagcgtg     480 gacccttatgt ctacagggag ttcagacaaa aggtcaacat caccttcaat gacaacgaca    540
ccgtgtcctt cgtggagaac cgcagcctcc atttccagcc tgacaagtcg catggctcag    600
agagtgacta cattgtactg cctaacatct tggtcctggg gggctcgata ttgatggaga    660
gcaagcctgt gagcctgaag ctgatgatga ccttggcgct ggtcaccatg ggccagcgtg    720
cttttatgaa ccgcacagtt ggtgagatcc tgtgggcta tgacgatccc ttcgtgcatt    780
ttctcaacac gtacctccca gacatgcttc ccataaaggg caaatttggc ctgtttgttg    840
```

```
ggatgaacaa ctcgaattct ggggtcttca ctgtcttcac gggcgtccag aatttcagca      900
ggatccatct ggtggacaaa tggaacggac tcagcaagat cgattattgg cattcagagc      960
agtgtaacat gatcaatggg acttccgggc agatgtgggc acccttcatg acacccgaat     1020
cctcgctgga attcttcagc ccggaggcat gcaggtccat gaagctgacc tacaacgaat     1080
caagggtgtt tgaaggcatt cccacgtatc gcttcacggc ccccgatact ctgtttgcca     1140
acgggtccgt ctaccacccc aacgaaggct tctgcccatg ccgagagtct ggcattcaga     1200
atgtcagcac ctgcaggttt ggtgcgcctc tgtttctctc ccaccccac ttttacaacg      1260 ccgaccctgt gttgtcagaa gctgttcttg gtctgaaccc taacccaaag gagcattcct     1320
tgttcctaga catccatccg gtcactggga tccccatgaa ctgttctgtg aagatgcagc     1380
tgagcctcta catcaaatct gtcaagggca tcgggcaaac agggaagatc gagccagtag     1440
ttctgccgtt gctgtggttc gaacagagcg agcaatgggt ggcaagccc ctgagcacgt      1500 tctacacgca gctggtgctg atgccccagg ttcttcacta cgcgcagtat gtgctgctgg     1560
ggcttggagg cctcctgttg ctggtgccca tcatctgcca actgcgcagc caggagaaat     1620 gcttttgtt ttggagtggt agtaaaaagg ctcccagga taaggaggcc attcaggcct       1680
actctgagtc cctgatgtca ccagctgcca agggcacggt gctgcaagaa gccaagctat     1740
agggtcctga agacactata agcccccccaa acctgatagc ttggtcagac cagccaccca     1800
gtccctacac cccgcttctt gaggactctc tcagcggaca gcccaccagt gccatggcct     1860
gagcccccag atgtcacacc tgtccgcacg cacggcacat ggatgcccac gcatgtgcaa     1920
aaacaactca gggaccaggg acagacctgc tgccaagtga gcctgatggg ccacaggtgt     1980
gctcttctaa atggcctgtg agccaggctg tgggaactct agctgctgtc agcccctcct     2040
gtaggagctg gccctgccca ggctcctgac ttccctcagg aagtctttct gtctttctcc     2100
atcagtctga aagccttagt tcccacagag gacggatctg tcactcctag gggctgggca     2160
tatgtcggcc tcttgtgcca aggccaggca agcagctcca ggtcctgacc agtttgcaca     2220
cacactctgg agctgtatct ggcgcttttt ctatcgtctc tgctatgtca ctgaattaac     2280
cactgtacgt ggcagaggtg gcaggcccct cagggtcctt attttcagg catggggtca      2340 aagctagagg tatgggccgt ctacaccccc ccgccccccg gcatctagtg tacctcacca     2400
gagggtattc ggaggcccag catcctgcaa ccgacccctt ttttctactg gaagagaaat     2460
tttatcatct tttgaaagga agtcatgact gaagcaataa accttttcac tgattcaaca     2520 aaaaaaaaa aaaa                                                       2534

<210> SEQ ID NO 8
<211> LENGTH: 8758
<212> TYPE: DNA
<213> ORGANISM: Homo sapiens

<400> SEQUENCE: 8
gtaaaggact ggggccccgc aactggcctc tcctgccctc ttaagcgcag cgccattta       60 gcaacgcaga agcccggcgc cgggaagcct cagctcgcct gaaggcaggt cccctctgac     120
gcctccggga gccaggtttt cccagagtcc ttggacgca gcgacgagtt gtgctgctat      180
cttagctgtc cttataggct ggccattcca ggtggtggta tttagataaa accactcaaa     240
ctctgcagtt tggtcttggg gtttggagga aagcttttat ttttcttcct gctccggttc     300
agaaggtctg aagctcatac ctaaccaggc ataacacaga atctgcaaaa caaaaacccc     360
```

| | |
|---|---|
| taaaaaagca gacccagagc agtgtaaaca cttctgggtg tgtccctgac tggctgccca | 420 |
| aggtctctgt gtcttcggag acaaagccat tcgcttagtt ggtctacttt aaaaggccac | 480 |
| ttgaactcgc tttccatggc gatttgcctt gtgagcactt tcaggagagc ctggaagctg | 540 |
| aaaaacggta gaaaaatttc cgtgcgggcc gtgggggggct ggcggcaact gggggggccgc | 600 |
| agatcagagt gggccactgg cagccaacgg cccccggggc tcaggcgggg agcagctctg | 660 |
| tggtgtggga ttgaggcgtt ttccaagagt gggttttcac gtttctaaga tttcccaagc | 720 |
| agacagcccg tgctgctccg atttctcgaa caaaaaagca aaacgtgtgg ctgtcttggg | 780 |
| agcaagtcgc aggactgcaa gcagttgggg gagaaagtcc gccatttgc cacttctcaa | 840 |
| ccgtccctgc aaggctgggg ctcagttgcg taatggaaag taaagccctg aactatcaca | 900 |
| ctttaatctt ccttcaaaag gtggtaaact atacctactg tccctcaaga gaacacaaga | 960 |
| agtgctttaa gaggtatttt aaaagttccg ggggttttgt gaggtgtttg atgacccgtt | 1020 |
| taaaatatga tttccatgtt tcttttgtct aaagtttgca gctcaaatct ttccacacgc | 1080 |
| tagtaattta agtatttctg catgtgtagt ttgcattcaa gttccataag ctgttaagaa | 1140 |
| aaatctagaa aagtaaaact agaaccatt tttaaccgaa gaactacttt ttgcctccct | 1200 |
| cacaaaggcg gcggaaggtg atcgaattcc ggtgatgcga gttgttctcc gtctataaat | 1260 |
| acgcctcgcc cgagctgtgc ggtaggcatt gaggcagcca gcgcaggggc ttctgctgag | 1320 |
| ggggcaggcg gagcttgagg aaaccgcaga taagttttt tctctttgaa agatagagat | 1380 |
| taatacaact acttaaaaaa tatagtcaat aggttactaa gatattgctt agcgttaagt | 1440 |
| ttttaacgta attttaatag cttaagattt taagagaaaa tatgaagact agaagagta | 1500 |
| gcatgaggaa ggaaaagata aaaggtttct aaaacatgac ggaggttgag atgaagcttc | 1560 |
| ttcatggagt aaaaaatgta tttaaagaa aattgagaga aaggactaca gagccccgaa | 1620 |
| ttaataccaa tagaagggca atgctttag attaaaatga aggtgactta aacagcttaa | 1680 |
| agtttagttt aaaagttgta ggtgattaaa ataatttgaa ggcgatcttt taaaaagaga | 1740 |
| ttaaaccgaa ggtgattaaa agaccttgaa atccatgacg cagggagaat tgcgtcattt | 1800 |
| aaagcctagt taacgcattt actaaacgca gacgaaaatg gaaagattaa ttgggagtgg | 1860 |
| taggatgaaa caatttggag aagatagaag tttgaagtgg aaaactggaa gacagaagta | 1920 |
| cgggaaggcg aagaaaagaa tagaagagat agggaaatta aagataaaa acatactttt | 1980 |
| agaagaaaaa agataaattt aaacctgaaa agtaggaagc agaagaaaaa agacaagcta | 2040 |
| ggaaacaaaa agctaagggc aaaatgtaca aacttagaag aaaattggaa gatagaaaca | 2100 |
| agatagaaaa tgaaaatatt gtcaagagtt tcagatagaa aatgaaaaac aagctaagac | 2160 |
| aagtattgga gaagtataga agatagaaaa atataaagcc aaaaattgga taaaatagca | 2220 |
| ctgaaaaaat gaggaaatta ttggtaacca atttatttta aaagcccatc aatttaattt | 2280 |
| ctggtggtgc agaagttaga aggtaaagct tgagaagatg agggtgttta cgtagaccag | 2340 |
| aaccaattta gaagaatact tgaagctaga aggggaagtt ggttaaaaat cacatcaaaa | 2400 |
| agctactaaa aggactggtg taatttaaaa aaaactaagg cagaaggctt ttggaagagt | 2460 |
| tagaagaatt tggaaggcct taaatatagt agcttagttt gaaaaatgtg aaggactttc | 2520 |
| gtaacggaag taattcaaga tcaagagtaa ttaccaactt aatgttttg cattggactt | 2580 |
| tgagttaaga ttattttta aatcctgagg actagcatta attgacagct gacccaggtg | 2640 |
| ctacacagaa gtggattcag tgaatctagg aagacagcag cagacaggat tccaggaacc | 2700 |
| agtgtttgat gaagctagga ctgaggagca agcgagcaag cagcagttcg tggtgaagat | 2760 |

```
aggaaaagag tccaggagcc agtgcgattt ggtgaaggaa gctaggaaga aggaaggagc    2820
gctaacgatt tggtggtgaa gctaggaaaa aggattccag gaaggagcga gtgcaatttg    2880
gtgatgaagg tagcaggcgg cttggcttgg caaccacacg gaggaggcga gcaggcgttg    2940
tgcgtagagg atcctagacc agcatgccag tgtgccaagg ccacagggaa agcgagtggt    3000
tggtaaaaat ccgtgaggtc ggcaatatgt tgttttactg gaacttactt atggtaacct    3060
tttatttatt ttctaatata atgggggagt ttcgtactga ggtgtaaagg gatttatatg    3120
gggacgtagg ccgatttccg ggtgttgtag gtttctcttt ttcaggctta tactcatgaa    3180
tcttgtctga agcttttgag ggcagactgc caagtcctgg agaaatagta gatggcaagt    3240
ttgtgggttt tttttttta cacgaatttg aggaaaacca aatgaatttg atagccaaat    3300
tgagacaatt tcagcaaatc tgtaagcagt ttgtatgttt agttgggta atgaagtatt    3360 tcagttttgt gaatagatga cctgttttta cttcctcacc ctgaattcgt tttgtaaatg    3420
tagagtttgg atgtgtaact gaggcggggg ggagttttca gtattttttt ttgtgggggt    3480
gggggcaaaa tatgttttca gttctttttc ccttaggtct gtctagaatc ctaaaggcaa    3540
atgactcaag gtgtaacaga aaacaagaaa atccaatatc aggataatca gaccaccaca    3600
ggtttacagt ttatagaaac tagagcagtt ctcacgttga ggtctgtgga agagatgtcc    3660
attggagaaa tggctggtag ttactctttt tccccccac cccttaatc agactttaaa    3720 agtgcttaac cccttaaact tgttattttt tacttgaagc attttgggat ggtcttaaca    3780
gggaagagag agggtggggg agaaaatgtt tttttctaag attttccaca gatgctatag    3840
tactattgac aaactgggtt agagaaggag tgtaccgctg tgctgttggc acgaacacct    3900
tcagggactg gagctgcttt tatccttgga agagtattcc cagttgaagc tgaaaagtac    3960
agcacagtgc agctttggtt catattcagt catctcagga gaacttcaga agagcttgag    4020
taggccaaat gttgaagtta agttttccaa taatgtgact tcttaaaagt tttattaaag    4080
gggaggggca atattggca attagttggc agtggcctgt tacggttggg attggtgggg    4140
tgggtttagg taattgttta gtttatgatt gcagataaac tcatgccaga gaacttaaag    4200
tcttagaatg gaaaaagtaa agaaatatca acttccaagt tggcaagtaa ctcccaatga    4260
tttagttttt tcccccag tttgaattgg gaagctgggg gaagttaaat atgagccact    4320
gggtgtacca gtgcattaat ttgggcaagg aaagtgtcat aatttgatac tgtatctgtt    4380
ttccttcaaa gtatagagct tttggggaag gaaagtattg aactgggggt tggtctggcc    4440
tactgggctg acattaacta caattatggg aaatgcaaaa gttgtttgga tatggtagtg    4500
tgtggttctc ttttggaatt ttttcaggt gatttaataa taatttaaaa ctactataga    4560
aactgcagag caaaggaagt ggcttaatga tcctgaaggg atttcttctg atggtagctt    4620
ttgtattatc aagtaagatt ctattttcag ttgtgtgtaa gcaagttttt tttagtgta    4680 ggagaaatac ttttccattg tttaactgca aaacaagatg ttaaggtatg cttcaaaaat    4740
tttgtaaatt gtttatttta aacttatctg tttgtaaatt gtaactgatt aagaattgtg    4800
atagttcagc ttgaatgtct cttagagggt gggcttttgt tgatgaggga ggggaaactt    4860
tttttttttc tatagacttt tttcagataa catcttctga gtcataacca gcctggcagt    4920
atgatggcct agatgcagag aaaacagctc cttggtgaat tgataagtaa aggcagaaaa    4980
gattatatgt catacctcca ttggggaata agcataaccc tgagattctt actactgatg    5040
agaacattat ctgcatatgc caaaaaattt taagcaaatg aaagctacca atttaaagtt    5100
```

```
acggaatcta ccattttaaa gttaattgct tgtcaagcta taaccacaaa aataatgaat     5160
tgatgagaaa tacaatgaag aggcaatgtc catctcaaaa tactgctttt acaaaagcag     5220
aataaaagcg aaaagaaatg aaaatgttac actacattaa tcctggaata aaagaagccg     5280
aaataaatga gagatgagtt gggatcaagt ggattgagga ggctgtgctg tgtgccaatg     5340
tttcgtttgc ctcagacagg tatctcttcg ttatcagaag agttgcttca tttcatctgg     5400
gagcagaaaa cagcaggcag ctgttaacag ataagtttaa cttgcatctg cagtattgca     5460
tgttagggat aagtgcttat ttttaagagc tgtggagttc ttaaatatca accatggcac     5520
tttctcctga ccccttccct agggatttc aggattgaga aattttttcca tcgagccttt     5580 ttaaaattgt aggacttgtt cctgtgggct tcagtgatgg gatagtacac ttcactcaga     5640
ggcatttgca tctttaaata atttcttaaa agcctctaaa gtgatcagtg ccttgatgcc     5700
aactaaggaa atttgtttag cattgaatct ctgaaggctc tatgaaagga atagcatgat     5760
gtgctgttag aatcagatgt tactgctaaa atttacatgt tgtgatgtaa attgtgtaga     5820
aaaccattaa atcattcaaa ataataaact attttttatta gagaatgtat acttttagaa     5880
agctgtctcc ttatttaaat aaaatagtgt ttgtctgtag ttcagtgttg gggcaatctt     5940
gggggggatt cttctctaat cttcagaaaa ctttgtctgc gaacactctt taatggacca     6000
gatcaggatt tgagcggaag aacgaatgta actttaaggc aggaaagaca aattttattc     6060
ttcataaagt gatgagcata taataattcc aggcacatgg caatagaggc cctctaaata     6120
aggaataaat aacctcttag acaggtggga gattatgatc agagtaaaag gtaattacac     6180
attttatttc cagaaagtca ggggtctata aattgacagt gattagagta atactttttc     6240
acatttccaa agtttgcatg ttaactttaa atgcttacaa tcttagagtg gtaggcaatg     6300
ttttacacta ttgaccttat ataggaagg aggggggtgc ctgtgggtt ttaaagaatt     6360 ttcctttgca gaggcatttc atccttcatg aagccattca ggattttgaa ttgcatatga     6420
gtgcttggct cttccttctg ttctagtgag tgtatgagac cttgcagtga gtttatcagc     6480
atactcaaaa ttttttttcct ggaatttgga gggatgggag ggggggtgg ggcttacttg     6540 ttgtagcttt ttttttttttt acagacttca cagagaatgc agttgtcttg acttcaggtc     6600
tgtctgttct gttggcaagt aaatgcagta ctgttctgat cccgctgcta ttagaatgca     6660
ttgtgaaacg actggagtat gattaaaagt tgtgttcccc aatgcttgga gtagtgattg     6720
ttgaaggaaa aaatccagct gagtgataaa ggctgagtgt tgaggaaatt tctgcagttt     6780
taagcagtcg tatttgtgat tgaagctgag tacattttgc tggtgtattt ttaggtaaaa     6840 tgcttttttgt tcatttctgg tggtgggagg ggactgaagc ctttagtctt ttccagatgc     6900
aaccttaaaa tcagtgacaa gaaacattcc aaacaagcaa cagtcttcaa gaaattaaac     6960
tggcaagtgg aaatgtttaa acagttcagt gatctttagt gcattgttta tgtgtgggtt     7020
tctctctccc ctcccttggt cttaattctt acatgcagga acactcagca gacacacgta     7080
tgcgaagggc cagagaagcc agacccagta agaaaaaata gcctatttac tttaaataaa     7140
ccaaacattc cattttaaat gtggggattg ggaaccacta gttctttcag atggtattct     7200
tcagactata gaaggagctt ccagttgaat tcaccagtgg acaaaatgag gaaacaggt     7260 gaacaagctt tttctgtatt tacatacaaa gtcagatcag ttatgggaca atagtattga     7320
atagatttca gctttatgct ggagtaactg gcatgtgagc aaactgtgtt ggcgtggggg     7380
tggaggggtg aggtgggcgc taagcctttt tttaagattt ttcaggtacc cctcactaaa     7440
ggcaccgaag gcttaaagta ggacaaccat ggagccttcc tgtggcagga gagacaacaa     7500
```

```
agcgctatta tcctaaggtc aagagaagtg tcagcctcac ctgatttttta ttagtaatga    7560 ggacttgcct caactccctc tttctggagt gaagcatccg aaggaatgct tgaagtaccc    7620
ctgggcttct cttaacattt aagcaagctg tttttatagc agctcttaat aataaagccc    7680
aaatctcaag cggtgcttga aggggaggga aaggggggaaa gcgggcaacc acttttccct    7740
agcttttcca gaagcctgtt aaaagcaagg tctccccaca agcaacttct ctgccacatc    7800
gccaccccgt gccttttgat ctagcacaga cccttcaccc ctcacctcga tgcagccagt    7860
agcttggatc cttgtgggca tgatccataa tcggtttcaa ggtaacgatg gtgtcgaggt    7920
cttggtgggg ttgaactatg ttagaaaagg ccattaattt gcctgcaaat tgttaacaga    7980
agggtattaa aaccacagct aagtagctct attataatac ttatccagtg actaaaacca    8040
acttaaacca gtaagtggag aaataacatg ttcaagaact gtaatgctgg gtgggaacat    8100
gtaacttgta gactggagaa gataggcatt tgagtggctg agagggcttt tgggtgggaa    8160
tgcaaaaatt ctctgctaag acttttttcag gtgaacataa cagacttggc caagctagca    8220
tcttagcgga agctgatctc caatgctctt cagtagggtc atgaaggttt ttcttttcct    8280
gagaaaacaa cacgtattgt tttctcaggt tttgcttttt ggcctttttc tagcttaaaa    8340
aaaaaaaaag caaaagatgc tggtggttgg cactcctggt ttccaggacg gggttcaaat    8400
ccctgcggcg tctttgcttt gactactaat ctgtcttcag gactctttct gtatttctcc    8460
ttttctctgc aggtgctagt tcttggagtt ttggggaggt gggaggtaac agcacaatat    8520 cttgaacta tatacatcct tgatgtataa tttgtcagga gcttgacttg attgtatatt      8580
catatttaca cgagaaccta atataactgc cttgtctttt tcaggtaata gcctgcagct    8640
ggtgttttga gaagccctac tgctgaaaac ttaacaattt tgtgtaataa aaatggagaa    8700
gctctaaatt gttgtggttc ttttgtgaat aaaaaaatct tgattgggga aaaaaaaa     8758
```

<210> SEQ ID NO 9
<211> LENGTH: 2759
<212> TYPE: DNA
<213> ORGANISM: Homo sapiens

<400> SEQUENCE: 9

```
gctcaggccc cgcccctgcc gccggaatcc tgaagcccaa ggctgccgg gggcggtccg       60 gcggcgccgg cgatggggca taaaaccact ggccacctgc cgggctgctc ctgcgtgcgc     120
tgccgtcccg gatccaccgt gcctctgcgg cctgcgtgcc cggagtcccc gcctgtgtcg     180
tctctgtcgc cgtccccgtc tcctgccagg cgcgagccc tgcagccgc gggtgggccc       240 caggcgcgca gacatgggct gctccgccaa agcgcgctgg gctgccgggg cgctgggcgt     300
cgcgggcgta ctgtgcgctg tgctgggcgc tgtcatgatc gtgatggtgc cgtcgctcat     360
caagcagcag gtccttaaga acgtgcgcat cgaccccagt agcctgtcct tcaacatgtg     420
gaaggagatc cctatcccct tctatctctc cgtctacttc tttgacgtca tgaaccccag     480
cgagatcctg aagggcgaga agccgcaggt gcgggagcgc gggccctacg tgtacaggga     540
gttcaggcac aaaagcaaca tcaccttcaa caacaacgac accgtgtcct tcctcgagta     600
ccgcaccttc cagttccagc cctccaagtc ccacggctcg agagcgact acatcgtcat     660 gcccaacatc ctggtcttgg gtgcggcggt gatgatggag aataagccca tgaccctgaa     720
gctcatcatg accttggcat tcaccaccct cggcgaacgt gccttcatga accgcactgt     780
gggtgagatc atgtggggct acaaggaccc ccttgtgaat ctcatcaaca gtactttcc     840
```

```
aggcatgttc cccttcaagg acaagttcgg attatttgct gagctcaaca actccgactc      900
tgggctcttc acggtgttca cggggggtcca gaacatcagc aggatccacc tcgtggacaa     960
gtggaacggg ctgagcaagg ttgacttctg gcattccgat cagtgcaaca tgatcaatgg    1020
aacttctggg caaatgtggc cgcccttcat gactcctgag tcctcgctgg agttctacag    1080
cccggaggcc tgccgatcca tgaagctaat gtacaaggag tcagggggtgt ttgaaggcat   1140 ccccacctat cgcttcgtgg ctcccaaaac cctgtttgcc aacgggtcca tctacccacc   1200
caacgaaggc ttctgcccgt gcctggagtc tggaattcag aacgtcagca cctgcaggtt   1260
cagtgccccc ttgtttctct ccatcctca cttcctcaac gctgacccgg ttctggcaga    1320
agcggtgact ggcctgcacc ctaaccagga ggcacactcc ttgttcctgg acatccaccc   1380
ggtcacggga atccccatga actgctctgt gaaactgcag ctgagcctct acatgaaatc   1440
tgtcgcaggc attggacaaa ctgggaagat tgagcctgtg gtcctgccgc tgctctggtt   1500
tgcagagagc ggggccatgg aggggagac tcttcacaca ttctacactc agctggtgtt    1560
gatgcccaag gtgatgcact atgcccagta cgtcctcctg gcgctgggct gcgtcctgct   1620
gctggtccct gtcatctgcc aaatccggag ccaagagaaa tgctatttat tttggagtag   1680
tagtaaaaag ggctcaaagg ataaggaggc cattcaggcc tattctgaat ccctgatgac   1740
atcagctccc aagggctctg tgctgcagga agcaaaactg tagggtcctg aggacaccgt   1800
gagccagcca ggcctggccg ctgggcctga ccggcccccc agcccctaca cccgcttct    1860 cccggactct cccagcggac agcccccag ccccacagcc tgagcctccc agctgccatg    1920
tgcctgttgc acacctgcac acacgccctg gcacacatac acacatgcgt gcaggcttgt   1980
gcagacactc agggatggag ctgctgctga agggacttgt agggagaggc tcgtcaacaa   2040
gcactgttct ggaaccttct ctccacgtgg cccacaggcc tgaccacagg ggctgtgggt   2100
cctgcgtccc cttcctcggg tgagcctggc ctgtcccgtt cagccgttgg gcccaggctt   2160
cctcccctcc aaggtgaaac actgcagtcc cggtgtggtg gctccccatg caggacgggc   2220
caggctggga gtgccgcctt cctgtgccaa attcagtggg gactcagtgc ccaggccctg   2280
gccacgagct ttggccttgg tctacctgcc aggccaggca aagcgccttt acacaggcct   2340
cggaaaacaa tggagtgagc acaagatgcc ctgtgcagct gcccgagggt ctccgcccac   2400
cccggccgga ctttgatccc cccgaagtct tcacaggcac tgcatcgggt tgtctggcgc   2460
ccttttcctc cagcctaaac tgacatcatc ctatggactg agccggccac tctctggccg   2520
aagtggccgc aggctgtgcc cccgagctgc ccccaccccc tcacagggtc cctcagatta   2580
taggtgccca ggctgaggtg aagaggcctg ggggccctgc cttccgggcg ctcctggacc   2640
ctggggcaaa cctgtgaccc ttttctactg gaatagaaat gagttttatc atctttgaaa   2700
aataattcac tcttgaagta ataaacgttt aaaaaaatgg gaaaaaaaaa aaaaaaaa    2759
```

```
<210> SEQ ID NO 10
<211> LENGTH: 16
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3), (14)..(16)
<223> OTHER INFORMATION: 2'-O-Me RNA

<400> SEQUENCE: 10
gcauucagug aacuag                                                      16
```

```
<210> SEQ ID NO 11
<211> LENGTH: 14
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (13)..(14)
<223> OTHER INFORMATION: 2'-O-Me RNA

<400> SEQUENCE: 11
gaagucauga cuga                                                          14

<210> SEQ ID NO 12
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1), (3)..(3), (14)..(16)
<223> OTHER INFORMATION: LNA
<220> FEATURE:
<221> NAME/KEY: misc_feature
<222> LOCATION: (2)..(2)
<223> OTHER INFORMATION: 5-methylcytosine LNA

<400> SEQUENCE: 12
gcattcagtg aactag                                                        16

<210> SEQ ID NO 13
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1), (3)..(3), (14)..(16)
<223> OTHER INFORMATION: LNA
<220> FEATURE:
<221> NAME/KEY: misc_feature
<222> LOCATION: (2)..(2)
<223> OTHER INFORMATION: 5-methylcytosine LNA

<400> SEQUENCE: 13
acaataaata ccgagg                                                        16

<210> SEQ ID NO 14
<211> LENGTH: 16
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3), (14)..(16)
<223> OTHER INFORMATION: 2'-O-Me RNA

<400> SEQUENCE: 14
ccucgguauu uauugu                                                        16

<210> SEQ ID NO 15
<211> LENGTH: 16
<212> TYPE: DNA
<213> ORGANISM: Artificial
<220> FEATURE:
```

```
<223> OTHER INFORMATION: Synthetic
<220> FEATURE:
<221> NAME/KEY: misc_feature
<222> LOCATION: (1)..(3), (15)..(16)
<223> OTHER INFORMATION: LNA
<220> FEATURE:
<221> NAME/KEY: misc_feature
<222> LOCATION: (14)..(14)
<223> OTHER INFORMATION: 5-methylcytosine LNA

<400> SEQUENCE: 15
agtactatag catctg                                                     16

<210> SEQ ID NO 16
<211> LENGTH: 16
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3), (14)..(16)
<223> OTHER INFORMATION: 2'-O-Me RNA

<400> SEQUENCE: 16
cagaugcuau aguacu                                                     16

<210> SEQ ID NO 17
<211> LENGTH: 2761
<212> TYPE: DNA
<213> ORGANISM: Mus musculus

<400> SEQUENCE: 17
gaactggcca gagagaccca agggatagtc agggacgggc agacatgcag ctagggttct      60
ggggcctgga caggggcagc caggccctgt gacgggaaga ccccgagctc cggcccgggg     120
aggggccatg gtgttgcctg cccaacatgt cagccgaagt gcggctgagg cagctccagc     180
agctggtgct ggacccaggc ttcctgggac tggagcccct gctcgacctt ctcctgggcg     240
tccaccagga gctgggtgcc tctcacctag cccaggacaa gtatgtggcc gacttcttgc     300
agtgggtgga gcccattgca gcaaggctta aggaggtccg actgcagagg gatgattttg     360
agattttgaa ggtgatcggg cgtggggcgt tcagcgaggt agcggtggtg aagatgaaac     420
agacgggcca agtgtatgcc atgaagatta tgaataagtg ggacatgctg aagagaggcg     480
aggtgtcgtg cttccgggaa gaaagggatg tattagtgaa aggggaccgg cgctggatca     540
cacagctgca ctttgccttc caggatgaga actacctgta cctggtcatg gaatactacg     600
tgggcgggga cctgctaacg ctgctgagca gtttgggga gcggatcccc gccgagatgg     660
ctcgcttcta cctggccgag attgtcatgg ccatagactc cgtgcaccgg ctgggctacg     720
tgcacaggga catcaaacca gataacattc tgctggaccg atgtgggcac attcgcctgg     780
cagacttcgg ctcctgcctc aaactgcagc ctgatggaat ggtgaggtcg ctggtggctg     840
tgggcacccc ggactacctg tctcctgaga ttctgcaggc cgttggtgga gggcctgggg     900
caggcagcta cgggccagag tgtgactggt gggcactggg cgtgttcgcc tatgagatgt     960
tctatgggca gacccccttc tacgcggact ccacagccga gacatatgcc aagattgtgc    1020
actacaggga acacttgtcg ctgccgctgg cagacacagt tgtccccgag gaagctcagg    1080
acctcattcg tggctgctg tgtcctgctg agataaggct aggtcgaggt ggggcaggtg    1140
atttccagaa acatccttc ttctttggcc ttgattggga gggtctccga gacagtgtac    1200 cccccttac accagacttc gagggtgcca cggacacatg caatttcgat gtggtggagg    1260
```

```
accggctcac tgccatggtg agcggggcg gggagacgct gtcagacatg caggaagaca    1320
tgccccttgg ggtgcgcctg cccttcgtgg gctactccta ctgctgcatg gccttcagag    1380
acaatcaggt cccggacccc acccctatgg aactagaggc cctgcagttg cctgtgtcag    1440
acttgcaagg gcttgacttg cagccccag tgtccccacc ggatcaagtg gctgaagagg    1500
ctgacctagt ggctgtccct gcccctgtgg ctgaggcaga gaccacggta acgctgcagc    1560
agctccagga agccctggaa gaagaggttc cacccggca gagcctgagc cgcgagctgg    1620
aggccatccg gaccgccaac cagaacttct ccagccaact acaggaggcc gaggtccgaa    1680
accgagacct ggaggcgcat gttcggcagc tacaggaacg gatggagatg ctgcaggccc    1740
caggagccgc agccatcacg ggggtcccca gtccccgggc cacggatcca ccttcccatc    1800
tagatggccc cccggccgtg gctgtgggcc agtgcccgct ggtggggcca ggccccatgc    1860
accgccgtca cctgctgctc cctgccagga tccctaggcc tggcctatcc gaggcgcgtt    1920
gcctgctcct gttcgccgct gctctggctg ctgccgccac actgggctgc actgggttgg    1980
tggcctatac cggcggtctc accccagtct ggtgtttccc gggagccacc ttcgcccct    2040
gaaccctaag actccaagcc atctttcatt taggcctcct aggaaggtcg agcgaccagg    2100
gagcgaccca aagcgtctct gtgcccatcg cgccccccc ccccccccac cgctccgctc    2160
cacacttctg tgagcctggg tccccaccca gctccgctcc tgtgatccag gcctgccacc    2220
tggcggccgg ggagggagga acagggctcg tgcccagcac ccctggttcc tgcagagctg    2280
gtagccaccg ctgctgcagc agctgggcat tcgccgacct tgctttactc agccccgacg    2340
tggatgggca aactgctcag ctcatccgat ttcactttt cactctccca gccatcagtt    2400
acaagccata agcatgagcc ccctatttcc agggacatcc cattcccata gtgatggatc    2460
agcaagacct ctgccagcac acacggagtc tttggcttcg acagcctca ctcctggggg    2520
ttgctgcaac tccttcccg tgtacacgtc tgcactctaa caacggagcc acagctgcac    2580
tccccctcc cccaaagcag tgtgggtatt tattgatctt gttatctgac tcactgacag    2640
actccgggac ccacgtttta gatgcattga gactcgacat tcctcggtat ttattgtctg    2700
tccccaccta cgacctccac tcccgaccct tgcgaataaa atacttctgg tctgccctaa    2760
a                                                                    2761
```

<210> SEQ ID NO 18
<211> LENGTH: 3243
<212> TYPE: DNA
<213> ORGANISM: Homo sapiens

<400> SEQUENCE: 18

```
gccacaagcc tccaccccag ctggtccccc acccaggctg cccagtttaa cattcctagt      60
cataggacct tgacttctga gaggcctgat tgtcatctgt aaataagggg taggactaaa     120
gcactcctcc tggaggactg agagatgggc tggaccggag cacttgagtc tgggatatgt     180
gaccatgcta cctttgtctc cctgtcctgt tccttccccc agccccaaat ccagggtttt     240
ccaaagtgtg gttcaagaac cacctgcatc tgaatctaga ggtactggat acaaccccac     300
gtctgggccg ttacccagga cattctacat gagaacgtgg gggtggggcc ctggctgcac     360
ctgaactgtc acctggagtc agggtggaag gtggaagaac tgggtcttat ttccttctcc     420
ccttgttctt tagggtctgt ccttctgcag actccgttac cccacccta ccatcctgca     480
caccccttgga gccctctggg ccaatgccct gtcccgcaaa gggcttctca ggcatctcac     540
```

| | | | | | |
|---|---|---|---|---|---|
| ctctatggga | gggcattttt | ggcccccaga | accttacacg | gtgtttatgt | ggggaagccc | 600 |
| ctgggaagca | gacagtccta | gggtgaagct | gagaggcaga | gagaagggga | gacagacaga | 660 |
| gggtggggct | ttcccccttg | tctccagtgc | cctttctggt | gaccctcggt | tcttttcccc | 720 |
| caccaccccc | ccagcggagc | ccatcgtggt | gaggcttaag | gaggtccgac | tgcagaggga | 780 |
| cgacttcgag | attctgaagg | tgatcggacg | cggggcgttc | agcgaggtag | cggtagtgaa | 840 |
| gatgaagcag | acgggccagg | tgtatgccat | gaagatcatg | aacaagtggg | acatgctgaa | 900 |
| gaggggcgag | gtgtcgtgct | tccgtgagga | gagggacgtg | ttggtgaatg | ggaccggcg | 960 |
| gtggatcacg | cagctgcact | tcgccttcca | ggatgagaac | tacctgtacc | tggtcatgga | 1020 |
| gtattacgtg | ggcggggacc | tgctgacact | gctgagcaag | tttggggagc | ggattccggc | 1080 |
| cgagatggcg | cgcttctacc | tggcggagat | tgtcatggcc | atagactcgg | tgcaccggct | 1140 |
| tggctacgtg | cacagggaca | tcaaacccga | caacatcctg | ctggaccgct | gtggccacat | 1200 |
| ccgcctggcc | gacttcggct | cttgcctcaa | gctgcgggca | gatggaacgg | tgcggtcgct | 1260 |
| ggtggctgtg | ggcacccccag | actacctgtc | ccccgagatc | ctgcaggctg | tgggcggtgg | 1320 |
| gcctgggaca | gcagctacg | ggcccgagtg | tgactggtgg | gcgctgggtg | tattcgccta | 1380 |
| tgaaatgttc | tatgggcaga | cgcccttcta | cgcggattcc | acggcggaga | cctatggcaa | 1440 |
| gatcgtccac | tacaaggagc | acctctctct | gccgctggtg | gacgaagggg | tccctgagga | 1500 |
| ggctcgagac | ttcattcagc | ggttgctgtg | tcccccggag | acacggctgg | gccggggtgg | 1560 |
| agcaggcgac | ttccggacac | atcccttctt | ctttggcctc | gactgggatg | gtctccggga | 1620 |
| cagcgtgccc | ccctttacac | cggatttcga | aggtgccacc | gacacatgca | acttcgactt | 1680 |
| ggtggaggac | gggctcactg | ccatggtgag | cggggcggg | gagacactgt | cggacattcg | 1740 |
| ggaaggtgcg | ccgctagggg | tccacctgcc | ttttgtgggc | tactcctact | cctgcatggc | 1800 |
| cctcagggac | agtgaggtcc | caggccccac | acccatggaa | ctggaggccg | agcagctgct | 1860 |
| tgagccacac | gtgcaagcgc | ccagcctgga | ccctcggtg | tccccacagg | atgaaacagc | 1920 |
| tgaagtggca | gttccagcgg | ctgtccctgc | ggcagaggct | gaggccgagg | tgacgctgcg | 1980 |
| ggagctccag | gaagccctgg | aggaggaggt | gctcacccgg | cagagcctga | gccgggagat | 2040 |
| ggaggccatc | cgcacggaca | accagaactt | cgccagtcaa | ctacgcgagg | cagaggctcg | 2100 |
| gaaccgggac | ctagaggcac | acgtccggca | gttgcaggag | cggatggagt | tgctgcaggc | 2160 |
| agagggagcc | acagctgtca | cgggggtccc | cagtccccgg | gccacggatc | caccttccca | 2220 |
| tctagatggc | cccccggccg | tggctgtggg | ccagtgcccg | ctggtggggc | caggccccat | 2280 |
| gcaccgccgc | cacctgctgc | tccctgccag | ggtccctagg | cctggcctat | cggaggcgct | 2340 |
| ttccctgctc | ctgttcgccg | ttgttctgtc | tcgtgccgcc | gccctgggct | gcattgggtt | 2400 |
| ggtggcccac | gccggccaac | tcaccgcagt | ctggcgccgc | ccaggagccg | cccgcgctcc | 2460 |
| ctgaacccta | gaactgtctt | cgactccggg | gccccgttgg | aagactgagt | gcccggggca | 2520 |
| cggcacagaa | gccgcgccca | ccgcctgcca | gttcacaacc | gctccgagcg | tgggtctccg | 2580 |
| cccagctcca | gtcctgtgat | ccgggcccgc | cccctagcgg | ccggggaggg | aggggccggg | 2640 |
| tccgcggccg | gcgaacgggg | ctcgaagggt | ccttgtagcc | gggaatgctg | ctgctgctgc | 2700 |
| tgctgctgct | gctgctgctg | ctgctgctgc | tgctgctgct | gctgctgctg | ctgctggggg | 2760 |
| ggatcacaga | ccatttcttt | ctttcggcca | ggctgaggcc | ctgacgtgga | tggcaaaact | 2820 |
| gcaggcctgg | gaaggcagca | agccgggccg | tccgtgttcc | atcctccacg | cacccccacc | 2880 |
| tatcgttggt | tcgcaaagtg | caaagctttc | ttgtgcatga | cgccctgctc | tggggagcgt | 2940 |
| ctggcgcgat | | | | | | |

```
ctctgcctgc ttactcggga aatttgcttt tgccaaaccc gcttttttcgg ggatcccgcg    3000 ccccctcct cacttgcgct gctctcggag ccccagccgg ctccgcccgc ttcggcggtt    3060
tggatattta ttgacctcgt cctccgactc gctgacaggc tacaggaccc ccaacaaccc    3120
caatccacgt tttggatgca ctgagacccc gacattcctc ggtatttatt gtctgtcccc    3180
acctaggacc cccaccccg accctcgcga ataaaaggcc ctccatctgc ccaaagctct    3240
gga                                                                  3243

<210> SEQ ID NO 19
<211> LENGTH: 29
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(6), (11)..(11), (16)..(16), (23)..(23), (26)..(26)
<223> OTHER INFORMATION: 2'-O-Me RNA

<400> SEQUENCE: 19
guauaaacau ucgcaucgca uagguucuu                                      29

<210> SEQ ID NO 20
<211> LENGTH: 27
<212> TYPE: RNA
<213> ORGANISM: Artificial
<220> FEATURE:
<223> OTHER INFORMATION: Synthetic
<221> NAME/KEY: misc_feature
<222> LOCATION: (4)..(4), (6)..(6), (8)..(8), (13)..(13), (19)..(19)
<223> OTHER INFORMATION: 2'-O-Me RNA

<400> SEQUENCE: 20
gaaccuaugc gaugcgaaug uuuauac                                        27

<210> SEQ ID NO 21
<211> LENGTH: 23
<212> TYPE: RNA
<213> ORGANISM: Artificial
<220> FEATURE:
<223> OTHER INFORMATION: Synthetic
<221> NAME/KEY: misc_feature
<222> LOCATION: (1)..(2), (5)..(5), (10)..(10), (17)..(17), (20)..(20)
<223> OTHER INFORMATION: 2'-O-Me RNA

<400> SEQUENCE: 21
acauucgcau cgcauagguu cuu                                            23

<210> SEQ ID NO 22
<211> LENGTH: 21
<212> TYPE: RNA
<213> ORGANISM: Artificial
<220> FEATURE:
<223> OTHER INFORMATION: Synthetic
<221> NAME/KEY: misc_feature
<222> LOCATION: (4)..(4), (6)..(6), (8)..(8), (13)..(13), (19)..(19)
<223> OTHER INFORMATION: 2'-O-Me RNA

<400> SEQUENCE: 22
gaaccuaugc gaugcgaaug u                                              21

<210> SEQ ID NO 23
<211> LENGTH: 4178
<212> TYPE: DNA
<213> ORGANISM: Mus musculus
```

<400> SEQUENCE: 23

```
ggaaaagcaa aaacccttcg gctttgacag ccaccgccac aagcctttcc gcctccccag    60
cctgcctagg tgctgggagc tgggagctgg attatggtgg cctgagcagc cgacgcagcc   120
gtaggagccc ggagtccctg tcggtcccca agctgcaaag cccgcctgga agaccccgaa   180
agctacgggc tcggatagcc atgcccgccc ctcccagccc cacaaggggc ccgatccccc   240
cgctggcggc cggcgtccag atgtagctgg gtccctgga tcgccatcgt cgtctcctct   300
cgtgcgctac ggatttctcc tgcccactct ccgccgcctg gaccgggaac tgagcgaggg   360
gcctgcagac tctgcagtcc tgatgccgcc gaggccgctc tcctgagaga agccaccacc   420
acccagactt aggggcaggc aagagggaca gtcaccaacc ggaccacaag gcccgggctc   480
actatggccc cagcgctgca ctggctcctg ctatgggtgg gctcgggaat gctgcctgcc   540
cagggaaccc atctcggcat ccggctgccc cttcgcagcg gcctggcagg gccacccctg   600
ggcctgaggc tgccccggga accgacgag gaatcggagg agcctggccg agagggcagc   660
tttgtggaga tggtggacaa cctgagggga aagtccggcc agggctacta tgtggagatg   720
accgtaggca gccccccaca gacgctcaac atcctggtgg acacgggcag tagtaacttt   780
gcagtggggg ctgccccaca ccctttcctg catcgctact accagaggca gctgtccagc   840
acatatcgag acctccgaaa gggtgtgtat gtgccctaca cccagggcaa gtgggagggg   900
gaactgggca ccgacctggt gagcatccct catggcccca acgtcactgt gcgtgccaac   960
attgctgcca tcactgaatc ggacaagttc ttcatcaatg gttccaactg ggagggcatc  1020
ctagggctgg cctatgctga gattgccagg cccgacgact ctttgagcc cttctttgac  1080
tccctggtga agcagaccca cattcccaac atcttttccc tgcagctctg tggcgctggc  1140
ttccccctca accagaccga ggcactggcc tcggtgggag ggagcatgat cattggtggt  1200
atcgaccact cgctatacac gggcagtctc tggtacacac ccatccggcg ggagtggtat  1260
tatgaagtga tcattgtacg tgtggaaatc aatggtcaag atctcaagat ggactgcaag  1320
gagtacaact acgacaagag cattgtggac agtgggacca ccaaccttcg cttgcccaag  1380
aaagtatttg aagctgccgt caagtccatc aaggcagcct cctcgacgga gaagttcccg  1440
gatggctttt ggctagggga gcagctggtg tgctggcaag caggcacgac cccttggaac  1500
attttcccag tcatttcact ttacctcatg ggtgaagtca ccaatcagtc cttccgcatc  1560
accatccttc ctcagcaata cctacggccg gtggaggacg tggccacgtc caagacgac  1620
tgttacaagt tcgctgtctc acagtcatcc acgggcactg ttatgggagc cgtcatcatg  1680
gaaggtttct atgtcgtctt cgatcgagcc cgaaagcgaa ttggctttgc tgtcagcgct  1740
tgccatgtgc acgatgagtt caggacgcg gcagtgaaag gtccgtttgt tacgcagac  1800
atggaagact gtggctacaa cattccccag acagatgagt caacacttat gaccatagcc  1860
tatgtcatgg cggccatctg cgccctcttc atgttccac tctgcctcat ggtatgtcag  1920
tggcgctgcc tgcgttgcct cgccaccag cacgatgact ttgctgatga catctcctg  1980
ctcaagtaag gaggcccgtg ggcagatgat ggagacgccc ctggaccaca tctgggtggt  2040
tcccttggt cacatgagtt ggagctatgg atggtacctg tggccagagc acctcaggac  2100
cctcaccaac ctgccaatgc ttctggcgtg acagaacaga gaaatcaggc aagctggatt  2160
acagggcttg cacctgtagg acacaggaga gggaaggaag cagcgttctg gtggcaggaa  2220
tatccttaga caccacaaac ttgagttgga aattttgctg cttgaagctt cagccctgac  2280
```

```
cctctgccca gcatccttta gagtctccaa cctaaagtat tctttatgtc cttccagaag    2340
tactggcgtc atactcaggc tacccggcat gtgtccctgt ggtaccctgg cagagaaagg    2400
gccaatctca ttccctgctg gccaaagtca gcagaagaaa gtgaagtttg ccagttgctt    2460
tagtgatagg gactgcagac tcaagcctac actggtacaa agactgcgtc ttgagataaa    2520
caagaaccta tgcgatgcga atgtttatac tcctgggggc agtcaagatg aggagacagg    2580
ataggataga gacaggaagg agatggtagc aaaactggga aaggcagaac tctgatcact    2640
ttctagttcc aagtttagac tcatctccaa gacagaagcc catctggact aagaggtatc    2700
attccccaat gtgcctgtgg ttgtagtctg aactgaaatg aaatgggga aaagggctt     2760 attagccaaa gagctctttt taacactctt agaggaacag tgctcatgag aaaagtccca    2820
ctggacagat gaattcctat cttgttaatt ctgtctctct ctgcttcttc aacatgctaa    2880
gtggcaccaa aatgacccaa ccccaaggtc ttaggtgccc tatgggacaa cagttagaat    2940
attgtagggc tagggatggt cttcccagca taggttcact ccaaccaagg tgctaaaagg    3000
aacagacagg agagtcctcc tctctgatcc acaaaggcag agccctcaag attcatccag    3060
cagggttagg gctgatgcat ttgcctctgc ctggattttg ttttttatttt ctttcttttt    3120 gcccagtggt acaaaacgat aagctctttta tggaatactg agtgggttca ttcctctctt    3180
gccctctcca atggcccctc tatttatctg gctaaggaaa caccacgcat tggctagtat    3240
taaacagcaa ctgtaagata gagggctttc tgttctatgt cattgccttc agtatcaagg    3300
ctgcctggag aaaggatggc agcctcaggg cttccttact ttcttctcct ttcctgacag    3360
agcagccttt ctgtcctgct ctctgctgcc cctcccaata taatccatgg gtacccaggc    3420
tggttcttgg gctaggttgt gggggccaca ctcacctctt ccctgccagt tctaacacga    3480
cagacatgaa gccagtgtta gtgggaagag ctgggttttc ccaggatgac cactgcatcc    3540
tctcctggta cgctctacac tgctttcagg ctggggacct gccaagtgtg ggacagttga    3600
tgaggaagag acattagcag ggcctctgga gttgctggcc cagccagctg cccacaagcc    3660
ataaaccaat aaaataagaa tcctgcgtca cagtttccag ctgggtcctc ttccttgccc    3720
tcgcactggt gctgctctgg ctgagtagga atacacccac agactgccag gaagatggag    3780
actgtccgct tccggctcag aactacagtg taattaagct tccaggatca ctaccatgaa    3840
aacgccgcat tctgctttat catttctacc catgttggga aaaactggct ttttccccat    3900
ttctttacag ggcaaaaaaa aaaaaaaaaa aagggagaga gagagagaac tcaacctagt    3960
tgttatttac cctagtaact ggtgttctat ttttttttaa aggggaaaaa tttgcattta    4020
tttttctttt gatggttaac tcctttgtat cataaaatta tgaactctga tatgtaaaac    4080
agaaaaaaat cttgacaaca gcttctcgct tgtaaaaata tgtattatac agctctattt    4140
tcaaagtctc ctgaaaaatg actgacctat ctccactg                           4178
```

<210> SEQ ID NO 24
<211> LENGTH: 16
<212> TYPE: DNA
<213> ORGANISM: Artificial
<220> FEATURE:
<223> OTHER INFORMATION: Synthetic

<400> SEQUENCE: 24
gcattcagtg aactag                                                      16

<210> SEQ ID NO 25
<211> LENGTH: 16

```
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3), (14)..(16)
<223> OTHER INFORMATION: 2'-O-Me RNA

<400> SEQUENCE: 25
gcattcagtg aacuag                                                   16

<210> SEQ ID NO 26
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1), (3)..(3), (7)..(7), (10)..(10), (12)..(12),
      (15)..(15)
<223> OTHER INFORMATION: LNA
<220> FEATURE:
<221> NAME/KEY: misc_feature
<222> LOCATION: (6)..(6), (14)..(14)
<223> OTHER INFORMATION: 5-methylcytosine LNA

<400> SEQUENCE: 26
tcagtctgat aagct                                                    15

<210> SEQ ID NO 27
<211> LENGTH: 15
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3), (13)..(15)
<223> OTHER INFORMATION: 2'-O-Me RNA

<400> SEQUENCE: 27
agcuuaucag acuga                                                    15

<210> SEQ ID NO 28
<211> LENGTH: 16
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1), (3)..(3), (14)..(16)
<223> OTHER INFORMATION: LNA
<220> FEATURE:
<221> NAME/KEY: misc_feature
<222> LOCATION: (2)..(2)
<223> OTHER INFORMATION: 5-methylcytosine LNA

<400> SEQUENCE: 28
gcauucagug aactag                                                   16

<210> SEQ ID NO 29
<211> LENGTH: 20
<212> TYPE: DNA
<213> ORGANISM: Artificial
<220> FEATURE:
<223> OTHER INFORMATION: Synthetic
<220> FEATURE:
<221> NAME/KEY: misc_feature
```

```
<222> LOCATION: (5)..(7), (18)..(20)
<223> OTHER INFORMATION: 2'-O-Me RNA
<220> FEATURE:
<221> NAME/KEY: misc_feature
<222> LOCATION: (8)..(17)
<223> OTHER INFORMATION: RNA

<400> SEQUENCE: 29
cttcgcauuc agugaacuag                                                  20

<210> SEQ ID NO 30
<211> LENGTH: 16
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (2)..(3), (14)..(15)
<223> OTHER INFORMATION: LNA
<220> FEATURE:
<221> NAME/KEY: misc_feature
<222> LOCATION: (1)..(1), (16)..(16)
<223> OTHER INFORMATION: 5-methylcytosine LNA

<400> SEQUENCE: 30
ctaguucacu gaatgc                                                      16
```